US005606032A

United States Patent [19]
Goodearl et al.

[11] Patent Number: 5,606,032
[45] Date of Patent: Feb. 25, 1997

[54] PROCESS FOR PREPARING GLIAL MITOGENIC FACTORS

[75] Inventors: Andrew Goodearl, Hertfordshire; Paul Stroobant, London, both of United Kingdom; Luisa Minghetti, Bagnacavallo, Italy; Michael Waterfield, Berkshire, United Kingdom; Mark Marchioni; Mario S. Chen, both of Arlington, Mass.; Ian Hiles, London, England

[73] Assignees: Ludwig Institute for Cancer Research, New York, N.Y.; Cambridge Neuroscience, Cambridge, Mass.

[21] Appl. No.: 469,569

[22] Filed: Jun. 6, 1995

Related U.S. Application Data

[60] Division of Ser. No. 36,555, Mar. 24, 1993, which is a continuation-in-part of Ser. No. 863,703, Apr. 3, 1992, abandoned, which is a continuation-in-part of Ser. No. 907,138, Jun. 30, 1992, abandoned, which is a continuation-in-part of Ser. No. 940,389, Sep. 3, 1992, abandoned, which is a continuation-in-part of Ser. No. 965,173, Oct. 23, 1992, abandoned.

[30] Foreign Application Priority Data

Apr. 10, 1991 [GB] United Kingdom ............... 9107566

[51] Int. Cl.⁶ ............... C07K 1/16; C07K 1/18; C07K 1/22; C07K 1/36
[52] U.S. Cl. ............... 530/416; 530/413; 530/417; 530/414; 530/415
[58] Field of Search ............... 530/413, 416, 530/417, 414, 415

[56] References Cited

PUBLICATIONS

Brockes et al, J. Neuroscience 4 (1984), 75–83.
Brockes et al J. Biol. Chem. 255(1980) 8374–8377.
Benveniste et al (PNAS 82 (1985), 3930–3934).
Holmes et al. Science (1992) 256:1205.
Davis et al. J. Cell. Biol., 110(1990), 1353–1360.

*Primary Examiner*—Howard F. Schain
*Attorney, Agent, or Firm*—Felfe & Lynch; Gregory B. Butler

[57] ABSTRACT

The invention involves the purification of various glial mitogenic factors. In one aspect of the invention, vertebrate brain material is extracted, and the extract is then subjected to chromatographic separation. The glial mitogenic factors which can be obtained include a basic polypeptide with a molecular weight of from about 30 to about 36 kD, by reference to SDS-PAGE, and a second basic polypeptide factor which is from about 55 to about 63 kD as determined by SDS-page.

12 Claims, 78 Drawing Sheets

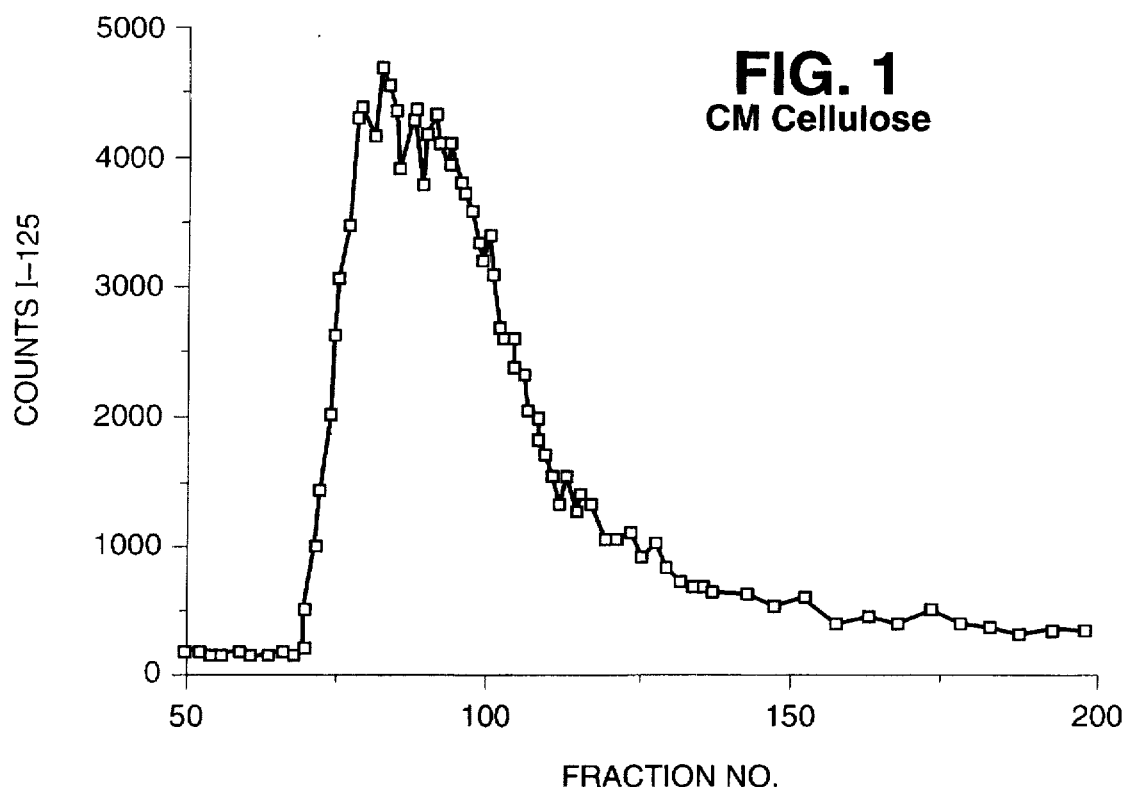
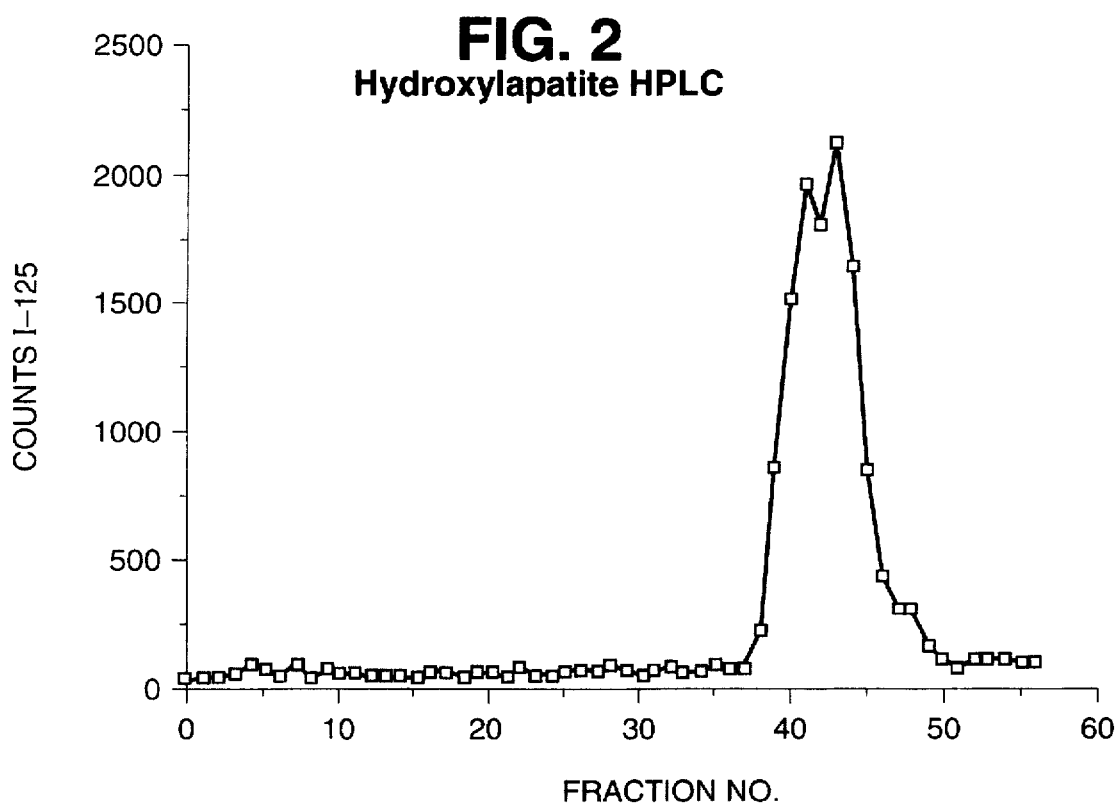

Mono S

Superose 12 Gel Filtration FPLC

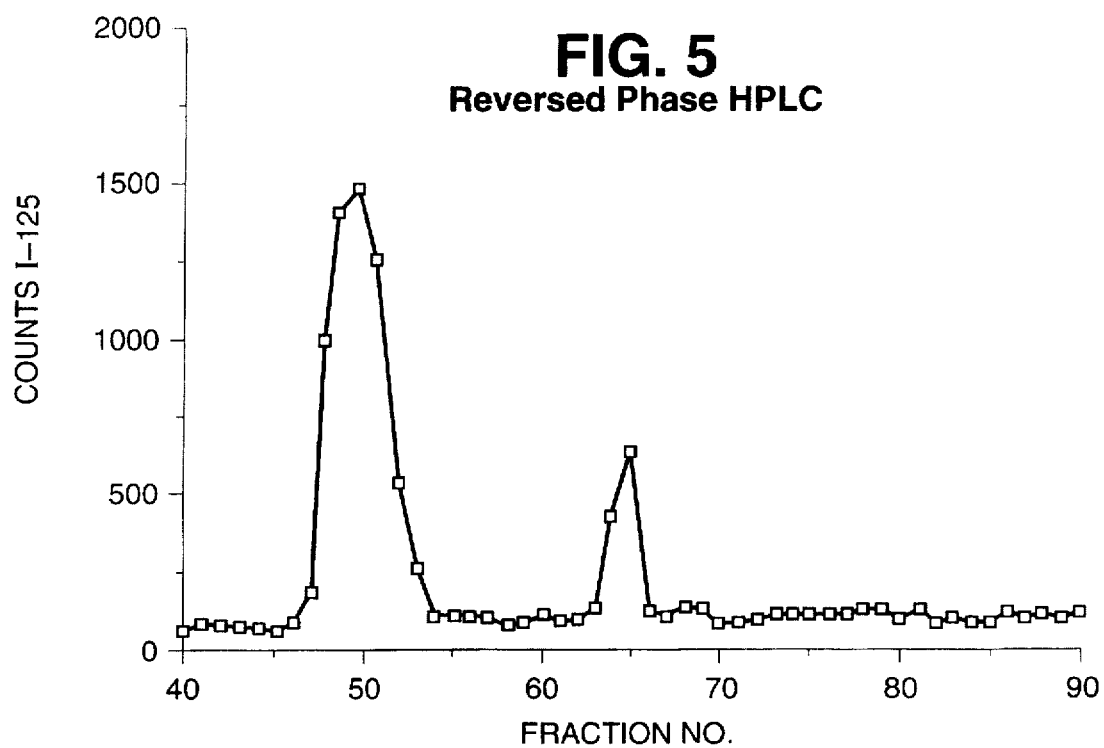
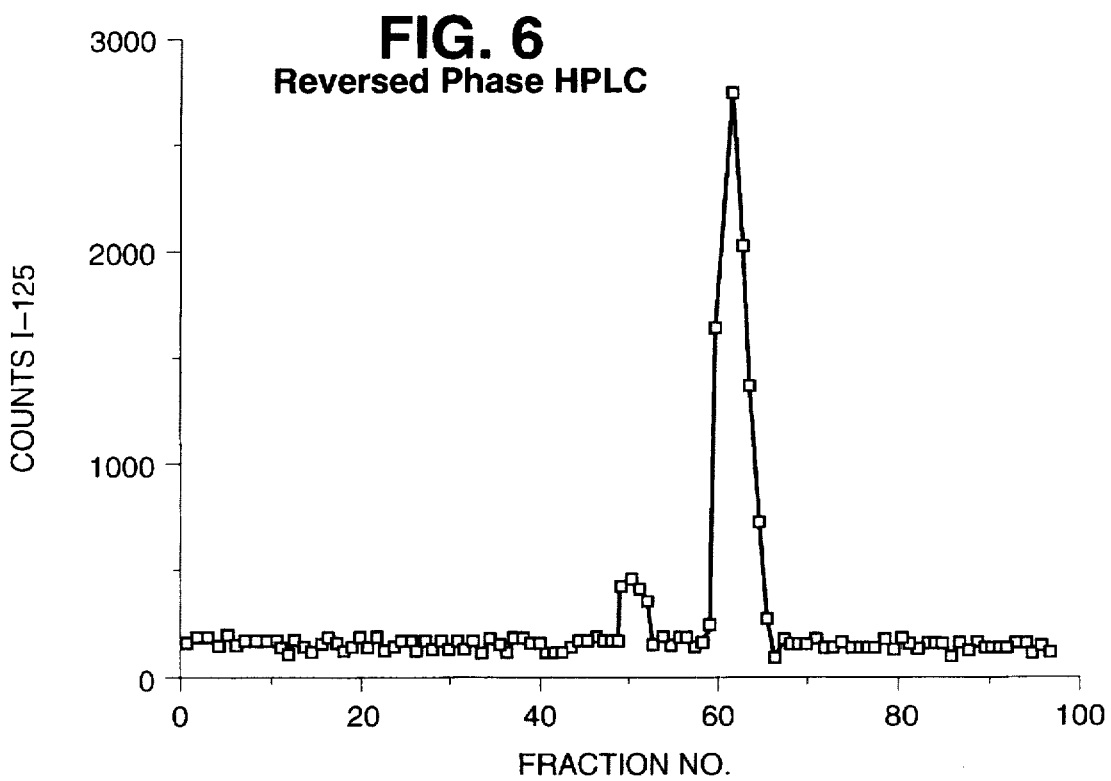

Factor-I Dose Response in Serum & Plasma

Factor-II Dose Response in Serum or Plasma

FIG. 9

```
           N-terminus
GGF-I 01   F K G D A H T E                              (SEQ ID NO: 1)

Trypsin peptides
GGF-I 02   K/R A S L A D E Y E Y M X K *                (SEQ ID NO: 2)
GGF-I 03   K/R T E T S S G L X L K                      (SEQ ID NO: 3)
GGF-I 04   K/R K L G E M W A E                          (SEQ ID NO: 4)    HMG-1
GGF-I 05   K/R L G E K R A                              (SEQ ID NO: 5)    HMG-1?
GGF-I 06   K/R I K S E H A G L S I G D T A K *          (SEQ ID NO: 6)    HMG-2
GGF-I 07   K/R A S L A D E Y E Y M R K *                (SEQ ID NO: 7)
GGF-I 08   K/R I K G E H P G L S I G D V A K *          (SEQ ID NO: 8)    HMG-1
GGF-I 09   K/R M S E Y A F F V Q T X R *                (SEQ ID NO: 9)    HMG-2
GGF-I 10   K/R S E H P G L S I G D T A K *              (SEQ ID NO: 10)   HMG-1
GGF-I 11   K/R A G Y F A E X A R                        (SEQ ID NO: 11)
GGF-I 12   K/R K L E F L X A K *                        (SEQ ID NO: 12)
GGF-I 13   K/R T T E M A S E Q G A                      (SEQ ID NO: 13)
GGF-I 14   K/R A K E A L A A L K *                      (SEQ ID NO: 14)
GGF-I 15   K/R F V L Q A K K *                          (SEQ ID NO: 15)
GGF-I 16   K/R L G E M W                                (SEQ ID NO: 16)   HMG-1

Protease V8 peptides
GGF-I 17   E T Q P D P G Q I L K K K V P M V I G A Y T  (SEQ ID NO: 169)
GGF-I 18   E Y K C L K F K W F K K K A T V M            (SEQ ID NO: 17)
GGF-I 19   E A K Y F S K X D A                          (SEQ ID NO: 18)
GGF-I 20   E X K F Y V P                                (SEQ ID NO: 19)   LH-alpha
GGF-I 21   E L S F A S V R L P G C P P G V D P M V S F P V A L  (SEQ ID NO: 20)   LH-beta
```

| | | | | | | | | | | | | | |
|---|---|---|---|---|---|---|---|---|---|---|---|---|---|
| GGF-I 01 | F | A | F | K | G | D | A | H | T | E | | | (SEQ ID NO: 1) |
| GGF-I 02 | A | S | L | A | D | E | Y | E | Y | M | X | K | (SEQ ID NO: 22) |
| GGF-I 03 | T | E | T | S | S | G | L | X | L | K | | | (SEQ ID NO: 23) |
| GGF-I 07 | A | S | L | A | D | E | Y | E | Y | M | R | K | (SEQ ID NO: 24) |
| GGF-I 11 | A | G | Y | F | A | E | X | A | R | | | | (SEQ ID NO: 25) |
| GGF-I 13 | T | T | E | M | A | S | E | Q | G | A | | | (SEQ ID NO: 26) |
| GGF-I 14 | A | K | E | A | L | A | A | L | K | | | | (SEQ ID NO: 27) |
| GGF-I 15 | F | V | L | Q | A | K | K | | | | | | (SEQ ID NO: 28) |
| GGF-I 17 | E | T | Q | P | D | P | G | Q | I | L | K | K | V P M V I G A Y T (SEQ ID NO: 29) |
| GGF-I 18 | E | Y | K | C | L | K | F | K | K | W | F | K | K A T V M (SEQ ID NO: 17) |

B

| | | | | | | | | |
|---|---|---|---|---|---|---|---|---|
| GGF-I 20 | E | X | K | F | Y | V | P | (SEQ ID NO: 19) |
| GGF-I 12 | K | L | E | F | L | X | A | K (SEQ ID NO: 32) |

FIG. 11

Trypsin peptides

| | | | |
|---|---|---|---|
| GGF-II 01 | K/R | V H Q V W A A K * | (SEQ ID NO: 33) |
| GGF-II 02 | K/R | Y I F F M E P E A X S S G | (SEQ ID NO: 34) |
| GGF-II 03 | K/R | L G A W G P P A F P V X Y | (SEQ ID NO: 35) |
| GGF-II 04 | K/R | W F V V I E G K * | (SEQ ID NO: 36) |
| GGF-II 05 | K/R | A L A A A G Y D V E K * | (SEQ ID NO: 164) |
| GGF-II 06 | K/R | L V L R * | (SEQ ID NO: 165) |
| GGF-II 07 | K/R | X X Y P G Q I T S N | (SEQ ID NO: 166) |
| GGF-II 08 | K/R | A S P V S V G S V Q E L V Q R * | (SEQ ID NO: 37) |
| GGF-II 09 | K/R | V C L L T V A A P P T | (SEQ ID NO: 38) |
| GGF-II 10 | K/R | D L L L X V | (SEQ ID NO: 39) |

Histone H1 (at GGF-II 05)
Trypsin (at GGF-II 06)

Lysyl Endopeptidase-C peptides

| | | |
|---|---|---|
| GGF-II 11 | K V H Q V W A A K * | (SEQ ID NO: 51) |
| GGF-II 12 | K A S L A D S G E Y M X K * | (SEQ ID NO: 52) |

| | | |
|---|---|---|
| GGF-II 01 | V H Q V W A A K | (SEQ ID NO: 45) |
| GGF-II 02 | Y I F F M E P E A X S S G | (SEQ ID NO: 46) |
| GGF-II 03 | L G A W G P P A F P V X Y | (SEQ ID NO: 47) |
| GGF-II 04 | W F V V I E G K | (SEQ ID NO: 48) |
| GGF-II 08 | A S P V S V G S V Q E L V Q R | (SEQ ID NO: 49) |
| GGF-II 09 | V C L L T V A A P P T | (SEQ ID NO: 50) |
| GGF-II 11 | K V H Q V W A A K | (SEQ ID NO: 51) |
| GGF-II 12 | K A S L A D S G E Y M X K | (SEQ ID NO: 52) |

B   Novel Factor II Peptides - others

| | | |
|---|---|---|
| GGF-II 10 | D L L L X V | (SEQ ID NO: 53) |

Comparison of BrdU-ELISA and [125 I]UdR Counting Method for the DNA Synthesis Assay in Schwann Cell Cultures Comparison of Br-UdR Immunoreactivity and Br-UdR Labelled Cell Number Comparison of Br-UdR Immunoreactivity and Br-UdR Labelled Cell Number

Mitogenic Response of Rat Sciatic Nerve Schwann cell to GGFs

DNA Synthesis in Rat Sciatic Nerve Schwann Cells and 3T3 Fibroblasts in the presence of GGFs

Mitogenic Response of BHK 21 C13 Cells to FCS and GGFs

Survival and Proliferation of BHK21 C13 Cell Microcultures After 48 Hours in Presence of GGFs Mitogenic Response
of C6 Cells to FCS Mitogenic Response of
C6 Cells to aFGF & GGFs Mitogenic Response of
C6 Cells to aFGF & GGFs

FIG. 21

Degenerate Oligonucleotide Probes for Factor I & Factor II

| Oligo | Sequence | Peptide | | | |
|---|---|---|---|---|---|
| 535 | TTYAARGGNGAYGCNCAYAC! | GGFI-1 | (SEQ | ID NO: | 54) |
| 536 | CATRTAYTCRTAYTCRTCNGC! | GGFI-2 | (SEQ | ID NO: | 55) |
| 537 | TGYTCNGANGCCATYTCNGT! | GGFI-13 | (SEQ | ID NO: | 56) |
| 538 | TGYTCRCTNGCCATYTCNGT! | GGFI-13 | (SEQ | ID NO: | 57) |
| 539 | CCDATNACCATNGGNACYTT! | GGFI-17 | (SEQ | ID NO: | 58) |
| 540 | GCNGCCCANACYTGRTGNAC! | GGFII-1 | (SEQ | ID NO: | 59) |
| 541 | GCYTCNGGYTCCATRAARAA! | GGFII-2 | (SEQ | ID NO: | 60) |
| 542 | CCYTCDATNACNACRAACCA! | GGFII-4 | (SEQ | ID NO: | 61) |
| 543 | TCNGCRAARTANCCNGC! | GGFI-11 | (SEQ | ID NO: | 62) |
| 544 | GCNGCNAGNGCYTCYTTNGC! | GGFI-14 | (SEQ | ID NO: | 63) |
| 545 | GCNGCYAANGCYTCYTTNGC! | GGFI-14 | (SEQ | ID NO: | 64) |
| 546 | TTYTTNGCYTGNAGNACRAA! | GGFI-15 | (SEQ | ID NO: | 65) |
| 551 | TTYTTNGCYTGYAANACRAA! | GGFI-15 | (SEQ | ID NO: | 66) |
| 568 | TGNACNAGYTCYTGNAC! | GGFII-8 | (SEQ | ID NO: | 67) |
| 569 | TGNACYAAYTCYTGNAC! | GGFII-8 | (SEQ | ID NO: | 68) |
| 609 | CATRTAYTCNCCNGARTCNGC! | GGFII-12 | (SEQ | ID NO: | 69) |
| 610 | CATRTAYTCNCCRCTRTCNGC! | GGFII-12 | (SEQ | ID NO: | 70) |
| 649 | NGARTCNGCYAANGANGCYTT! | GGFII-12 | (SEQ | ID NO: | 71) |
| 650 | NGARTCNGCNAGNGANGCYTT! | GGFII-12 | (SEQ | ID NO: | 72) |
| 651 | RCTRTCNGCYAANGANGCYTT! | GGFII-12 | (SEQ | ID NO: | 73) |
| 652 | RCTRTCNGCNAGNGANGCYTT! | GGFII-12 | (SEQ | ID NO: | 74) |
| 653 | NGARTCNGCYAARCTNGCYTT! | GGFII-12 | (SEQ | ID NO: | 75) |
| 654 | NGARTCNGCNAGRCTNGCYTT! | GGFII-12 | (SEQ | ID NO: | 76) |
| 655 | RCTRTCNGCYAARCTNGCYTT! | GGFII-12 | (SEQ | ID NO: | 78) |
| 656 | RCTRCTNGCNAGRCTNGCYTT! | GGFII-12 | (SEQ | ID NO: | 79) |
| 659 | ACNACNGARATGGCTCNNGA! | GGFI-13 | (SEQ | ID NO: | 80) |
| 660 | ACNACNGARATGGCAGYNGA! | GGFI-13 | (SEQ | ID NO: | 81) |
| 661 | CAYCARGTNTGGGCNGCNAA! | GGFII-1 | (SEQ | ID NO: | 82) |
| 662 | TTYGTNGTNATHGARGGNAA! | GGFII-4 | (SEQ | ID NO: | 83) |
| 663 | AARGGNGAYGCNCAYACNGA! | GGFI-1 | (SEQ | ID NO: | 84) |
| 664 | GARGCNYTNGCNGCNYTNAA! | GGDI-14 | (SEQ | ID NO: | 85) |
| 665 | GTNGGNTCNGTNCARGARYT! | GGFII-8 | (SEQ | ID NO: | 86) |
| 666 | GTNGGNAGYGTNCARGARYT! | GGFII-8 | (SEQ | ID NO: | 87) |
| 694 | NACYTTYTTNARHATYTGNCC! | GGFI-17 | (SEQ | ID NO: | 88) |

FIG. 22
Putative Bovine Factor II Gene Sequences

```
SEQ ID NO: 89:

TCTAA AAC TAC AGA GAC TGT ATT TTC ATG ATC ATC ATA GTT CTG TGA AAT ATA    53
      Asn Tyr Arg Asp Cys Ile Phe Met Ile Ile Ile Val Leu Xaa Asn Ile

CTT AAA CCG CTT TGG TCC TGA TCT TGT AGG AAG TCA GAA CTT CGC ATT         101
Leu Lys Pro Leu Trp Ser Xaa Ser Cys Arg Lys Ser Glu Leu Arg Ile

AGC AAA GCG TCA CTG GCT GAT TCT GGA GAA TAT ATG TGC AAA GTG ATC         149
Ser Lys Ala Ser Leu Ala Asp Ser Gly Glu Ser Met Cys Lys Val Ile

AGC AAA CTA GGA AAT GAC AGT GCC TCT GCC AAC ATC ACC ATT GTG GAG         197
Ser Lys Leu Gly Asn Asp Ser Ala Ser Ala Asn Ile Arg Ile Val Glu

TCA AAC GGT AAG AGA TGC CTA CTG CGT GCT ATT TCT CAG TCT CTA AGA         245
Ser Asn Gly Lys Arg Cys Leu Leu Arg Ala Ile Ser Gln Ser Leu Arg

GGA GTG ATC AAG GTA TGT GGT CAC ACT TGA ATC ACG CAG GTG TGT GAA         293
Gly Val Ile Lys Val Cys Gly His Thr Xaa Ile Thr Gln Val Cys Glu

ATC TCA TTG TGA ACA AAT AAA AAT CAT GAA AGG AAA ACT CTA TGT TTG         341
Ile Ser Cys Xaa Thr Asn Lys Asn His Glu Arg Lys Thr Leu Cys Leu

AAA TAT CTT ATG GGT CCT CCT GTA AAG CTC TTC ACT CCA TAA GGT GAA         389
Lys Tyr Leu Met Gly Pro Pro Val Lys Leu Phe Thr Pro Xaa Gly Glu

ATA GAC CTG AAA TAT ATA TAG ATT ATT T                                   417
Ile Asp Leu Lys Tyr Ile Xaa Ile Ile
```

FIG. 23A
PCR Primers for Factor I & Factor II

Degenerate PCR Primers

| Oligo | Sequence | Peptide | |
|---|---|---|---|
| 657 | CCGAATTCTGCAGGARACNCARCCNGAYCCNGG! | GGFI-17 | (SEQ ID NO: 90) |
| 658 | AAGGATCCTGCAGNGTRTANGCNCCHATNACCATNGG! | GGFI-17 | (SEQ ID NO: 91) |
| 667 | CCGAATTCTGCAGGCNGAYTCNGGNGARTAYATG! | GGFII-12 | (SEQ ID NO: 92) |
| 668 | CCGAATTCTGCAGGCNGAYATYGGNGARTAYAT! | GGFII-12 | (SEQ ID NO: 93) |
| 669 | AAGGATCCTGCAGNNNCATRTAYTCNCCNGARTC! | GGFII-12 | (SEQ ID NO: 94) |
| 670 | AAGGATCCTGCAGNNNCATRTAYTCNCCRRTRTC! | GGFII-12 | (SEQ ID NO: 95) |
| 671 | CCGAATTCTGCAGCAYCARGTNTGGCNGCNAA! | GGFI-1 | (SEQ ID NO: 96) |
| 672 | CCGAATTCTGCAGATRTYTTYATGGARCCNGARG! | GGFII-2 | (SEQ ID NO: 97) |
| 673 | CCGAATTCTGCAGGGGNCCNCCNGCNTTYCCNGT! | GGFII-3 | (SEQ ID NO: 98) |
| 674 | CCGAATTCTGCAGTGGTTYGTNGTNATHGARGG! | GGFII-4 | (SEQ ID NO: 99) |
| 677 | AAGGATCCTGCAGYTTNGCNGCCCANACYTGRTG! | GGFI-1 | (SEQ ID NO: 100) |
| 678 | AAGGATCCTGCAGGCYTCNGGYTCCATRAARAA! | GGFII-2 | (SEQ ID NO: 101) |
| 679 | AAGGATCCTGCAGACNGGRAANGCNGGNGGNCC! | GGFII-3 | (SEQ ID NO: 102) |
| 680 | AAGGATCCTGCAGYTNCCYTCDATNACNACRAAC! | GGFII-4 | (SEQ ID NO: 103) |
| 681 | CATRTAYTCRTAYTCTCNGCAAGRGGNGAYGCNCAYACNGA! | GGFI-2 | (SEQ ID NO: 104) |
| 682 | CCGAATTCTGCAGAARGGNGAYGCNCAYACNGA! | GGFI-1 | (SEQ ID NO: 105) |
| 683 | GCNGCYAANGCYRCYTTNGCAAGGATCCTGCAG! | GGFI-14 | (SEQ ID NO: 106) |
| 684 | GCNGCNAGNGCYTCYTTNGCAAGGATCCTGCAG! | GGFI-14 | (SEQ ID NO: 107) |
| 685 | TCNGCRAARTANCNGCAAGGATCCTGCAG! | GGFI-1 | (SEQ ID NO: 108) |

FIG. 23B
PCR Primers for Factor I & Factor II

Unique PCR Primers for Factor II

| Oligo | Sequence | Comment | |
|---|---|---|---|
| 711 | CATCGATCTGCAGGCTGATTCTGGAGAATATATGTGCA! | 3' RACE | (SEQ ID NO: 109) |
| 712 | AAGGATCCTGCAGCCACACATCTCGAGTCGACATCGATT! | 3' RACE | (SEQ ID NO: 110) |
| 713 | CCGAATTCTGCAGTGATCAGCAAACTAGGAAATGACA! | 3' RACE | (SEQ ID NO: 111) |
| 721 | CATCGATCTGCAGCCTAGTTTGCTGATCACTTTGCAC! | 5' RACE | (SEQ ID NO: 112) |
| 722 | AAGGATCCTGCAGTATATTCTCCAGAATCAGCCAGTG! | 5' RACE; ANCHORED | (SEQ ID NO: 113) |
| 725 | AAGGATCCTGCAGGCACGCAGTAGGCATCTCTTA! | EXON A | (SEQ ID NO: 114) |
| 726 | CCGAATTCTGCAGCAGAACTTCGCATTAGCAAAGC! | EXON A | (SEQ ID NO: 115) |
| 771 | CATCCCGGGATGAAGAGTCAGGAGTCTGTGGCA! | EXONS B+A | (SEQ ID NO: 116) |
| 772 | ATACCCGGGCTGCAGACAATGAGATTTCACACACCTGCG! | | (SEQ ID NO: 117) |
| 773 | AAGGATCCTGCAGTTTGGAACCTGCCACAGACTCCT! | ANCHORED | (SEQ ID NO: 118) |
| 776 | ATACCCGGGCTGCAGATGAGATTTCACACACCTGCCGTGA! | EXONS B+A | (SEQ ID NO: 119) |

Summary of Contiguous GGF-II cDNA Structures & Sequences

Alternative Gene Products of Putative Bovine GGF-II

FIG. 27

GGF-II Peptides Identified in Deduced Amino Acid Sequences of Putative Bovine GGF-II Proteins

| Peptide | Pos. | Sequence match | ID Sequences |
|---|---|---|---|
| II-1 | | VHQVWAAK | |
| | 1: | HQVWAAK AAGLK | (SEQ ID NO:120) |
| II-10 | | DLLLXV | |
| | 14: | GGLKK dslltv RLGAW | (SEQ ID NO:121) |
| II-03 | | LGAWGPPAFPVXY | (SEQ ID NO:122) |
| | 21: | LLTVR lgawghpafpscg RLKED | (SEQ ID NO:123) |
| II-02 | | YIFFMEPEAXSSG | (SEQ ID NO:124) |
| | 41: | KEDSR YIFFMEPEANSSG GPGRL | (SEQ ID NO:125) |
| II-6 | | LVLR | |
| | 103: | VAGSK LVLR CETSS | (SEQ ID NO:126) |
| I-18 | | EYKCLKFKWFKKATVM | (SEQ ID NO:127) |
| | 112: | CETSS eysslkfkwfkngsel SRKNK | (SEQ ID NO:128) |
| II-12 | | KASLADSGEYMXK | (SEQ ID NO:129) |
| | 151: | ELRIS KASLADSGEYMCK VISKL | (SEQ ID NO:130) |
| I-07 | | ASLADEYEYMRK | (SEQ ID NO:131) |
| | 152: | LRISK asladsgeymck VISKL | (SEQ ID NO:132) |

FIG. 28A

SEQ ID NO: 133:

```
                                                                                                  CCTGCAG CAT CAA GTG TGG GCG AAA GCC GGG GGC TTG AAG AAG GAC TCG CTG   55
                                                His Gln Val Trp Ala Lys Ala Gly Gly Leu Lys Lys Asp Ser Leu

CTC ACC GTG CGC CTG GAG GAG AAG GCC GGG GCC CCC GCC CAC CCC GCC TTG AAG TTC CCC TCC TGC          103
Leu Thr Val Arg Leu Glu Glu Lys Ala Gly Ala Pro Ala His Pro Ala Phe Pro Ser Cys

GGG CGC CTC AAG GAG GAC GAG AGC AGG AGG TAC ATC TTC TTC ATG GAG CCC GAG                          151
Gly Arg Leu Lys Glu Asp Glu Ser Arg Arg Tyr Ile Phe Phe Met Glu Pro Glu

GCC AAC AGC AGC GGC GGG CCC CGC GGC CCG CTT CCG AGC CTC CTT CCC CCC                              199
Ala Asn Ser Ser Gly Gly Pro Arg Gly Pro Leu Pro Ser Leu Leu Pro Pro

TCT CGA GAC GGG CCC GAA CCT CAA GGA GGT CAG CCG GGT GCT GTG                                      247
Ser Arg Asp Gly Pro Glu Pro Gln Gly Gly Gln Pro Gly Ala Val

CAA CGG TGC GCC TTG CCT CCC CGC TTG CCC ATG GAG AAA AAG ATG CAG GAG                              295
Gln Arg Cys Ala Leu Pro Pro Arg Leu Pro Met Glu Lys Lys Met Gln Glu

TCT GTG GCA GGT TCC CTC AAA CTA GTG CTT CGG TGC GAG AGT TCT GAA                                  343
Ser Val Ala Gly Ser Leu Lys Leu Val Leu Arg Cys Glu Ser Ser Glu

TAC TCC TCT CTC AAG TTC TGG AAG TTC TTC AAG AAT GGG AGT TTA AGC                                  391
Tyr Ser Ser Leu Lys Phe Trp Lys Phe Phe Lys Asn Gly Ser Leu Ser

CGA AAG AAC CCA ATT AGC GAA ATC ATA CAG CTG GCT TCT CCG GGG AAG                                  439
Arg Lys Asn Pro Ile Ser Glu Ile Ile Gln Leu Ala Ser Pro Gly Lys

TCA GAA CTT CGC AGC AGC AAA CTA GGA AAT GAC AGT GCC TCT GAA TAT                                  487
Ser Glu Leu Arg Ser Ser Lys Leu Gly Asn Asp Ser Ala Ser Glu Tyr

ATG TGC AAA GTG ATC ATC TCA AAC GGT ATC AAG GTA TCT GCC TCT GCC AAC                              535
Met Cys Lys Val Ile Ile Ser Asn Gly Ile Lys Val Ser Ala Ser Asn

ATC ACC ATT GTG GAG TCA AAC GGT AAG AGA TGC CTA CTG CGT GCT ATT                                  583
Ile Thr Ile Val Glu Ser Asn Gly Lys Arg Cys Leu Leu Arg Ala Ile

TCT CAG TCT CTA AGA GGA ATC GTG AAG GTA TGT CAC ACT                                              625
Ser Gln Ser Leu Arg Gly Ile Val Lys Val Cys His Thr

TGAATCACGC AGGTGTGTGA AATCTCATTG TGAACAAATA AAAATCATGA AAGGAAAAAA                                685

AAAAAAAAAA AATCGATGTC GACTCGAGAT GTGGCTGCAG GTCGACTCTA GAGGATCCC                                 744
```

FIG. 28B

Nucleotide Sequences & Deduced Amino Acid Sequences of GGF2BPP2

SEQ ID NO: 134:

```
CCTGCAG CAT GTG CAA TGG GCG GCG AAA GCC GGG GGC TTG AAG AAG GAC TCG CTG     55
        His Val Gln Trp Ala Ala Lys Ala Gly Gly Leu Lys Lys Asp Ser Leu

CTC ACC GTG CGC CTG GGC GCC TGG GGC CAC CCC GCC TTC CCC TCC TGC            103
Leu Thr Val Arg Leu Gly Ala Trp Gly His Pro Ala Phe Pro Ser Cys

GGG CGC CTC AAG GAG GAC AGC AGG TAC ATC TTC TTC ATG GAG CCC GAG            151
Gly Arg Leu Lys Glu Asp Ser Arg Tyr Ile Phe Phe Met Glu Pro Glu

GCC AAC AGC GGC GGG CCC GGC CGC CTT CCG AGC CTC CTT CCC CCC               199
Ala Asn Ser Gly Gly Pro Gly Arg Leu Pro Ser Leu Leu Pro Pro

TCT CGA GAC GGG CCG CCT CAA GAA GGA GGT CAG CCG GCT GTG                   247
Ser Arg Asp Gly Pro Pro Gln Glu Gly Gly Gln Pro Ala Val

CAA CGG TGC GCC TTG CCT CCC CGC TTG AAA GAG ATG AAG CAG GAG               295
Gln Arg Cys Ala Leu Pro Pro Arg Leu Lys Glu Met Lys Gln Glu

TCT GTG GCA GGT TCC AAA CTA GTG CTT CGG TGC GAG ACC AGT GAA               343
Ser Val Ala Gly Ser Lys Leu Val Leu Arg Cys Glu Thr Ser Glu

TAC TCC TCT CTC AAG TTC TGG TTC AAG AAT GGG AGT TTA AGC                   391
Tyr Ser Ser Leu Lys Phe Trp Phe Lys Asn Gly Ser Leu Ser

CGA AAG AAC CCA GAA AAC ATC ATA CAG CAG AAA AGG CCG GGG AAG               439
Arg Lys Asn Pro Glu Asn Ile Ile Gln Gln Lys Arg Pro Gly Lys

TCA GAA CTT CGC ATT AGC AAA GCG TCA CTG GCT GAT TCT GGA GAA TAT           487
Ser Glu Leu Arg Ile Ser Lys Ala Ser Leu Ala Asp Ser Gly Glu Tyr

ATG TGC AAA GTG ATC AGC AAA CTA GGA AAT GAC AGT GCC TCT GCC AAC           535
Met Cys Lys Val Ile Ser Lys Leu Gly Asn Asp Ser Ala Ser Ala Asn
```

FIG. 28C

Nucleotide Sequences & Deduced Amino Acid Sequences of GG2BPP2

```
ATC ACC ATT GTG GAG TCA AAC GCC ACA TCC ACA TCT ACA GCT GGG ACA      583
Ile Thr Ile Val Glu Ser Asn Ala Thr Ser Thr Ser Thr Ala Gly Thr

AGC CAT CTT GTC AAG TGT GCA GAG AAG ACT TTC TGT GTG AAT              631
Ser His Leu Val Lys Cys Ala Glu Lys Thr Phe Cys Val Asn

GGA GGC TGC ATG GTG AAA GAC CTT TCA AAT CCC TCA AGA TAC              679
Gly Gly Cys Met Val Lys Asp Leu Ser Asn Pro Ser Arg Tyr

TTG TGC AAG TGC CAA CCT GGA TTC ACT GGA GCG AGA TGT ACT GAG AAT      727
Leu Cys Lys Cys Gln Pro Gly Phe Thr Gly Ala Arg Cys Thr Glu Asn

GTG CCC ATG AAA GTC CAA ACC CAA GAA AGT GCC CAA ATG AGT TTA CTG      775
Val Pro Met Lys Val Gln Thr Gln Glu Ser Ala Gln Met Ser Leu Leu

GTG ATC GCT GCC AAA ACT ACG TAATGGCCAG CTTCTACAGT ACGTCCACTC         826
Val Ile Ala Ala Lys Thr Thr

CCTTTCTGTC TCTGCCCTGAA TAGCGCATCT CAGTCGGTGC CGCTTTCTTG TTGCCGCATC   886

TCCCCTCAGA TTCCTCCTAG AGCTAGATGC GTTTACCAG GTCTAACATT GACTGCCTCT     946

GCCTGTCGCA TGAGAACATT AACACAAGCG ATTGTATGAC TTCCCTCTGTC CGTGACTAGT   1006

GGGCTCTGAG CTACTCGTAG GTGCGTAAGG CTCCAGTGTT TCTGAAATTG ATCTTGAATT    1066

ACTGTGATAC GACATGATAG TCCCCTCTCAC CCAGTGCAAT GACAATAAAG GCCTTGAAAA   1126

GTCAAAAAAA AAAAAAAAAA AAAAAATCGA TGTCGACTCG AGATGTGGCT GCAGGTCGAC    1186

TCTAGAG                                                              1193
```

FIG. 28D

Nucleotide Sequences & Deduced Amino Acid Sequences of GGF2BPP3

SEQ ID NO: 135:

```
CCTGCAG CAT CAA GTG TGG GCG GCG AAA GCC GGG GGC TTG AAG AAG GAC TCG CTG  55
        His Gln Val Trp Ala Ala Lys Ala Gly Gly Leu Lys Lys Asp Ser Leu

CTC ACC GTG CGC CTG GGC GCC TGG GCC CAC CCC GCC TTC CCC TCC TGC         103
Leu Thr Val Arg Leu Gly Ala Trp Ala His Pro Ala Phe Pro Ser Cys

GGG CGC CTC AAG GAG GAC AGC TAC AGG AGG TTT ATC TTC ATG GAG CCC GAG     151
Gly Arg Leu Lys Glu Asp Ser Arg Arg Tyr Ile Phe Met Glu Pro Glu

GCC AAC AGC GGC GGG CCC CGC CTT CCG AGC CTC CTT CCC CCC                 199
Ala Asn Ser Gly Gly Pro Arg Leu Pro Ser Leu Leu Pro Pro

TCT CGA GAC GGG CCG GAA CCT CAA GGA GAA CAG CAG CCG GGT GCT GTG         247
Ser Arg Asp Gly Pro Glu Pro Gln Glu Gln Gln Pro Gly Ala Val

CAA CGG TGC GCC TTG CCT CCC CGC TTG AAA ATG AAG AGT CAG GAG             295
Gln Arg Cys Ala Leu Pro Pro Arg Leu Lys Met Lys Ser Gln Glu

TCT GTG GCA GGT TCC AAA CTA GTG CTT CGG TGC GAG ACC AGT TCT GAA         343
Ser Val Ala Gly Ser Lys Leu Val Leu Arg Cys Glu Thr Ser Ser Glu

TAC TCC CTC CTC AAG TTC TGG AAG TTC AAG ATA GGG AGT TTA AGC             391
Tyr Ser Leu Leu Lys Phe Trp Lys Phe Lys Ile Gly Ser Leu Ser

CGA AAG AAC CCA GAA AAC ATC AAG CAG AAA AGG CCG GGG AAG                 439
Arg Lys Asn Pro Glu Asn Ile Lys Gln Lys Arg Pro Gly Lys

TCA GAA CTT CGC ATT AGC AAA GCG TCA CTG GCT GAT TCT GGA GAA TAT         487
Ser Glu Leu Arg Ile Ser Lys Ala Ser Leu Ala Asp Ser Gly Glu Tyr
```

FIG. 28E

Nucleotide Sequences & Deduced Amino Acid Sequences of GGF2BPP3

```
ATG TGC AAA GTG ATC AGC AAA CTA GGA AAT GAC AGT GCC TCT GCC AAC          535
Met Cys Lys Val Ile Ser Lys Leu Gly Asn Asp Ser Ala Ser Ala Asn

ATC ACC ATT GTG GAG TCA AAC GCC ACA TCC ACA TCT ACA GCT GGG ACA          583
Ile Arg Ile Val Glu Ser Asn Ala Thr Ser Thr Ser Thr Ala Gly Thr

AGC CAT CTT GTC AAG TGT GCA GAG AAG ACT TTC TGT GTG AAT          631
Ser His Leu Val Lys Cys Ala Glu Lys Thr Phe Cys Val Asn

GGA GGC GAG TGC TTC ATG GTG AAA GAC CTT TCA AAT CCC TCA AGA TAC          679
Gly Gly Glu Cys Phe Met Val Lys Asp Leu Ser Asn Pro Ser Arg Tyr

TTG TGC AAG TGC CCA AAT GAG TTT ACT GGT GAT CGC TGC CAA AAC TAC          727
Leu Cys Lys Cys Pro Asn Glu Phe Thr Gly Asp Arg Cys Gln Asn Tyr

GTA ATG GCC AGC TTC TAC AGT ACG TCC CCC TTT CTG TCT CTG CCT          775
Val Met Ala Ser Phe Tyr Ser Thr Ser Pro Phe Leu Ser Leu Pro

GAA TAGCGCATCT CAGTCGGTGC CGCTTTCTTG TTGCCGCATC TCCCCCTCAGA TTCCGCCTAG   838
Glu

AGCTAGATGC GTTTTACCAG GTCTAACATT GACTGCCTCT GCCTGTCGCA TGAGAACATT        898

AACACAAGCG ATTGTATGAC TTCCCTCTGTC CGTGACTAGT GGGCTCTGAG CTACTCGTAG       958

GTGCGTAAGG CTCCAGTGTT TCTGAAATTG ATCTTGAATT ACTGTGATAC GACATGATAG       1018

TCCCTCTCAC CCAGTGCAAT GACAATAAAG GCCTTGAAAA GTCAAAAAAA AAAAAAAAAA       1078

AAAAATCGAT GTCGACTCGA GATGTGGCTG                                        1108
```

FIG. 31A

Coding Segments of Glial Growth Factor/Heregulin Gene

```
CODING SEGMENT F: (SEQ ID NO: 136 (bovine) and 173 (human))

AGTTTCCCCC CCCAACTTGT CGGAACTCTG GGCTCGGCGC CAGGGCAGGA GCGGAGCGGC        60

GGCGGCTGCC CAGGCGATGC GAGCGCGGGC CGGACGGTAA TCGCCTCTCC CTCCTCGGGC       120

TGCGAGCGCG CCGGACCGAG GCAGCGACAG GAGCGGACCG CGGCGGGAAC CGAGGACTCC       180

CCAGCGGCGC GCCAGCAGGA GCCACCCCGC GAGNCGTGCG ACCGGGACGG AGCGCCCGCC       240

AGTCCCCAGGT GGCCCCGGACC GCACGTTGCG TCCCCGCGCT CCCCGCCGGC GACAGGAGAC    300

GCTCCCCCCC ACGCCGCGCG CGCCCTCGGCC CGGTCGCTGG CCCGCCTCCA CTCCGGGGAC     360
                                   CGCGAG       CGCCTCAGCG CGGCCGCTCG CTCTC..CCC CTCGAGGGAC

AAACTTTTCC CGAAGCCGAT CCCAGCCCTC GGACCCAAAC TTGTCGCGCG TCGCCTTCGC       420
                                                                       |||||||
AAACTTTTCC CAAACCCGAT CCGAGCCCTT GGACCAAA..  .........C TCGCCTGCGC

Met Ser Glu Arg Arg
CGGGAGCCGT CCGGCGCAGAG CGTGCACTTC TCGGGGCGAG ATG TCG GAG CGC AGA        474
|||||||||| |||||||||| |||||||||| |||||||||| ||| ||| ||| ||| |||
CGAGAGCCGT CCGGGTAGAG CGCTC.CGTC TCCGGGCGAG ATG TCC GAG CGC AAA
                                                                K

Glu Gly Lys Gly Lys Gly Lys Asp Arg Arg Gly Ser Gly
GAA GGC AAA GGC AAG GGC AAG GAC CGA CGC GGC TCC GGG                    522
||| ||| ||| ||| ||| ||| ||| ||| ||| ||| ||| ||| |||
GAA GGC AGA GGC AAA GGC AAG GAG CGA GAG CGA TCC GGC
 R                                E

Lys Lys Pro Val Pro Ala Ala Gly Gly Pro Ser Pro Ala
AAG AAG CCC GTG CCC GCG GCT GGC GGC CCG AGC CCA G                      559
||| ||| ||| ||| ||| ||| ||| ||| ||| ||| ||| ||| |
AAG AAG CCG GAG TCC GCG GCG TCC CAG AGC CCA G
         E  S
```

FIG. 31B

CODING SEGMENT E: (SEQ ID NO: 137)

```
CC CAT CAN GTG TGG GCG GCG AAA GCC GGG GGC TTG AAG AAG GAC TCG      47
   His Gln Val Trp Ala Ala Lys Ala Gly Gly Leu Lys Lys Asp Ser

CTG CTC ACC GTG CGC CGC CTG GGC TGG GGC CAC CCC GCC TTC CCC TCC     95
Leu Leu Thr Val Arg Arg Leu Gly Trp Gly His Pro Ala Phe Pro Ser

TGC GGG CGC CTC AAG GAG GAC AGC TAC ATC TTC ATG GAG CCC            143
Cys Gly Arg Leu Lys Glu Asp Ser Tyr Ile Phe Met Glu Pro

GAG GCC AAC AGC GGG GGC CCC GGG CGC CTT CCG AGC CTC CCC            191
Glu Ala Asn Ser Gly Gly Pro Gly Arg Leu Pro Ser Leu Pro

CCC TCT CGA GAC CCG GAA CCT CAA GGA GGT CAG CCG GGT GCT            239
Pro Ser Arg Asp Pro Glu Pro Gln Gly Gly Gln Pro Gly Ala

GTG CAA CGG TGC G                                                  252
Val Gln Arg Cys
```

FIG. 31C

CODING SEGMENT B: (SEQ ID NO: 138 (bovine) and 174 (human))

```
    Leu Pro Arg Leu Lys Glu His Lys Ser Gln Glu Ser Val Ala Gly
    CCT CCC CGC CTC AAG GCT TGA AGA AGA TGA AGG AGT CTG TGG CAG      48
    ||| ||| ||  ||| ||| ||| ||| ||| ||| ||| ||| ||| ||| ||| |||
    CCT TGC CCC CTC GAT TGA AGA AGA TGA AGG AGT CTG CGG CAG
                Q                                        A

Ser Lys Leu Val Leu Arg Cys Glu Thr Ser Ser Ser Tyr Ser Leu
    GTT CCA AAC TAG TGC TTC GGT GCG AGA CCA AAA CCA GTT AAT CCT CTC    96
    ||| ||| ||| ||| ||| ||| ||| ||| ||| ||| ||| ||| ||| ||| ||| |||
    GTT CCA AAC TAG TGC TCC GGT GTG AGA CTG AAA CCA GTT AAT CCT CTC

Lys Phe Lys Trp Phe Lys Asn Gly Ser Glu Leu Ser Arg Lys Asn Lys
    TCA AGT TCA AGT GGT TCA AGA ATG GGA GTG AAT TAA GCC GAA AGA ACA    144
    ||| ||| ||| ||  ||| ||| ||| ||| ||| ||| ||| ||| ||  ||| ||| |||
    TCA GAT TCA AGT GGT TCA AGA ATG GGA ATG AAT TGA ATC GAA AAA ACA
    R                               N              N

Pro Gly Asn Ile Gln Lys Ile Lys Arg Pro Gly
    AAC CAC AAA ATA TCA AGA TAC AAA GGC CGG G                         178
    ||| ||| ||| ||| ||| ||| ||| ||| ||| ||| |
    AAC CAC AAA ATA TCA AGA TAC AAA AGC CAG G
                                    K
```

FIG. 31D

CODING SEGMENT A: (SEQ ID NO: 139 (bovine) and 175 (human))

```
    Lys Ser Glu Leu Arg Ile Ser Lys Ala Ser Leu Ala Asp Ser Gly
G   AAG TCA GAA CTT CGC ATT AGC AAA GCG TCA CTG GCT GAT TCT GGA
     |   |   |   |   |   |   |       |   |   |   |   |   |   |
     |   |   |   |   |   |   |       |   |   |   |   |   |   |
G   AAG TCA GAA CTT CGC ATT AAC AAA GCA TCA CTG GCT GAT TCT GGA       46
                         N

Glu Tyr Met Cys Lys Val Ile Ser Lys Leu Gly Asn Asp Ser Ala Ser
    GAA TAT ATG TGC AAA GTG ATC AGC AAA CTA GGA AAT GAC AGT GCC TCT
     |   |   |   |   |   |   |   |   |   |   |   |   |   |   |   |
     |   |   |   |   |   |   |   |   |   |   |   |   |   |   |   |
    GAG TAT ATG TGC AAA GTG ATC AGC AAA TTA GGA AAT GAC AGT GCC TCT   94

Ala Asn Ile Thr Ile Val Glu Ser Asn Ala
    GCC AAC ATC ACC ATT GTG GAG TCA AAC G
     |   |   |   |   |   |   |   |   |
     |   |   |   |   |   |   |   |   |
    GCC AAT ATC ACC ATC GTG GAA TCA AAC G                              122
```

FIG. 31E

CODING SEGMENT A': (SEQ ID NO: 140)

```
TCTAAAACTA CAGAGACTGT ATTTCATGA TCATCATAGT TCTGTGAAAT ATACTTAAAC         60

CGCTTTGGTC CTGATCTTGT AGG AAG TCA GAA CTT CGC ATT AGC AAA GCG          110
                         Lys Ser Glu Leu Arg Ile Ser Lys Ala

TCA CTG GCT GAT TCT GGA GAA TAT ATG TGC AAA GTG ATC AGC AAA CTA        158
Ser Leu Ala Asp Ser Gly Glu Tyr Met Cys Lys Val Ile Ser Lys Leu

GGA AAT GAC AGT GCC TCT GCC AAC ATC ACC ATT GTG GAG TCA AAC GGT        206
Gly Asn Asp Ser Ala Ser Ala Asn Ile Thr Ile Val Glu Ser Asn Gly

AAG AGA TGC CTA CTG CGT GCT ATT TCT CAG TCT CTA AGA GGA GTG ATC        254
Lys Arg Cys Leu Leu Arg Ala Ile Ser Gln Ser Leu Arg Gly Val Ile

AAG GTA TGT GGT CAC ACT TGAATCACGC AGGTGTGTGA AATCTCATTG                302
Lys Val Cys Gly His Thr

TGAACAAATA AAAATCATGA AAGGAAAACT CTATGTTTGA AATATCTTAT GGGTCCTCCT       362

GTAAAGCTCT TCACTCCATA AGGTGAAATA GACCTGAAAT ATATATAGAT TATTT            417
```

FIG. 31F

CODING SEGMENT G: (SEQ ID NO: 141 (bovine) and 176 (human))

```
       Glu Ile Thr Thr Gly Met Pro Ala Ser Thr Glu Thr Ala Tyr Val Ser
        AG ATC ACC ACT GGC ATG CCA GCC TCA ACT GAG ACA GCG TAT GTG TCT                47
        ||  ||| ||| ||| ||| ||| ||| ||| ||| ||| ||| ||| | | ||| ||| |||
        AG ATC ACT GGT ATG CCA GCC TCA ACT GAA GGA GCA TAT GTG TCT
                I                                   G

Ser Glu Ser Pro Ile Arg Ile Ser Val Ser Thr Glu Gly Thr Asn Thr
       TCA GAG TCT CCC ATT AGA ATA TCA GTA TCA ACA GAA GGA ACA AAT ACT          95
       ||| ||| ||| ||| ||| ||| ||| ||| ||| ||  ||| ||| ||| ||| ||| |||
       TCA GAG TCT CCC ATT AGA ATA TCA GTA TCC ACA GAA GGA GCA AAT ACT
                                                                 A

Ser Ser Ser
       TCT TCA T                                                                102
       ||| ||| |
       TCT TCA T
```

FIG. 31G

CODING SEGMENT C: (SEQ ID NO: 160 (bovine) and 177 (human))

```
       Thr Ser Thr Ser Ala Gly Thr Ser His Leu Val Lys Cys Ala
    CC ACA TCC ACA TCT ACA GCT GGG ACA AGC CAT CTT GTC AAG TGT GCA
       ||| ||| ||| ||| ||| ||| ||| ||| ||| ||| ||| ||| ||| ||| |||
    CT ACA TCT ACA TCC ACC ACT GGG ACA AGC CAT CTT GTA AAA TGT GCG
                            T                                           47

Glu Lys Thr Phe Cys Val Asn Gly Gly Cys Phe Met Val
       GAG AAA ACT TTC TGT GTG AAT GGA GGC TGC TTC ATG GTG
       ||| ||| ||| ||| ||| ||| ||| ||| ||| ||| ||| ||| |||
       GAG AAA GAG ACT TTC TGT GTA AAT GGA GGG GAG TGC TTC ATG GTG
                                                                        95

Lys Asp Leu Ser Asn Pro Ser Arg Tyr Leu Cys
       AAA GAC CTT TCA AAT CCC TCA AGA TAC TTG TGC
       ||| ||| ||| ||| ||| ||| ||| ||| ||| ||| |||
       AAA GAC CTT TCA AAC CCC TCG AGA TAC TTG TGC
                                                                       128
```

FIG. 31H

CODING SEGMENT C/D: (SEQ ID NO: 142 (bovine) and 178 (human))

```
     Lys Cys Gln Pro Gly Phe Thr Gly Ala Arg Cys Thr Glu Asn Val Pro
     AAG TGC CAA CCT GGA TTC ACT GGA GCG AGA TGT ACT GAG AAT GTG CCC
     ||| ||| ||| ||| ||| ||| ||| ||| ||| ||| ||| ||| ||| ||| ||| |||                              48
     AAG TGC CAA CCT GGA TTC ACT GGA GCA AGA TGT ACT GAG AAT GTG CCC

Met Lys Val Gln Thr Gln Glu
     ATG AAA GTC CAA ACC CAA GAA
     ||| ||| ||| ||| ||| ||| |||                                                                   69
     ATG AAA GTC CAA AAC CAA GAA
                      N
```

FIG. 31I

CODING SEGMENT D: (SEQ ID NO: 143 (bovine) and 179 (human))

```
Lys Cys Pro Asn Glu Phe Thr Gly Asp Arg Cys Gln Asn Tyr Val Met
AAG TGC CCA AAT GAG TTT ACT GGT GAT CGC TGC CAA AAC TAC GTA ATG    48
||| ||| ||| ||| ||| ||| ||| ||| ||| ||| ||| ||| ||| ||| ||| |||
AAG TGC CCA AAT GAG TTT ACT GGT GAT CGC TGC CAA AAC TAC GTA ATG

Ala Ser Phe Tyr
GCC AGC TTC TAC                                                    60
||| ||| ||| |||
GCC AGC TTC TAC
```

FIG. 31J

CODING SEGMENT D: (SEQ ID NO: 144 (bovine) and 180 (human))

```
Ser Thr Ser Thr Pro Phe Leu Ser Leu Pro Glu *
AGT ACG TCC ACT CCC TTT CTG TCT CTG CCT GAA TAG                    36
||| ||| ||| ||| ||| ||| ||| ||| ||| ||| ||| |||
AGT ACG TCC ACT CCC TTT CTG TCT CTG CCT GAA TAG
```

FIG. 31K

CODING SEGMENT D': (SEQ ID NO: 145 (bovine))

```
Lys His Leu Gly Ile Glu Phe Met Glu
AAG CAT CTT GGG ATT GAA TTT ATG GAG                                27
```

FIG. 31L

CODING SEGMENT H: (SEQ ID NO: 146 (bovine) and 181 (human))

```
Lys Ala Glu Glu Leu Tyr Gln Lys Arg Val Leu Thr Ile Thr Gly Ile
AAA GCG GAG GAG CTC TAC CAG AAG AGA GTG CTC ACC ATT ACC GGC ATT       48
||| ||| ||| ||| ||| ||| ||| ||| ||| ||| ||| ||| ||| ||| ||| |||
AAG GCG GAG GAG CTG TAC CAG AAG AGA GTG CTG ACC ATA ACC GGC ATC

Cys Ile Ala Leu Leu Val Gly Ile Met Cys Val Val Tyr Cys
TGC ATC GCG CTG CTC GTG GTT GGC ATC ATG TGT GTG GTC TAC TGC           96
||| ||| ||| ||| ||| ||| ||| ||| ||| ||| ||| ||| ||| ||| |||
TGC ATC GCC CTC CTT GTG GTG GGC ATC ATG TGT GTG GTG GCC TAC TGC
                                                    A

Lys Thr Lys Lys Gln Arg Lys Lys Leu His Asp Arg Leu Arg Gln Ser
AAA ACC AAG AAG CAA CGG AAA AAG CTT CAT GAC CGG CTT CGG CAG AGC       144
||| ||| ||| ||| ||| ||| ||| ||| ||| ||| ||| ||| ||| ||| ||| |||
AAA ACC AAG AAG CAG CGG AAA AAG CTG CAT GAC CGT CTT CGG CAG AGC

Leu Arg Ser Glu Arg Asn Thr Met Met Asn Val Ala Asn Gly Pro His
CTT CGG TCT GAA AGA AAC ACC ATG ATG AAC GTA GCC AAC GGG CCC CAC       192
||| ||| ||| ||| ||| ||| ||| ||| ||| ||| ||| ||| ||| ||| ||| |||
CTT CGG TCT GAA CGA AAC AAT ATG ATG AAC ATT GCC AAT GGG CCT CAC
                          N                     I

His Pro Asn Pro Pro Pro Glu Asn Val Gln Leu Val Asn Gln Tyr Val
CAC CCC AAT CCG CCC CCC GAG AAC GTG CAG CTG GTG AAT CAA TAC GTA       240
||| ||| ||| ||| ||| ||| ||| ||| ||| ||| ||| ||| ||| ||| ||| |||
CAT CCT AAC CCA CCC CCC GAG AAT GTC CAG CTG GTG AAT CAA TAC GTA

Ser Lys Asn Val Ile Ser Ser Glu His Ile Val Glu Arg Glu Ala Glu
TCT AAA AAT GTC ATC TCT AGC GAG CAT ATT GTT GAG AGA GCG GAG           288
||| ||| ||| ||| ||| ||| ||| ||| ||| ||| ||| ||| ||| ||| ||| |||
TCT AAA AAC GTC ATC TCC AGT GAG CAT ATT GTT GAG AGA GAA GCA GAG
```

FIG. 31M

```
Ser Ser Phe Ser Thr Ser His Tyr Thr Ser Thr Ala His His Ser Thr
AGC TCT TTT TCC ACC AGT CAC TAC ACT TCG ACA GCT CAT CAT TCC ACT
||| ||| ||| ||| ||| ||| ||| ||| ||| ||| ||| ||| ||| ||| ||| |||                                336
ACA TCC TTT TCC AGT CAC TAT ACT TCC ACA GCC CAT CAC TCC ACT
  T

Thr Val Thr Gln Thr Pro Ser His Ser Trp Ser Asn Gly His Thr Glu
ACT GTC ACT CAG ACT CCC AGT CAC AGC TGG AGC AAT GGA CAC ACT GAA
||| ||| ||| ||| ||| ||| | | ||| ||| ||| ||| ||| ||| ||| ||| |||                                384
ACT GTC ACC CAG ACC CCT AGC CAC AGC TGG AGC AAC GGA CAC ACT GAA

Ser Ile Ile Ser Glu Ser His Ser Val Ile Val Met Ser Ser Val Glu
AGC ATC ATT TCG GAA AGC CAC TCT GTC ATC GTG ATG TCA TCC GTA GAA
||| ||| ||| ||  ||| ||| ||| ||| ||| ||| ||| ||| ||| ||| ||| |||                                432
AGC ATC ATC CTT TCC GAA AGC CAC TCT GTA ATC GTG ATG TCA TCC GTA GAA
          L

Asn Ser Arg His Ser Pro Arg Glu Cys Asn Ser Phe Leu Arg His Ala Arg
AAC AGT AGG CAC AGC CCG GGC ACT GGG AGA GGA CCA AGA GGA TCA CCG GTA GAA
||| ||| ||| ||| ||| ||| ||| ||| ||| ||| ||| ||| ||| ||| ||| ||| |||                            480
AAC AGT AGG CAC AGC CCA AGA GGA CGT CTT AAT

Gly Leu Gly Gly Pro Arg Asp Ser Tyr Arg Asp Ser Pro His Ser Glu Arg
GGC TTG GGA GGC CCT CGT GAA TGT AAC AGC TTC CTC AGG CAT GCC AAT
||| ||| ||| ||| ||| ||| ||| ||| ||| ||| ||| ||| ||| ||| |||                                    528
GGC ACA GGA GGC CCT CGT GAA TGT AAC AGC TTC CTC AGG CAT GCC AAT
    T

Glu Thr Pro Asp Ser Tyr Arg Asp Ser Pro His Ser Glu Arg
GAA ACC CCT GAC TCC TAC CGA GAC TCT CAT AGT GAA AG
||| ||| ||| | | ||| ||| ||| ||| ||| ||| ||| ||                                                 569
GAA ACC CCT GAT TCC TAC CGA GAC TCT CAT AGT GAA AG
```

FIG. 31N

CODING SEGMENT K: (SEQ ID NO: 161)

```
A CAT AAC CTT ATA GCT GAG CTA AGG AGA AAC AAG GCC CAC AGA TCC   46
  His Asn Leu Ile Ala Glu Leu Arg Arg Asn Lys Ala His Arg Ser

AAA TGC ATG CAG ATC CAG CTT TCC GCA ACT CAT CTT AGA GCT TCT TCC   94
Lys Cys Met Gln Ile Gln Leu Ser Ala Thr His Leu Arg Ala Ser Ser

ATT CCC CAT TGG GCT TCA TTC TCT AAG ACC CCT TGG CCT TTA GGA AG   141
Ile Pro His Trp Ala Ser Phe Ser Lys Thr Pro Trp Pro Leu Gly Arg
```

FIG. 31O

CODING SEGMENT L: (SEQ ID NO: 147 (bovine) and 182 (human))

```
    Tyr Val Ser Ala Met Thr Pro Ala Arg Met Ser Pro Val Asp
G   TAT GTA TCA GCA ATG ACC ACC CCG GCT CGT ATG TCA CCT GTA GAT       46
    ||| ||| ||  ||  ||| ||| ||| ||| ||| ||| ||| ||| ||| ||| |||
G   TAT GTG TCA GCC ATG ACC ACC CCG GCT CGT ATG TCA CCT GTA GAT

Phe His Thr Pro Ser Ser Pro Lys Ser Pro Pro Ser Glu Met Ser Pro
    TTC CAC ACG CCA AGC TCC CCC AAG TCA CCC CCT TCG GAA ATG TCC CCG   94
    ||| ||| ||  ||  ||| ||  ||| ||  ||  ||| ||| ||  ||| ||| ||  ||
    TTC CAC ACG CCA AGC TCC CCC AAA TCG CCC CCT TCG GAA ATG TCT CCA

Pro Val Ser Ser Thr Thr Val Ser Met Pro Ser Met Ala Val Ser Pro
    CCC GTG TCC AGC ACG ACG GTC ATG TCC ATG GCG GTC GCC CCC         142
    ||| ||| ||  ||| ||  ||  ||| ||| ||  ||| ||  ||| ||  |||
    CCC GTG TCC AGC ACG ACG GTC ATG TCC ATG GCG GTC AGC CCC
                                 M

Phe Val Glu Glu Arg Pro Leu Leu Leu Val Thr Pro Pro Arg Leu
    TTC GTG GAA GAG AGA CCC CTG CTC CTT GTG ACG CCA CCA CGG CTG      190
    ||| ||| ||| ||| ||  ||| ||| ||  ||  ||| ||  ||| ||| ||| |||
    TTC ATG GAA GAA GAG AGA CCT CTG CTC GTG ACA CCA CCA AGG CTG
        N

Arg Glu Lys    -    Tyr Asp His His Ala Gln Gln Phe Asn Ser Phe His
    CGG GAG AAG    ...  TAT GAC CAC CAC GCC CAG CAA TTC AAC TCG TTC CAC   238
    ||| ||| |||         ||| ||  ||  ||  ||  ||| ||  ||| ||  ||  ||| |||
    CGG GAG AAG         TTT GAC CAT CAC CCT CAG CAG TTC AGC TCC TTC CAC
            K           F              P

Cys Asn Pro Ala His Glu Ser Asn Leu Pro Ser Pro Leu Arg
    TGC AAC CCC GCG CAT GAG AGC AAC CTG CCC AGC CCC TTG AGG          286
    ||| ||  ||| ||  ||  ||| ||  ||  ||  ||| ||| ||  ||| |||
    CAC AAC CCC CAT GAC AGT AAC AGC CTC CCT AGC CCT AGG
                  D                             A
                  N
```

FIG. 31P

```
                                                            334
Ile Val Glu Asp Glu Glu Tyr Glu Thr Thr Gln Glu Tyr Glu Pro Ala
ATA GTG GAG GAT GAG GAA TAT GAA ACG ACC CAG GAG TAC GAA CCA GCT
=== === === === === === === === === === === === === === === ===
ATA GTG GAG GAT GAG GAG TAT GAA ACG ACC CAA GAG TAC GAG CCA GCC

382
Gln Glu Pro Val Lys Lys Leu Thr Asn Ser Ser Arg Arg Ala Lys Arg
CAA GAG CCG GTT AAG AAA CTC ACC AAC AGC AGC CGG CGG GCC AAA AGA
=== === === === === === === === === === === === === === === ===
CAA GAG CCT GTT AAG AAA CTC GCC ..T AGC CGG CGG GCC AAA AGA
                                    A

430
Thr Lys Pro Asn Gly His Ile Ala His Arg Leu Glu Met Asp Asn Asn
ACC AAG CCC AAT GGT CAC ATT GCC CAC AGG TTG GAA ATG GAC AAC AAC
=== === === === === === === === === === === === === === === ===
ACC AAG CCC AAT GGC CAC ATT GCT AAC AGA TTG GAA GTG GAC AGC AAC
                            N                       V         S

478
Thr Gly Ala Asp Ser Ser Asn Ser Glu Ser Glu Thr Glu Asp Glu Arg
ACA GGC GCT GAC AGC AGT AAC TCA GAG AGC GAG ACA GAG GAT GAA AGA
=== === ===     === === === === === === === === === === === ===
ACA AGC GAC     CAG AGT AAC TCA GAG AGT GAG ACA GAG GAT GAA AGA
    S   Q
```

FIG. 31Q

```
        Val Gly Glu Asp Thr Pro Phe Leu Ala Ile Gln Asn Pro Leu Ala Ala
        GTA GGA GAA GAT ACG CCT TTC CTG GCC ATA CAG AAC CCC CTG GCA GCC    526
        ||| ||| ||| ||| ||| ||| ||| ||| ||| ||| ||| ||| ||| ||| ||| |||
        GTA GGT GAA GAT ACG CCT TTC CTG GCC ATA CAG AAC CCC CTG GCA GCC
              A

Ser Leu Glu Ala Ala Pro Ala Phe Arg Leu Val Asp Ser Arg Thr Asn
        AGT CTC GAG GCG GCC CCT GCC TTC CGC CTG GTC GAC AGC AGG ACT AAC    574
        ||| ||| ||| ||| ||| ||| ||| ||| ||| ||| ||| ||| ||| ||| ||| |||
        AGT CTT GAG GCA GCA CCT GCC TTC CGC CTG GTC GAC AGC AGG ACT AAC
                        T       G

Pro Thr Gly Gly Phe Ser Pro Gln Glu Glu Leu Gln Ala Arg Leu Ser
        CCA ACA GGC GGC TTC TCT CCG CAG GAA CTG TTG CAG GCC AGG CTC TCC    622
        ||| ||| ||| ||| ||| ||| ||| ||| ||| ||| ||| ||| ||| ||| ||| |||
        CCA GCA GGC CGC TTC TCG ACA CAG GAA GAA ATC CAG GCC AGG CTG TCT
                    A       R       T               I

Gly Val Ile Ala Asn Gln Asp Pro Ile Ala Val  *
        GGT GTA ATC GCT AAC CAA GAC CCT ATC GCT GTC TAA AAC CGA AAT ACA    672
        ||| ||| ||| ||| ||| ||| ||| ||| ||| ||| ||| ||| ||| ||| ||| |||
        AGT GTA ATT GCT AAC CAA GAC CCT ATT GCT GTA TAA AAC CTA AGT ATT AAA
        S

CCC ATA GAT TCA CCT GTA AAA CTT TAT TTT ATA TAA TAA AGT ATT CCA    718
        ||| ||| ||| ||| ||| ||| ||| ||| ||| ||| ||| ||| ||| ||| ||| |||
        CAC ATA GAT TCA CCT GTA AAA CTT TAT TTT ATA TAA TAA AGT ATT CCA

CCT TAA ATT AAA CAA                                                733
        ||| ||| ||| ||| |||
        CCT TAA ATT AAA CAA
```

FIG. 31R

HUMAN CODING SEGMENT E:
(SEQ ID NO: 163)

```
ATG AGA TGG CGA CGC GCC CCG CGC TCC GGG CGT CCC GGC CCC CGG         48
Met Arg Trp Arg Arg Ala Pro Arg Ser Gly Arg Pro Gly Pro Arg

GCC CAG CGC CCC GGG GAG TCC CGC CGC GCC CCG CCG CTG CCG CTG         96
Ala Gln Arg Pro Gly Glu Ser Arg Arg Ala Pro Pro Leu Pro Leu

CTG CCA CTA CTG CTG CTG CTG CTG GGG CGC ACC CTG GCG CCG GCG        144
Leu Pro Leu Leu Leu Leu Leu Leu Gly Arg Thr Leu Ala Pro Ala

GCG GCC AAC GGG GCG GCT CCC GCG GGG GAG CTG GCG GCG GGG GCG        192
Ala Ala Asn Gly Ala Ala Pro Ala Gly Glu Leu Ala Ala Gly Ala

TCC CCG CCC AGC GGA GTG TCG CAG CAC CCC GAG GCG CAG CAG GGG GCA    240
Ser Pro Pro Ser Gly Val Ser Gln His Pro Glu Ala Gln Gln Gly Ala

GTG GTG ATC GAG AAG GGA GCG GCG GCG GAG CGG CGA CGG CAG CAG GCA    288
Val Val Ile Glu Lys Gly Ala Ala Ala Glu Arg Arg Arg Gln Gln Ala

CTC GAC AGG AAG GCG GCG GCG GCG GCA CCG GCG GCA CAG CAG GGG GGT    336
Leu Asp Arg Lys Ala Ala Ala Ala Ala Pro Ala Ala Gln Gln Gly Gly

GGC GAT CGC GAG GAG GCC GCG GCG GGG CCA GGG GGG CTG GGG CCC CCC    384
Gly Asp Arg Glu Glu Ala Ala Ala Gly Pro Gly Gly Leu Gly Pro Pro

GCC GAG GAG CCG GAG CAC GGG GCG GCG GGG ACC GTG CCC TCT TGG CCC    432
Ala Glu Glu Pro Glu His Gly Ala Ala Gly Thr Val Pro Ser Trp Pro

ACC GTG AAG AAA CAG CAG TGG TGG GGG GAG GAG GCC GGG GCA CCC TAT    480
Thr Val Lys Lys Gln Gln Trp Trp Gly Glu Glu Ala Gly Ala Pro Tyr

CTG GTG AAG CAC CAG CTC ACC GTG GGG CTG TGG CCG TTG CTC CCC AAG    528
Leu Val Lys His Gln Leu Thr Val Gly Leu Trp Pro Leu Leu Pro Lys

AAG GAC TCG AGG AAC AAC GAC AAG GAG AGC GCC GGC CAC ATC TTC GCC    576
Lys Asp Ser Arg Asn Asn Asp Lys Glu Ser Ala Gly His Ile Phe Ala

TTC CCC TGC TGT GGG CTC GAT AGC ACG AGG TAC TGG AGG ATC TTC TTC    624
Phe Pro Cys Cys Gly Leu Asp Ser Thr Arg Tyr Trp Arg Ile Phe Phe

ATG GAG CCC GAC GCC AGC AGC ACG ACG GGC GCC CCG GCC TTC CGA        672
Met Glu Pro Asp Ala Ser Ser Thr Thr Gly Ala Pro Ala Phe Arg

GCC TCT TTC CCT CTG ACG GGG CGG AAC CTC AAG AAG AAG GAG GTC        720
Ala Ser Phe Pro Leu Thr Gly Arg Asn Leu Lys Lys Lys Glu Val

AGC CGG GTG CTG TGC AAG CGG TGC G                                  745
Ser Arg Val Leu Cys Lys Arg Cys
```

FIG. 32A

GGF2BPP5 Nucleotide Sequence & Deduced Protein Sequence

SEQ ID NO: 148:

```
AGTTTCCCCC CCCAACTTGT CGGAACTCTG GGCTCGCGCG CAGGGCAGGA GCGGAGCGGC     60
GGCGGCTGCC CAGGGCGATGC GAGCGCGGGC CGGACGGTAA TCGCCTCTCC CTCCTCGGGC   120
TGCGAGCGCG CCGGACCGAG GCAGCGACAG GAGCGGGACCG CGGCGGGAAC CGAGGACTCC   180
CCAGCGGCGC GCCAGCAGGA GCCACCCCGC GAGCGGTGCGA CCGGGACGGA GCGCCCCGCCA  240
GTCCCAGGTG GCCCGGACCG CACGTTGCGT CCCCGCGCTC CCCGCCGGCG ACAGGAGACG    300
CTCCCCCCCA CGCCGCGCGC GCCTCGGCCC GGTCGCTGGC CCGCCTCCAC TCCGGGGACA    360
AACTTTTCCC GAAGCCGATC CCAGCCCTCG GACCCAAACT TGTCGCGCGT CGCCTTCGCC    420
GGGAGCCGTC CGGCAGAGC GTGCACTTCT CGGGCGAG ATG TCG GAG CGC AGA          475
                                        Met Ser Glu Arg Arg

GAA GGC AAA GGC AAG GGG AAG GGC GGC GGG AAG GAC CGA GGC TCC GGG      523
Glu Gly Lys Gly Lys Gly Lys Gly Gly Gly Lys Asp Arg Gly Ser Gly

AAG AAG CCC GTG CCC GCG GCT GGC GGC GGG AGC CCA GCC TTG CCT CCC      571
Lys Lys Pro Val Pro Ala Ala Gly Gly Gly Ser Pro Ala Leu Pro Pro

CGC TTG AAA GAG ATG AAG CAG GAG TCT GTG GCA GGT TCC AAA CTA          619
Arg Leu Lys Glu Met Lys Ser Gln Glu Val Ala Gly Ser Lys Leu

GTG CTT CGG TGC GAG ACC AGT TCT GAA TAC TCC TCT AAG TTC CTC AAG      667
Val Leu Arg Cys Glu Thr Ser Ser Glu Tyr Ser Ser Lys Phe Lys

TGG TTC AAG AAT GGG AGT GAA TTA AGC CGA AAG AAA CCA CAA AAC          715
Trp Phe Lys Asn Gly Ser Glu Leu Ser Arg Lys Lys Pro Gln Asn

ATC AAG ATA CAG AGG CCG GGG AAG TCA GAA CTT CGC ATT AGC AAA          763
Ile Lys Ile Gln Arg Pro Gly Lys Ser Glu Leu Arg Ile Ser Lys

GCG TCA CTG GCT GAT TCT GGA GAA TAT ATG TGC AAA GTG ATC AGC AAA      811
Ala Ser Leu Ala Asp Ser Gly Glu Tyr Met Cys Lys Val Ile Ser Lys
```

FIG. 32B

GGF2BPP5 Nucleotide Sequence & Deduced Protein Sequence

```
CTA GGA AAT GAC AGT GCC TCT GCC AAC ATC ACC ATT GTG GAG TCA AAC      859
Leu Gly Asn Asp Ser Ala Ser Ala Asn Ile Thr Ile Val Glu Ser Asn

GAG ATC ACC ACT GGC ATG CCA GCC TCA ACT GAG ACA GCG TAT GTG TCT      907
Glu Ile Thr Thr Gly Met Pro Ala Ser Thr Glu Thr Ala Tyr Val Ser

TCA GAG TCT CCC ATT AGA ATA TCA GTA TCA ACA GAA GGA ACA AAT ACT      955
Ser Glu Ser Pro Ile Arg Ile Ser Val Ser Thr Glu Gly Thr Asn Thr

TCT TCA TCC ACA TCT ACA GCT GGG ACA AGC CAT CTT GTC AAG             1003
Ser Ser Ser Thr Ser Thr Ala Gly Thr Ser His Leu Val Lys

TGT GCA GAG AAA GAG CTT TTC TGT AAT GTG GTG AAT TAC TTG TGC CCA     1051
Cys Ala Glu Lys Glu Leu Phe Cys Asn Val Val Asn Tyr Leu Cys Pro

ATG GTG AAA GAC CTT TCA AAT CCC TCA AGA CGC TGC AAG TGC GAG TTC     1099
Met Val Lys Asp Leu Ser Asn Pro Ser Arg Arg Cys Lys Cys Glu Phe

AAT GAG TTT ACT GGT GAT CGC TGC CAA AAC TAC GTA ATG GCC AGC TTC     1147
Asn Glu Phe Thr Gly Asp Arg Cys Gln Asn Tyr Val Met Ala Ser Phe

TAC AGT ACG TCC ACT CCC TTT CTG TCT CCT GAA TAGGCGCATG              1193
Tyr Ser Thr Ser Thr Pro Phe Leu Ser Pro Glu

CTCAGTCGGT GCCGCTTTCT TGTTGCCGCA TCTCCCCTCA GATTCAACCT AGAGCTAGAT   1253

GCGTTTTACC AGGTCTAACA TTGACTGCCT CTGCCTGTCG CATGAGAACA TTAACACAAG   1313

CGATTGTATG ACTTCCTCTG TCCGTGACTA GTGGGCTCTG AGCTACTCGT AGGTGCGTAA   1373

GGCTCCAGTG TTTCTGAAAT TGATCTTGAA TTACTGTGAT ACGACATGAT AGTCCCTCTC   1433

ACCCAGTGCA ATGACAATAA AGGCCTTGAA AAGTCTCACT TTTATTGAGA AAATAAAAAT   1493

CGTTCCACGG GACAGTCCCT CTTCTTTATA AAATGACCCT ATCCTTGAAA AGGAGGTGTG   1553

TTAAGTTGTA ACCAGTACAC ACTTGAAATG ATGGTAAGTT CGCTTCGGTT CAGAATGTGT   1613

TCTTTCTGAC AAATAAACAG AATAAAAAAA AAAAAAAAAA A                       1654
```

FIG. 33A

GGF2BPP2 Nucleotide Sequence & Deduced Protein Sequence

SEQ ID NO: 149:

```
CAT CAN GTG TGG GCG AAA GCC GGG GGC TTG AAG AAG GAC TCG CTG      48
His Gln Val Trp Ala Lys Ala Gly Gly Leu Lys Lys Asp Ser Leu

CTC ACC GTG CGC CTG GGC TGG GGC CAC CCC GCC TTC CCC GCC TCC      96
Leu Thr Val Arg Leu Gly Ala Trp Gly His Pro Ala Phe Pro Ser Cys

GGG CGC CTC AAG GAG GAC AGC TAC ATC TTC ATG TTC ATG GAG CCC GAG 144
Gly Arg Leu Lys Glu Asp Ser Tyr Ile Phe Met Glu Pro Glu

GCC AAC AGC AGC GGG GGC CCC CGC CTT CCG AGC CTC CTT CCC CCC     192
Ala Asn Ser Ser Gly Gly Pro Gly Arg Leu Pro Ser Leu Pro Pro

TCT CGA GAC CCG GAA CCT CAA GGA GGT CAG CCG GGT GCT GTG         240
Ser Arg Asp Gly Pro Glu Pro Gln Glu Gly Gln Pro Gly Ala Val

CAA CGG TGC GCC TTG GCC CGC GTG AAA AAG GAG ATG AAG CCG GAG     288
Gln Arg Cys Ala Leu Ala Arg Val Lys Lys Glu Met Lys Gln Glu

TCT GTG GCA GGT TCC AAG CTT CTT CGG TGC ACC GAG AGT CAG TCT GAA 336
Ser Val Ala Gly Ser Lys Leu Leu Arg Cys Thr Glu Ser Glu

TAC TCC TCT CTC AAG TTC TGG TTC AAT GGG AGT TTA AGC             384
Tyr Ser Ser Leu Lys Phe Lys Trp Phe Lys Asn Gly Ser Leu Ser

CGA AAG AAC CCA GAA ATC ATA CAG AAA AGG CCG GGG AAG             432
Arg Lys Asn Lys Pro Glu Ile Ile Gln Lys Arg Pro Gly Lys

TCA GAA CTT CGC ATT AGC GCG TCA CTG GCT GAT TCT GGA GAA TAT     480
Ser Glu Leu Arg Ile Ser Ala Ser Leu Ala Asp Ser Gly Glu Tyr

ATG TGC AAA GTG ATC AGC AAA CTA GGA AAT GAC ACT TCT GCC AAC     528
Met Cys Lys Val Ile Ser Lys Leu Gly Asn Asp Ser Ala Asn
```

FIG. 33B

GGF2BPP2 Nucleotide Sequence & Deduced Protein Sequence

```
ATC ACC ATT GTG GAG TCA AAC GCC ACA TCC ACA TCT ACA GCT GGG ACA    576
Ile Thr Ile Val Glu Ser Asn Ala Thr Ser Thr Ser Thr Ala Gly Thr

AGC CAT CTT GTC AAG TGT GCA GAG AAG GAG AAA ACT TTC TGT GTG AAT    624
Ser His Leu Val Lys Cys Ala Glu Lys Glu Lys Thr Phe Cys Val Asn

GGA GGC GAG TGC TTC ATG GTG AAA GAC CTT TCA AAT CCC TCA AGA TAC    672
Gly Gly Glu Cys Phe Met Val Lys Asp Leu Ser Asn Pro Ser Arg Tyr

TTG TGC AAG TGC CAA CCT GGA TTC ACT GGA GCG AGA TGT ACT GAG AAT    720
Leu Cys Lys Cys Gln Pro Gly Phe Thr Gly Ala Arg Cys Thr Glu Asn

GTC CCC ATG AAA GTC CAA ACC CAA GAA AAG TGC CCA AAT GAG TTT ACT    768
Val Pro Met Lys Val Gln Thr Gln Glu Lys Cys Pro Asn Glu Phe Thr

GGT GAT CGC TGC CAA TGC CGC AAC TAC GTA ATG GCC AGC TTC TAC ACG TCC    816
Gly Asp Arg Cys Gln Cys Arg Asn Tyr Val Met Ala Ser Phe Tyr Thr Ser

ACT CCC TTT CTG TCT CTG CCT GAA TAGCGCATCT CAGTCGGTGC CGCTTTCTTG    870
Thr Pro Phe Leu Ser Leu Pro Glu

TTGCCGCATC TCCCCCTCAGA TTCCNCCTAG AGCTAGATGC GTTTTACCAG GTCTAACATT    930

GACTGCCTCT GCCTGTCGCA TGAGAACATT AACACAAGCG ATTGTATGAC TTCCTCTGTC    990

CGTGACTAGT GGGCTCTGAG CTACTCGTAG GTGCGTAAGG CTCCAGTGTT TCTGAAATTG   1050

ATCTTGAATT ACTGTGATAC GACATGATAG TCCCCTCTCAC CCAGTGCAAT GACAATAAAG   1110

GCCTTGAAAA GTCAAAAAAA AAAAAAAAAA                                    1140
```

FIG. 34A

GGF2BPP4 Nucleotide Sequence & Deduced Protein Sequence

SEQ ID NO: 150:

```
G AAG TCA GAA CTT CGC ATT AGC AAA GCG TCA CTA GCT GAT TCT GGA GAA          49
  Lys Ser Glu Leu Arg Ile Ser Lys Ala Ser Leu Ala Asp Ser Gly Glu

TAT ATG TGC AAA GTG ATC AGC GAG CTA GGA AAT GAC AGT GCC TCT GCC           97
Tyr Met Cys Lys Val Ile Ser Glu Leu Gly Asn Asp Ser Ala Ser Ala

AAC ATC ACC ATT GTG TCA AAC GCC ACA TCC ACA TCT ACA GCT GGG              145
Asn Ile Thr Ile Val Ser Asn Ala Thr Ser Thr Ser Thr Ala Gly

ACA AGC CAT CTT GTC AAG TGT GCA GAG AAG GAG ACT TTC TGT GTG              193
Thr Ser His Leu Val Lys Cys Ala Glu Lys Glu Thr Phe Cys Val

AAT GGA GGC GAC TGC ATG GTG AAA GAC CTT TCA AAT CCC TCA AGA              241
Asn Gly Gly Asp Cys Met Val Lys Asp Leu Ser Asn Pro Ser Arg

TAC TTG TGC AAG TGC CAA CCT GGA TTC ACT GGA GCG AGA TGT ACT GAG          289
Tyr Leu Cys Lys Cys Gln Pro Gly Phe Thr Gly Ala Arg Cys Thr Glu

AAT GTG CCC ATG AAA GTC CAA ACC CAA GAA AAA GCG GAG CTG TAC              337
Asn Val Pro Met Lys Val Gln Thr Gln Glu Lys Ala Glu Leu Tyr

CAG AAG AGA GTG CTC ACC ATT GGC ATC TGC AAG ACC CTT CTG GTG              385
Gln Lys Arg Val Leu Thr Ile Gly Ile Cys Lys Thr Leu Leu Val

GTT GGC ATC ATG TGT GTC GTC CAG AGC TAC TGG CTT CGG AGA CGG              433
Val Gly Ile Met Cys Val Val Gln Ser Tyr Trp Leu Arg Arg Arg

AAA CTT CAT GAC CGG CTT CGG CAG AGC TCT CGG AGA AGA AAC              481
Lys Leu His Asp Arg Leu Arg Gln Ser Ser Arg Arg Arg Asn

ACC ATG ATG AAC GTA GCC AAC GGG CCC CAC CAC CCC AAT CCG CCC              529
Thr Met Met Asn Val Ala Asn Gly Pro His His Pro Asn Pro Pro

GAG AAC GTG CAG CTG GTG AAT CAA TAC GTA TCT AAA AAT GTC ATC TCT          577
Glu Asn Val Gln Leu Val Asn Gln Tyr Val Ser Lys Asn Val Ile Ser
```

FIG. 34B

GGF2BPP4 Nucleotide Sequence & Deduced Protein Sequence

```
AGC GAG CAT ATT GTT GAG AGA GAG GCG GAG AGC TCT TTT TCC ACC AGT      625
Ser Glu His Ile Val Glu Arg Glu Ala Glu Ser Ser Phe Ser Thr Ser

CAC TAC ACT TCG ACA GCT CAT CAT CAC TCC ACT GTC CAG ACT CCC          673
His Tyr Thr Ser Thr Ala His His His Ser Thr Val Gln Thr Pro

AGT CAC AGC TGG AGC AAT GGA CAC ACT GAA AGC ATT TCG GAA AGC          721
Ser His Ser Trp Ser Asn Gly His Thr Glu Ser Ile Ser Glu Ser

CAC TCT GTC ATC GTG ATG TCA GAA GTA GAA AAC AGT CAC AGC AGC          769
His Ser Val Ile Val Met Ser Glu Val Glu Asn Ser His Ser Ser

CCG ACT GGG GGC CCG AGA CGT CAT AAT CTC GCC AGA AAC GGA GGC CCT CGT  817
Pro Thr Gly Gly Pro Arg Arg His Asn Leu Ala Arg Asn Gly Gly Pro Arg

GAA ACT AGC TTC CTC CAT AGG AGA AGT GAA CAT CGA CTT GCT GAG CTA TAC  865
Glu Thr Ser Phe Leu His Arg Arg Ser Glu His Arg Leu Ala Glu Leu Tyr

CGA GAC TCT CCT CAT AGT AGA GAA AAC AAT TGC ATG CAG ATC CTT TCC AGG  913
Arg Asp Ser Pro His Ser Arg Glu Asn Asn Cys Met Gln Ile Leu Ser Arg

AGA AAC AAG GCC CAC AGA AGA TCC AAA CAT CCC ATT TGG GCT TCA TTC TCC GCA 961
Arg Asn Lys Ala His Arg Arg Ser Lys His Pro Ile Trp Ala Ser Phe Ser Ala

ACT CAT CTT AGA GCT TCT TCT CCC ATT TAT GTA TCA GCA ATG ACC ATG CCG GCT 1009
Thr His Leu Arg Ala Ser Ser Pro Ile Tyr Val Ser Ala Met Thr Met Pro Ala

ACC CCT TGG CCT TTA GGA AGG TAT GTT TCA AGC CCA ATG TCC ACC CCG GCT CCC 1057
Thr Pro Trp Pro Leu Gly Arg Tyr Val Ser Ser Pro Met Ser Thr Pro Ala

CGT ATG TCA CCT GTA GAT TTC CAC ACG CCA TTC CAC CCC AAG TCA CCC        1105
Arg Met Ser Pro Val Asp Phe His Thr Pro Phe His Pro Lys Ser Pro

CCT TCG GAA ATG TCC CCC GTG TCC AGC ACG ACG GTC TCC ATG CCC            1153
Pro Ser Glu Met Ser Pro Val Ser Ser Thr Thr Val Ser Met Pro
```

FIG. 34C

GGF2BPP4 Nucleotide Sequence & Deduced Protein Sequence

```
TCC ATG GCG GTC AGT CCC TTC GTG GAA GAG AGA CCC CTG CTC CTT    1201
Ser Met Ala Val Ser Pro Phe Val Glu Glu Arg Pro Leu Leu Leu

GTG ACG CCA CCA CGG CTG CGG GAG AAG TAT GAC CAC GCC CAG CAA    1249
Val Thr Pro Pro Arg Leu Arg Glu Lys Tyr Asp His Ala Gln Gln

TTC AAC TCG TTC CAC TGC AAC CCC GCG CAT GAG AGC AAC CTG CCC    1297
Phe Asn Ser Phe His Cys Asn Pro Ala His Glu Ser Asn Leu Pro

CCC AGC CCC TTG AGG ATA GTG GAG GAT GAA TAT GAA ACG ACC CAG    1345
Pro Ser Pro Leu Arg Ile Val Glu Asp Glu Tyr Glu Thr Thr Gln

GAG TAC GAA GCT CAA GAG CCG GTT AAG AAA CTC ACC AAC AGC AGC    1393
Glu Tyr Glu Ala Gln Glu Pro Val Lys Lys Leu Thr Asn Ser Ser

CGG GCC AAA AGA ACC AAG CCC AAT GGT CAC ATT GCC CAC AGG TTG    1441
Arg Ala Lys Arg Thr Lys Pro Asn Gly His Ile Ala His Arg Leu

GAA ATG GAC AAC AAC ACA GCT GGC GAC AGT CCT TTC AAC TCA GAG    1489
Glu Met Asp Asn Asn Thr Gly Ala Asp Ser Pro Phe Asn Ser Glu

ACA GAG GAT GAA AGA GTA GGA GAA CTC GGA GAT ACG GCC CTG ATA CAG    1537
Thr Glu Asp Glu Arg Val Gly Glu Leu Gly Asp Thr Ala Leu Ile Gln

AAC CCC CTG GCA GCC AGT GCC GAG CTC GAG GGC GCG CCT TTC CGC CTG GTC    1585
Asn Pro Leu Ala Ala Ser Ala Glu Leu Glu Ala Ala Pro Arg Leu Val

GAC AGC AGG ACT AAC CCA ACA GGA GGC TTC TCT CCG CAG GAA GAA TTG    1633
Asp Ser Arg Thr Asn Pro Thr Gly Gly Phe Ser Pro Gln Glu Glu Leu

CAG GCC AGG CTC TCC GGT GTA ATC GCT AAC CAA GAC CCT ATC GCT GTC    1681
Gln Ala Arg Leu Ser Gly Val Ile Ala Asn Gln Asp Pro Ile Ala Val

TAAAACCGAA ATACACCCAT AGATTCACCT GTAAAACTTT ATTTTATATA ATAAAGTATT   1741

CCACCTTAAA TTAAACAAAA AAA                                            1764
```

FIG. 35

```
GGF2bpp5 (SEQ ID NO: 151)  KCAEKEKTFCVNGGECFMVKDLSNPSRYLCKCPNEFTGDRCQNYVMASFY
GGF2bpp4 (SEQ ID NO: 152)  KCAEKEKTFCVNGGDCFMVKDLSNPSRYLCKCQPGFTGARCTENVPMKVQ
hEGF     (SEQ ID NO: 153)  ECLRKYKDFCIH-GECKYVKELRAPS---CKCQQEYFGERCGEKSNKTHS
```

200 kDa Tyrosine Phosphorylation Compared with Mitogenic Activity

FIG. 37A  GGF/Heregulin Splicing Variants

```
F-B-A'                          F-E-B-A'

F-B-A-C-C/D-D                   F-E-B-A-C-C/D-D
F-B-A-C-C/D-H                   F-E-B-A-C-C/D-H
F-B-A-C-C/D-H-L                 F-E-B-A-C-C/D-H-L
F-B-A-C-C/D-H-K-L               F-E-B-A-C-C/D-H-K-L
F-B-A-C-C/D-D'-H                F-E-B-A-C-C/D-D'-H
F-B-A-C-C/D-D'-H-L              F-E-B-A-C-C/D-D'-H-L
F-B-A-C-C/D-D'-H-K-L            F-E-B-A-C-C/D-D'-H-K-L
F-B-A-C-C/D'-D                  F-E-B-A-C-C/D'-D
F-B-A-C-C/D'-H                  F-E-B-A-C-C/D'-H
F-B-A-C-C/D'-H-L                F-E-B-A-C-C/D'-H-L
F-B-A-C-C/D'-H-K-L              F-E-B-A-C-C/D'-H-K-L
F-B-A-C-C/D'-D'-H               F-E-B-A-C-C/D'-D'-H
F-B-A-C-C/D'-D'-H-L             F-E-B-A-C-C/D'-D'-H-L
F-B-A-C-C/D'-D'-H-K-L           F-E-B-A-C-C/D'-D'-H-K-L
F-B-A-C-C/D-C/D'-D              F-E-B-A-C-C/D-C/D'-D
F-B-A-C-C/D-C/D'-H              F-E-B-A-C-C/D-C/D'-H
F-B-A-C-C/D-C/D'-H-L            F-E-B-A-C-C/D-C/D'-H-L
F-B-A-C-C/D-C/D'-H-K-L          F-E-B-A-C-C/D-C/D'-H-K-L
F-B-A-C-C/D-C/D'-D'-H           F-E-B-A-C-C/D-C/D'-D'-H
F-B-A-C-C/D-C/D'-D'-H-L         F-E-B-A-C-C/D-C/D'-D'-H-L
F-B-A-C-C/D-C/D'-D'-H-K-L       F-E-B-A-C-C/D-C/D'-D'-H-K-L

F-B-A-G-C-C/D-D                 F-E-B-A-G-C-C/D-D
F-B-A-G-C-C/D-H                 F-E-B-A-G-C-C/D-H
F-B-A-G-C-C/D-H-L               F-E-B-A-G-C-C/D-H-L
F-B-A-G-C-C/D-H-K-L             F-E-B-A-G-C-C/D-H-K-L
F-B-A-G-C-C/D-D'-H              F-E-B-A-G-C-C/D-D'-H
F-B-A-G-C-C/D-D'-H-L            F-E-B-A-G-C-C/D-D'-H-L
F-B-A-G-C-C/D-D'-H-K-L          F-E-B-A-G-C-C/D-D'-H-K-L
F-B-A-G-C-C/D'-D                F-E-B-A-G-C-C/D'-D
F-B-A-G-C-C/D'-H                F-E-B-A-G-C-C/D'-H
F-B-A-G-C-C/D'-H-L              F-E-B-A-G-C-C/D'-H-L
F-B-A-G-C-C/D'-H-K-L            F-E-B-A-G-C-C/D'-H-K-L
F-B-A-G-C-C/D'-D'-H             F-E-B-A-G-C-C/D'-D'-H
F-B-A-G-C-C/D'-D'-H-L           F-E-B-A-G-C-C/D'-D'-H-L
F-B-A-G-C-C/D'-D'-H-K-L         F-E-B-A-G-C-C/D'-D'-H-K-L
F-B-A-G-C-C/D-C/D'-D            F-E-B-A-G-C-C/D-C/D'-D
F-B-A-G-C-C/D-C/D'-H            F-E-B-A-G-C-C/D-C/D'-H
F-B-A-G-C-C/D-C/D'-H-L          F-E-B-A-G-C-C/D-C/D'-H-L
F-B-A-G-C-C/D-C/D'-H-K-L        F-E-B-A-G-C-C/D-C/D'-H-K-L
F-B-A-G-C-C/D-C/D'-D'-H         F-E-B-A-G-C-C/D-C/D'-D'-H
F-B-A-G-C-C/D-C/D'-D'-H-L       F-E-B-A-G-C-C/D-C/D'-D'-H-L
F-B-A-G-C-C/D-C/D'-D'-H-K-L     F-E-B-A-G-C-C/D-C/D'-D'-H-K-L
```

FIG. 37B
GGF/Heregulin Splicing Variants

E-B-A'

E-B-A-C-C/D-D
E-B-A-C-C/D-H
E-B-A-C-C/D-H-L
E-B-A-C-C/D-H-K-L
E-B-A-C-C/D-D'-H
E-B-A-C-C/D-D'-H-L
E-B-A-C-C/D-D'-H-K-L
E-B-A-C-C/D'-D
E-B-A-C-C/D'-H
E-B-A-C-C/D'-H-L
E-B-A-C-C/D'-H-K-L
E-B-A-C-C/D'-D'-H
E-B-A-C-C/D'-D'-H-L
E-B-A-C-C/D'-D'-H-K-L
E-B-A-C-C/D-C/D'-D
E-B-A-C-C/D-C/D'-H
E-B-A-C-C/D-C/D'-H-L
E-B-A-C-C/D-C/D'-H-K-L
E-B-A-C-C/D-C/D'-D'-H
E-B-A-C-C/D-C/D'-D'-H-L
E-B-A-C-C/D-C/D'-D'-H-K-L

E-B-A-G-C-C/D-D
E-B-A-G-C-C/D-H
E-B-A-G-C-C/D-H-L
E-B-A-G-C-C/D-H-K-L
E-B-A-G-C-C/D-D'-H
E-B-A-G-C-C/D-D'-H-L
E-B-A-G-C-C/D-D'-H-K-L
E-B-A-G-C-C/D'-D
E-B-A-G-C-C/D'-H
E-B-A-G-C-C/D'-H-L
E-B-A-G-C-C/D'-H-K-L
E-B-A-G-C-C/D'-D'-H
E-B-A-G-C-C/D'-D'-H-L
E-B-A-G-C-C/D'-D'-H-K-L
E-B-A-G-C-C/D-C/D'-D
E-B-A-G-C-C/D-C/D'-H
E-B-A-G-C-C/D-C/D'-H-L
E-B-A-G-C-C/D-C/D'-H-K-L
E-B-A-G-C-C/D-C/D'-D'-H
E-B-A-G-C-C/D-C/D'-D'-H-L
E-B-A-G-C-C/D-C/D'-D'-H-K-L

FIG. 38
EGFL1

SEQ ID NO: 154:

```
AGC CAT CTT GTC AAG TGT GCA GAG AAG GAG AAA ACT TTC TGT GTG AAT       48
Ser His Leu Val Lys Cys Ala Glu Lys Glu Lys Thr Phe Cys Val Asn

GGA GGC GAG TGC TTC ATG GTG AAA GAC CTT TCA AAT CCC TCA AGA TAC       96
Gly Gly Glu Cys Phe Met Val Lys Asp Leu Ser Asn Pro Ser Arg Tyr

TTG TGC AAG TGC CCA AAT GAG TTT ACT GGT GAT CGC TGC CAA AAC TAC      144
Leu Cys Lys Cys Pro Asn Glu Phe Thr Gly Asp Arg Cys Gln Asn Tyr

GTA ATG GCC AGC TTC TAC AGT ACG TCC ACT CCC TTT CTG TCT CTG CCT      192
Val Met Ala Ser Phe Tyr Ser Thr Ser Thr Pro Phe Leu Ser Leu Pro

GAA TAG                                                              198
Glu
```

FIG. 39
EGFL2

SEQ ID NO: 155:

```
AGC CAT CTT GTC AAG TGT GCA GAG AAG GAG AAA ACT TTC TGT GTG AAT   48
Ser His Leu Val Lys Cys Ala Glu Lys Glu Lys Thr Phe Cys Val Asn

GGA GGC GAG TGC TTC ATG GTG AAA GAC CTT TCA AAT CCC TCA AGA TAC   96
Gly Gly Glu Cys Phe Met Val Lys Asp Leu Ser Asn Pro Ser Arg Tyr

TTG TGC AAG TGC CAA CCT GGA TTC ACT GGA GCG AGA TGT ACT GAG AAT  144
Leu Cys Lys Cys Gln Pro Gly Phe Thr Gly Ala Arg Cys Thr Glu Asn

GTG CCC ATG AAA GTC CAA ACC CAA GAA AAA GCG GAG GAG CTC TAC TAA  192
Val Pro Met Lys Val Gln Thr Gln Glu Lys Ala Glu Glu Leu Tyr
```

FIG. 40
EGFL3

SEQ ID NO: 156:

```
AGC CAT CTT GTC AAG TGT GCA GAG AAG GAG AAA ACT TTC TGT GTG AAT      48
Ser His Leu Val Lys Cys Ala Glu Lys Glu Lys Thr Phe Cys Val Asn

GGA GGC GAG TGC TTC ATG GTG AAA GAC CTT TCA AAT CCC TCA AGA TAC      96
Gly Gly Glu Cys Phe Met Val Lys Asp Leu Ser Asn Pro Ser Arg Tyr

TTG TGC AAG TGC CCA AAT GAG TTT ACT GGT GAT CGC TGC CAA AAC TAC     144
Leu Cys Lys Cys Pro Asn Glu Phe Thr Gly Asp Arg Cys Gln Asn Tyr

GTA ATG GCC AGC TTC TAC AAA GCG GAG CTC TAC TAA                     183
Val Met Ala Ser Phe Tyr Lys Ala Glu Leu Tyr
```

FIG. 41
EGFL4

SEQ ID NO: 157:

| | | | | | | | | | | | | | | | |
|---|---|---|---|---|---|---|---|---|---|---|---|---|---|---|---|
|AGC|CAT|CTT|GTC|AAG|TGT|GCA|GAG|AAG|GAG|AAA|ACT|TTC|TGT|GTG|AAT 48|
|Ser|His|Leu|Val|Lys|Cys|Ala|Glu|Lys|Glu|Lys|Thr|Phe|Cys|Val|Asn|

|GGA|GGC|GAG|TGC|TTC|ATG|GTG|AAA|GAC|CTT|TCA|AAT|CCC|TCA|AGA|TAC 96|
|---|---|---|---|---|---|---|---|---|---|---|---|---|---|---|---|
|Gly|Gly|Glu|Cys|Phe|Met|Val|Lys|Asp|Leu|Ser|Asn|Pro|Ser|Arg|Tyr|

|TTG|TGC|AAG|TGC|CCA|AAT|GAG|TTT|ACT|GGT|GAT|CGC|TGC|CAA|AAC|TAC 144|
|---|---|---|---|---|---|---|---|---|---|---|---|---|---|---|---|
|Leu|Cys|Lys|Cys|Pro|Asn|Glu|Phe|Thr|Gly|Asp|Arg|Cys|Gln|Asn|Tyr|

|GTA|ATG|GCC|AGC|TTC|TAC|AAG|CAT|CTT|GGG|ATT|GAA|TTT|ATG|GAG|AAA 192|
|---|---|---|---|---|---|---|---|---|---|---|---|---|---|---|---|
|Val|Met|Ala|Ser|Phe|Tyr|Lys|His|Leu|Gly|Ile|Glu|Phe|Met|Glu|Lys|

|GCG|GAG|GAG|CTC|TAC|TAA 210|
|---|---|---|---|---|---|
|Ala|Glu|Glu|Leu|Tyr| |

FIG. 42
EGFL5

SEQ ID NO: 158:

```
AGC CAT CTT GTC AAG TGT GCA GAG AAG GAG AAA ACT TTC TGT GTG AAT    48
Ser His Leu Val Lys Cys Ala Glu Lys Glu Lys Thr Phe Cys Val Asn

GGA GGC GAG TGC TTC ATG GTG AAA GAC CTT TCA AAT CCC TCA AGA TAC    96
Gly Gly Glu Cys Phe Met Val Lys Asp Leu Ser Asn Pro Ser Arg Tyr

TTG TGC AAG TGC CAA CCT GGA TTC ACT GGA GCG AGA TGT ACT GAG AAT   144
Leu Cys Lys Cys Gln Pro Gly Phe Thr Gly Ala Arg Cys Thr Glu Asn

GTC CCC ATG AAA GTC CAA ACC CAA GAA AAG TGC CCA AAT GAG TTT ACT   192
Val Pro Met Lys Val Gln Thr Gln Glu Lys Cys Pro Asn Glu Phe Thr

GGT GAT CGC TGC CAA AAC TAC GTA ATG GCC AGC TTC TAC AGT ACG TCC   240
Gly Asp Arg Cys Gln Asn Tyr Val Met Ala Ser Phe Tyr Ser Thr Ser

ACT CCC TTT CTG TCT CTG CCT GAA TAG                                267
Thr Pro Phe Leu Ser Leu Pro Glu
```

FIG. 43
EGFL6

SEQ ID NO: 159:

```
AGC CAT CTT GTC AAG TGT GCA GAG AAA GAG AAA ACT TTC TGT GTG AAT    48
Ser His Leu Val Lys Cys Ala Glu Lys Glu Lys Thr Phe Cys Val Asn

GGA GGC GAG TGC TTC ATG GTG AAA GAC CTT TCA AAT CCC TCA AGA TAC    96
Gly Gly Glu Cys Phe Met Val Lys Asp Leu Ser Asn Pro Ser Arg Tyr

TTG TGC AAG TGC CAA CCT GGA TTC ACT GGA GCG AGA TGT ACT GAG AAT   144
Leu Cys Lys Cys Gln Pro Gly Phe Thr Gly Ala Arg Cys Thr Glu Asn

GTG CCC ATG AAA GTC CAA ACC CAA GAA AAG TGC CCA AAT GAG TTT ACT   192
Val Pro Met Lys Val Gln Thr Gln Glu Lys Cys Pro Asn Glu Phe Thr

GGT GAT CGC TGC CAA AAC TAC GTA ATG GCC AGC TTC TAC AAA GCG GAG   240
Gly Asp Arg Cys Gln Asn Tyr Val Met Ala Ser Phe Tyr Lys Ala Glu

GAG CTC TAC TAA                                                   252
Glu Leu Tyr
```

GGF2HBS5

FIG. 45A

Nucleotide Sequence & Deduced Acid Sequence of GGF2HBS5

SEQ ID NO: 21:

```
GGAATTCCTT TTTTTTTTT TTTTTTTCTT NNTTTTTTTT TGCCCTTATA CCTCTTCGCC        60
TTTCTGTGGT TCCATCCACT TCTTCCCCCT CCTCCTCCCA TAAACAACTC TCCTACCCCT       120
GCACCCCCAA TAAATAAATA AAGGAGGAG GCAAGGGGG GAGGAGGAGG AGTGGTGCTG         180
CGAGGGAAG GAAAAGGGAG GCAGCGCGAG AAGAGCCGGG CAGAGTCCGA ACCGACAGCC        240
AGAAGCCCGC ACGCACCTCG CACC ATG AGA TGG CGA CGC GCC CCG CGC CGC         291
                         Met Arg Trp Arg Arg Ala Pro Arg Arg

TCC GGG CGT CCC GGC CCC CGG GCC CAG CGC CCC GGC TCC GCC GCC CGC        339
Ser Gly Arg Pro Gly Pro Arg Ala Gln Arg Pro Gly Ser Ala Ala Arg
                                                      GGF-II 09

TCG CCG CCG CTG CCG CTG CCA CTA CTG CTG CTG CTG CTG CTG GGG ACC        387
Ser Ser Pro Pro Leu Pro Leu Pro Leu Leu Leu Leu Leu Leu Gly Thr
                                    Val Cys Leu Leu Leu Thr Val
                                                      GGF-II 09

GCC GCC CTG GCG GCG CCG GGC GCG GCC AAC GAG GCG GCT CCC CCG            435
Ala Ala Leu Ala Ala Pro Gly Ala Ala Ala Gly Asn Glu Ala Ala Pro Ala
Ala Ala Leu Pro Pro

GGG GCC TCG GTG TGC TAC TCG TCC CCG CCC AGC GTG GGA TCG GTG CAG        483
Gly Ala Ser Val Cys Tyr Ser Ser Pro Pro Ser Val Gly Ser Val Gln
                                                      GGF-II 08
                    Ala Ser Pro Val Ser Val Gly Ser Val Gln

GAG CTA GCT CAG CGC|GCC GCG GCG GTG ATC GAG GTG GTG GGA AAG GTG CAC CCG  531
Glu Leu Ala Gln Arg|Ala Val Ala Ile Glu Val Val Gly Lys Val His Pro
Glu Leu Val Gln Arg|Trp Val Phe Val Ile Glu Ile Glu Gly Lys
                                          GGF-II 04
```

FIG. 45B

Nucleotide Sequence & Deduced Acid Sequence of GGF2HBS5

```
CAG CGG CAG CAG GGG GCA CTC GAC AGG AAG GCG GCG GCG GCG              579
Gln Arg Gln Gln Gly Ala Leu Asp Arg Lys Ala Ala Ala Ala

GGC GAG GCA GGG GCG TGG GGC GGC GAT CGC GAG CCA GCC GCG GGC          627
Gly Glu Ala Gly Ala Trp Gly Gly Asp Arg Glu Pro Pro Ala Gly

CCA CGG GCG CTG GGG CCC GCC GCC GAG CTG CTC GCC GCC AAC              675
Pro Arg Ala Leu Gly Pro Ala Ala Glu Leu Leu Ala Ala Asn

GGG ACC GTG CCC TCT TGG CCC ACC GCC CCC AGC GCC GGC GAG              723
Gly Thr Val Pro Ser Trp Pro Thr Ala Pro Ser Ala Gly Glu

CCC GGG GAG GAG GCG CCC TAT CTG GTG AAG GTG CAC CAG GTG TGG GCG      771
Pro Gly Glu Glu Ala Pro Tyr Leu Val Lys Val His Gln Val Trp Ala
                                Lys Val His Glu Val Trp Ala
                                      GGF-II 01 & GGF-II 11

GTG AAA GCC GGG GGC TTG AAG AAG GAC TCG CTG CTC ACC GTG CGC CTG      819
Val Lys Ala Gly Gly Leu Lys Lys Asp Ser Leu Leu Thr Val Arg Leu
Ala Lys                           Asp Leu Leu Leu Xaa Val      Leu
                                        GGF-II 10

GGG ACC TGG GGC CAC CCC GCC TTC CCC TCC TGC GGG AGG CTC AAG GAG      867
Gly Thr Trp Gly His Pro Ala Phe Pro Ser Cys Gly Arg Leu Lys Glu
Gly Ala Trp Gly Pro Pro Ala Phe Pro Val Xaa Tyr
      GGF-II 03

GAC AGG TAC ATC TTC TTC ATG GAG CCC GAC GCC AAC AGC ACC AGC          915
Asp Ser Arg Tyr Ile Phe Phe Met Glu Pro Asp Ala Asn Ser Thr Ser
      Tyr Ile Phe Phe Met Glu Pro Gla Ala Xaa Ser Ser Gly
                                  GGF-II 02
```

FIG. 45C

Nucleotide Sequence & Deduced Acid Sequence of GGF2HBS5

```
CGC GCG CCG GCC TTC CGA GCC TCT TTC CCC CCT CTG GAG ACG GGC      963
Arg Ala Pro Ala Phe Arg Ala Ser Phe Pro Pro Leu Glu Thr Gly

CGG AAC CTC AAG AAG GAG GTC AGC CGG GTG CTG TGC AAG CGG TGC GCC  1011
Arg Asn Leu Lys Lys Glu Val Ser Arg Val Leu Cys Lys Arg Cys Ala

TTG CCT CCC CAA TTG AAA GAG ATG AAA AGC CAG GAA TCG GCT GCA GGT  1059
Leu Pro Pro Gln Leu Lys Glu Met Lys Ser Gln Glu Ser Ala Ala Gly

TCC AAA CTA GTC CTT CGG TGT GAA ACC AGT TCT GAA TAC TCC TCT CTC  1107
Ser Lys Leu Val Leu Arg Cys Glu Thr Ser Ser Glu Tyr Ser Ser Leu
        Leu Val Leu Arg
        GGF-II 06

AGA TTC AAG TGG TTC AAG AAT GGG AAT GAA TTG AAT CGA AAA AAC AAA  1155
Arg Phe Lys Trp Phe Lys Asn Gly Asn Glu Leu Asn Arg Lys Asn Lys

CCA CAA AAT ATC AAG ATA CAA AAG AAG CCA GGG AAG TCA GAA CTT CGC  1203
Pro Gln Asn Ile Lys Ile Gln Lys Lys Pro Gly Lys Ser Glu Leu Arg

ATT AAC AAA GCA TCA CTG GCT GAT TCT GGA GAG TAT ATG TGC AAA GTG  1251
Ile Asn Lys Ala Ser Leu Ala Asp Ser Gly Glu Tyr Met Cys Lys Val
Lys Ala Ser Leu Ala Asp Ser Gly Glu Tyr Met Xaa Lyx
                    GGF-II 12

ATC AGC AAA TTA GGA AAT GAC AGT GCC TCT GCC AAT ATC ACC ATC GTG  1299
Ile Ser Lys Leu Gly Asn Asp Ser Ala Ser Ala Asn Ile Thr Ile Val

GAA TCA AAC GCT ACA TCT ACA ACC ACT GGG ACA AGC CAT CTT GTA      1347
Glu Ser Asn Ala Thr Ser Thr Thr Thr Gly Thr Ser His Leu Val
```

FIG. 45D

Nucleotide Sequence & Deduced Acid Sequence of GGF2HBS5

```
AAA TGT GCG GAG AAG GAG AAA ACT TTC TGT GTG AAT GGA GGG GAG TGC    1395
Lys Cys Ala Glu Lys Glu Lys Thr Phe Cys Val Asn Gly Gly Glu Cys

TTC ATG GTG AAA GAC CTT TCA AAC CCC TCG AGA TAC TTG TGC AAG TGC    1443
Phe Met Val Lys Asp Leu Ser Asn Pro Ser Arg Tyr Leu Cys Lys Cys

CCA AAT GAG TTT ACT GGT GAT CGC TGC CAA AAC TAC GTA ATG GCC AGC    1491
Pro Asn Glu Phe Thr Gly Asp Arg Cys Gln Asn Tyr Val Met Ala Ser

TTC TAC AGT ACG TCC ACT CCC TTT CTG TCT CTG CCT GAA                1530
Phe Tyr Ser Thr Ser Thr Pro Phe Leu Ser Leu Pro Glu

TAGGAGCATG CTCAGTTGGT GCTGCTTTCT TGTTGCTGCA TCTCCCCTCA GATTCCACCT  1590

AGAGCTAGAT GTGTCTTACC AGATCTAATA TTGACTGCCT CTGCCTGTCG CATGAGAACA  1650

TTAACAAAAG CAATTGTATT ACTTCCTCTG TTCGCGACTA GTTGGCTCTG AGATACTAAT  1710

AGGTGTGTGA GGCTCCGGAT GTTTCTGGAA TTGATATTGA ATGATGTGAT ACAAAATTGAT 1770

AGTCAATATC AAGCAGTGAA ATATGATAAT AAAGGCATTT CAAAGTCTCA CTTTTATTGA  1830

TAAAATAAAA ATCATTCTAC TGAACAGTCC ATCTTCTTTA TACAATGACC ACATCCTGAA  1890

AAGGGTGTTG CTAAGCTGTA ACCGATATGC ACTTGAAATG ATGGTAAGTT AATTTTGATT  1950

CAGAATGTGT TATTTGTCAC AAATAAACAT AATAAAAGGA AAAAAAAAAA AAA         2003
```

Schwann Cell Proliferation Assay

Schwann Cell Assay/Baculovirus Clones

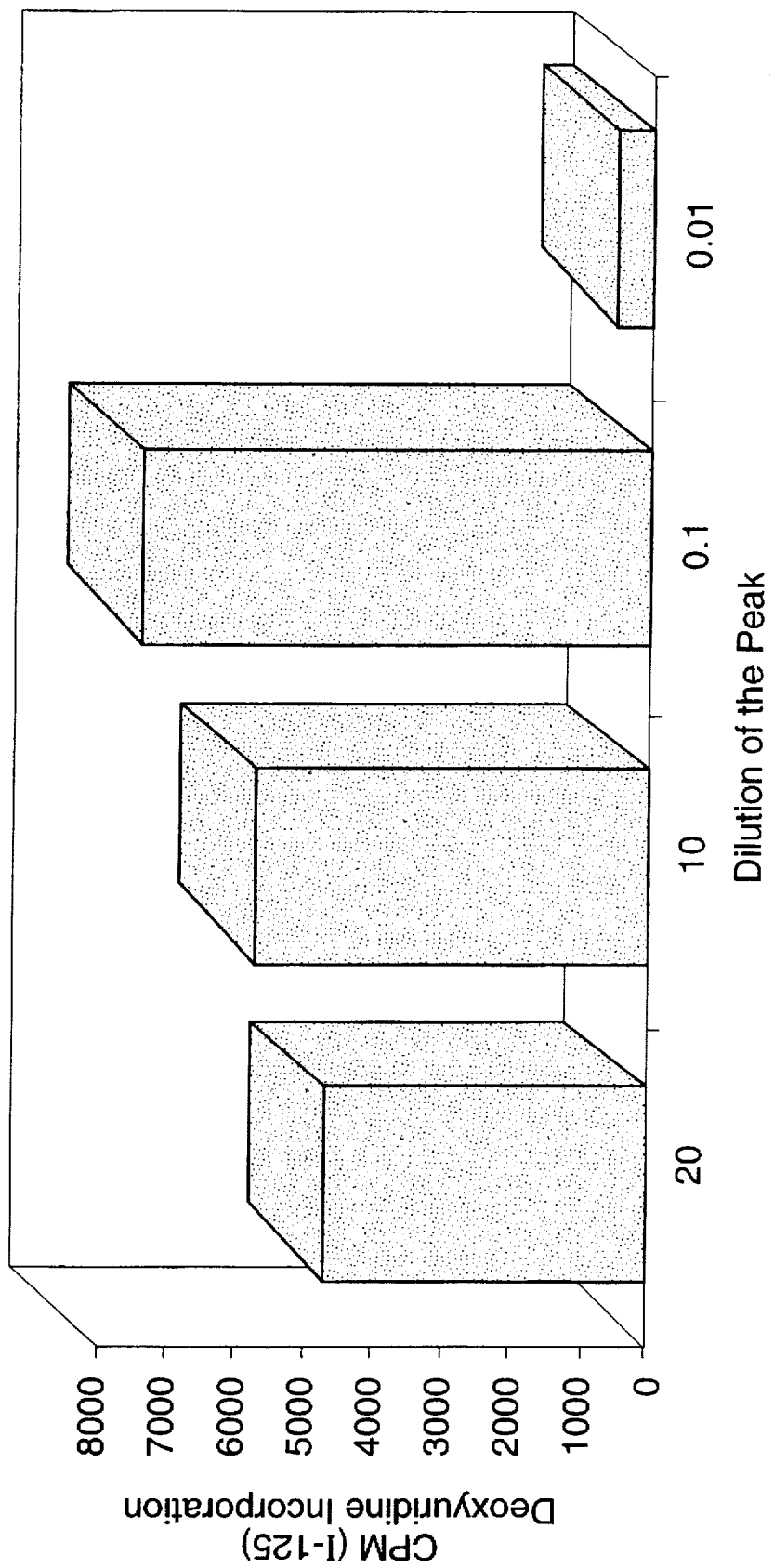

rGGF Purification on Cation Exchange Column

Deduced Sequences of Human & Bovine Glial Growth Factors

PROCESS FOR PREPARING GLIAL MITOGENIC FACTORS

CROSS REFERENCE TO RELATED APPLICATION

This application is a divisional of application Ser. No. 08/036,555 filed Mar. 24, 1993, which is a continuation-in-part of Ser. No. 07/863,703 filed Apr. 3, 1992 (abandoned), which in turn is a continuation-in-part of Ser. No. 07/907,138 filed Jun. 30, 1992 (abandoned), which is a continuation-in-part of Ser. No. 07/940,389 filed Sep. 3, 1992 (abandoned), which is a continuation-in-part of Ser. No. 07/965,173 filed Oct. 23, 1992 (abandoned).

BACKGROUND OF THE INVENTION

This invention relates to polypeptides found in vertebrate species, which polypsprides are mitogenic growth factors for glial cells, including Schwann cells. The invention is also concerned with processes capable of producing such factors, and the therapeutic application of such factors.

The glial cells of vertebrates constitute the specialized connective tissue of the central and peripheral nervous systems. Important glial cells include Schwann cells which provide metabolic support for neurons and which provide myelin sheathing around the axons of certain peripheral neurons, thereby forming individual nerve fibers. Schwann cells support neurons and provide a sheath effect by forming concentric layers of membrane around adjacent neural axons, twisting as they develop around the axons. These myelin sheaths are a susceptible element of many nerve fibers, and damage to Schwann cells, or failure in growth and development, can be associated with significant demyelination or nerve degeneration characteristic of a number of peripheral nervous system diseases and disorders. In the development of the nervous system, it has become apparent that cells require various factors to regulate their division and growth, and various such factors have been identified in recent years, including some found to have an effect on Schwann cell division or development.

Thus, Brockes etal., inter alia, in J. Neuroscience, 4(1984) 75–83 describe a protein growth factor present In extracts from bovine brain and pituitary tissue, which was named Glial Growth Factor (GGF). This factor stimulated cultured rat Schwann cells to divide against a background medium containing ten percent fetal calf serum. The factor was also described as having a molecular weight of 31,000 Daltons and as readily dimerizing. In Meth. Enz., 147 (1987), 217–225, Brockes describes a Schwann cell-based assay for GGF.

Brockes etal., supra, also describes a method of purification of GGF to apparent homogeneity. In brief, one large-scale purification method described involves extraction of the lyophilized bovine anterior lobes and chromatography of material obtained thereby using NaCl gradient elution from CM cellulose. Gel filtration is then carried out with an Ultrogel column, followed by elution from a phosphocellulose column, and finally, small-scale SDS gel electrophoresis. Alternatively, the CM-cellulose material was applied directly to a phosphocellulose column, fractions from the column were pooled and purified by preparative native gel electrophoresis, followed by a final SDS gel electrophoresis.

Brockes etal. observe that in previously reported gel filtration experiments (Brockes etal., J. Biol. Chem. 255 (1980) 8374–8377), the major peak of growth factor activity was observed to migrate with a molecular weight of 56,000 Daltons, whereas in the first of the above-described procedures activity was predominantly observed at molecular weight 31,000. It is reported that the GGF dimer is largely removed as a result of the gradient solution from CM-cellulose in this procedure.

Benveniste etal. (PNAS, 82 (1985), 3930–3934) describe a T lymphocyte-derived glial growth promoting factor. This factor, under reducing conditions, exhibits a change in apparent molecular weight on SDS gels.

Kimura etal. (Nature, 348 (1990), 257–260) describe a factor they term Schwannoma-derived growth factor (SDGF) which is obtained from a sciatic nerve sheath tumor. The authors state that SDGF does not stimulate the incorporation of tritium-labelled TdR into cultured Schwann cells under conditions where, in contrast, partially purified pituitary fraction containing GGF is active. SDGF has an apparent molecular weight of between 31,000 and 35,000.

Davis and Stroobant (J. Cell. Biol., 110 (1990), 1353–1360) describe the screening of a number of candidate mitogens. Rat SChwann cells were used, the chosen candidate substances being examined for their ability to stimulate DNA synthesis in the Schwann cells in the presence of 10% FCS (fetal calf serum), with and without forskolin. One of the factors tested was GGF-carboxymethyl cellulose fraction (GGF-CM), which was mitogenic in the presence of FCS, with and without forskolin. The work revealed that in the presence of forskolin, inter alia, platelet derived growth factor (PDGF) was a potent mitogen for Schwann cells, PDGF having previously been thought to have no effect on Schwann cells.

Holmes etal. Science (1992) 256: 1205 and Wen et al. Cell (1992) 69: 559 demonstrate that DNA sequences which encode proteins binding to a receptor ($p185^{erbB2}$) are associated with several human tumors.

The $p185^{erbB2}$ protein is a 185 kilodalton membrane spanning protein with tyrosine kinase activity. The protein is encoded by the erbB2 proto-oncogene (Yarden and Ullrich Ann. Rev. Biochem. 57: 443 (1988)). The erbB2 gene, also referred to as HER-2 (in human cells) and neu (in rat cells), is closely related to the receptor for epidermal growth factor (EGF). Recent evidence indicates that proteins which interact with (and activate the kinass of) $p185^{erbB2}$ induce proliferation in the cells bearing $p185^{erbB2}$ (Holmes et al. Science 256: 1205 (1992); Dobashi et al. Proc. Natl. Acad. Sci. 88: 8582 (1991); Lupu et al. Proc. Natl. Acad. Sci. 89: 2287 (1992)). Furthermore, it is evident that the gene encoding $p185^{erbB2}$ binding proteins produces a number of variably-sized, differentially-spliced RNA transcripts that give rise to a series of proteins, which are of different lengths and contain some common peptide sequences and some unique peptide sequences. This is supported by the differentially-spliced RNA transcripts recoverable from human breast cancer (MDA-MB-231) (Holmes et al. Science 256: 1205 (1992)). Further support derives from the wide size range of proteins which act as (as disclosed herein) ligands for the $p185^{erbB2}$ receptor (see below).

SUMMARY OF THE INVENTION

In general the invention provides methods for stimulating glial cell (in particular, Schwann cell and glia of the central nervous system) mitogenesis, as well as new proteins exhibiting such glial cell mitogenic activity. In addition, DNA encoding these proteins and antibodies which bind these and related proteins are provided.

The novel proteins of the invention include alternative splicing products of sequences encoding known polypsprides. Generally, these known proteins are members of the GGF/p185$^{erbB2}$ family of proteins.

Specifically, the invention provides polypeptides of a specified formula, and DNA sequences encoding those polypsprides. The polypeptides have the formula

WYBAZCX wherein WYBAZCX is composed of the amino acid sequences shown in FIG. 31 (SEQ ID Nos. 136–139, 141–147, 160, 161); wherein W comprises the polypeptide segment F, or is absent; wherein Y comprises the polypeptide segment E, or is absent; wherein Z comprises the polypeptide segment G or is absent; and wherein X comprises the polypeptide segments C/D HKL, C/D H, C/D HL, C/D D, C/D' HL, C/D' HKL, C/D' H, C/D' D, C/D C/D' HKL, C/D C/D' H, C/D C/D' HL, C/D C/D' D, C/D D' H, C/D D' HL, C/D D' HKL, C/D' D' H, C/D' D' HL, C/D' D' HKL, C/D C/D' D' H, C/D C/D' D' HL, or C/D C/D' D' HKL; provided that, either a) at least one of F, Y, B, A, Z, C, or X is of bovine origin; or b) Y comprises the polypeptide segment E; or c) X comprises the polypeptide segments C/D HKL, C/D D, C/D' HKL, C/D C/D' HKL, C/D C/D' D, C/D D' H, C/D D' HL, C/D D' HKL, C/D' D' H, C/D' D' HKL, C/D C/D' D' H, C/D C/D' D' HL, C/D C/D' D' HKL, C/D'H, C/D C/D'H, or C/D C/D' HL.

In addition, the invention includes the DNA sequence comprising coding segments $^5$'FBA$^3$' as well as the with corresponding polypeptide segments having the amino acid sequences shown in FIG. 31 (SEQ ID Nos. 136, 138, 139);

the DNA sequence comprising the coding segments $^5$'FBA'$^3$' as well as the corresponding polypeptide segments having the amino acid sequences shown in FIG. 31 (SEQ ID Nos. 136, 138, 140);

the DNA sequence comprising the coding segments $^5$'FEBA$^3$' as well as the corresponding polypeptide segments having the amino acid sequences shown in FIG. 31 (SEQ ID Nos. 136–139);

the DNA sequence comprising the coding segments $^5$'FEBA'$^3$' as well as the corresponding polypeptide segments having the amino acid sequences shown An FIG. 31 (SEQ ID Nos. 136–138, 140); and the DNA sequence comprising the polypeptide coding segments of the GGF2HBS5 cDNA clone (ATCC Deposit No. 75298, deposited Sep. 2, 1992).

The invention further includes peptides of the formula FBA, FEBA, FBA' FEBA' and DNA sequences encoding these peptides wherein the polypeptide segments correspond to amino acid sequences shown in FIG. 31, SEQ ID Nos. (136, 138 and 139), (136–139) and (136, 138 and 140) and (136–138 and 140) respectively. The purified GGF-II polypeptide (SEQ ID No. 167) is also included as a part of the invention.

Further included as an aspect of the invention are peptides and DNA encoding such peptides which are useful for the treatment of glia and in particular oligodendrocytes, microgila and astrocytes, of the central nervous system and methods for the administration of these peptides.

The invention further includes vectors including DNA sequences which encode the amino acid sequences, as defined above. Also included are a host cell containing the isolated DNA encoding the amino acid sequences, as defined above. The invention further includes those compounds which bind the p185$^{erbB2}$ receptor and stimulate glial cell mitogenesis in vivo and/or in vitro.

Also a part of the invention are antibodies to the novel peptides described herein. In addition, antibodies to any of the peptides described herein may be used for the purification of polypeptides described herein. The antibodies to the polypeptides may also be used for the therapeutic inhibition of glial cell mitogenesis.

The invention further provides a method for stimulating glial cell mitogenesis comprising contacting glial cells with a polypeptide defined by the formula

WYBAZCX wherein WYBAZCX is composed of the polypeptide segments shown in FIG. 31 (SEQ ID Nos. 136–139, 141–147, 160, 161); wherein W comprises the polypeptide segment F, or is absent wherein Y comprises the polypeptide segment E, or is absent; wherein Z comprises the polypeptide segment G or is absent; and wherein X comprises the polypeptide segment C/D HXL, C/D H, C/D HL, C/D D, C/D' HL, C/D' HKL, C/D' H, C/D' D, C/D C/D' HKL, C/D C/D' H, C/D C/D' HL, C/D C/D' D, C/D D' H, C/D D' HL, C/D D' HKL, C/D' D' H, C/D' D' HL, C/D' D' HKL, C/D C/D' D' H, C/D C/D' D' HL, or C/D C/D' D' HKL.

The invention also includes a method for the preparation of a glial cell mitogenic factor which consist of culturing modified host cells as defined above under conditions permitting expression of the DNA sequences of the invention.

The peptides of the invention can be used to make a pharmaceutical or veterinary formulation for pharmaceutical or veterinary use. Optionally, the formulation may be used together with an acceptable diluent, carrier or excipient and/or in unit dosage form.

A method for stimulating mitogenesis of a glial cell by contacting the glial cell with a polypeptide defined above as a glial cell mitogen in vivo or in vitro is also an aspect of the invention. A method for producing a glial cell mitogenic effect in a vertebrate (preferably a mammal, more preferably a human) by administering an effective amount of a polypeptide as defined is also a component of the invention.

Methods for treatment of diseases and disorders using the polypsprides described are also a part of the invention. For instance, a method of treatment or prophylaxis for a nervous disease or disorder can be effected with the polypeptides described. Also included are a method for the prophylaxis or treatment of a pathophysiological condition of the nervous system in which a cell type is involved which is sensitive or responsive to a polypeptide as defined are a part of the invention.

Included in the invention as well, are methods for treatment when the condition involves peripheral nerve damage; nerve damage in the central nervous system; neurodegenerative disorders; demyelination in peripheral or central nervous system; or damage or loss of Schwann cells oligodendrocytes, microgila, or astrocytes. For example a neuropathy of sensory or motor nerve fibers; or the treatment of a neurodegenerative disorder are included. In any of these cases, treatment consists of administering an effective amount of the polypeptide.

The invention also includes a method for inducing neural regeneration and/or repair by administering an effective amount of a polypeptide as defined above. Such a medicament is made by administering the polypeptide with a pharmaceutically effective carrier.

The invention includes the use of a polypeptide as defined above in the manufacture of a medicament.

The invention further includes the use of a polypeptide as defined above to immunize a mammal for producing antibodies, which can optionally be used for therapeutic or diagnostic purposes in a competitive assay to identify or quantify molecules having receptor binding characteristics corresponding to those of the polypeptide; and/or for contacting a sample with a polypeptide, as mentioned above, along with a receptor capable of binding specifically to the polypeptide for the purpose of detecting competitive inhibition of binding to the polypeptide.

in an affinity isolation process, optionally affinity chromatography, for the separation of a corresponding receptor.

The invention also includes a method for the prophylaxis or treatment of a glial tumor. This method consists of administering an effective amount of a substance which inhibits the binding of a factor as defined by the peptides above.

Furthermore, the invention includes a method of stimulating glial cell mitogenic activity by the application to the glial cell of a 30 kD polypeptide factor isolated from the MDA-MB 231 human breast cell line; or 35 kD polypeptide factor isolated from the rat I-EJ transformed fibroblast cell line to the glial cell or 75 kD polypeptide factor isolated from the SKBR-3 human breast cell line; or 44 kD polypeptide factor isolated from the rat I-EJ transformed fibroblast cell line; or 25 kD polypeptide factor isolated from activated mouse peritoneal macrophages; or 45 kD polypeptide factor isolated from the MDA-MB 231 human breast cell; or 7 to 14 kD polypeptide factor isolated from the ATL-2 human T-cell line to the glial cell; or 25 kD polypeptide factor isolated from the bovine kidney cells; or 42 kD polypeptide factor (ARIA) isolated from brains.

The invention further includes a method for the use of the EGFL1, EGFL2, EGFL3, EGFL4, EGFL5, and EGFL6 polypeptides, FIG. 38 to 43 and SEQ ID Nos. 154 to 159, respectively, for the stimulation of glial cell mitogenesis in vivo and in vitro.

Also included in the invention is the administration of the GGF-II polypeptide whose sequence is shown in FIG. 45 for the stimulation of glial cell mitogenesis.

An additional aspect of the invention includes the use of the above-referenced peptides for the purpose of stimulating Schwann cells to produce growth factors which may, in turn, be harvested for scientific or therapeutic use.

Furthermore, the peptides described herein may be used to induce central glial proliferation and remyelination for treatment of diseases, e.g., MS, where re-myelination is desired.

In an additional aspect of the invention, the novel polypeptides described herein may be used to stimulate the synthesis of acetylcholine receptors.

As mentioned above, the invention provides new glial growth factors from mammalian sources, including bovine and human, which are distinguished from known factors. These factors are mitogenic for Schwann cells against a background of fetal calf plasma (FCP). The invention also provides processes for the preparation of these factors, and an improved method for defining activity of these and other factors. Therapeutic application of the factors is a further significant aspect of the invention.

Thus, important aspects of the invention are:

(a) a basic polypeptide factor having glial cell mitogenic activity, more specifically, Schwann cell mitogenic activity in the presence of fetal calf plasma, a molecular weight of from about 30 kD to about 36 kD, end including within its amino acid sequence any one or more of the following peptide sequences:

| F | K | G | D | A | H | T | E |   |   |   |   |   |   |   |   |
|---|---|---|---|---|---|---|---|---|---|---|---|---|---|---|---|
| A | S | L | A | D | E | Y | E | Y | M | X | K |   |   |   |   |
| T | E | T | S | S | S | G | L | X | L | K |   |   |   |   |   |
| A | S | L | A | D | E | Y | E | Y | M | R | K |   |   |   |   |
| A | G | Y | F | A | E | X | A | R |   |   |   |   |   |   |   |
| T | T | E | M | A | S | E | Q | G | A |   |   |   |   |   |   |
| A | K | E | A | L | A | A | L | K |   |   |   |   |   |   |   |
| F | V | L | Q | A | K | K |   |   |   |   |   |   |   |   |   |
| E | T | Q | P | D | P | G | Q | I | L | K | K | V | P | M | V | I | G | A | Y | T |
| E | Y | K | C | L | K | F | K | W | F | K | K | A | T | V | M |
| E | X | K | F | Y | V | P |   |   |   |   |   |   |   |   |   |
| K | L | E | F | L | X | A | K; and |

(b) a basic polypeptide factor which stimulates glial cell mitogenesis, particularly the division of Schwann cells, in the presence of fetal calf plasma, has a molecular weight of from about 55 kD to about 63 kD, and including within its amino acid sequence any one or more of the following peptide sequences:

| V | H | Q | V | W | A | A | K |   |   |   |   |   |   |
|---|---|---|---|---|---|---|---|---|---|---|---|---|---|
| Y | I | F | F | M | E | P | E | A | X | S | S | G |   |
| L | G | A | W | G | P | P | A | F | P | V | X | Y |   |
| W | F | V | V | I | E | G | K |   |   |   |   |   |   |
| A | S | P | V | S | V | G | S | V | Q | E | L | Q | R |
| V | C | L | L | T | V | A | A | L | P | P | T |   |   |
| K | V | H | Q | V | W | A | A | K |   |   |   |   |   |
| K | A | S | L | A | D | S | G | E | Y | M | X | K |   |
| D | L | L | L | X | V |   |   |   |   |   |   |   |   |
| E | G | K | V | H | P | Q | R | R | G | A | L | D | R | K |
| P | S | C | G | R | L | K | E | D | S | R | Y | I | F | F | M | E |
| E | L | N | R | K | N | K | P | Q | N | I | K | I | Q | K | K |

The novel peptide sequences set out above, derived from the smaller molecular weight polypeptide factor, and from the larger molecular weight polypeptide factor, are also aspects of this invention in their own right. These sequences are useful as probe sources for polypeptide factors of the invention, for investigating, isolating or preparing such factors (or corresponding gene sequences) from a range of different species, or preparing such factors by recombinant technology, and in the generation of corresponding antibodies, by conventional technologies, preferably monoclonal antibodies, which are themselves useful investigative tools and are possible therapeutics. The invention also includes an isolated glial cell mitogenic activity encoding gene sequence, or fragment thereof, obtainable by the methods set out above for the novel peptide sequences of the invention.

The availability of short peptides from the highly purified factors of the invention has enabled additional sequences to be determined (see Examples to follow).

Thus, the invention further embraces a polypeptide factor having glial cell mitogenic activity and including an amino acid sequence encoded by:

(a) a DNA sequence shown in any one of FIGS. 28a, 28b or 28c, SEQ ID Nos. 133–135, respectively;

(b) a DNA sequence shown in FIG. 22, SEQ ID No. 89;

(c) the DNA sequence represented by nucleotides 281–557 of the sequence shown in FIG. 28a, SEQ ID No. 133; or (d) a DNA sequence hybridizable to any one of the DNA sequences according to (a), (b) or (c).

The invention further includes sequences which have greater than 60%, preferably 80%, sequence identity of homology to the sequences indicated above.

While the present invention is not limited to a particular set of hybridization conditions, the following protocol gives general guidance which may, if desired, be followed:

DNA probes may be labelled to high specific activity (approximately $10^8$ to $10^9$ $^{32}$Pdmp/µg) by nick-translation or by PCR reactions according to Schowalter and Sommer (Anal. Biochem., 177:90–94, 1989) and purified by desalting on G-150 Sephadex columns. Probes may be denatured (10 minutes in boiling water followed by immersion into ice water), then added to hybridization solutions of 80% buffer B (2 g polyvinylpyrolidine, 2 g Ficoll-400, 2 g bovine serum albumin, 50 ml 1M Tris HCL (pH 7.5), 58 g NaCl, 1 g sodium pyrophosphate, 10 g sodium dodecyl sulfate, 950 ml $H_2O$) containing 10% dextran sulfate at $10^6$ dpm $^{32}$P per ml and incubated overnight (approximately 16 hours) at 60° C. The filters may then be washed at 60° C., first in buffer B for 15 minutes followed by three 20-minute washes in 2× SSC, 0.1% SDS then one for 20 minutes in 1× SSC, 0.1% SDS.

In other respects, the invention provides:

(a) a basic polypeptide factor which has, if obtained from bovine pituitary material, an observed molecular weight, whether in reducing conditions or not, of from about 30 kD to about 36 kD on SDS-polyacrylamide gel electrophoresis using the following molecular weight standards:

| Lysozyme (hen egg white) | 14,400 |
| Soybean trypsin inhibitor | 21,500 |
| Carbonic anhydrase (bovine) | 31,000 |
| Ovalbumin (hen egg white) | 45,000 |
| Bovine serum albumin | 66,200 |
| Phosphorylase B (rabbit muscle) | 97,400; | which factor has glial cell mitogenic activity including stimulating the division of rat Schwann cells in the presence of fetal calf plasma, and when isolated using reversed-phase HPLC retains at least 50% of said activity after 10 weeks incubation in 0.1% trifluoroacetic acid at 4° C.; and (b) a basic polypeptide factor which has, if obtained from bovine pituitary material, an observed molecular weight, under non-reducing conditions, of from about 55 kD to about 63 kD on SDS-polyacrylamide gel electrophoresis using the following molecular weight standards:

| Lysozyme (hen egg white) | 14,400 |
| Soybean trypsin inhibitor | 21,500 |
| Carbonic anhydrase (bovine) | 31,000 |
| Ovalbumin (hen egg white) | 45,000 |
| Bovine serum albumin | 66,200 |
| Phosphorylase B (rabbit muscle) | 97,400; | which factor the human equivalent of which is encoded by DNA clone GGF2HBS5 described herein and which factor has glial cell mitogenic activity including stimulating the division of rat Schwann cells in the presence of fetal calf plasma, and when isolated using reversed-phase HPLC retains at least 50% of the activity after 4 days incubation in 0.1% trifluoroacetic acid at 4° C.

For convenience of description only, the lower molecular weight and higher molecular weight factors of this invention are referred to hereafter as "GGF-I" and "GGF-II", respectively. The "GGF2" designation is used for all clones isolated with peptide sequence data derived from GGF-II protein (i.e., GGF2HBS5, GGF2BPP3).

It will be appreciated that the molecular weight range limits quoted are not exact, but are subject to slight variations depending upon the source of the particular polypeptide factor. A variation of, say, about 10% would not, for example, be impossible for material from another source.

Another important aspect of the invention is a DNA sequence encoding a polypeptide having glial cell mitogenic activity and comprising:

(a) a DNA sequence shown in any one of FIGS. 28a, 28b or 28c, SEQ ID Nos. 133–135:

(b) a DNA sequence shown in FIG. 22, SEQ ID No. 89;

(c) the DNA sequence represented by nucleotides 281–557 of the sequence shown in FIG. 28a, SEQ ID No. 133; or (d) a DNA sequence hybridizable to any one of the DNA sequences according to (a), (b) or (c).

Another aspect of the present invention uses the fact that the Glial Growth Factors and p185$^{erbB2}$ ligand proteins are encoded by the same gene. A variety of messenger RNA splicing variants (and their resultant proteins) are derived from this gene and many of these products show p185$^{erbB2}$ binding and activation. Several of the (GGF-II) gene products have been used to show Schwann cell mitogenic activity. This invention provides a use for all of the known products of the GGF/p185$^{erbB2}$ ligand gene (described in the references listed above) as Schwann cell mitogens.

This invention also relates to other, not yet naturally isolated splicing variants of the Glial Growth Factor gene. FIG. 30, shows the known patterns of splicing derived from polymerass chain reaction experiments (on reverse transcribed RNA) and analysis of cDNA clones (as presented within) and derived from what has been published as sequences encoding p185$^{erbB2}$ Zigands (Pales etal., Cell 69:205 (1992) and Wen etal., Cell 69:559 (1992)). These patterns, as well as additional ones disclosed herein, represent probable splicing variants which exist. Thus another aspect of the present invention relates to the nucleotide sequences encoding novel protein factors derived from this gene. The invention also provides processes for the preparation of these factors. Therapeutic application of these new factors is a further aspect of the invention.

Thus other important aspects of the invention are:

(a) A series of human and bovine polypeptide factors having glial cell mitogenic activity including stimulating the division of Schwann cells. These peptide sequences are shown in FIGS. 31, 32, 33 and 34, SEQ ID Nos. 136–137, respectively.

(b) A series of polypeptide factors having glial cell mitogenic activity including stimulating the division of Schwann cells and purified and characterized according to the procedures outlined by Lupu et al. Science 249: 1552 (1990); Lupu et al. Proc. Natl. Acad. Sci USA 89: 2287 (1992); Holmes et al. Science 256: 1205 (1992); Pales et al. 69: 205 (1992); Yarden and Peles Biochemistry 30: 3543 (1991); Dobashi et al. Proc. Natl. Acad. Sci. 88: 8582 (1991); Davis et al. Biochem. Biophys. Res. Commun. 179: 1536 (1991); Beaumont et al., patent application PCT/US91/03443 (1990); Greene et al. patent application POT/US91/02331 (1990); Usdin and Fischbach, J. Cell. Biol. 103:493–507 (1986); Falls et al., Cold Spring Harbor Symp. Quant. Biol. 55:397–406 (1990); Harris et al., Proc. Natl. Acad. Sci. USA 88:7664–7668 (1991); and Falls et al., Cell 72:801–815 (1993).

(c) A polypeptide factor (GGFBPP5) having glial cell mitogenic activity including stimulating the division of Schwann cells. The amino acid sequence is shown in FIG. 32, SEQ ID No. 148, and is encoded by the bovine DNA sequence shown in FIG. 32, SEQ ID No. 148.

The novel human peptide sequences described above and presented in FIGS. 31, 32, 33 and 34, SEQ ID Nos. 136–150, respectively, represent a series of splicing variants which can be isolated as full length complementary DNAs (cDNAs) from natural sources (cDNA libraries prepared from the appropriate tissues) or can be assembled as DNA constructs with individual exons (e.g., derived as separate exons) by someone skilled in the art.

Other compounds in particular, peptides, which bind specifically to the p185$^{erbB2}$ receptor can also be used according to the invention as a glial cell mitogen. A candidate compound can be routinely screened for p185$^{erbB2}$ binding, and, if it binds, can then be screened for glial cell mitogenic activity using the methods described herein.

The invention includes any modifications or equivalents of the above polypeptide factors which do not exhibit a significantly reduced activity. For example, modifications in which amino acid content or sequence is altered without substantially adversely affecting activity are included. By way of illustration, in EP-A 109748 mutations of native proteins are disclosed in which the possibility of unwanted disulfide bonding is avoided by replacing any cysteine in the native sequence which is not necessary for biological activity with a neutral amino acid. The statements of effect and use contained herein are therefore to be construed accordingly, with such uses and effects employing modified or equivalent factors being part of the invention.

The new sequences of the invention open up the benefits of recombinant technology. The invention thus also includes the following aspects:

(a) DNA constructs comprising DNA sequences as defined above in operable reading frame position within vectors (positioned relative to control sequences so as to permit expression of the sequences) in chosen host cells after transformation thereof by the constructs (preferably the control sequence includes regulatable promoters, e.g. Trp). It will be appreciated that the selection of a promoter and regulatory sequences (if any) are matters of choice for those of skill in the art;

(b) host cells modified by incorporating constructs as defined in (a) immediately above so that said DNA sequences may be expressed An said host cells—the choice of host is not critical, and chosen cells may be prokaryotic or eukaryotic and may be genetically modified to incorporate said constructs by methods known in the art; and, (c) a process for the preparation of factors as defined above comprising cultivating the modified host cells under conditions permitting expression of the DNA sequences. These conditions can be readily determined, for any particular embodiment, by those of skill in the art of recombinant DNA technology. Glial cell mitogens prepared by this means are included in the present invention.

None of the factors described in the art has the combination of characteristics possessed by the present new polypeptide factors.

As indicated, the Schwann cell assay used to characterize the present factors employs a background of fetal calf plasma. In all other respects, the assay can be the same as that described by Brockes et al. in Meth. Enz., supra, but with 10% PCP replacing 10% FCS. This difference in assay techniques is significant, since the absence of platelet-derived factors in fetal calf plasma (as opposed to serum) enables a more rigorous definition of activity on Schwann cells by eliminating potentially spurious effects from some other factors.

The invention also includes a process for the preparation of a polypeptide as defined above, extracting vertebrate brain material to obtain protein, subjecting the resulting extract to chromatographic purification by hydroxylapatite HPLC and then subjecting these fractions to SDS-polyacrylamide gel electrophoresis. The fraction which has an observed molecular weight of about 30 kD to 36 kD and/or the fraction which has an observed molecular weight of about 55 kD to 63 kD is collected. In either case, the fraction is subjected to SDS-polyacrylamide gel electrophoresis using the following molecular weight standards:

| | |
|---|---|
| Lysozyme (hen egg white) | 14,400 |
| Soybean trypsin inhibitor | 21,500 |
| Carbonic anhydrase (bovine) | 31,000 |
| Ovalbumin (hen egg white) | 45,000 |
| Bovine serum albumin | 66,200 |
| Phosphorylase B (rabbit muscle) | 97,400 |

In the case of the smaller molecular weight fraction, the SDS-polyacrylamide gel is run in non-reducing conditions in reducing conditions or, and in the case of the larger molecular weight fraction the gel is run under non-reducing conditions. The fractions are then tested for activity stimulating the division of rat Schwann cells against a background of fetal calf plasma.

Preferably, the above process starts by isolating a relevant fraction obtained by carboxymethyl cellulose chromatography, e.g. from bovine pituitary material. It is also preferred that hydroxylapatite HPLC, cation exchange chromatography, gel filtration, and/or reversed-phase HPLC be employed prior to the SDS-Polyacrylamide gel electrophoresis. At each stage in the process, activity may be determined using Schwann cell incorporation of radioactive iododeoxyuridine as a measure in an assay generally as described by Brockes in Meth. Enz., supra, but modified by substituting 10% FCP for 10% FCS. As already, noted, such as assay is an aspect of the invention in its own substance for CNS or PNS cell, e.g. Schwann cell, mitogenic effects.

Thus, the invention also includes an assay for glial cell mitogenic activity in which a background of fetal calf plasma is employed against which to assess DNA synthesis in glial cells stimulated (if at all) by a substance under assay.

Another aspect of the invention is a pharmaceutical or veterinary formulation comprising any factor as defined above formulated for pharmaceutical or veterinary use, respectively, optionally together with an acceptable diluent, carrier or excipient and/or in unit dosage form. In using the factors of the invention, conventional pharmaceutical or veterinary practice may be employed to provide suitable formulations or compositions.

Thus, the formulations of this invention can be applied to parenteral administration, for example, intravenous, subcutaneous, intramuscular, intraorbital, opthalmic, intraventricular, intracranial, intracapsular, intraspinal, intracisternal, intraperitoneal, topical, intranasal, aerosol, scarification, and also oral, buccal, rectal or vaginal administration.

The formulations of this invention may also be administered by the transplantation into the patient of host cells expressing the DNA of the instant invention or by the use of surgical implants which release the formulations of the invention.

Parenteral formulations may be in the form of liquid solutions or suspensions; for oral administration, formulations may be in the form of tablets or capsules; and for intranasal formulations, in the form of powders, nasal drops, or aerosols.

Methods well known in the art for making formulations are to be found in, for example, "Remington's Pharmaceutical Sciences." Formulations for parenteral administration may, for example, contain as excipients sterile water or saline, polyalkylene glycols such as polyethylene glycol, oils of vegetable origin, or hydrogenated naphthalenes, biocompatible, biodegradable lactide polymer, or polyoxyethylene-polyoxypropylene copolymers may be used to control the release of the present factors. Other potentially useful parenteral delivery systems for the factors include ethylene-vinyl acetate copolymer particles, osmotic pumps, implantable infusion systems, and liposomes. Formulations for inhalation may contain as excipients, for example, lactose, or may be aqueous solutions containing, for example, polyoxyethylene-9-lauryl ether, glycocholate and deoxycholate, or may be oily solutions for administration in the form of nasal drops, or as a gel to be applied intranasally. Formulations for parenteral administration may also include glycocholate for buccal administration, methoxysalicylate for rectal administration, or citric acid for vaginal administration.

The present factors can be used as the sole active agents, or can be used in combination with other active ingredients, e.g., other growth factors which could facilitate neuronal survival in neurological diseases, or peptidase or protease inhibitors.

The concentration of the present factors in the formulations of the invention will vary depending upon a number of issues, including the dosage to be administered, and the route of administration.

In general terms, the factors of this invention may be provided in an aqueous physiological buffer solution containing about 0.1 to 10% w/v compound for parenteral administration. General dose ranges are from about 1 mg/kg to about 1 g/kg of body weight per day; a preferred dose range is from about 0.01 mg/kg to 100 mg/kg of body weight per day. The preferred dosage to be administered is likely to depend upon the type and extent of progression of the pathophysiological condition being addressed, the overall health of the patient, the make up of the formulation, and the route of administration.

As indicated above, Schwann cells (the glial cells of the peripheral nervous system) are stimulated to divide in the presence of the factors of the invention. Schwann cells of the peripheral nervous system are involved in supporting neurons and in creating the myelin sheath around individual nerve fibers. This sheath is important for proper conduction of electrical impulses to muscles and from sensory receptors.

There are a variety of peripheral neuropathies in which Schwarm cells end nerve fibers are damaged, either primarily or secondarily. There are many neuropathies of both sensory and motor fibers (Adams and Victor, Principles of Neurology). The most important of those neuropathies are probably the neuropathies associates with diabetes, multiple sclerosis, Landry-Guillain-Barr syndrome, neuropathies caused by carcinomas, and neuropathies caused by toxic agents (some of which are used to treat carcinomas).

The invention, however, envisages treatment or prophylaxis of conditions where nervous system damage has been brought about by any basic cause, e.g. infection or injury. Thus, in addition to use of the present factors in the treatment of disorders or diseases of the nervous system where demyelination or loss of Schwann cells is present, such glial growth factors can be valuable in the treatment of disorders of the nervous system that have been caused by damage to the peripheral nerves. Following damage to peripheral nerves, the regeneration process is led by the growth or the re-establishment of Schwann cells, followed by the advancement of the nerve fibre back to its target. By speeding up the division of Schwann cells one could promote the regenerative process following damage.

Similar approaches could be used to treat injuries or neurodegenerative disease of the central nervous system (brain and spinal cord).

Furthermore, there are a variety of tumors of glial cells the most common of which is probably neurofibromatosis, which is a patchy small tumor created by overgrowth of glial cells. Also, it has been found that an activity very much like GGF can be found in some Schwann cell tumors, and therefore inhibitors of the action of the present factors on their recaptols provides a therapy of a glial tumor, which comprises administering an effective amount of a substance which inhibits the binding of a factor, as defined above, to a receptor.

In general, the invention includes the use of present polypeptide factors An the prophylaxis or treatment of any pathophysiological condition of the nervous system in which a factor-sensitive or factor-responsive cell type is involved.

The polypeptide factors of the invention can also be used as immunogens for making antibodies, such as monoclonal antibodies, following standard techniques. Such antibodies are included within the present invention. These antibodies can, in turn, be used for therapeutic or diagnostic purposes. Thus, conditions perhaps associated with abnormal levels of the factor may be tracked by using such antibodies. In vitro techniques can be used, employing assays on isolated samples using standard methods. Imaging methods in which the antibodies are, for example, tagged with radioactive isotopes which can be imaged outside the body using techniques for the art of rumour imaging may also be employed.

The invention also includes the general use of the present factors as glial cell mitogens in vivo or in vitro, and the factors for such use. One specific embodiment is thus a method for producing a glial cell mitogenic effect in a vertebrate by administering an effective amount of a factor of the invention. A preferred embodiment is such a method in the treatment or prophylaxis of a nervous system disease or disorder.

A further general aspect of the invention is the use of a factor of the invention in the manufacture of a medicament, preferably for the treatment of a nervous disease or disorder, or for neural regeneration or repair.

Also included in the invention are the use of the factors of the invention in competitive assays to identify or quantify molecules having receptor binding characteristics corresponding to those of said polypsprides. The polypeptides may be labelled, optionally with a radioisotope. A competitive assay can identify both antagonists and agonists of the relevant receptor.

In another aspect, the invention provides the use of each one of the factors of the invention in an affinity isolation process, optionally affinity chromatography, for the separation of a respective corresponding receptor. Such processes for the isolation of recaptots corresponding to particular proteins are known in the art, and a number of techniques are available and can be applied to the factors of the present invention. For example, in relation to IL-6 and IFNγ the reader is referred to Novick, D.; et al., J. Chromatogr. (1990) 510: 331–7. With respect to gonadotropin releasing hormone reference is made to Hazum, E., J. (1990) Chromatogr. 510:233–8. In relation to G-CSF reference is made to Fukunaga, R., et al., J. Biol. Chem., 265:13386–90. In relation to IL-2 reference is made to Smart, J. E., et al., (1990) J. Invest. Dermatol., 94:158S–163S, and in relation to human IFN-gamma reference is made to Stefanos, S, et al., (1989) J. Interraton Res., 9:719–30.

BRIEF DESCRIPTION OF THE DRAWINGS

The drawings will first be described.
Drawings

FIGS. 1 to 8 relate to Example 1, and are briefly described below:

FIG. 1 is the profile for product from carboxymethyl cellulose chromatography;

FIG. 2 is the profile for product from hydroxylapatite HPLC;

FIG. 3 is the profile for product from Mono S FPLC;

FIG. 4 is the profile for product from Gel filtration FPLC;

FIGS. 5 and 6 depict the profiles for the two partially purified polypeptide products from reversed-phase HPLC; and FIGS. 7 and 8 depict dose-response curves for the GGF-I and GGF-II fractions from reversed-phase HPLC using either a fetal calf serum or a fetal calf plasma background;

FIGS. 9 to 12 depict the peptide sequences derived from GGF-I and GGF-II, SEQ ID Nos. 1–20, 22–29, 32–53 and 169, (see Example 2 hereinafter), FIGS. 10 and 12 specifically depict novel sequences:

In FIG. 10, Panel A, the sequences of GGF-I peptides used to design degenerate oligonucleotide probes and degenerate PCR primers are listed (SEQ ID Nos. 20, 1, 22–29, and 17). Some of the sequences in Panel A were also used to design synthetic peptides. Panel B is a listing of the sequences of novel peptides that were too short (less than 6 amino acids) for the design of degenerate probes or degenerate PCR primers (SEQ ID Nos. 17 and 52);

In FIG. 12, Panel A, is a listing of the sequences of GGF-II peptides used to design degenerate oligonucleotide probes and degenerate PCR primers (SEQ ID Nos. 45–52). Some of the sequences in Panel A were used to design synthetic peptides. Panel B is a listing of the novel peptide that was too short (less than 6 amino acids) for the design of degenerate probes or degenerate PCR primers (SEQ ID No. 53);

FIGS. 21 to 28 (a, b and c) relate to Example 4, below and are briefly described below:

FIG. 21 is a listing of the degenerate oligonucleotide probes (SEQ ID Nos. 54–88) designed from the novel peptide sequences in FIG. 10, Panel A and FIG. 12, Panel A;

FIG. 22 (SEQ ID No. 89) depicts a stretch of the putative bovine GGF-II gene sequence from the recombinant bovine genomic phage GGF2BG1, containing the binding site of degenerate oligonucleotide probes 609 and 650 (see FIG. 21, SEQ ID NOs. 69 and 72, respectively). The figure is the coding strand of the DNA sequence and the deduced amino acid sequence in the third reading frame. The sequence of peptide 12 from factor 2 (bold) is part of a 66 amino acid open reading frame (nucleotides 75272);

FIG. 23 is the degenerate PCR primers (Panel A, SEQ IS Nos. 90–108) and unique PCR primers (Panel B, SEQ ID Nos. 109–119) used in experiments to isolate segments of the bovine GGF-II coding sequences present in RNA from posterior pituitary;

FIG. 24 depicts of the nine distinct contiguous bovine GGF-II cDNA structures and sequences that were obtained in PCR amplification experiments using the list of primers in FIG. 7, Panels A and B, and RNA from posterior pituitary. The top line of the Figure is a schematic of the coding sequences which contribute to the cDNA structures that were characterized;

FIG. 25 is a physical map of bovine recombinant phage of GGF2BG1. The bovine fragment is roughly 20 kb in length and contains two exons (bold) of the bovine GGF-II gene. Restriction sites for the enzymes XbaI, SpeI, NdeI, EcoRI, KpnI, and SstI have been placed on this physical map. Shaded portions correspond to fragments which were subcloned for sequencing;

FIG. 26 is a schematic of the structure of three alternative gene products of the putative bovine GGF-II gene. Exons are listed A through E in the order of their discovery. The alternative splicing patterns 1, 2 and 3 generate three overlapping deduced protein structures (GGF2BPP1, 2, and 3), which are displayed in the various FIGS. 28a, b, c (described below);

FIG. 27 (SEQ ID Nos. 120–132) is a comparison of the GGF-I and GGF-II sequences identified in the deduced protein sequences shown in FIGS. 28a, 28b and 28c (described below) with the novel peptide sequences listed in FIGS. 10 and 12. The Figure shows that six of the nine novel GGF-II peptide sequences are accounted for in these deduced protein sequences. Two peptide sequences similar to GGF-I sequences are also found;

FIG. 28a (SEQ ID No. 133) is a listing of the coding strand DNA sequence and deduced amino acid sequence of the cDNA obtained from splicing pattern number 1 in FIG. 26. This partial cDNA of the putative bovine GGF-II gene encodes a protein of 206 amino acids in length. Peptides in bold were those identified from the lists presented in FIGS. 10 and 12. Potential glycosylation sites are underlined (along with polyadenylation signal AATAAA);

FIG. 28b (SEQ ID No. 134) is a listing of the coding strand DNA sequence and deduced amino acid sequence of the cDNA obtained from splicing pattern number 2 in FIG. 26. This partial cDNA of the putative bovine GGF-II gene encodes a protein of 281 amino acids in length. Peptides in bold are those identified from the lists presented in FIGS. 10 and 12. Potential glycosylation sites are underlined (along with polyadenylation signal AATAAA);

FIG. 28c (SEQ ID No. 135) is a listing of the coding strand DNA sequence and deduced amino acid sequence of the cDNA obtained from splicing pattern number 3 in FIG. 26. This partial cDNA of the putative bovine GGF-II gene encodes, a protein of 257 amino acids in length. Peptides in bold are those identified from the lists in FIGS. 10 and 12. Potential glycosylation sites are underlined (along with polyadenylation signal AATAAA).

FIG. 28D is the nucleotide and deduced amino acid sequences of GGF2BPP3 (SEQ ID NO: 135).

FIG. 28E continues the figure started in figure 28D.

FIG. 31 (SEQ ID Nos. 136–147, 160, 161) is a listing of the DNA sequences and predicted peptide sequences of the coding segments of GGF. Line 1 is a listing of the predicted amino acid sequences of bovine GGF, line 2 is a listing of the nucleotide sequences of bovine GGF, line 3 is a listing of the nucleotide sequences of human GGF (heregulin) (nucleotide base matches are indicated with a vertical line) and line 4 is a listing of the predicted amino acid sequences of human GGF/heregulin where it differs from the predicted bovine sequence. Coding segments E, A' and K represent only the bovine sequences. Coding segment D' represents only the human (heregulin) sequence.

FIG. 32 (SEQ ID No. 148) is the predicted GGF2 amino acid sequence and nucleotide sequence of BPP5. The upper line is the nucleotide sequence and the lower line is the predicted amino acid sequence.

FIG. 33 (SEQ ID No. 149) is the predicted amino acid sequence and nucleotide sequence of GGF2BPP2. The upper line is the nucleotide sequence and the lower line is the predicted amino acid sequence.

FIG. 34 (SEQ ID No. 150) is the predicted amino acid sequence and nucleotide sequence of GGF2BPP4. The upper line is the nucleotide sequence and the lower line is the predicted amino acid sequence.

FIG. 35 (SEQ ID Nos. 151–152) depicts the alignment of two GGF peptide sequences (GGF2bpp4 and GGF2bpp5) with the human EGF (hEGF). Asterisks indicate positions of conserved cysteines.

FIG. 32 depicts the level of GGF activity (Schwann cell mitogenic assay) and tyrosine phosphorylation of a ca. 200 kD protein (intensity of a 200 kD band on an autoradiogram of a Western blot developed with an antiphosphotyrosine polyclonal antibody) in response to increasing amounts of GGF.

FIG. 37 is a list of splicing variants derived from the sequences shown in FIG. 31.

FIG. 38 is the predicted amino acid sequence, bottom, and nucleic sequence, top, of EGFL1 (SEQ ID No. 154).

FIG. 39 is the predicted amino acid sequence, bottom, and nucleic sequence, top, of EGFL2 (SEQ ID No. 155).

FIG. 40 is the predicted amino acid sequence, bottom, and nucleic sequence, top, of EGFL3 (SEQ ID No. 156).

FIG. 41 is the predicted amino acid sequence, bottom, and nucleic sequence, top, of EGFL4 (SEQ ID No. 157).

FIG. 42 is the predicted amino acid sequence, bottom, and nucleic sequence, top, of EGFL5 (SEQ ID No. 158).

FIG. 43 is the predicted amino acid sequence, bottom, and nucleic sequence, top, of EGFL6 (SEQ ID No. 159).

FIG. 45 is the predicted amino acid sequence (middle) and nucleic sequence (top) of GGF2HBS5 (SEQ ID No. 167). The bottom (intermittent) sequence represents peptide sequences derived from GGF-II preparations (see FIGS. 11, 12).

FIG. 51 (A) is a graph showing the purification of rhGGF-II (CHO cell produced) on cation exchange column by fraction; (B) is a photograph of a Western blot using fractions as depicted in (A) and a rhGGF-II specific antibody.

DETAILED DESCRIPTION

Figure 3:
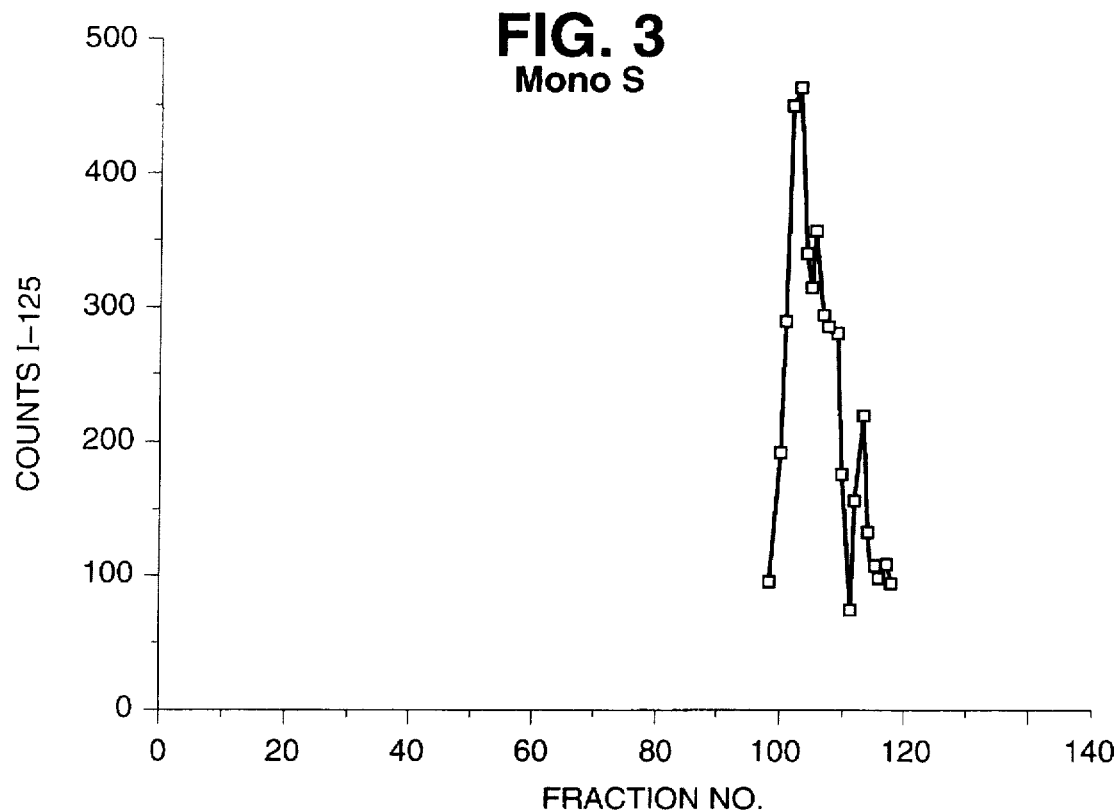
Figure 4:
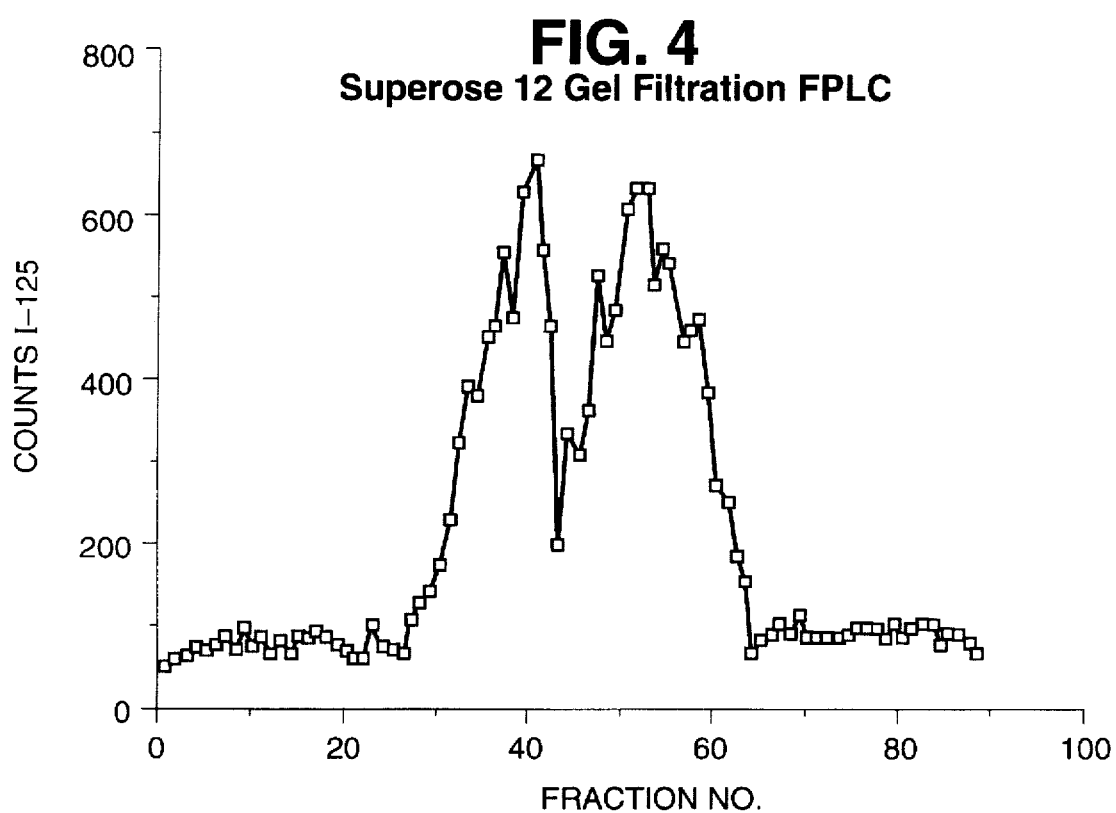

The invention pertains to the isolation and purification of novel Glial Growth factors and the cloning of DNA sequences encoding these factors. Other components of the invention are several gene splicing variants which potentially encode a series of glial growth factors, in particular the GGF2HBS5 in particular a variant which encodes the human equivalent of bovine GGF-II. It is evident that the gene encoding GGF's and p185$^{erbB2}$ binding proteins produces a number of variably-sized, differentially-spliced RNA transcripts that give rise to a series of proteins, which are of different lengths and contain some common peptide sequences and some unique peptide sequences. This is supported by the differentially-spliced sequences which are recoverable from bovine posterior pituitary RNA (as presented herein), human breast cancer (MDA-MB-231) (Holmes et al. Science 256: 1205 (1992) and chicken brain RNA (Falls et al. Cell 72:1–20 (1993)). Further support derives from the wide size range of proteins which act as both mitogens for Schwann cells (as disclosed herein) and as ligands for the p185$^{erbB2}$ receptor (see below).

Further evidence to support the fact that the genes encoding GGF and p185$^{erbB}$2 are homologous comes from nucleotide sequence comparison. Science, 256 (1992), 1205–1210) Holmes et al. demonstrate the purification of a 45-kilodalton human protein (Heregulin-α) which specifically interacts with the receptor protein p185$^{erbB}$2, which is associated with several human malignancies. Several complementary DNA clones encoding Heregulin-α were isolated. Peles et al. (Cell 69:205 (1992)) and Wen et al (Cell 69:559 (1992)) describe a complementary DNA isolated from rat cells encoding a protein called "neu differentiation factor" (NDF). The translation product of the NDF cDNA has p185$^{erbB2}$ binding activity. Usdin and Fischbach, J. Cell. Biol. 103:493–507 (1986); Falls et al., Cold Spring Harbor Syrup. Quant. Biol. 55:397–406 (1990); Harris et al., Proc. Natl. Acad. Sci. USA 88:7664–7668 (1991); and Falls et al., Cell 72:801–815 (1993) demonstrate the purification of a 42 Kd glycoprotein which interacts with a receptor protein p185$^{erbB2}$ and several complementary cDNA clones were isolated (Falls et al. Cell 72:801–815 (1993). Several other groups have reported the purification of proteins of various molecular weights with p185$^{erbB2}$ binding activity. These groups include Lupu et al. (1992) Proc. Natl. Acad. Sci. USA 89:2287; Yarden and Pales (1991) Biochemistry 30:3543; Lupu et al. (1990) Science 249:1552); Dobashi et al. (1991) Biochem. Biophys. Res. Comm. 179:1536; and Huang et al. (1992) J. Biol. Chem. 257:11508–11512.

Other Embodiments

The invention includes any protein which is substantially homologous to the coding segments in FIG. 31 (SEQ ID Nos. 136–147, 160, and 161) as well as other naturally occurring GGF polypeptides. Also included are: allelic variations; natural mutants; induced mutants; proteins encoded by DNA that hybridizes under high or low stringency conditions to a nucleic acid naturally occurring (for definitions of high and low stringency see Current Protocols in Molecular Biology, John Wiley & Sons, New York, 1989, 6.3.1–6.3.6, hereby incorporated by reference); and polypeptides or proteins specifically bound by antisera to GGF polypeptide. The term also includes chimeric polypsprides that include the GGF polypsprides comprising sequences from FIG. 31.

The following examples are not intended to limit the invention, but are provided to usefully illustrate the same, and provide specific guidance for effective preparative techniques.

As will be seen from Example 3, below, the present factors exhibit mitogenic activity on a range of cell types.

The activity in relation to fibroblasts indicates a wound repair ability, and the invention encompasses this use. The general statements of invention above in relation to formulations and/or medicaments and their manufacture should clearly be construed to include appropriate products and uses. This is clearly a reasonable expectation for the present invention, given reports of similar activities for fibroblast growth factors (FGFs). Reference can be made, for example, to Sporn et al., "Peptide Growth Factors and their Receptors I", page 396 (Baird and Bohlen) in the section headed "FGFs in Wound Healing and Tissue Repair".

Example 1

Purification of GGF-I and GGF-II from Bovine Pituitaries

I. Preparation of Factor-CM Fraction 4,000 frozen whole bovine pituitaries (c.a. 12 kg) were thawed overnight, washed briefly with water and then homogenized in an equal volume of 0.15M ammonium sulphate in batches in a Waring Blender. The homogenate was taken to pH 4.5 with 1.0M HCl and centrifuged at 4,900 g for 80 minutes. Any fatty material in the supernatant was removed by passing it through glass wool. After taking the pH of the supernatant to 6.5 using 1.0M NaOH, solid ammonium sulphate was added to give a 36% saturated solution. After several hours stirring, the suspension was centrifuged at 4,900 g for 80 minutes and the precipitate discarded. After filtration through glass wool, further solid ammonium sulphate was added to the supernatant to give a 75% saturated solution which was once again centrifuged at 4,900 g for 80 minutes after several hours stirring. The pellet was resuspended in c.a. 2 L of 0.1M sodium phosphate pH 6.0 and dialyzed against 3×40 L of the same buffer. After confirming that the conductivity of the dialysate was below 20.0 μSiemens, it was loaded onto a Bioprocess column (120×113 mm, Pharmacia) packed with carboxymethyl cellulose (CM-52, Whatman) at a flow rate of 2 ml min$^{-1}$. The column was washed with 2 volumes of 0.1M sodium phosphate pH 6.0, followed by 2 volumes of 50 mM NaCl, and finally 2 volumes of 0.2M NaCl both An the same buffer. During the final step, 10 mL (5 minute) fractions were collected. Fractions 73 to 118 inclusive were pooled, dialyzed against 10 volumes of 10 mM sodium phosphate pH 6.0 twice and clarified by centrifugation at 100,000 g for 60 minutes.

II. Hydroxylapatite HPLC

Hydroxylapatite HPLC is not a technique hitherto used in isolating glial growth factors, but proved particularly efficacious in this invention. The material obtained from the above CM-cellulose chromatography was filtered through a 0.22 μm filter (Nalgene), loaded at room temperature on to a high performance hydroxylapatite column (50×50 mm, Biorad) equipped with a guard column (15×25 mm, Biorad) and equilibrated with 10 mM potassium phosphate pH 6.0. Elution at room temperature was carried out at a flow rate of 2 ml.minute$^{-1}$ using the following programmed linear gradient:

| time (min) | % B | Solvent A: | 10 mM potassium phosphate pH 6.0 |
|---|---|---|---|
| 0.0 | 0 | | |
| 5.0 | 0 | Solvent B: | 1.0M potassium phosphate pH 6.0 |
| 7.0 | 20 | | |
| 70.0 | 20 | | |
| 150.0 | 100 | | |
| 180.0 | 100 | | |
| 185.0 | 0 | | |

6.0 mL (3 minutes) fractions were collected during the gradient elution. Fractions 39–45 were pooled and dialyzed against 10 volumes of 50 mM sodium phosphate pH 6.0.

III. Mono S FPLC

Mono S FPLC enabled a more concentrated material to be prepared for subsequent gel filtration.

Any particulate material in the pooled material from the hydroxylapatite column was removed by a clarifying spin at 100,000 g for 60 minutes prior to loading on to a preparative HR10/10Mono S cation exchange column (100×10 mm, Pharmacia) which was then re-equilibrated to 50 mM sodium phosphate pH 6.0 at room temperature with a flow rate of 1.0 ml/minute$^{-1}$. Under these conditions, bound protein was eluted using the following programmed linear gradient:

| time (min) | % B | Solvent A: | 50 mM potassium phosphate pH 6.0 |
|---|---|---|---|
| 0.0 | 0 | | |
| 70.0 | 30 | Solvent B: | 1.2M sodium chloride, 50 mm sodium phosphate pH 6.0 |
| 240.0 | 100 | | |
| 250.0 | 100 | | |
| 260.0 | 0 | | |

1 mL (1 minute) fractions were collected throughout this gradient program. Fractions 99 to 115 inclusive were pooled.

IV. Gel Filtration FPLC

This step commenced the separation of the two factors of the invention prior to final purification, producing enriched fractions.

For the purposes of this step, a preparative Suparose 12 FPLC column (510×20 mm, Pharmacia) was packed according to the manufacturers' instructions. In order to standardize this column, a theoretical plates measurement was made according to the manufacturers' instructions, giving a value of 9,700 theoretical plates.

The pool of Mono Seluted material was applied at room temperature in 2.5 Ml aliquots to this column in 50 mM sodium phosphate, 0.75 NaCl pH 6.0 (previously passed through a C18 reversed phase column (Sep-pak, Millipore) at a flow rate of 1.0 mL/minute$^{-1}$. 1 mL (0.5 minute) fractions were collected from 35 minutes after each sample was applied to the column. Fractions 27 to 41 (GGF-II) and 42 to 57 (GGF-I) inclusive from each run were pooled.

V. Reversed-Phase HPLC

The GGF-I and GGF-II pools from the above Supsrose 12 runs were each divided into three equal aliquots. Each aliquot was loaded on to a C8 reversed-phase column (Aquapore RP-300 7 μC8 220×4.6 mm, Applied Biosystems) protected by a guard cartridge (RP-8, 15×3.2 mm, Applied Biosystems) and equilibrated to 40° C. at 0.5 mL.minute. Protein was eluted under these conditions using the following programmed linear gradient:

| time (min) | %B | Solvent A: | 0.2% trifluoroacetic acid (TFA) acid (TFA) |
|---|---|---|---|
| 0 | | | |
| 60 | 66.6 | Solvent B: | 90% acetonitrile, 0.1% TFA |
| 62.0 | 100 | | |
| 72.0 | 100 | | |
| 75.0 | 0 | | |

200 μL (0.4 minute) fractions were collected in siliconized tubes (Multilube tubes, Bioquote) from 15.2 minutes after the beginning of the programmed gradient.

VI. SDS-Polyacrylamide Gel Electrophoresis

In this step, protein molecular weight standards, low range, catalogue no. 161–0304, from Bio-Rad Laboratories Limited, Warford, England were employed. The actual proteins used, and their molecular weight standards, have been listed herein previously.

Fractions 47 to 53 (GGF-I) and fractions 61 to 67 (GGFII) inclusive from the reversed-phase runs were individually pooled. 7 μL of the pooled material was boiled in an equal volume of 0.0125M Tris-Cl, 4% SDS, 20% glycerol, and 10% β-mercaptoethanol for GGF-I, for 5 minutes and loaded on to an 11% polyacrylamide Laemmli gel with a 4% stacking gel and run at a constant voltage of 50 V for 16 hours. This gel was then fixed and stained using a silver staining kit (Amersham). Under these conditions, the factors are each seen as a somewhat diffuse band at relative molecular weights 30,000 to 36,000 Daltons (GGF-I) and 55,000 to 63,000 Daltons (GGFII) as defined by molecular weight markers. From the gel staining, it is apparent that there are a small number of other protein species present at equivalent levels to the GGF-I and GGF-II species in the material pooled from the reversed-phase runs.

VII. Stability in Trifluoroacetic Acid

Stability data were obtained for the present Factors in the presence of trifluoroacetic acid, as follows:

GGF-I: Material from the reversed-phase HPLC, in the presence of 0.1% TFA and acetonitrile, was assayed within 12 hours of the completion of the column run and then after 10 weeks incubation at 40° C. Following incubation, the GGF-I had at least 50% of the activity of that material assayed directly off the column.

GFG-II: Material from the reversed-phase HPLC, in the presence of 0.1% TFA and acetonitrile, and stored at −20° C., was assayed after thawing and then after 4 days incubation at 40° C. Following incubation, the GGF-II had at least 50% of the activity of that material freshly thawed.

It will be appreciated that the trifluoroacetic acid concentration used in the above studies is that most commonly used for reversed-phase chromatography.

VIII. Activity Assay Conditions

Unless otherwise indicated, all operations were conducted at 37° C., and, with reference to FIGS. 1 to 6, activity at each stage was determined using the Brockes (Meth. Enz., supra) techniques with the following modifications. Thus, in preparing Schwann cells, 5 μM forskolin was added in addition to DMEM (Dulbecco's modified Eagle's medium), FCS and GGF. Cells used in the assay were fibroblast-free Schwann cells at passage number less than 10, and these cells were removed from flasks with trypsin and plated into flat-bottomed 96-well plates at 3.3 thousand cells per microwell.

[$^{125}$I] IUdR was added for the final 24 hours after the test solution addition. The background (unstimulated) incorporation to each assay was less than 100 cpm, and maximal incorporation was 20 to 200 fold over background depending on Schwann cell batch and passage number.

Figure 7:
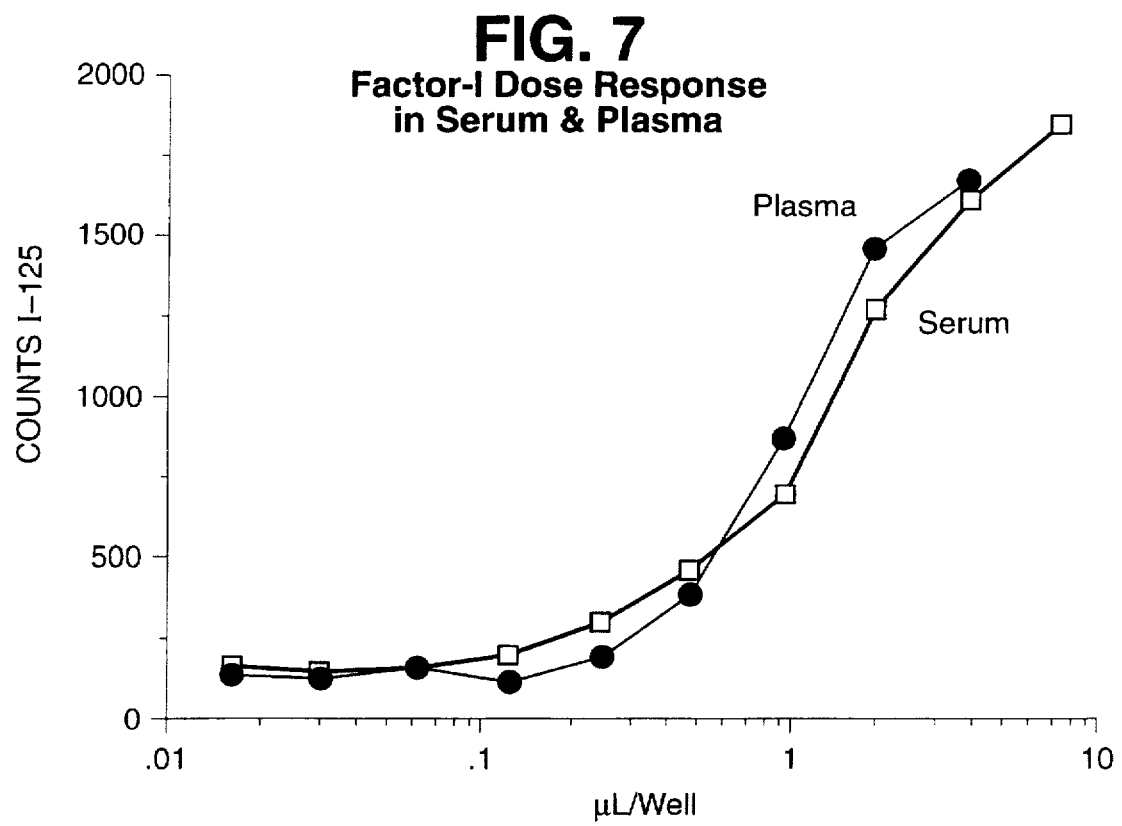
Figure 8:
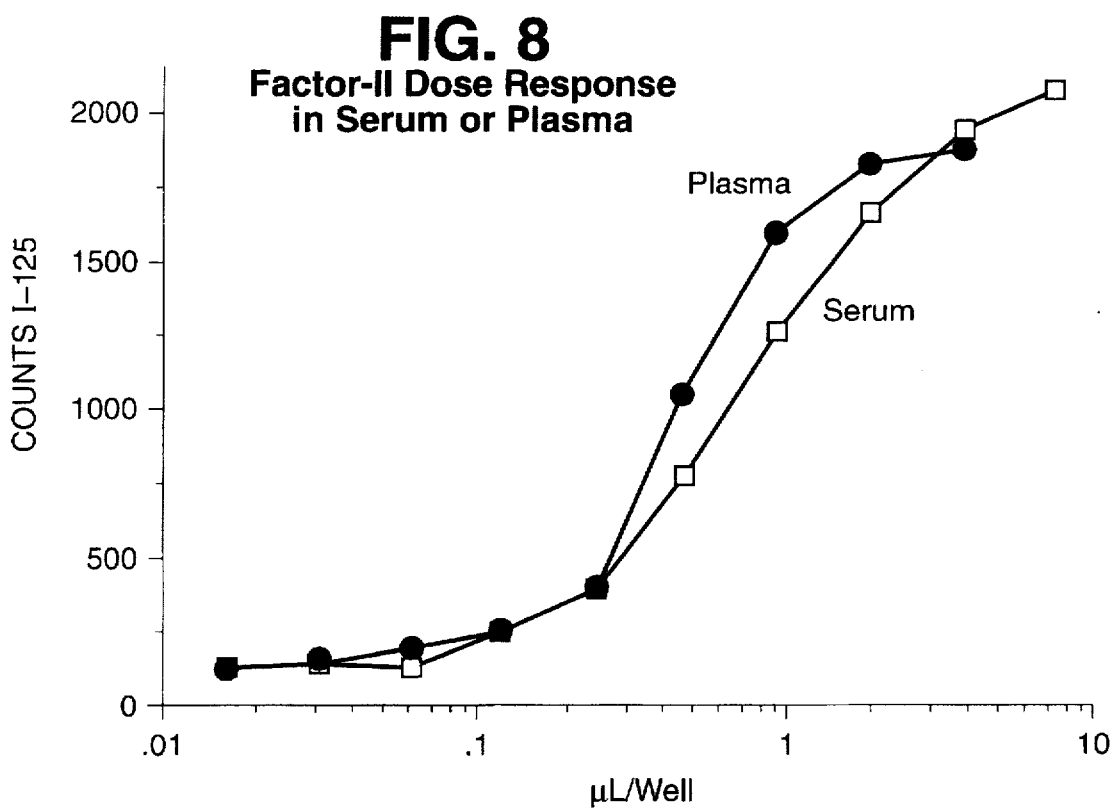

In the case of the GGF-I and GGF-II fractions from reversed-phase HPLC as described above, two dose response curves were also produced for each factor, using exactly the above method for one of the curves for each factor, and the above method modified in the assay procedure only by substituting foetal calf plasma for fetal calf serum to obtain the other curve for each factor. The results are in FIGS. 7 and 8.

EXAMPLE 2

Amino Acid Sequences of Purified GGF-1 and GGF-II

Amino acid sequence analysis studies were performed using highly purified bovine pituitary GGF-I and GGF-II. The conventional single letter code was used to describe the sequences. Peptides were obtained by lysyl endopeptidase and protease V8 digests, carried out on reduced and carboxymethylated samples, with the lysyl endopeptidase digest of GGF-II carried out on material eluted from the 55–65 RD region of a 11% SDS-PAGE (MW relative to the above-quoted markers).

A total of 21 peptide sequences (see FIG. 9, SEQ ID Nos. 1–20, 169) were obtained for GGF-I, of which 12 peptides (see FIG. 10, SEQ ID Nos. 1, 22–29, 17, 19, and 32) are not present in current protein databases and therefore represent unique sequences. A total of 12 peptide sequences (see FIG. 11, SEQ ID Nos. 33–44) were obtained for GGF-II, of which 10 peptides (see FIG. 12, SEQ ID Nos. 45–53) are not present in current protein databases and therefore represent unique sequences (an exception is peptide GGF-II 06 which shows identical sequences in many proteins which are probably of no significance given the small number of residues). These novel sequences are extremely likely to correspond to portions of the true amino acid sequences of GGFs I and II.

Particular attention can be drawn to the sequences of GGF-I 07 and GGF-II 12, which are clearly highly related. The similarities indicate that the sequences of these peptides are almost certainly those of the assigned GGF species, and are most unlikely to be derived from contaminant proteins.

In addition, in peptide GGF-II 02, the sequence X S S is consistent with the presence of an N linked carbohydrate moiety on an asparagine at the position denoted by X.

In general, in FIGS. 9 and 11, X represents an unknown residue denoting a sequencing cycle where a single position could not be called with certainty either because there was more than one signal of equal size in the cycle or because no signal was present. As asterisk denotes those peptides where the last amino acid called corresponds to the last amino acid present in that peptide. In the remaining peptides, the signal strength after the last amino acid called was insufficient to continue sequence calling to the end of that peptide. The right hand column indicates the results of a computer database search using the GCG package FASTA and TFASTA programs to analyze the NBRF and EMBL sequence databases. The name of a protein in this column denotes identity of a portion of its sequence with the peptide amino acid sequence called allowing a maximum of two mismatches. A question mark denotes three mismatches allowed. The abbreviations used are as follows:

| HMG-1 | High Mobility Group protein-1 |
| HMG-2 | High Mobility Group protein-2 |
| LH-alpha | Luteinizing hormone alpha subunit |
| LH-beta | Luteinizing hormone beta subunit |

EXAMPLE 3

Mitogenic Activity of Purified GGF-I and GGF-II

The mitogenic activity of a highly purified sample containing both GGFs I and II was studied using a quantitative method, which allows a single microculture to be examined for DNA synthesis, cell morphology, cell number and expression of cell antigens. This technique has been modified from a method previously reported by Muir et al., Analytical Biochemistry 185, 377–382, 1990. The main modifications are: 1) the use of uncoated microtiter plates, 2) the cell number per well, 3) the use of 5% Foetal Bovine Plasma (FBP) instead of 10% Foetal Calf Serum (FCS), and 4) the time of incubation in presence of mitogens and bromodeoxyuridine (BrdU), added simultaneously to the cultures. In addition the Cell monolayer was not washed before fixation to avoid loss of cells, and the incubation time of monoclonal mouse anti-BrdU antibody and peroxidase conjugated goat anti-mouse immunoglobulin (IgG) antibody were doubled to increase the sensitivity of the assay. The assay, optimized for rat sciatic nerve Schwann cells, has also been used for several cell lines, after appropriate modifications to the cell culture conditions.

I. Methods of Mitogenesis Testing

On day 1, purified Schwann cells were plated onto uncoated 96 well plates in 5% FBP/Dulbecco's Modified Eagle Medium (DMEM) (5,000 cells/well). On day 2, GGFs or other test factors were added to the cultures, as well as BrdU at a final concentration of 10 μm. After 48 hours (day 4) BrdU incorporation was terminated by aspirating the medium and cells were fixed with 200 μl/well of 70% ethanol for 20 min at room temperature. Next, the cells were washed with water and the DNA denatured by incubation with 100 μl 2N HCl for 10 min at 37° C. Following aspiration, residual acid was neutralized by filling the wells with 0.1M borate buffer, pH 9.0, and the cells were washed with phosphate buffered saline (PBS). Cells were then treated with 50 μl of blocking buffer (PBS containing 0.1% Triton X 100 and 2% normal goat serum) for 15 min at 37° C. After aspiration, monoclonal mouse anti-BrdU antibody (Dako Corp., Santa Barbara, Calif.) (50 μl/well, 1.4 μg/ml diluted in blocking buffer) was added and incubated for two hours at 37° C. Unbound antibodies were removed by three washes in PBS containing 0.1% Triton X-100 and peroxidase-conjugated goat ant-mouse IgG antibody (Dako Corp., Santa Barbara, Calif.) (50 μl/well, 2 μg/ml diluted in blocking buffer) was added and incubated for one hour at 37° C. After three washes in PBS/Triton and a final rinse in PBS, wells received 100 μl/well of 50 mM phosphate/citrate buffer, pH 5.0, containing 0.05% of the soluble chromogan o-phenylenediamine (OPD) and 0.02% $H_2O_2$. The reaction was terminated after 5–20 min at room temperature, by pipetting 80 μl from each well to a clean plate containing 40 μl/well of 2N sulfuric acid. The absorbance was recorded at 490 nm using a plate reader (Dynatech Labs). The assay plates containing the cell monolayers were washed twice with PBS and immunocytochemically stained for BrdU-DNA by adding 100 μl/well of the substrate diaminobenzidine (DAB) and 0.02% $H_2O_2$ to generate an insoluble product. After 10–20 min the staining reaction was stopped by washing with water, and BrdU-positive nuclei observed and counted using an inverted microscope. occasionally, negative nuclei were counterstained with 0.001% Toluidine blue and counted as before.

II. Cell lines used for Mitogenesis Assays

Swiss 3T3 Fibroblasts: Cells, from Flow Labs, were maintained in DMEM supplemented with 10% FCS, penicillin and streptomycin, at 37° C. in a humidified atmosphere of 10% $CO_2$ in air. Cells were fed or subcultured every two days. For mitogenic assay, cells were plated at a density of 5,000 cells/well in complete medium and incubated for a week until cells were confluent and quiescent. The serum containing Medium was removed and the cell monolayer washed twice with serum free-medium. 100 μl of serum free medium containing mitogens and 10 μM of BrdU were added to each well and incubated for 48 hours. Dose responses to GGFs and serum or PDGF (as a positive control) were performed.

BHK (Baby Hamster Kidney) 21 C13 Fibroblasts: Cells from European Collection of Animal Cell Cultures (ECACC), were maintained in Glasgow Modified Eagle Medium (GMEM) supplemented with 5% tryprose phosphate broth, 5% FCS, penicillin and streptomycin, at 37° C. in a humidified atmosphere of 5% $CO_2$ in air. Cells were fed or subcultured every two to three days. For mitogenic assay, cells were plated at a density of 2,000 cell/well in complete medium for 24 hours. The serum containing medium was then removed and after washing with serum free medium, replaced with 100 µl of 0.1% FCS containing GMEM or GMEM alone. GGFs and FCS or bFGF as positive controls were added, coincident with 10 µM BrdU, and incubated for 48 hours. Cell cultures were then processed as described for Schwann cells.

C6 Rat Glioma Cell Line: Cells, obtained at passage 39, were maintained in DMEM containing 5% FCS, 5% Horse serum (HS), penicillin and streptomycin, at 37° C. in a humidified atmosphere of 10% $CO_2$ in air. Cells were fed or subcultured every three days. For mitogenic assay, cells were plated at a density of 2,000 cells/well in complete medium and incubated for 24 hours. Then medium was replaced with a mixture of 1:1 DMEM and F12 medium containing 0.1% FCS, after washing in serum free medium. Dose responses to GGFs, FCS and aFGF were then performed and cells were processed through the ELISA as previously described for the other cell types.

PC12 (Rat Adrenal Pheochromocytoma Cells): Cells from ECACC, were maintained in RPMI 1640 supplemented with 10% MS, 5% FCS, penicillin and streptomycin, in collagen coated flasks, at 37° C. in a humidified atmosphere of 5% $CO_2$ in air. Cells were fed every three days by replacing 80% of the medium. For mitogenic assay, cells were plated at a density of 3,000 cells/well in complete medium, on collagen coated plates (50 µl/well collagen, Vitrogen Collagen Corp., diluted 1: 50, 30 min at 37° C.) and incubated for 24 hours. The medium was then placed with fresh RPMI either alone or containing 1 mM insulin or 1% FCS. Dose responses to FCS/HS (1:2) as positive control and to GGFs were performed as before. After 48 hours cells were fixed and the ELISA performed as previously described.

III. Results of Mitogenesis Assays

All the experiments presented in this Example were performed using a highly purified sample from a Sepharose 12 chromatography purification step (see Example 1, section D) containing a mixture of GGF-I and GGF-II (GGFs).

First, the results obtained with the BrdU incorporation assay were compared with the classical incorporation into DNA of dividing cells, described by J. P. Brockes (Methods Enzymol. 147:217, 1987).

Figure 13:
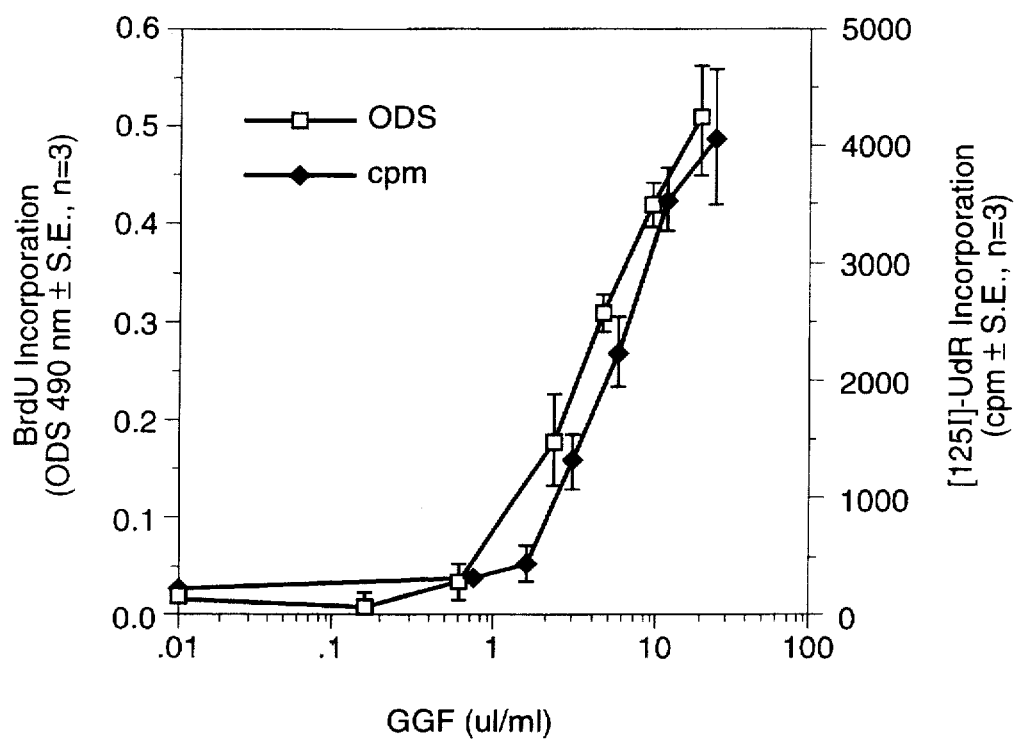
FIGS. 13 to 20 relate to Example 3, below and depict the mitogenic activity of factors of the invention.

FIG. 13 shows the comparison of data obtained with the two assays, performed in the same cell culture conditions (5,000 cells/well, in 5% FBP/DMEM, incubated in presence of GGFs for 48 hrs). As clearly shown, the results are comparable, but BrdU incorporation assay appears to be slightly more sensitive, as suggested by the shift of the curve to the left of the graph, i.e. to lower concentrations of GGFS.

As described under the section "Methods of Mitogenesis Testing", after the immunoreactive BrdU-DNA has been quantitated by reading the intensity of the soluble product of the OPD peroxidase reaction, the original assay plates containing cell monolayers can undergo the second reaction resulting in the insoluble DAB product, which stains the BrdU positive nuclei. The microcultures can then be examined under an inverted microscope, and cell morphology and the numbers of BrdU-positive and negative nuclei can be observed.

Figure 14A:
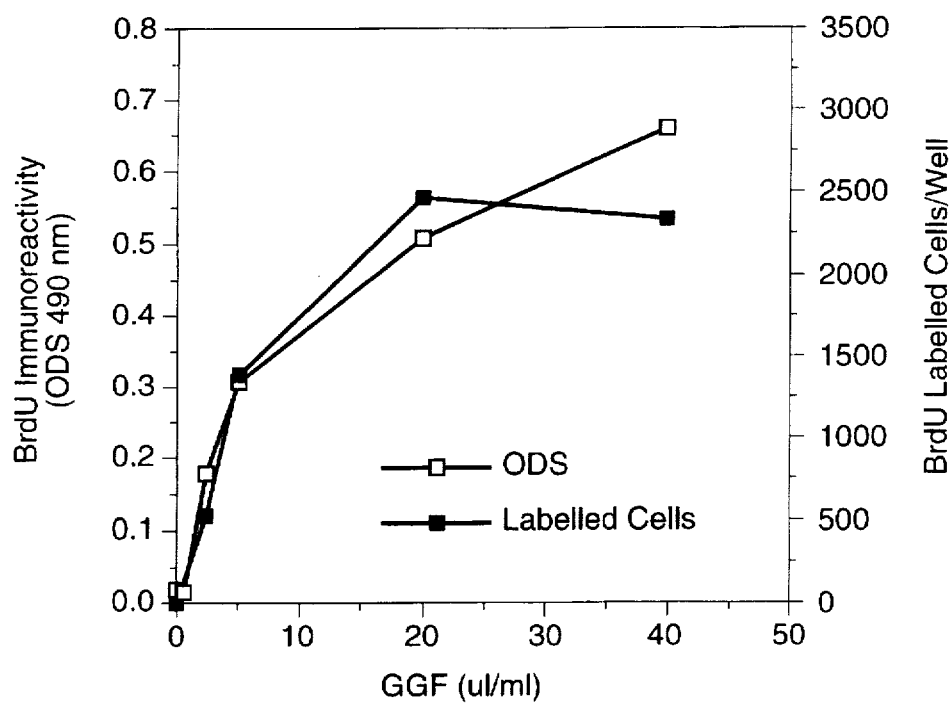
Figure 14B:
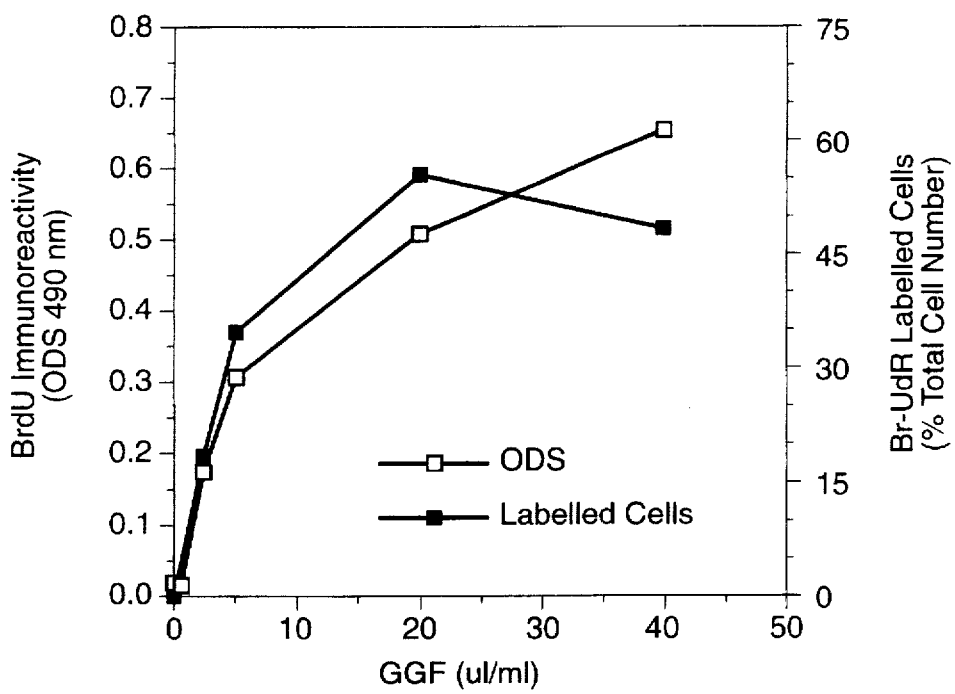

In FIG. 14a and FIG. 14b the BrdU-DNA immunoreactivity, evaluated by reading absorbance at 490 nm, is compared to the number of BrdU-positive nuclei and to the percentage of BrdU-positive nuclei on the total number of cells per well, counted in the same cultures. Standard deviations were less than 10%. The two evaluation methods show a very good correlation and the discrepancy between the values at the highest dose of GGFs can be explained by the different extent of DNA synthesis in cells detected as BrdU-positive.

Figure 15:
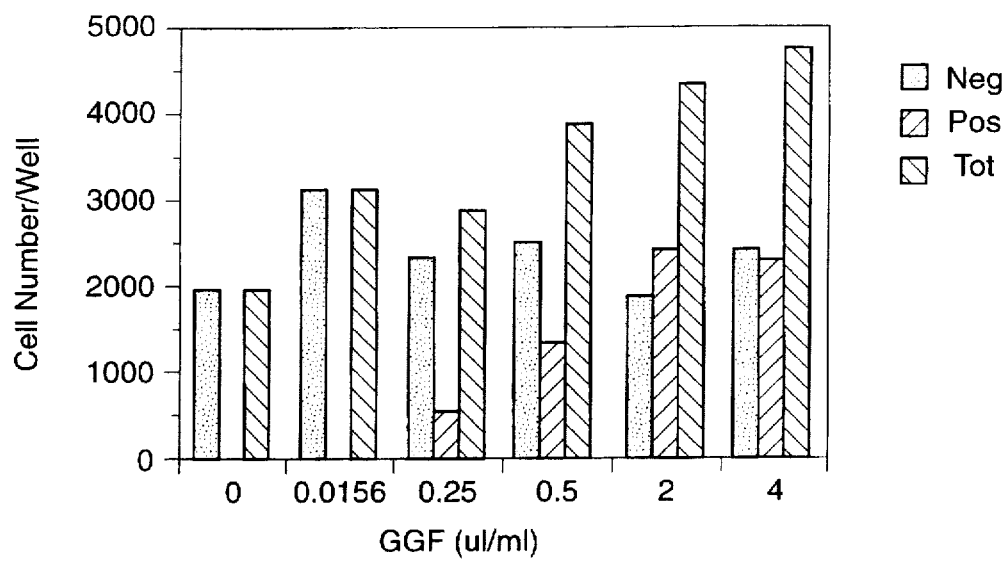

The BrdU incorporation assay can therefore provide additional useful information about the biological activity of polypsprides on Schwann cells when compared to the (125) I-UdR incorporation assay. For example, the data reported in FIG. 15 show that GGFs can act on Schwann cells to induce DNA synthesis, but at lower doses to increase the number of negative cells present in the microculture after 48 hours.

Figure 16:
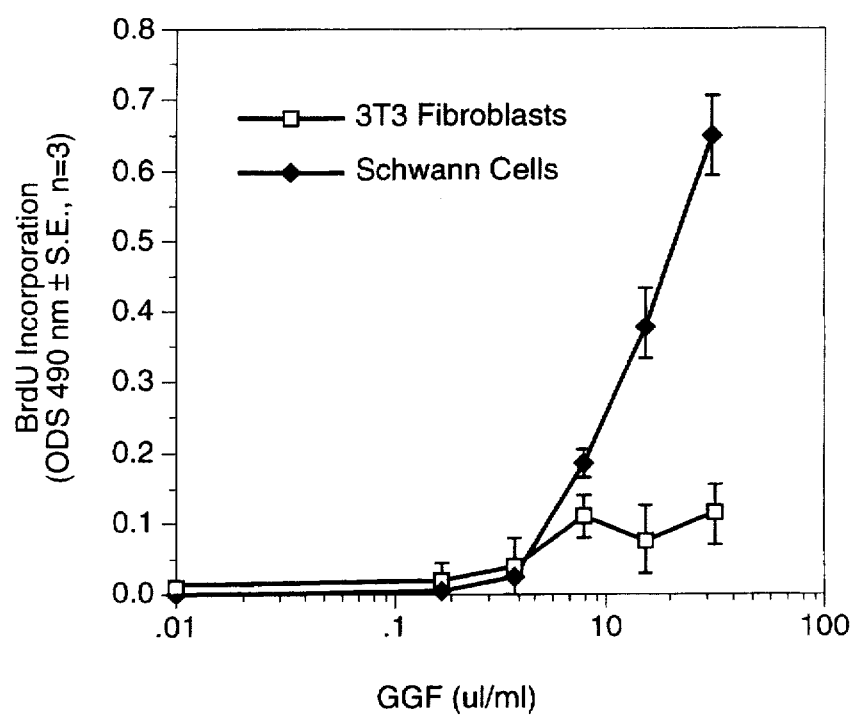

The assay has then been used on several cell Lines of different origin. In FIG. 16 the mitogenic responses of Schwann cells and Swiss 3T3 fibroblasts to GGFs are compared; despite the weak response obtained in 3T3 fibroblasts, some clearly BrdU-positive nuclei were detected in these cultures. Control cultures were run in parallel in presence of several doses of FCS or human recombinant PDGF, showing that the cells could respond to appropriate stimuli (not shown).

Figure 17:
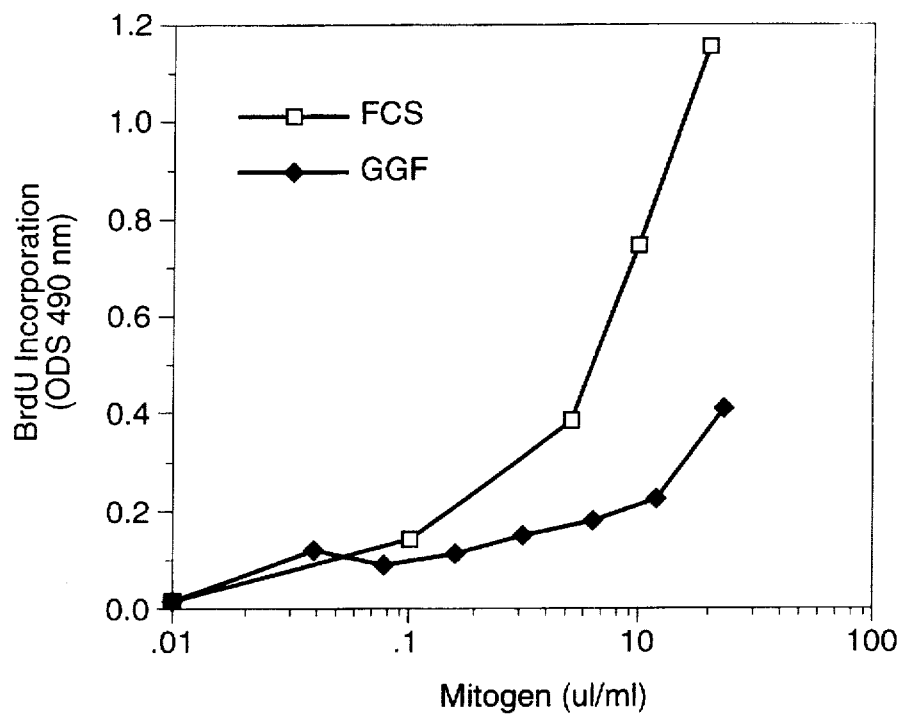
Figure 18:
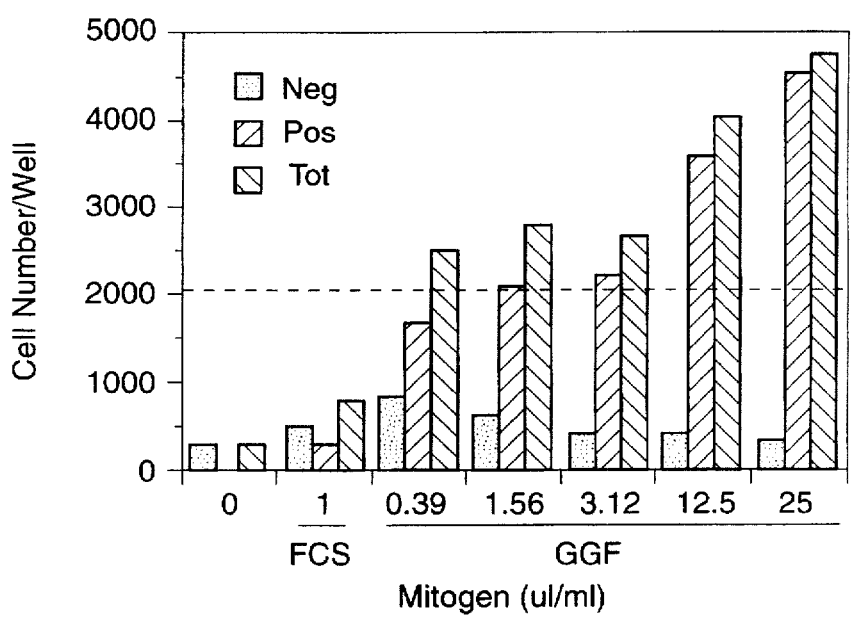

The ability of fibroblasts to respond to GGFs was further investigated using the BHK 21 C13 cell line. These fibroblasts, derived from kidney, do not exhibit contact inhibition or reach a quiescent state when confluent. Therefore the experimental conditions were designed to have a very low background proliferation without compromising the cell viability. GGFs have a significant mitogenic activity on BHK21 C13 cells as shown by FIG. 17 and FIG. 18. FIG. 17 shows the Brdu incorporation into DNA by BHK 21 C13 cells stimulated by GGFS in the presence of 0.1% FCS. The good mitogenic response to FCS indicates that cell culture conditions were not limiting. In FIG. 18 the mitogenic effect of GGFs is expressed as the number of BrdU-positive and BrdU-negative cells and as the total number of cells counted per well. Data are representative of two experiments run in duplicates; at least three fields per well were counted. As observed for Schwann cells in addition to a proliferative effect at low doses, GGFs also increase the numbers of nonresponding cells surviving. The percentage of BrdU positive cells is proportional to the increasing amounts of GGFs added to the cultures. The total number of cells after 48 hours in presence of higher doses of GGFs is at least doubled, confirming that GGFs induce DNA synthesis and proliferation in BHK21 C13 cells. Under the same conditions, cells maintained for 48 hours in the presence of 2% FCS showed an increase of about six fold (not shown).

Figure 19:
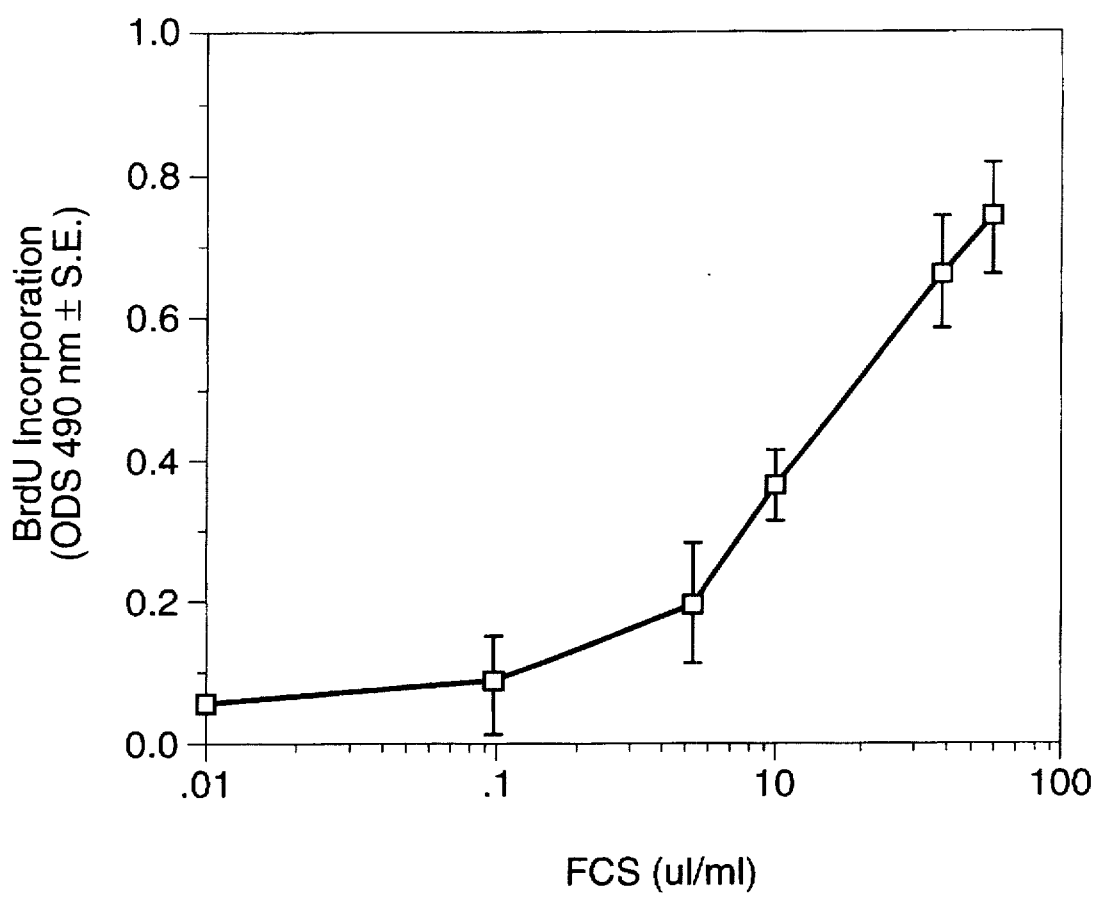

C6 glioma cells have provided a useful model to study glial cell properties. The phenotype expressed seems to be dependent on the cell passage, the cells more closely resembling an astrocyte phenotype at an early stage, and an oligodendrocyte phenotype at later stages (beyond passage 70). C6 cells used in these experiments were from passage 39 to passage 52. C6 cells are a highly proliferating population, therefore the experimental conditions were optimized to have a very low background of BrdU incorporation. The presence of 0.1% serum was necessary to maintain cell viability without significantly affecting the mitogenic responses, as shown by the dose response to FCS (FIG. 19).

Figure 20B:
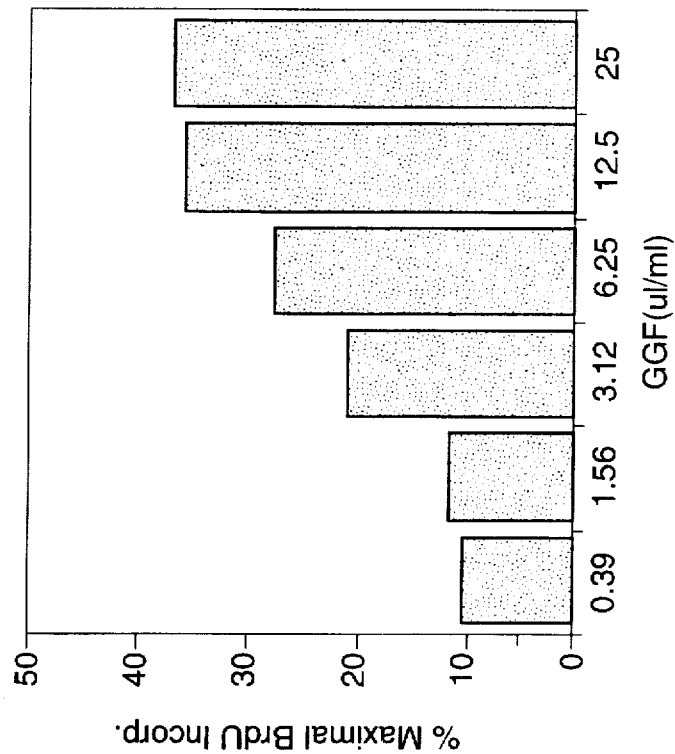
Figure 20A:
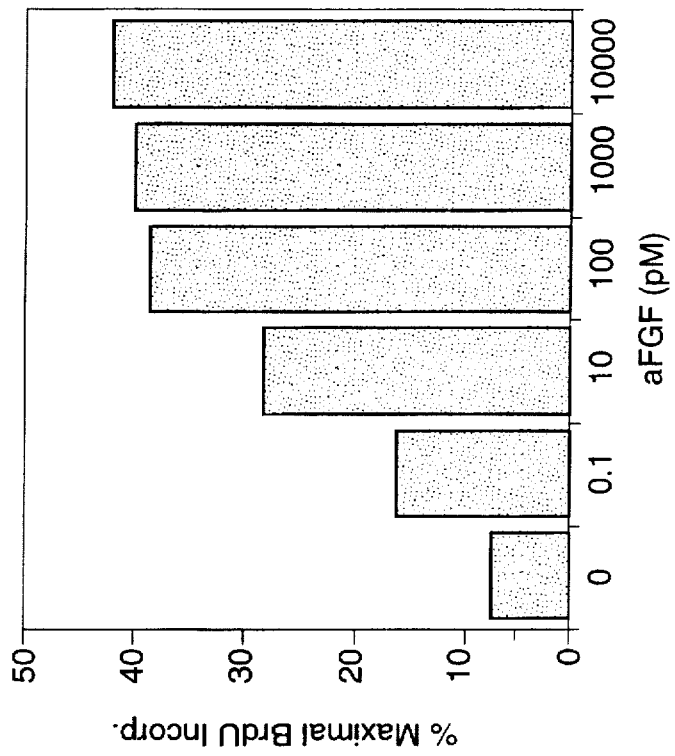

In FIG. 20 the mitogenic responses to aFGF (acidic Fibroblast growth factor) and GGFs are expressed as the percentages of maximal BrdU incorporation obtained in the presence of FCS (8%). Values are averages of two experiments, run in duplicates. The effect of GGFs was comparable to that of a pure preparation of aFGF. aFGF has been described as a specific growth factor for C6 cells (Lim R. et al., Cell Regulation 741–746, 1990) and for that reason it was used as a positive control. The direct counting of BrdU positive and negative cells was not possible because of the high cell density in the microcultures. In contrast to the cell lines so far reposed, PC12 cells did not show any evident responsiveness to GGFS, when treated under culture conditions in which PC12 could respond to sera (mixture of FCS and HS as used routinely for cell maintenance). Nevertheless the number of cells plated per well seems to affect the behavior of PC12 cells, and therefore further experiments are required.

EXAMPLE 4

Isolating and cloning of Nucleotide Sequences Encoding Proteins Containing GGF-I and GGF-II Peptides Isolation and cloning of the GGF-II nucleotide sequences was performed as outlined herein, using peptide sequence information and library screening, and was performed as set out below. It will be appreciated that the peptides of FIGS. 4 and 5 can be used as the starting point for isolation and cloning of GGF-I sequences by following the techniques described herein. Indeed, FIG. 21, SEQ ID Nos. 54–88) shows possible degenerate oligonucleotide probes for this purpose, and FIG. 23, SEQ ID Nos. 90–119, lists possible PCR primers. DNA sequence and polypeptide sequence should be obtainable by this means as with GGF-II, and also DNA constructs and expression vectors incorporating such DNA sequence, host cells genetically altered by incorporating such constructs/vectors, and protein obtainable by cultivating such host cells. The invention envisages such subject matter.

I. Design and Synthesis of oligonucleotide Probes and Primers

Degenerate DNA oligomer probes were designed by backtranslating the amino acid sequences (derived from the peptides generated from purified GGF protein) into nucleotide sequences. Oligomers represented either the coding strand or the non-coding strand of the DNA sequence. When satins, arginine or leucine were included in the oligomer design, then two separate syntheses were prepared to avoid ambiguities. For example, serine was encoded by either TCN or AGY as in 537 and 538 or 609 and 610. Similar codon splitting was done for arginine or leucine (e.g. 544, 545). DNA oligomers were synthesized on a Biosearch 8750 4-column DNA synthesizer using β-cyanoethyl chemistry operated at 0.2 micromole scale synthesis. Oligomers were cleaved off the column (500 angstrom CpG resins) and deprotected An concentrated ammonium hydroxide for 6–24 hours at 55°–60° C. Deprotected oligomers were dried under vacuum (Speedvac) and purified by electrophoresis in gels of 15% acrylamide (20 mono: 1 bis), 50 mM Tris-borate-EDTA buffer containing 7M urea. Full-length oligomers were detected An the gels by UV shadowing, then the bands were excised and DNA oligomers eluted into 1.5 mls H20 for 4–16 hours with shaking. The eluate was dried, redissolved in 0.1 ml H$_2$O and absorbance measurements were taken at 260 nm.

Concentrations were determined according to the following formula:

(A 260× units/ml) (60.6/length=x µM)

All oligomers were adjusted to 50 µM concentration by addition of H$_2$O.

Degenerate probes designed as above are shown in FIG. 21, SEQ ID Nos. 54–88.

PCR primers were prepared by essentially the same procedures that were used for probes with the following modifications. Linkers of thirteen nucleotides containing restriction sites were included at the 5' ends of the degenerate oligomers for use in cloning into vectors. DNA synthesis was performed at 1 micromole scale using 1,000 angstrom CpG resins and inosine was used at positions where all four nucleotides were incorporated normally into degenerate probes. Purifications of PCR primers included an ethanol precipitation following ;he gel electrophoresis purification.

II. Library Construction and Screening

A bovine genomic DNA library was purchased from Stratagems (Catalogue Number: 945701). The library contained 2×10$^6$ 15–20 kb Sau3A1 partial bovine DNA fragments cloned into the vector lambda DashII. A bovine total brain CDNA library was purchased from Clonetech (Catalogue Number: BL 10139). Complementary DNA libraries were constructed (In Vitrogen; Stratagene) from mRNA prepared from bovine total brain, from bovine pituitary and from bovine posterior pituitary. In Vitrogen prepared two cDNA libraries: one library was in the vector lambda g10, the other in vector pcDNAI (a plasmid library). The Stratagems libraries were prepared in the vector lambda unizap. Collectively, the cDNA libraries contained 14 million primary recombinant phage.

The bovine genomic library was plated on *E. coli* K12 host strain LE392 on 23×23 cm plates (Nunc) at 150,000 to 200,000 phage plaques per plate. Each plate represented approximately one bovine genome equivalent. Following an overnight incubation at 37° C., the plates were chilled and replicate filters were prepared according to procedures of Manjarls et al. (2:60–81). Four plaque lifts were prepared from each plate onto uncharged nylon membranes (Pall Biodyne A or MSI Nitropure). The DNA was immobilized onto the membranes by cross-linking under UV light for 5 minutes or, by baking at 80° C. under vacuum for two hours. DNA probes were labelled using T4 polynucleotide kinase (New England Biolabs) with gamma 32P ATP (New England Nuclear; 6500 Ci/mmol) according to the specifications of the suppliers. Briefly, 50 pmols of degenerate DNA oligomer were incubated in the presence of 600 µCi gamma $^{32}$P-ATP and 5 units T4 polynucleotide kiness for 30 minutes at 37° C. Reactions were terminated, gel electrophoresis loading buffer was added and then radiolabelled probes were purified by electrophoresis. 32P labelled probes were excised from gel slices and eluted into water. Alternatively, DNA probes were labelled via PCR amplification by incorporation of α-32P-dATP or α-32P dCTP according to the protocol of Schowalter and Sommer, Anal. Biochem 177:90–94 (1989). Probes labelled in PCR reactions were purified by desalting on Sephadex G-150 columns.

Prehybridization and hybridization were performed in GMC buffer (0.52M NaPi, 7% SDS, 1% BSA, 1.5 mM EDTA, 0.1M NaCl 10 mg/ml tRNA). Washing was performed in oligowash (160 ml 1M Na$_2$HPO$_4$, 200 ml 20% SDS, 8.0 ml 0.5M EDTA, 100 ml 5M NaCl, 3632 ml H$_2$O). Typically, 20 filters (400 sq. centimeters each) representing replicate copies of ten bovine genome equivalents were incubated in 200 ml hybridization solution with 100 pmols of degenerate oligonucleotide probe (128–512 fold degenerate). Hybridization was allowed to occur overnight at 5° C. below the minimum melting temperature calculated for the degenerate probe. The calculation of minimum melting temperature assumes 2° C. for an AT pair and 4° C. for a GC pair.

Filters were washed in repeated changes of oligowash at the hybridization temperatures four to five hours and finally, in 3.2M tetramethylammonium chloride, 1% SDS twice for 30 min at a temperature dependent on the DNA probe length. For 20 mers, the final wash temperature was 60° C. Filters were mounted, then exposed to X-ray film (Kodak XAR5) using intensifying screens (Dupont Cronex Lightening Plus). Usually, a three to five day film exposure at minus 80° C. was sufficient to detect duplicate signals in these library screens. Following analysis of the results, filters could be stripped and reprobed. Filters were stripped by incubating through two successive cycles of fifteen minutes in a microwave oven at full power in a solution of 1% SDS containing 10 mM EDTA pH8. Filters were taken through at least three to four cycles of stripping and reprobing with various probes.

III. Recombinant Phage Isolation. Growth and DNA Preparation

These procedures followed standard protocol as described in Recombinant DNA (Maniatis et al 2:60–2:81).

IV. Analysis of Isolated Clones Using DNA Digestion and Southern Blots

Recombinant Phage DNA samples (2 micrograms) were digested according to conditions recommended by the restriction endonuclease supplier (New England Biolabs). Following a four hour incubation at 37° C., the reactions products were precipitated in the presence of 0.1M sodium acetate and three volumes of ethanol. Precipitated DNA was collected by centrifugation, rinsed in 75% ethanol and dried. All resuspended samples were loaded onto agarose gels (typically 1% in TAE buffer; 0.04M Tris acetate, 0.002M EDTA). Gel runs were at 1 volt per centimeter from 4 to 20 hours. Markers included lambda Hind III DNA fragments and/or Ø174HaeIII DNA fragments (New England Biolabs). The gels were stained with 0.5 micrograms/ml of ethidium bromide and photographed. For southern blotting, DNA was first depurinated in the gel by treatment with 0.125N HCl, denatured in 0.5N NaOH and transferred in 20× SSC (3M sodium chloride, 0.03M sodium citrate) to uncharged nylon membranes. Blotting was done for 6 hours up to 24 hours, then the filters were neutralized in 0.5 Tris HCl pH 7.5, 0.15M sodium chloride, then rinsed briefly in 50 mM Tris-borate EDTA.

For cross-linking, the filters were wrapped first in transparent plastic wrap, then the DNA side exposed for five minutes to an ultraviolet light. Hybridization and washing was performed as described for library screening (see section 2 of this Example). For hybridization analysis to determine whether similar genes exist in other species slight modifications were made. The DNA filter was purchased from Clonetach (Catalogue Number 7753-1) and contains 5 micrograms of EcoRI digested DNA from various species per lane. The probe was labelled by PCR amplification reactions as described in section 2 above, and hybridizations were done in 80% buffer B(2 g polyvinylpyrrolidine, 2 g Ficoll-400, 2 g bovine serum albumin, 50 ml 1M Tris-HCl (pH 7.5) 58 g NaCl, 1 g sodium pyrophosphate, 10 g sodium dodecyl sulfate, 950 ml H$_2$O) containing 10% dextran sulfate. The probes were denatured by boiling for ten minutes then rapidly cooling in ice water. The probe was added to the hybridization buffer at 10$^6$ dpm $^{32}$P per ml and incubated overnight at 60° C. The filters were washed at 60° C. first in buffer B followed by 2× SSC, 0.1% SDS then in 1× SSC, 0.1% SDS. For high stringency, experiments, final washes were done in 0.1× SSC, 1% SDS and the temperature raised to 65° C.

Southern blot data were used to prepare a restriction map of the genomic clone and to indicate which subfragments hybridized to the GGF probes (candidates for subcloning).

V. Subcloning of Segments of DNA Homologous to Hybridization Probes

DNA digests (e.g. 5 micrograms) were loaded onto 1% agarose gels then appropriate fragments excised from the gels following staining. The DNA was purified by adsorption onto glass beads followed by solution using the protocol described by the supplier (Bio 101). Recovered DNA fragments (100–200 ng) were ligated into linearized dephosphorylated vectors, e.g. pT3T7 (Ambion), which is a derivative of pUC18, using T4 ligase (New England Biolabs). This vector carries the E. coil β lactamase gene, hence, transformants can be selected on plates containing ampicillin. The vector also supplies β-galactosidase complementation to the host cell, therefore non-recombinants (blue) can be detected using isopropylthiogalactoside and Bluogal (Bethesda Research Labs). A portion of the ligation reactions was used to transforms E. coli K12 XL1 blue competent cells (Stratagene Catalogue Number: 200236) and then the transformants were selected on LB plates containing 50 micrograms per ml ampicillin. White colonies were selected and plasmid mini preps were prepared for DNA digestion and for DNA sequence analysis. Selected clones were retested to determine if their insert DNA hybridized with the GGF probes.

VI. DNA Sequencing

Double stranded plasmid DNA templates were prepared from 5 ml cultures according to standard protocols. Sequencing was by the dideoxy chain termination method using Sequenase 2.0 and a dideoxynucleotide sequencing kit (U.S. Biochemical) according to the manufacturers protocol (a modification of Sanger et al. PNAS; USA 74:5463 (1977)]. Alternatively, sequencing was done in a DNA thermal cycler (Perkin Elmer, model 4800) using a cycle sequencing kit (New England Biolabs; Bethesda Research Laboratories) and was performed according to manufacturers instructions using a 5'-end labelled primer. Sequence primers were either those supplied with the sequencing kits or were synthesized according to sequence determined from the clones. Sequencing reactions were loaded on and resolved on 0.4 mm thick sequencing gels of 6% polyacrylamide. Gels were dried and exposed to X-Ray film. Typically, 35S was incorporated when standard sequencing kits were used and a 32P end labelled primer was used for cycle sequencing reactions. Sequences were read into a DNA sequence editor from the bottom of the gel to the top (5' direction to 3') and data were analyzed using programs supplied by Genetics Computer Group (GCG, University of Wisconsin).

VII. RNA Preparation and PCR Amplification

Open reading frames detected in the genomic DNA and which contained sequence encoding GGF peptides were extended via PCR amplification of pituitary RNA. RNA was prepared from frozen bovine tissue (Palfreeze) according to the guanidine neutral-CsCl procedure (Chirgwin et. al. Biochemistry 18:5294(1979).) Polyadenylated RNA was selected by oligo-dT cellulose column chromatography (Aviv and Leder PNAS (USA) 69:1408 (1972)).

Specific DNA target sequences were amplified beginning with either total RNA or polyadenylated RNA samples that had been converted to cDNA using the Perkin Elmer PCR/RNA Kit Number: N808-0017. First strand reverse transcription reactions used 1 μg template RNA and either primers of oligo dT with restriction enzyme recognition site linkers attached or specific antisense primers determined from cloned sequences with restriction sites attached. To produce the second strand, the primers either were plus strand unique sequences as used in 3' RACE reaction; (Frohman et. al., PNAS (USA) 85:8998 (1988)) or were oligo dT primers with restriction sites attached if the second target site had been added by terminal transferass tailing first strand reaction products with dATP (e.g. 5' race reactions, Frohman et. al., ibid). Alternatively, as in anchored PCR reactions the second strand primers were degenerate, hence, representing particular peptide sequences.

The amplification profiles followed the following general scheme: 1) five minutes soak file at 95° C.; 2) thermal cycle file of 1 minute, 95° C.; 1 minute ramped down to an annealing temperature of 45° C., 50° C. or 55° C.; maintain the annealing temperature for one minute; ramp up to 72° C. over one minute; extend at 72° C. for one minute or for one minute plus a 10 second auto extension; 3) extension cycle at 72° C., five minutes, and; 4) soak file 4° C. for infinite time. Thermal cycle files (#2) usually were run for 30 cycles. A sixteen µl sample of each 100 µl amplification reaction was analyzed by electrophoresis in 2% Nusieve 1% agarose gels run in TAE buffer at 4 volts per centimeter for three hours. The gels were stained, then blotted to uncharged nylon membranes which were probed with labelled DNA probes that were internal to the primers.

Specific sets of DNA amplification products could be identified in the blotting experiments and their positions used as a guide to purification and reamplification. When appropriate, the remaining portions of selected samples were loaded onto preparative gels, then following electrophoresis four to five slices of 0.5 mm thickness (bracketing the expected position of the specific product) were taken from the gel. The agarose was crushed, then soaked in 0.5 ml of electrophoresis buffer from 2–16 hours at 40° C. The crushed agarose was centrifuged for two minutes and the aqueous phase was transferred to fresh tubes.

Reamplification was done on five microliters (roughly 1% of the product) of the eluted material using the same sets of primers and the reaction profiles as in the original reactions. When the reamplification reactions were completed, samples were extracted with chloroform and transferred to fresh tubes. Concentrated restriction enzyme buffers and enzymes were added to the reactions in order to cleave at the restriction sites present in the linkers. The digested PCR products were purified by gel electrophoresis, then subcloned into vectors as described in the subcloning section above. DNA sequencing was done described as above.

VIII. DNA Sequence Analysis

DNA sequences were assembled using a fragment assembly program and the amino acid sequences deduced by the GCG programs GelAssemble, Map and Translate. The deduced protein sequences were used as a query sequence to search protein sequence databases using WordSearch. Analysis was done on a VAX Station 3100 workstation operating under VMS 5.1. The database search was done on SwissProt release number 21 using GCG Version 7.0.

IX. Results of Cloning and Sequencing of genes encoding GGF-I and GGF-II

As indicated above, to identify the DNA sequence encoding bovine GGF-II degenerate oligonucleotide probes were designed from GGF-II peptide sequences. GGF-II 12 (SEQ ID No. 44), a peptide generated via lysyl endopeptidase digestion of a purified GGF-II preparation (see FIGS. 11 and 12) showed strong amino acid sequence homology with GGF-I 07 (SEQ ID No. 39), a tryptic peptide generated from a purified GGF-I preparation. GGF-II 12 was thus used to create ten degenerate oligonucleotide probes (see oligos 609, 610 and 649 to 656 in FIG. 21, SEQ ID Nos. 69, 70, 71 and 79, respectively). A duplicate set of filters were probed with two sets (set 1=609, 610; set 2=649–5656) of probes encoding two overlapping portions of GGF-II 12. Hybridization signals were observed, but, only one clone hybridized to both probe sets. The clone (designated GGF2BG1) was purified.

Southern blot analysis of DNA from the phage clone GGF2BG1 confirmed that both sets of probes hybridized with that bovine DNA sequence, and showed further that both probes reacted with the same set of DNA fragments within the clone. Based on those experiments a 4 kb Eco RI sub-fragment of the original clone was identified, subcloned and partially sequenced. FIG. 22 shows the nucleotide sequence, SEQ ID No. 89) and the deduced amino acid sequence of the initial DNA sequence readings that included the hybridization sites of probes 609 and 650, and confirmed that a portion of this bovine genomic DNA encoded peptide 12 (KASLADSGEYM).

Further sequence analysis demonstrated that GGF-II 12 resided on a 66 amino acid open reading frame (see below) which has become the starting point for the isolation of overlapping sequences representing a putative bovine GGF-II gene and a cDNA.

Figure 24:
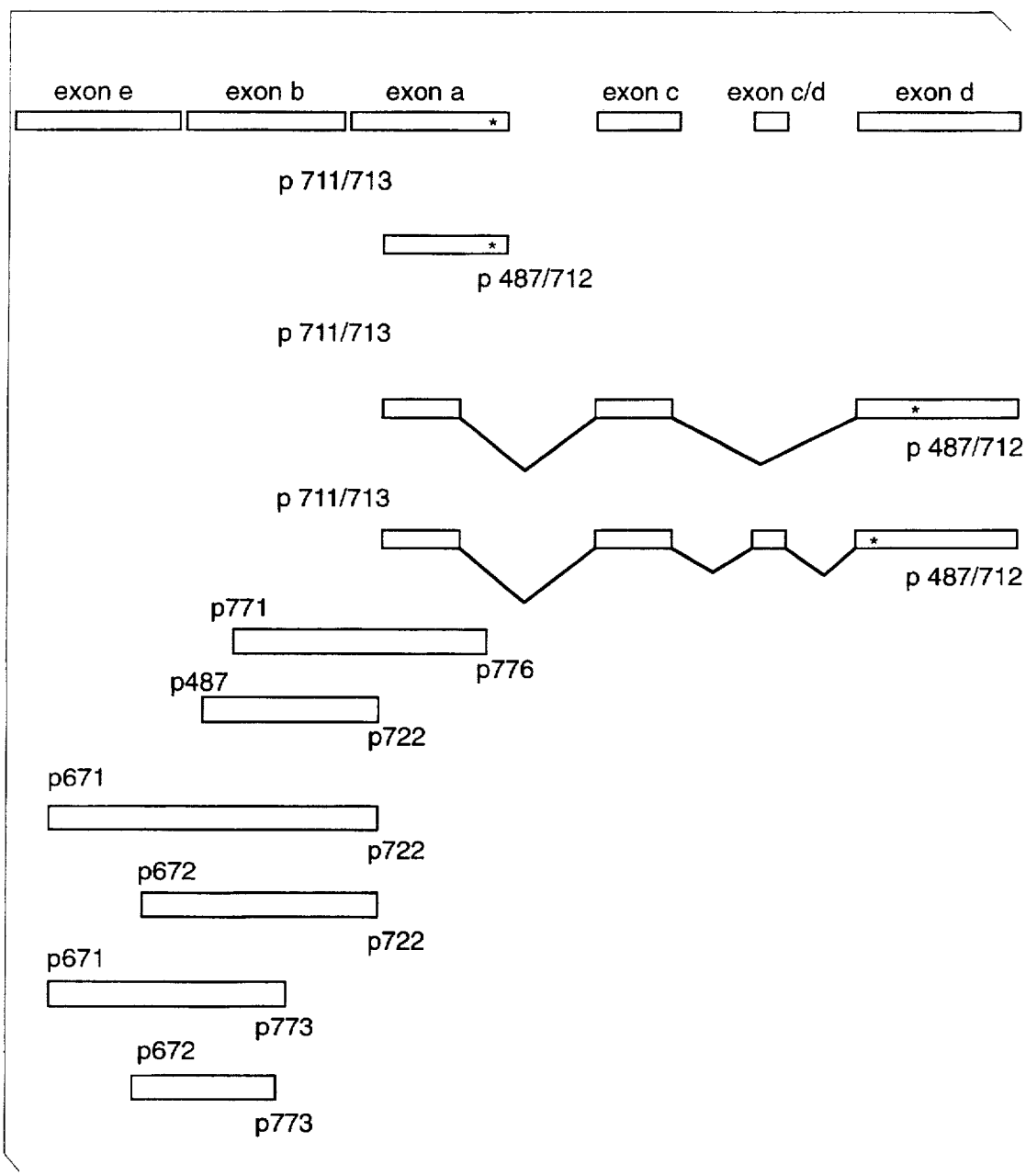

Several PCR procedures were used to obtain additional coding sequences for the putative bovine GGF-II gens. Total RNA and oligo dT-selected (poly A containing) RNA samples were prepared from bovine total pituitary, anterior pituitary, posterior pituitary, and hypothalamus. Using primers from the list shown in FIG. 23, SEQ ID Nos. 109–119, one-sided PCR reactions (RACE) were used to amplify cDNA ends in both the 3' and 5' directions, and anchored PCR reactions were performed with degenerate oligonucleotide primers representing additional GGF-II peptides. FIG. 24 summarizes the contiguous DNA structures and sequences obtained in those experiments. From the 3' RACE reactions, three alternatively spliced cDNA sequences were produced, which have been cloned and sequenced. A 5' RACE reaction led to the discovery of an additional exon containing coding sequence for at least 52 amino acids. Analysis of that deduced amino acid sequence revealed peptides GGF-II-6 and a sequence similar to GGF-I-18 (see below). The anchored PCR reactions led to the identification of (cDNA) coding sequences of peptides GGF-II-1, 2, 3 and 10 contained within an additional cDNA segment of 300 bp. The 5' limit of this segment (i.e., segment E, see FIG. 31) is defined by the oligonucleotide which encodes peptide GGF-II-1 and which was used in the PCR reaction (additional 5' sequence data exists as described for the human clone in Example 6). Thus this clone contains nucleotide sequences encoding six out of the existing total of nine novel GGF-II peptide sequences.

Figure 25:
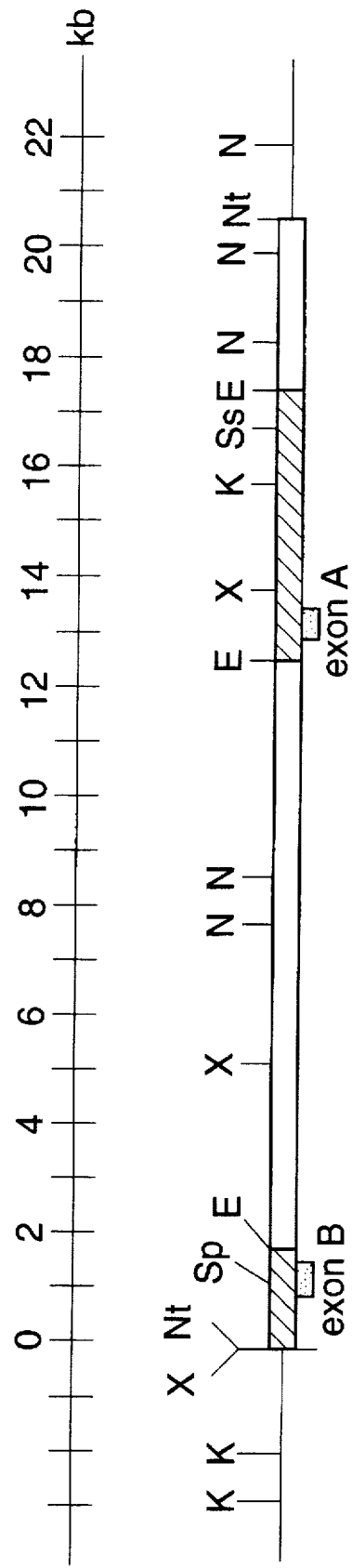
Figure 26:
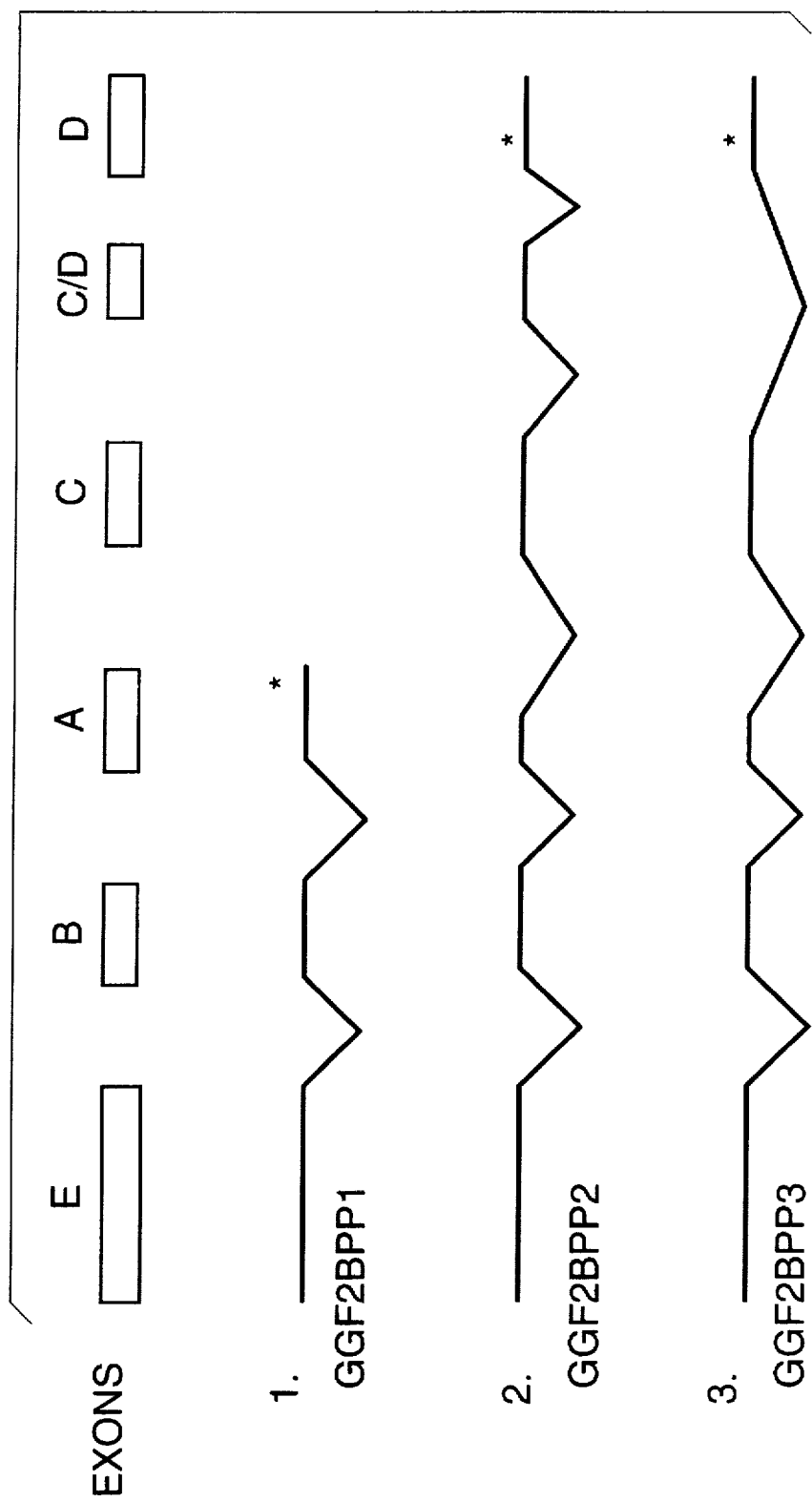

The cloned gene was characterized first by constructing a physical map of GGF2BG1 that allowed us to position the coding sequences as they were found (see below, FIG. 25). DNA probes from the coding sequences described above have been used to identify further DNA fragments containing the exons on this phage clone and to identify clones that overlap in both directions. The putative bovine GGF-II gene is divided into at least 5 coding segments. Coding segments are defined as discrete lengths of DNA sequence which can be translated into polypeptide sequences using the universal genetic code. The coding segments described in FIG. 31 and referred to in the present application are: 1) particular exons present within the GGF gene (e.g. coding segment a), or 2) derived from sets of two or more exons that appear in specific subgroups of mRNAs, where each set can be translated into the specific polypeptide segments as in the gene products shown. The polypeptide segments referred to in the claims are the translation products of the analogous DNA coding segments. Only coding segments A and B have been defined as exons and sequenced and mapped thus far. The summary of the contiguous coding sequences identified is shown in FIG. 26. The exons are listed (alphabetically) in the order of their discovery. It is apparent from the intron/exon boundaries that exon B may be included in cDNAs that connect coding segment E and coding segment A. That is, exon B cannot be spliced out without compromising the reading frame. Therefore, we suggest that three alternative splicing patterns can produce putative bovine GGF-II cDNA sequences 1, 2 and 3. The coding sequences of these, designated GGF2BPP1.CDS, GGF2BPP2.CDS and GGF2BPP3.CDS, respectively, are given in FIGS. 28a (SEQ ID No. 133), 28b (SEQ ID No. 134), and 28c (SEQ ID No. 135), respectively. The deduced amino acid sequence of the three cDNAs is also given in FIGS. 28a, (SEQ ID No. 133), 28b (SEQ ID No. 134), and 28c (SEQ ID No. 135).

The three deduced structures encode proteins of lengths 206, 281 and 257 amino acids. The first 183 residues of the deduced protein sequence are identical in all three gene products. At position 184 the clones differ significantly. A codon for glycine GGT in GGF2BPP1 also serves as a splice donor for GGF2BPP2 and GGF2BPP3, which alternatively add on exons C, C/D, C/D' and D or C, C/D and D, respectively, and shown in FIG. 33, SEQ ID No. 149). GGFIIBPP1 is a truncated gene product which is generated by reading past the coding segment A splice junction into the following intervening sequence (intron). This represents coding segment A' in FIG. 31 (SEQ ID No. 140). The transcript ends adjacent to a canonical AATAAA polyadenylation sequence, and we suggest that this truncated gens product represents a bonafide mature transcript. The other two longer gene products share the same 3' untranslated sequence and polyadenylation site.

All three of these molecules contain six of the nine novel GGF-II peptide sequences (see FIG. 12) and another peptide is highly homologous to GGF-I-18 (see FIG. 27). This finding gives a high probability that this recombinant molecule encodes at least a portion of bovine GGF-II. Furthermore, the calculated isoelectric points for the three peptides are consistent with the physical properties of GGF-I and II. Since the molecular size of GGF-II is roughly 60 kD, the longest of the three cDNAs should encode a protein with nearly one-half of the predicted number of amino acids.

Figure 30:
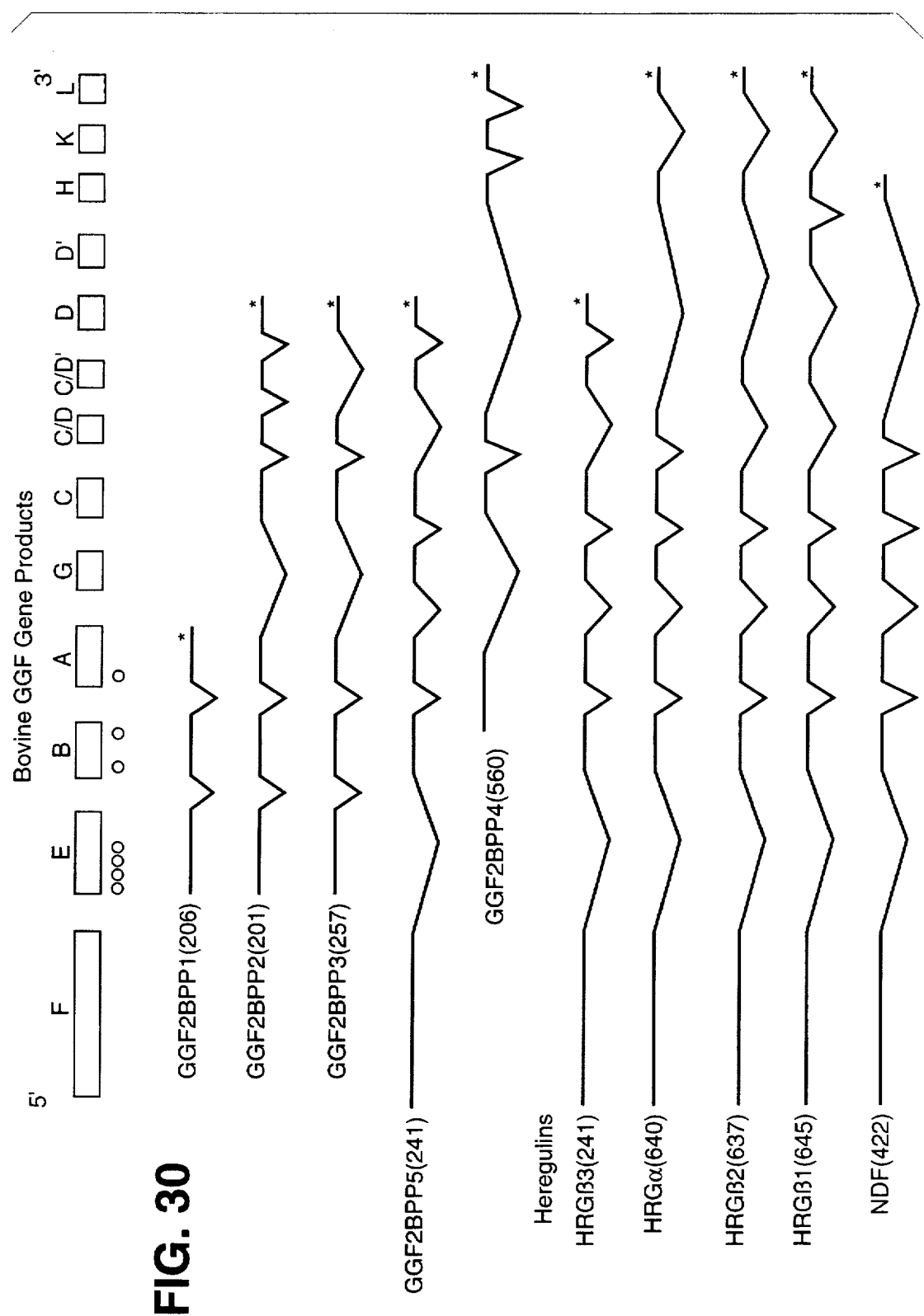
FIG. 30 is a diagram of representative splicing variants. The coding segments are represented by F, E, B, A, G, C, C/D, C/D', D, D', H, K and L. The location of the peptide sequences derived from purified protein are indicated by "o".

A probe encompassing the B and A exons was labelled via PCR amplification and used to screen a cDNA library made from RNA isolated from bovine posterior pituitary. One clone (GGF2BPP5) showed the pattern indicated in FIG. 30 and contained an additional DNA coding segment (G) between coding segments A and C. The entire nucleic acid sequence is shown in FIG. 32 (SEQ ID No. 148). The predicted translation product from the longest open reading frame is 241 amino acids. A portion of a second cDNA (GGF2BPP4) was also isolated from the bovine posterior pituitary library using the probe described above. This clone showed the pattern indicated in FIG. 30. This clone is incomplete at the 5' end, but is a splicing variant in the sense that it lacks coding segments G and D. BPP4 also displays a novel 3' end with regions H, K and L beyond region C/D. The sequence of BPP4 is shown in FIG. 34 (SEQ ID No. 150).

EXAMPLE 5

GGF Sequences in Various Species

Figure 29:
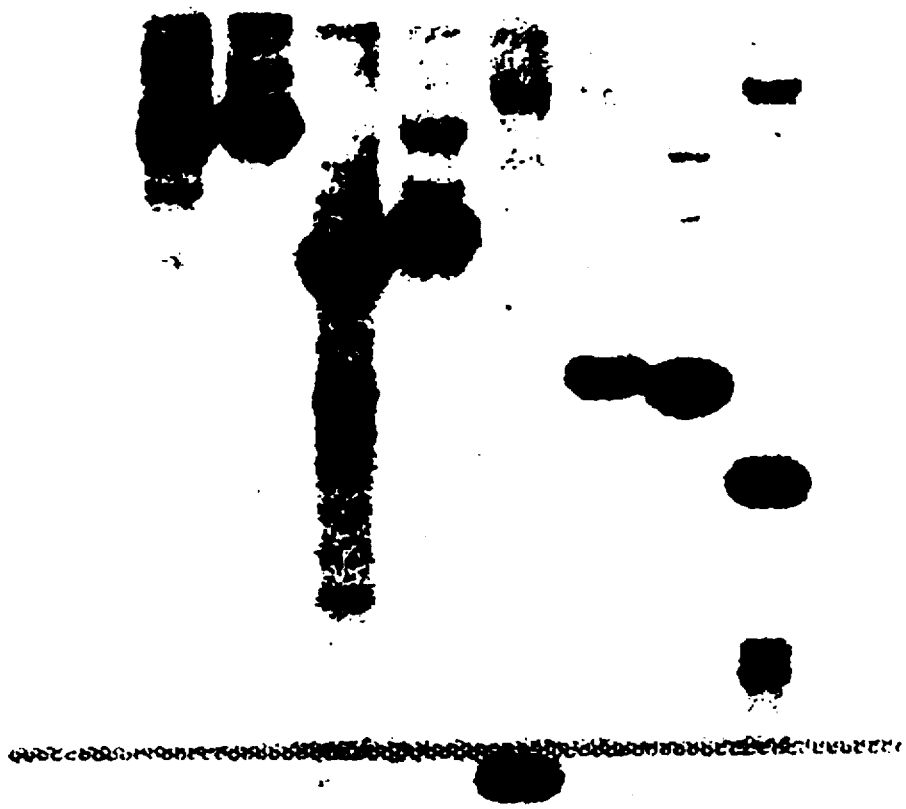
FIG. 29, which relates to Example 6 hereinafter, is an autoradiogram of a cross hybridization analysis of putative bovine GGF-II gene sequences to a variety of mammalian DNAs on a southern blot. The filter contains lanes of EcoRI-digested DNA (5 µg per lane) from the species listed in the Figure. The probe detects a single strong band in each DNA sample, including a four kilobase fragment in the bovine DNA as anticipated by the physical map in FIG. 25. Bands of relatively minor intensity are observed as well, which could represent related DNA sequences. The strong hybridizing band from each of the other mammalian DNA samples presumably represents the GGF-II homologue of those species.

Database searching has not revealed any meaningful similarities between any predicted GGF translation products and known protein sequences. This suggests that GGF-II is the first member of a new family or superfamily of proteins. In high stringency cross hybridization studies (DNA blotting experiments) with other mammalian DNAs we have shown, clearly, that DNA probes from this bovine recombinant molecule can readily detect specific sequences in a variety of samples tested. A highly homologous sequence is also detected in human genomic DNA. The autoradiogram is shown in FIG. 29. The signals in the lanes containing rat and human DNA represent the rat and human equivalents of the GGF gens, the sequences of several cDNA's encoded by this gene have been recently reported by Holmes et al. (Science 256: 1205 (1992)) and Wen et al. (Cell 69: 559 (1992)).

EXAMPLE 6

Isolation of a Human Sequence Encoding Human GGF2

Several human clones containing sequences from the bovine GGFII coding segment E were isolated by screening a human cDNA library prepared from brain stem (Stratagens catalog #935206). This strategy was pursued based on the strong link between most of the GGF2 peptides (unique to GGF2) and the predicted peptide sequence from clones containing the bovine E segment. This library was screened as described in Example 4, Section II using the oligonucleotide probes 914–919 listed below.

```
914TCGGGCTCCATGAAGAAGATGTA
915TCCATGAAGAAGATGTACCTGCT
916ATGTACCTGCTGTCCTCCTTGA
917TTGAAGAAGGACTCGCTGCTCA
918AAAGCCGGGGGCTTGAAGAA
919ATGARGTGTGGGCGGCGAAA
```

Figure 44:
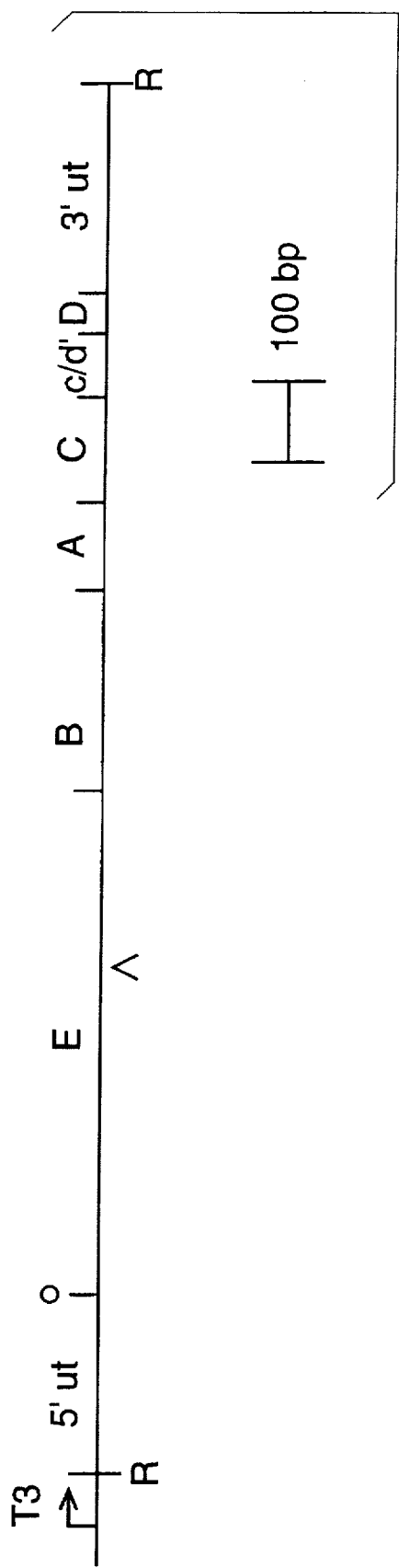
FIG. 44 is a scale coding segment map of the clone. T3 refers to the bacteriophage promoter used to produce mRNA from the clone. R=flanking EcoRI restriction enzyme sites. 5' UT refers to the 5' untranslated region. E, B, A, C, C/D', and D refer to the coding segments. O=the translation start site. ∧=the 5' limit of the region homologous to the bovine E segment (see example 6) and 3' UT refers to the 3' untranslated region.

Clones detected with these probes were further analyzed by hybridization. A probe derived from coding segment A (see FIG. 21), which was produced by labeling a polymerase chain reaction (PCR) product from segment A, was also used to screen the primary library. Several clones that hybridized with both A and E derived probes were selected and one particular clone, GGF2HBS5, was selected for further analysis. This clone is represented by the pattern of coding segments (EBACC/D'D as shown in FIG. 31). The E segment in this clone is the human equivalent of the truncated bovine version of E shown in FIG. 37. GGF2HBS5 is the most likely candidate to encode GGF-II of all the "putative" GGF-II candidates described. The length of coding sequence segment E is 786 nucleotides plus 264 bases of untranslated sequence. The predicted size of the protein encoded by GGF2HBS5 is approximately 423 amino acids (approximately 45 kilodaltons, see FIG. 45, SEQ ID NO: 167), which is similar to the size of the deglycosylated form of GGF-II (see Example 16). Additionally, seven of the GGF-II peptides listed in FIG. 27 have equivalent sequences which fall within the protein sequence predicted from region E. Peptides II-6 and II-12 are exceptions, which fall in coding segment B and coding segment A, respectively. RNA encoding the GGF2HBS5 protein was produced in an in vitro transcription system driven by the bacteriophage T7 promoter resident in the vector (Bluescript SK [Stratagene Inc.] see FIG. 44) containing the GGF2HBS5 insert. This RNA was translated in a cell free (rabbit reticulocyte) translation system and the size of the protein product was 45 Kd. Additionally, the cell-free product has been assayed in a Schwann cell mitogenic assay to confirm biological activity. Schwann cells treated with conditioned medium show both increased proliferation as measured by incorporation of $^{125}$I-Uridine and phosphorylation on tyrosine of a protein in the 185 kilodalton range. Thus the size of the product encoded by GGF2HBS5 and the presence of DNA sequences which encode human peptides highly homologous to the bovine peptides shown in FIG. 12 confirm that GGF2HBS5 encodes the human equivalent of bovine GGF2. The fact that conditioned media prepared from cells transformed with this clone elicits Schwann cell mitogenic activity confirms that the GGFIIHBS5 gene produce (unlike the BPP5 gene product) is secreted. Additionally the GGFI-IBPP5 gene product seems to mediate the Schwann cell proliferation response via a receptor tyrosine kinase such as p185$^{erbB2}$ or a closely related receptor (see Example 14).

EXAMPLE 7

Expression of Human Recombinant GGF2 in Mammalian and Insect Cells

Figure 46:
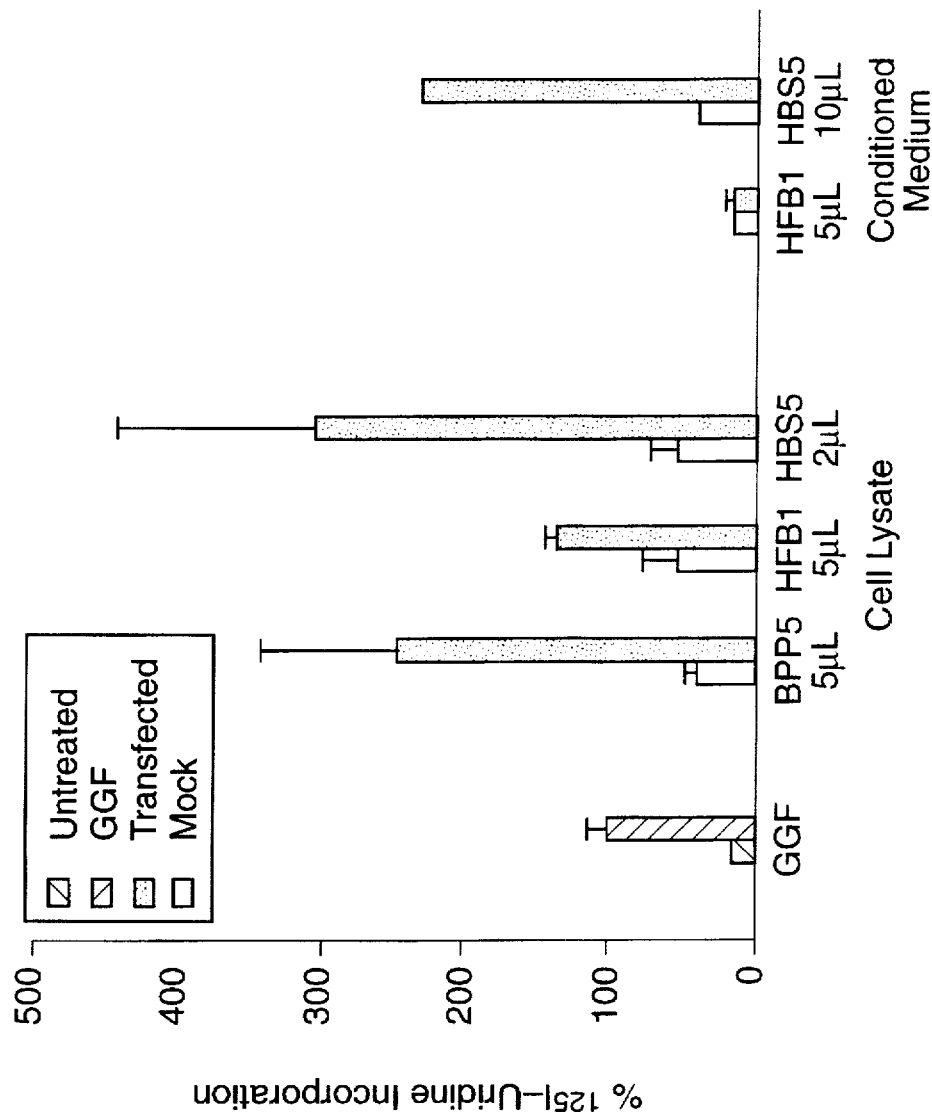
FIG. 46 is a graph depicting the Schwann cell mitogenic activity of recombinant human and bovine glial growth factors.

The GGF2HBS5 cDNA clone encoding human GGF2 (as described in Example 6 and also referred to herein as HBS5) was cloned into vector pcDL-SRα296 (Takebe et al. Mol. Cell. Biol. 8:466–472 (1988) and COS-7 cells were transfected in 100 mm dishes by the DEAE-dextran method (Sambrook et al. Molecular Cloning: A Laboratory Manual 2nd ed. CSH Laboratory N.Y. (1989). Cell lysates or conditioned media from transiently expressing COS cells were harvested at 3 or 4 days post-transfection. To prepare lysates, cell monolayers were washed with PBS, scraped from the dishes, lysed by three freeze/thaw cycles in 150 µl of 0.25M Tris-HCl, pH 8. Cell debris was pelleted and the supernatant recovered. Conditioned media samples (7 ml.) were collected, then concentrated and buffer exchanged with 10 mM Tris, pH 7.4 using Centiprep-10 and Centricon-10 units as described by the manufacturer (Amicon, Beverly, Mass.). Rat nerve Schwann cells were assayed for incorporation of DNA synthesis precursors, as described (see Example 3). Conditioned media or cell lysate samples were tested in the Schwann cell proliferation assay as described in Example 3. The mitogenic activity data are shown in FIG. 46. The cDNA, GGF2HBS5, encoding GGF2 directed the secretion of the protein product to the medium. A small proportion of total activity was detectable inside the cells as determined by assays using cell lysates. GGF2HFB1 and GGFBPP5 cDNA's failed to direct the secretion of the product to the extracellular medium. GGF activity from these clones was detectable only in cell lysates (FIG. 46).

Figure 47:
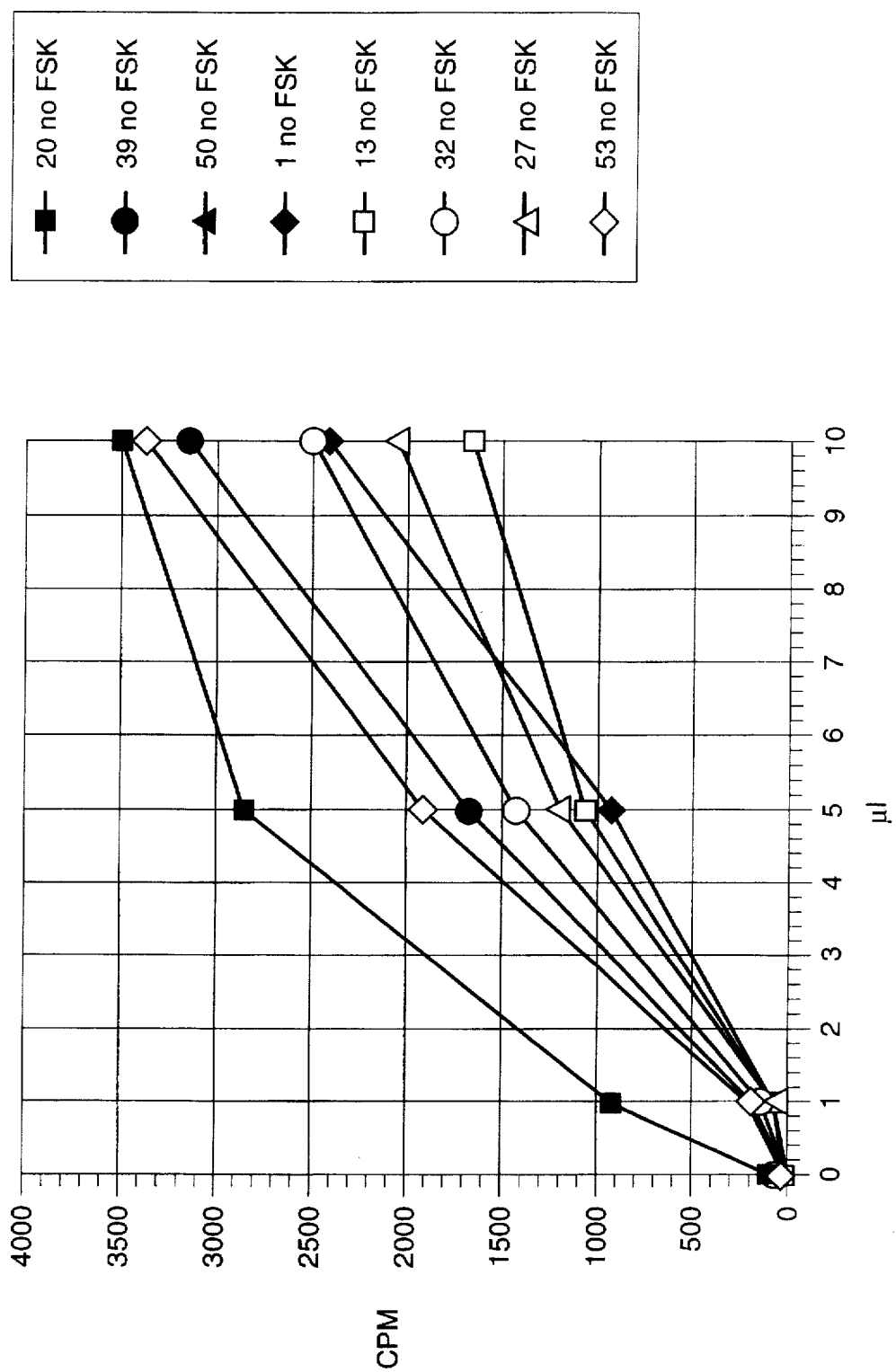
FIG. 47 is a dose-response curve depicting Schwann cell proliferation activity data resulting from administration of different size aliquots of CHO cell conditioned medium.
Figure 49:
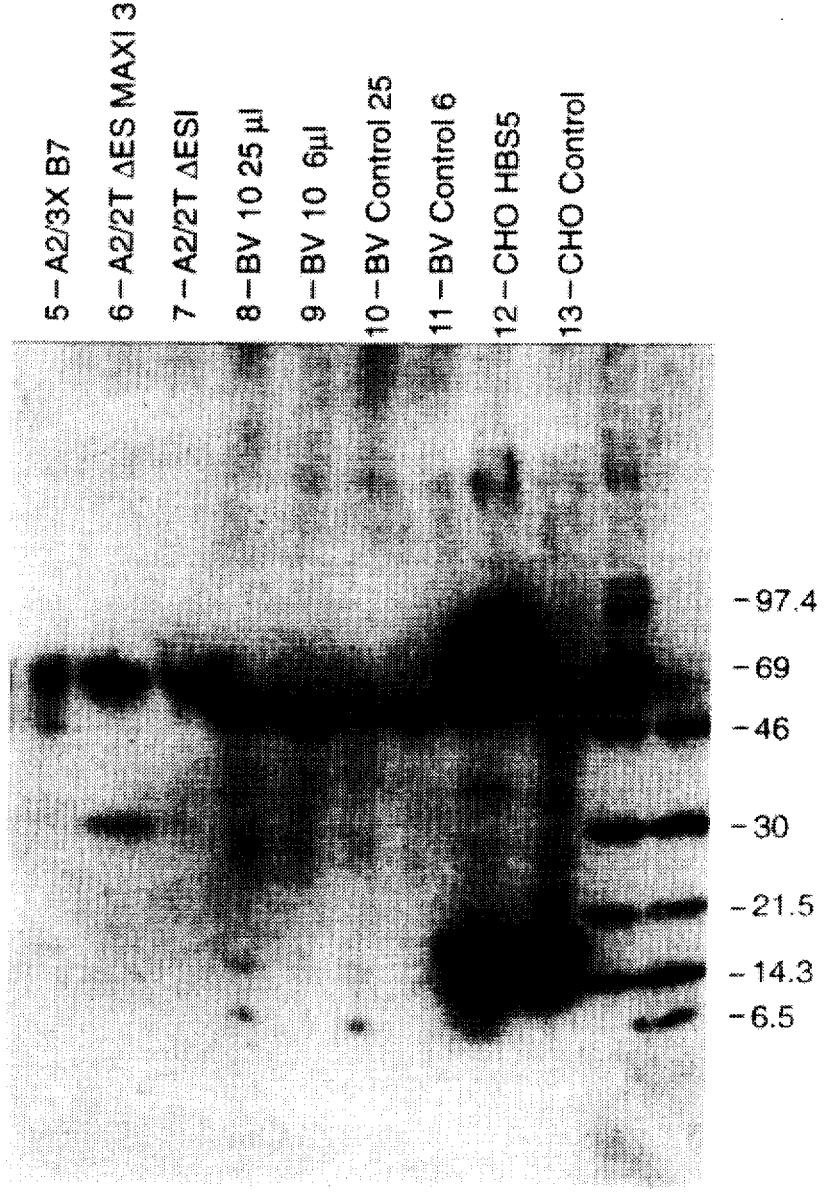
FIG. 49 is a Western blot of recombinant CHO cell conditioned medium using a GGF peptide antibody.
Figure 54:
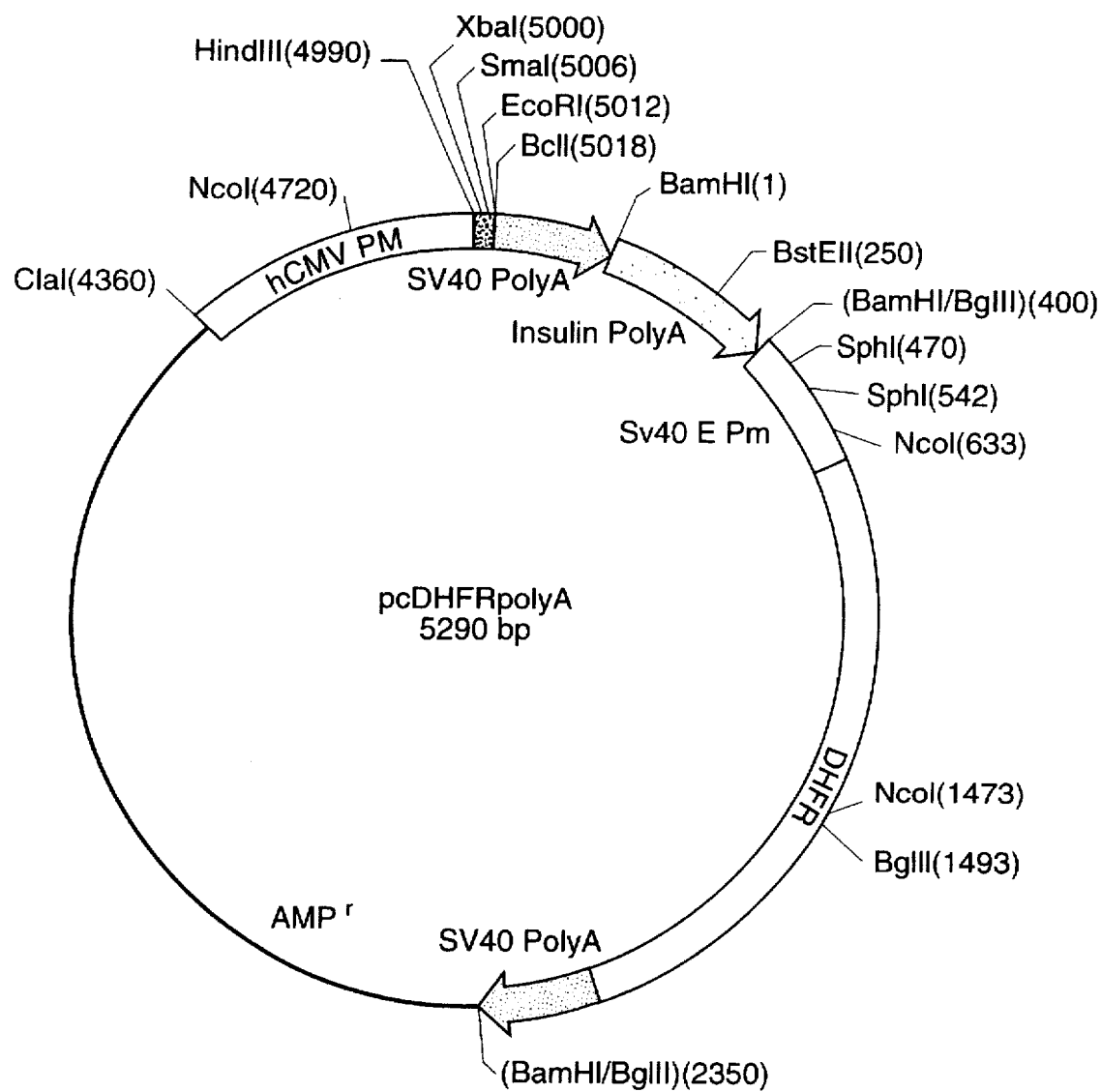
FIG. 54 is a map of the CHO cell-expression vector pcDHFRpolyA.

Recombinant GGF2 was also expressed in CHO cells. The GGF2HBS5 cDNA encoding GGF2 was cloned into the EcoRI site of vector pcdhfrpolyA (FIG. 54) and transfected into the DHFR negative CHO cell line (DG44) by the calcium phosphate coprecipitation method (Graham and Van Der Eb, Virology 52:456–467 (1973). Clones were selected in nucleotide and nucleoside free α medium (Gibco) in 96-well plates. After 3 weeks, conditioned media samples from individual clones were screened for expression of GGF by the Schwann cell proliferation assay as described in Example 3. Stable clones which secreted significant levels of GGF activity into the medium were identified. Schwann cell proliferation activity data from different volume aliquots of CHO cell conditioned medium were used to produce the dose response curve shown in FIG. 47 (ref., Graham and Van Der Eb, Virology 52:456, 1973). This material was analyzed on a Western blot probed with polyclonal antisera raised against a GGF2 specific peptide. A broad band of approximately 69–90 Kd (the expected size of GGF2 extracted from pituitary and higher molecular weight glycoforms) is specifically labeled (FIG. 49, lane 12).

Figure 48:
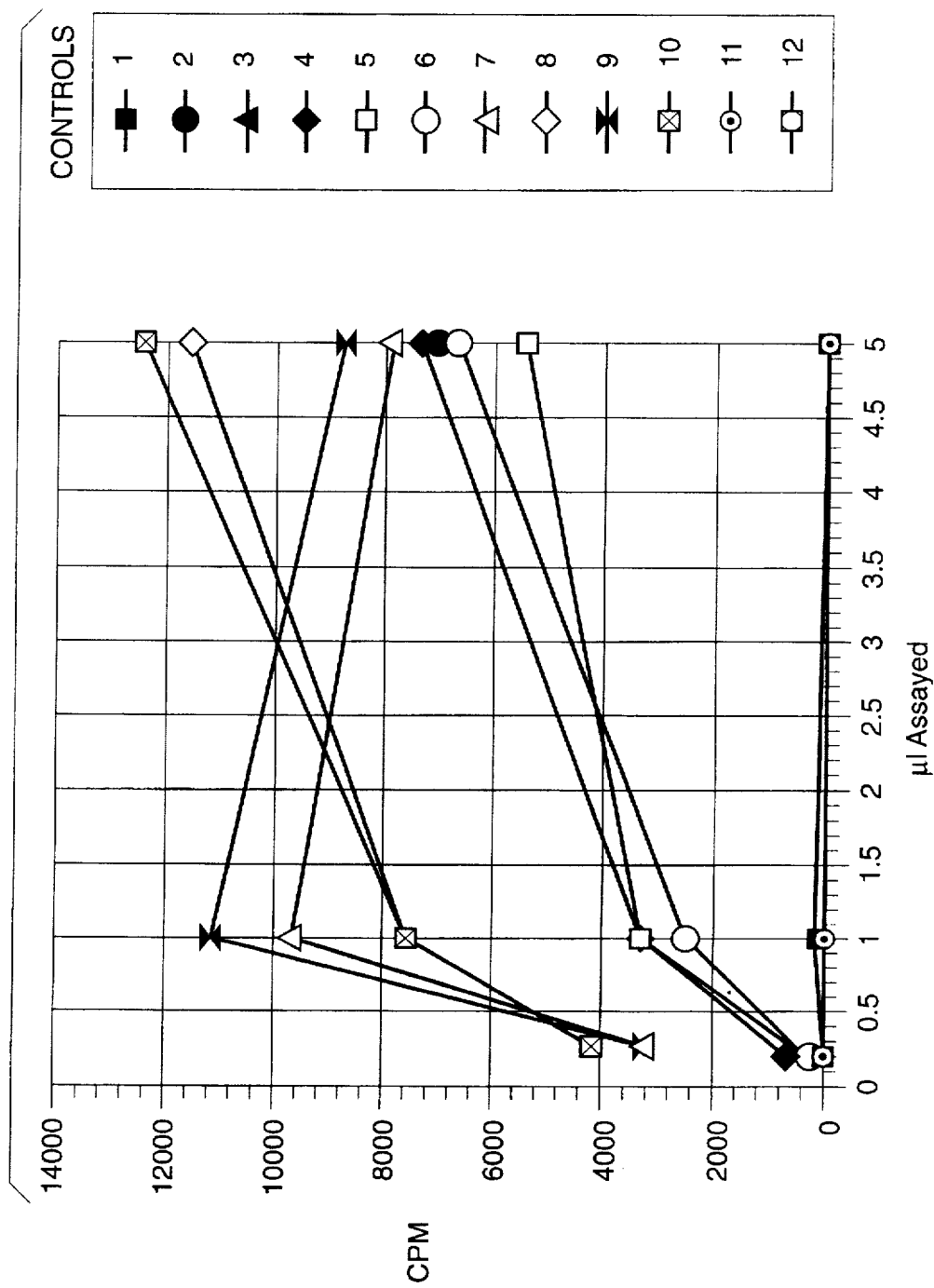
FIG. 48 is a dose-response curve depicting Schwann cell mitogenic activity secreted into the extracellular medium by SF9 insect cells infected with baculovirus containing the GGF2HBS5 cDNA clone.

Recombinant GGF2 was also expressed in insect cells using Baculovirus expression. Sf9 insect cells were infected with baculovirus containing the GGF2HBS5 cDNA clone at a multiplicity of 3–5 (10$^6$ cells/ml) and cultured in Sf900-II medium (Gibco). Schwann cell mitogenic activity was secreted into the extracellular medium (FIG. 48). Different volumes of insect cell conditioned medium were tested in the Schwann cell proliferation assay in the absence of forskolin and the data used to produce the dose response curve shown in FIG. 48.

This material was also analyzed on a Western blot (FIG. 47) probed with the GGF II specific antibody described above. A band of 45 Kd, the size of deglycosylated GGF-II (see Example 16) was seen.

Figure 53:
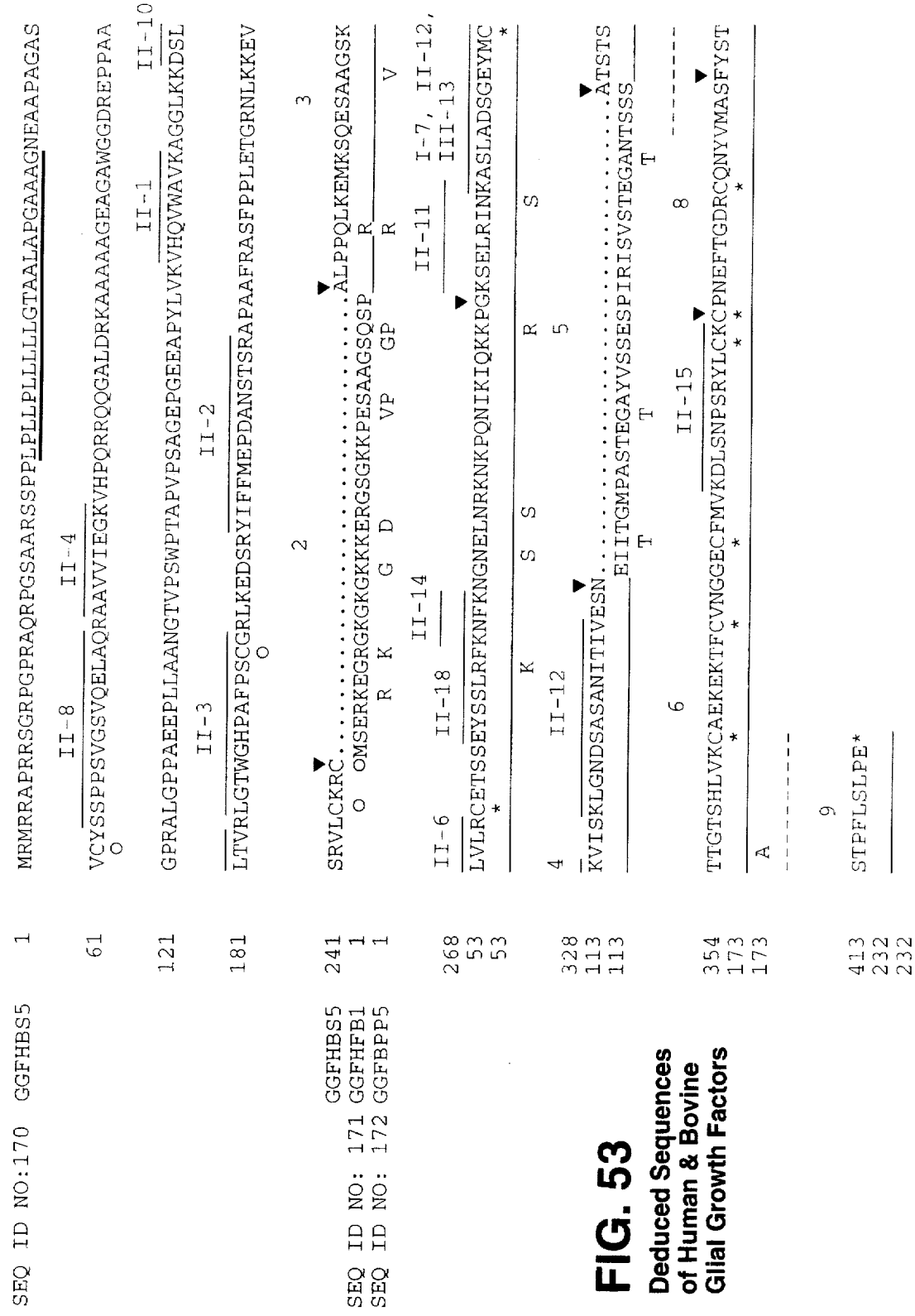
FIG. 53 is the sequences of GGFHBS5, GGFHFB1 and GGFBPP5 polypeptides (SEQ ID NOS: 170, 171, and 172).

The methods used in this example were as follows:

Schwann cell mitogenic activity of recombinant human and bovine glial growth factors was determined as follows: Mitogenic responses of cultured Schwann cells were measured in the presence of 5 µM forskolin using crude recombinant GGF preparations obtained from transient mammalian expression experiments. Incorporation of [$^{125}$I]-Uridine was determined following an 18–24 hour exposure to materials obtained from transfected or mock transfected COS cells as described in the Methods. The mean and standard deviation of four sets of data are shown. The mitogenic response to partially purified native bovine pituitary GGF (carboxymethyl cellulose fraction; Goodearl et al., submitted) is shown (GGF) as a standard of one hundred percent activity.

cDNAs (FIG. 53) were cloned into pcDL-SRα296 (Takebe et al., Mol. Cell Biol. 8:466–472 (1988)), and COS-7 cells were transfected in 100 mm dishes by the DEAE-dextran method (Sambrook et al., In Molecular Cloning. A Laboratory Manual, 2nd. ed. (Cold Spring Harbor Laboratory Press, Cold Spring Harbor, N.Y., 1989)). Cell lysates or conditioned media were harvested at 3 or 4 days post-transfection. To prepare lysates, cell monolayers were washed with PBS, scraped from the dishes, and lysed by three freeze/thaw cycles in 150 µl of 0.25M Tris-HCl, pH 8. Cell debris was pelleted and the supernate recovered. Conditioned media samples (7 mls) were collected, then concentrated and buffer exchanged with 10 mM Tris, pH 7.4 using Centriprep-10 and Centricon-10 units as described by the manufacturer (Amicon, Beverly, Mass.). Rat sciatic nerve Schwann cells were assayed for incorporation of DNA synthesis precursors, as described (Davis and Stroobant, J. Cell Biol. 110:1353–1360 (1990); Brockes et al., Brain Res. 165:105–118 (1979)).

Western blots of recombinant CHO cell conditioned medium were performed as follows: A recombinant CHO clone was cultured in 7 ml. of MCDB302 protein-free medium for 3 days. 2 ml of conditioned medium was concentrated, buffer exchanged against 10 mM Tris-HCl, pH 7.4 and lyophilized to dryness. The pellet was resuspended in SDS-PAGE sample buffer, subjected to reducing SDS gel electrophoresis and analyzed by Western blotting with a GGF peptide antibody. A CHO control was done by using conditioned medium from untransfected CHO-DG44 host and the CHO HBS5 levels were assayed using conditioned medium from a recombinant clone.

EXAMPLE 8

Isolation of Other Human Sequences Related to Bovine GGF

The result in Examples 5 and 6 indicate that GGF related sequences from human sources can also be easily isolated by using DNA probes derived from bovine GGF sequences. Alternatively the procedure described by Holmes et el. (Science 256: 1205 (1992)) can be used. In this example a human protein (heregulin α), which binds to and activates the p185$^{erbB2}$ receptor (and is related to GGF), is purified from a tumor cell line and the derived peptide sequence is used to produce oligonucleotide probes which were utilized to clone the cDNA's encoding heregulin. The biochemical assay for p185$^{erbB2}$ receptor activation is distinguished from Schwann cell proliferation. This is a similar approach to that used in examples 1–4 for the cloning of GGF sequences from pituitary cDNAs. The heregulin protein and complementary DNAs were isolated from tumor cell lines according to the following procedures. Heregulin was purified from medium conditioned by MDA-MB-231 breast cancer cells (ATCC #HTB 26) grown on Parcell Biolytica microcarrier beads (Hyclone Labs). The medium (10 liters) was concentrated ~25-fold by filtration through a membrane (10-kD cutoff) (Millipore) and clarified by centrifugation and filtration through a filter (0.22 µm). The filtrate was applied to a heparin Sepharose column (Pharmacia) and the proteins were eluted with steps of 0.3, 0.6, and 0.9M NaCl in phosphate-buffered saline. Activity in the various chromatographic fractions was measured by quantifying the increase in tyrosine phosphorylation of p185$^{erbB2}$ in MCF-7 breast tumor cells (ATCC #HTB 22). MCF-7 cells were plated in 24-well Costar plates in F12 (50%) Dulbecco's minimum essential medium (50%) containing serum (10%) ($10^5$ cells per well), and allowed to attach for at least 24 hours. Prior to assay, cells were transferred into medium without serum for a minimum of 1 hour. Column fractions (10 to 100 µl) were incubated for 30 min. at 37°. Supernatants were then aspirated and the reaction was stopped by the addition of SDS-PAGE sample buffer 100 µl). Samples were heated for 5 min. at 100° C., and portions (10 to 15 µl) were applied to a tris-glycine gel (4 to 20%) (Novex). After electrophoresis, proteins were electroblotted onto a polyvinylidenedifluoride (PVDF) membrane and then blocked with bovine serum albumin (5%) in tris-buffered saline containing Tween-20 (0.05%) (TBST). Blots were probed with a monoclonal antibody (1:1000 dilution) to phosphotyrosine (Upstate Biotechnology) for a minimum of 1 hour at room temperature. Blots were washed with TBST, probed with an antibody to mouse immunoglobulin G conjugated to alkaline phosphatase (Promega) (diluted 1:7500) for a minimum of 30 min. at room temperature. Reactive bands were visualized with 5-bromo-4-chloro-3-indoyl-1-phosphate and nitro-blue tetrazolium. Immunoblots were scanned with a Scan Jet Plus (Hewlett-Packard) densitometer. Signal intensities for unstimulated MCF-7 cells were 20 to 30 units. Fully stimulated p185$^{erbB2}$ yielded signals of 180 to 200 units. The 0.6M NaCl pool, which contained most of the activity, was applied to a polyaspartic acid (PolyLC) column equilibrated in 17 mM sodium phosphate (pH 6.8) containing ethanol (30%). A linear gradient from 0.3M to 0.6M NaCl in the equilibration buffer was used to elute bound proteins. A peak of activity (at ~0.45M NaCl) was further fractionated on a C4 reversed-phase column (SynChropak RP-4) equilibrated in buffer containing TFA (0.1%) and acetonitrile (15%). Proteins were eluted from this column with an acetonitrile gradient from 25 to 40% over 60 min. Fractions (1 ml) were collected, assayed for activity, and analyzed by SDS-PAGE on tris-glycine gels (4–20%, Novex). HPLC-purified HRG-α was digested with lysine C in SDS (0.1%), 10 mM dithiothreitol, 0.1M $NH_4HCO_3$ (pH 8.0) for 20 hours at 37° C. and the resultant fragments were resolved on a Synchrom C4 column (4000A°, 0.2 by 10 cm).

The column was equilibrated in 0.1% TFA and eluted with a 1-propanol gradient in 0.1% TFA (W. J. Henzel, J. T. Stults, C. Hsu, D. W. Aswad, J. Biol. Chem. 264:15905 (1989)). Peaks from the chromatographic run were dried under vacuum and sequenced. One of the peptides (eluting at ~24% 1-propanol) gave the sequence [A]AEKEKTF[C]VNGGEXFMVKDLXNP (SEQ ID No. 162). Residues in brackets were uncertain and an X represents a cycle in which it was not possible to identify the amino acid. The initial yield was 8.5 pmol and the sequence did not correspond to any known protein. Residues 1, 9, 15, and 22 were later identified in the cDNA sequence as cysteine. Direct sequencing of the ~45-kD band from a gel that had been overloaded and blotted onto a PVDF membrane revealed a low abundance sequence XEXKE[G][R]GK[G]K[G]KKKEXGXG[K] (SEQ ID No. 163) with a very low initial yield (0.2 pmol). This corresponded to amino acid residues 2 to 22 of heregulin-α (FIG. 31), suggesting that serine 2 is the $NH_2$-terminus of proHRG-α. Although the $NH_2$ terminus was blocked, it was observed that occasionally a small amount of a normally blocked protein may not be posttranslationally modified. The $NH_2$ terminal assignment was confirmed by mass spectrometry of the protein after digestion with cyanogen bromide. The COOH-terminus of the isolated protein has not been definitely identified; however, by mixture sequencing of proteolytic digests, the mature sequence does not appear to extend past residue 241. Abbreviations for amino residues are: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr. As a source of cDNA clones, an oligo(dT)-primed λgt10 (T. V. Huynn, R. A. Young, R. W. Davis, λgt10 and λgt11 DNA Cloning Techniques: A Practical Approach, D. Glover, Ed. (IRC Press, Oxford, (1984)) cDNA library was constructed (U. Gubler and B. J. Hoffman, Gene25, 263 (1983)) with mRNA purified (J. M. ChiNin, A. E. Przbyla, R. J. MacDonald, W. J. Rutter, Biochemistry 18, 5294 (1979)) from MDA-MB-231 cells. The following eightfold degenerate antisense deoxyoligonucleotide encoding the 13-amino acid sequence AEKEKTFCVNGGE (SEQ ID No. 164)(13) was designed on the basis of human codon frequency optima (R. Lathe, J. Mol. Biol. 183, 1 (1985)) and chemically synthesized: 5'-CTCGCC (G OR T) CC (A OR G) TTCAC (A OR G) CAGAAGGTCTTCTCCTTCT-CAGC-3' (SEQ ID No. 165). For the purpose of probe design a cysteine was assigned to an unknown residue in the amino acid sequence. The probe was labeled by phosphorylation and hybridized under low-stringency conditions to the cDNA library. The proHRG-α protein was identified in this library. HRB-β1 cDNA was identified by probing a second oligo(dT)-primed λgt10 library made from MDA-MB-231 cell mRNA with sequences derived from both the 5' and 3' ends of proHRG-α. Clone 13 (FIG. 2A) was a product of screening a primed (5'-CCTCGCTCCTTCTTCT-TGCCCTTC-3' primer (SEQ ID No. 166); proHRG-α antisense nucleotides 33 to 56) MDA-MB-231 λgt10 library with 5' HRG-α sequence. A sequence corresponding to the 5' end of clone 13 as the probe was used to identify proHRGβ2 and proHRGβ3 in a third oligo(dT)-primed λgt10 library derived from MDA-MB-231 cell mRNA. Two cDNA clones encoding each of the four HRGs were sequenced (F. Sanger, S. Milken, A. R. Coulson, Proc. Natl. Acad. Sci. U.S.A. 74, 5463 1977]). Another cDNA designated clone 84 has an amino acid sequence identical to proHRGβ2 through amino acid 420. A stop codon at position 421 is followed by a different 3'-untranslated sequence.

EXAMPLE 9

Isolation of a Further Splicing Variant

The methods in Example 6 produced four closely related sequences (heregulin α, β1, β2, β3) which arise as a result of splicing variation. Peles et al. (Cell 69, 205 (1992)), and Wen et al. (Cell 69, 559 (1992)) have isolated another splicing variant (from rat) using a similar purification and cloning approach to that described in Examples 1–4 and 6 involving a protein which binds to p185$^{erbB2}$. The cDNA clone was obtained as follows (via the purification and sequencing of a p185$^{erbB2}$ binding protein from a transformed rat fibroblast cell line).

A p185$^{erbB2}$ binding protein was purified from conditioned medium as follows. Pooled conditioned medium from three harvests of 500 roller bottles (120 liters total) was cleared by filtration through 0.2μ filters and concentrated 31-fold with a Pelicon ultrafiltration system using membranes with a 20 kd molecular size cutoff. All the purification steps were performed by using a Pharmacia fast protein liquid chromatography system. The concentrated material was directly loaded on a column of heparin-Sepharose (150 ml, preequilibrated with phosphate-buffered saline (PBS)). The column was washed with PBS containing 0.2M NaCl until no absorbance at 280 nm wavelength could be detected. Bound proteins were then eluted with a continuous gradient (250 ml) of NaCl (from 0.2M to 1.0M), and 5 ml fractions were collected. Samples (0.01 ml of the collected fractions were used for the quantitative assay of the kinass stimulatory activity. Active fractions from three column runs (total volume =360 ml) were pooled, concentrated to 25 ml by using a YM10 ultrafiltration membrane (Amicon, Danvets, Mass.), and ammonium sulfate was added to reach a concentration of 1.7M. After clearance by centrifugation (10, 000× g, 15 min.), the pooled material was loaded on a phenyl-Superose column (HR10/10, Pharmacia). The column was developed with a 45 ml gradient of $(NH_4)_2SO_4$ (from 1.7M to no salt) in 0.1M $Na_2PO_4$ (pH 7.4), and 2 ml fractions were collected and assayed (0.002 ml per sample) for kinase stimulation (as described in Example 6). The major peak of activity was pooled and dialyzed against 50 mM sodium phosphate buffer (pH 7.3). A Mono-S cation-exchange column (HR5/5, Pharmacia) was preequilibrated with 50 mM sodium phosphate. After loading the active material (0.884 mg of protein; 35 ml), the column was washed with the starting buffer and then developed at a rate of 1 ml/min. with a gradient of NaCl. The kinase stimulatory activity was recovered at 0.45–0.55M salt and was spread over four fractions of 2 ml each. These were pooled and loaded directly on a Cu$^{+2}$ chelating columns (1.6 ml, HR2/5 chelating Superose, Pharmacia). Most of the proteins adsorbed to the resin, but they gradually eluted with a 30 ml linear gradient of ammonium chloride (0–1M). The activity eluted in a single peak of protein at the range of 0.05 to 0.2M $NH_4Cl$. Samples from various steps of purification were analyzed by gel electrophoresis followed by silver staining using a kit from ICN (Costa Mesa, Calif.), and their protein contents were determined with a Coomassie blue dye binding assay using a kit from Bio-Rad (Richmond, Calif.).

The p44 protein (10 μg) was reconstituted in 200 μl of 0.1M ammonium bicarbonate buffer (pH 7.8). Digestion was conducted with L-1-tosyl-amide 2-phenylethyl chloromethyl ketone-treated trypsin (Serra) at 37° C. for 18 hr. at an enzyme-to-substrate ratio of 1:10. The resulting peptide mixture was separated by reverse-phase HPLC and monitored at 215 nm using a Vydac C4 micro column (2.1 mm i.d.×15 cm, 300 Å) and an HP 1090 liquid chromatographic system equipped with a diode-array detector and a workstation. The column was equilibrated with 0.1% trifluoroacetic acid (mobile phase A), and elution was effected with a linear gradient from 0%–55% mobile phase B (90% acetonitrile in 0.1% trifluoroacetic acid) over 70 min. The flow rate was 0.2 ml/min. and the column temperature was controlled at 25° C. One-third aliquots of the peptide peaks collected manually from the HPLC system were characterized by N-terminal sequence analysis by Edman degradation. The fraction eluted after 27.7 min. (T27.7) contained mixed amino acid sequences and was further rechromatographed after reduction as follows: A 70% aliquot of the peptide fraction was dried in vacuo and reconstituted in 100 μl of 0.2M ammonium bicarbonate buffer (pH 7.8). DTT (final concentration 2 mM) was added to the solution, which was then incubated at 37° C. for 30 min. The reduced peptide mixture was then separated by reverse-phase HPLC using a Vydac column (2.1 mm i.d.×15 cm). Elution conditions and flow ratwere identical to those described above. Amino acid sequence analysis of the peptide was performed with a Model 477 protein sequencer (Applied Biosystems, Inc., Foster City, Calif.) equipped with an on-line phenylthiohydantoin (PTH) amino acid analyzer and a Model 900 data analysis system (Hunkapiller et al. (1986) In *Methods of Protein Microcharacterization*, J. E. Shively, ed. (Clifton, N.J.: Humana Press p. 223–247). The protein was loaded onto a trifluoroacetic acid-treated glass fiber disc precycled with polybrene and NaCl. The PTH-amino acid analysis was performed with a micro liquid chromatography system (Model 120) using dual syringe pumps and reverse-phase (C-18) narrow bore columns (Applied Biosystems, 2.1 mm×250 mm).

RNA was isolated from Rat1-EJ cells by standard procedures (Manjarls et al., Molecular Cloning: A Laboratory Manual (Cold Spring Harbor, N.Y. (1982) and poly (A)$^+$ was selected using an mRNA Separator kit (Clontech Lab, Inc., Palo Alto, Calif.). cDNA was synthesized with the Superscript kit (from BRL Life Technologies, Inc., Bethesda, Md.). Column-fractionated double-strand cDNA was ligated into an SalI- and NotI-digested pJT-2 plasmid vector, a derivative of the pCD-X vector (Okayama and Berg, Mol. Cell Biol. 3: 280 (1983)) and transformed into DH10B *E. coli* cells by electropotation (Dower et al., Nucl. Acids Res. 16:6127 (1988)). Approximately 5×10$^5$ primary transformants were screened with two oligonucleotide probes that were derived from the protein sequences of the N-terminus of NDF (residues 5–24) and the T40.4 tryptic peptide (residues 7–12). Their respective sequences were as follows (N indicates all 4 nt):

```
(1) 5'-ATA GGG AAG GGC GGG GGA AGG GTC NCC CTC NGC
        A                             T
    AGG GCC GGG CTT GCC TCT GGA GCC TCT-3'

(2) 5'-TTT ACA CAT ATA TTC NCC-3'
        C   G       G   C
```

(1: SEQ ID No. 167; 2: SEQ ID No. 168)

The synthetic oligonucleotides were end-labeled with [γ-$^{32}$P]ATP with T4 polynucleotide kinass and used to screen replicate sets of nitrocellulose filters. The hybridization solution contained 6× SSC, 50 mM sodium phosphate (pH 6.8), 0.1% sodium pyrophosphate, 2× Denhardt's solution, 50 µg/ml salmon sperm DNA, and 20% formamide (for probe 1) or no formamide (for probe 2). The filters were washed at either 50° C. with 0.5× SSC, 0.2% SDS, 2 mM EDTA (for probe 1) or at 37° C. with 2× SSC, 0.2% SDS, 2 mM EDTA (for probe 2). Autoradiography of the filters gave ten clones that hybridized with both probes. These clones were purified by replating and probe hybridization as described above. The cDNA clones were sequenced using an Applied Biosystems 373A automated DNA sequencer and Applied Biosystems Taq DyeDeoxy™ Terminator cycle sequencing kits following the manufacture's instructions. In some instances, sequences were obtained using [$^{35}$S]dATP (Amersham) and Sequenase™ kits from U.S. Biochemicals following the manufacturer's instructions. Both strands of the cDNA clone 44 were sequenced by using synthetic oligonucleotides as primers. The sequence of the most 5' 350 nt was determined in seven independent cDNA clones. The resultant clone demonstrated the pattern shown in FIG. 30 (NDF).

EXAMPLE 10

Strategies for Detecting Other Possible Splicing Variants

Alignment of the deduced amino acid sequences of the cDNA clones and PCR products of the bovine, and the published human (FIG. 31) and rat sequences show a high level of similarity, indicating that these sequences are derived from homologous genes within the three species. The variable number of messenger RNA transcripts detectable at the cDNA/PCR product level is probably due to-extensive tissue-specific splicing. The patterns obtained and shown in FIG. 30 suggests that other splicing variants exist. A list of probable splicing variants is indicated in FIG. 37. Many of these variants can be obtained by coding segment specific probing of cDNA libraries derived from different tissues and by PCR experiments using primer pairs specific to particular coding segments. Alternatively, the variants can be assembled from specific cDNA clones, PCR products or genomic DNA regions via cutting and splicing techniques known to one skilled in the art. For example, a rare restriction enzyme cutting site in a common coding segment (e.g., A), can be used to connect the FBA amino terminus of GGF2BPP5 to carboxy terminal sequences of GGF2BPP1, GGFBPP2, GGFBPP3, or GGFBPP4. If the presence or the absence of coding segment E and/or G provide benefit for contemplated and stated uses, then these coding segments can be included in expression constructs. These variant sequences can be expressed in recombinant systems and the recombinant products can be assayed to determine their level of Schwann cell mitogenic activity as well as their ability to bind and activate the p185$^{erbB2}$ receptor.

EXAMPLE 11

Identification of Functional Elements of GGF

The deduced structures of the family of GGF sequences indicate that the longest forms (as represented by GGF2BPP4) encode transmembrane proteins where the extracellular part contains a domain which resembles epidermal growth factor (see Carpenter and Wahl in Peptide Growth Factors and Their Receptors I pp. 69–133, Springer-Verlag, N.Y. 1991). The positions of the cysteine residues in coding segments C and C/D or C/D' peptide sequence are conserved with respect to the analogous residues in the epidermal growth factor (EGF) peptide sequence (see FIG. 35, SEQ ID Nos. 151–153). This suggests that the extracellular domain functions as receptor recognition and biological activation sites. Several of the variant forms lack the H, K, and L coding segments and thus may be expressed as secreted, diffusible biologically active proteins. GGF DNA sequences encoding polypeptides which encompass the EGF-like domain (EGFL) can have full biological activity for stimulating glial cell mitogenic activity.

Membrane bound versions of this protein may induce Schwann cell proliferation if expressed on the surface of neurons during embryogenesis or during nerve regeneration (where the surfaces of neurons are intimately associated with the surfaces of proliferating Schwann cells).

Secreted (non membrane bound) GGFs may act as classically diffusible factors which can interact with Schwann cells at some distance from their point of secretion. Other forms may be released from intracells by sources via tissue injury and cell disruption. An example of a secreted GGF is the protein encoded by GGF2HBS5 (see example 6); this is the only GGF known which has been found to be directed to the exterior of the cell (example 7). Secretion is probably mediated via an N-terminal hydrophobic sequence found only in region E, which is the N-terminal domain contained within recombinant GGF-II encoded by GGF2HBS5.

Other GGF's appear to be non-secreted (see example 6). These GGFs may be injury response forms which are released as a consequence of tissue damage.

Other regions of the predicted protein structure of GGF-II (encoded by. GGF2HBS5) and other proteins containing regions B and A exhibit similarities to the human basement membrane heparin sulfate proteoglycan core protein (Kallunk, P. and Tryggvason, K., Cell Biology Vol. 116, p. 559–571 (1992)). The peptide ADSGEY, which is located next to the second cysteine of the C2 immunoglobulin fold in these GGF's, occurs in nine of twenty-two C-2 repeats found in that basal lamina protein. This evidence strongly suggests that these proteins may associate with matrix proteins such as those associated with neurons and glia, and may suggest a method for sequestration of glial growth factors at target sites.

EXAMPLE 12

Purification of GGFs from Recombinant Cells

In order to obtain full length or portions of GGFs to assay for biological activity, the proteins can be overproduced using cloned DNA. Several approaches can be used. A recombinant E. coli cell containing the sequences described above can be constructed. Expression systems such as pNH8a or pHH16a (Stratagens, Inc.) can be used for this purpose by following manufacturers procedures. Alternatively, these sequences can be inserted in a mammalian expression vector and an overproducing cell line can be constructed. As an example, for this purpose DNA encoding a GGF, clone GGF2BPP5 has been expressed in both COS cells and Chinese hamster ovary cells (see Example 7) (J. Biol. Chem. 263, 3521–3527, (1981)). This vector containing GGF DNA sequences can be transfected into host cells using established procedures.

Transient expression can be examined or G418-resistant clones can be grown in the presence of methotrexate to select for cells that amplify the dhfr gene (contained on the pMSXND vector) and, in the process, co-amplify the adjacent GGF protein encoding sequence. Because CHO cells can be maintained in a totally serum-free, protein-free medium (Hamilton and Ham, In Vitro 13, 537–547 (1977)), the desired protein can be purified from the medium. Western analysis using the antisera produced in Example 9 can be used to detect the presence of the desired protein in the conditioned medium of the overproducing cells.

Figure 50B:
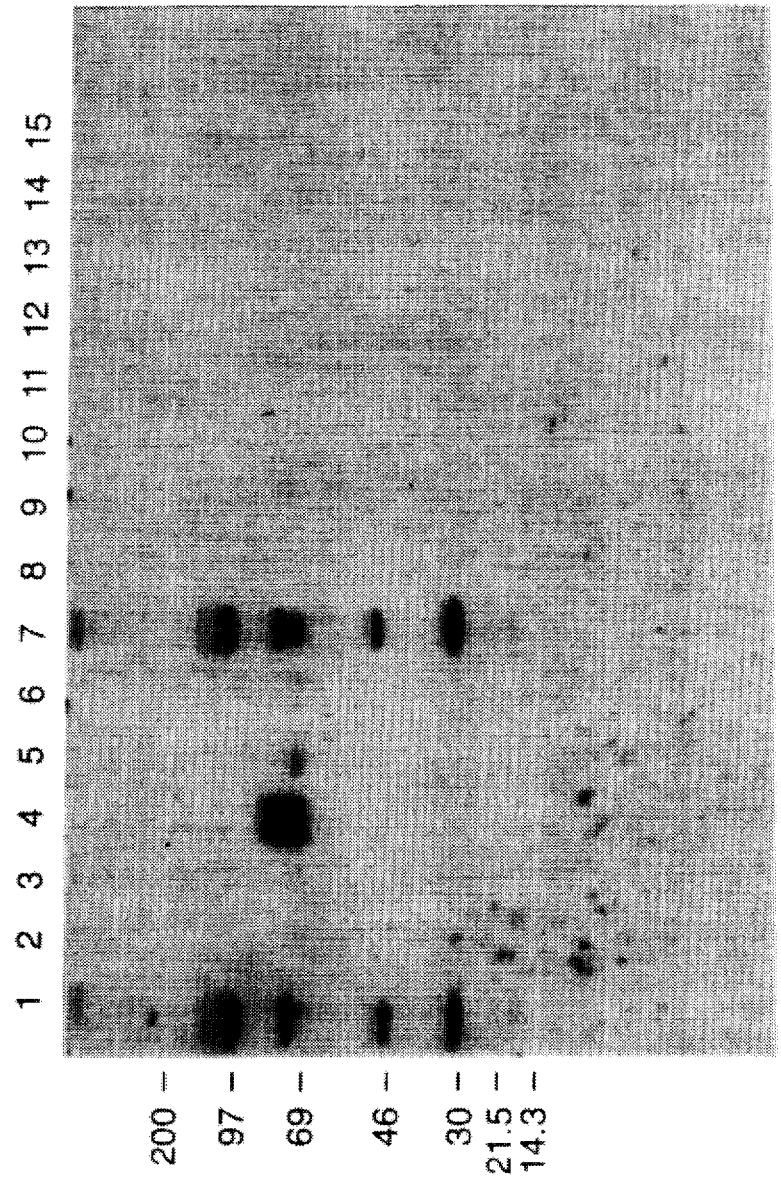
FIG. 50 (a) is a graph of Schwann cell proliferation activity of recombinant (COS cell produced) human GGF-II (rhGGF-II) peak eluted from the cation exchange column; (B) is an immunoblot against recombinant GGFII peak using polyclonal antibody made against specific peptide of rhGGFII.
Figure 51:
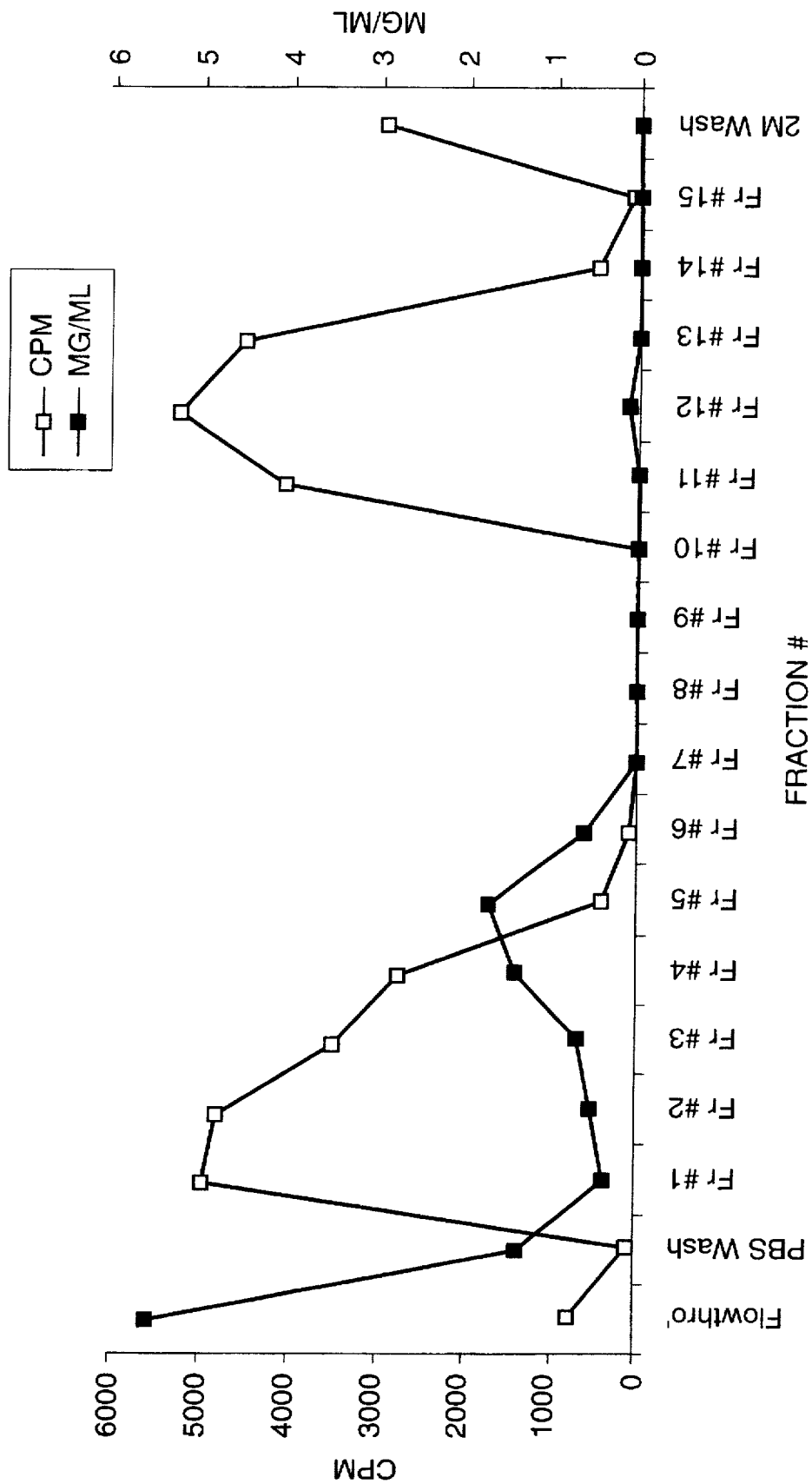
FIG. 51 shows purification of rGGF on a cation exchange column

The desired protein (rGGF-II) was purified from the medium conditioned by transiently expressing COS cells as follows. rGGF-II was harvested from the conditioned medium and partially purified using Cation Exchange Chromatography (POROS-HS). The column was equilibrated with 33.3 mM MES at pH 6.0. Conditioned media was loaded at flow rate of 10 ml/min. The peak containing Schwann cell proliferation activity and immunoreactive (using the polyclonal antisera was against a GGFII peptide described above) was eluted with 50 mM Tris, 1M NaCl pH 8.0. (FIG. 50A and 50B respectively).

rGGF-II is also expressed using a stable Chinese Hamster Ovary cell line. rGGF-II from the harvested conditioned media was partially purified using Cation Exchange Chromatograph (POROS-HS). The column was equilibrated with PBS pH 7.4. Conditioned media was loaded at 10 ml/min. The peak containing the Schwann Cell Proliferative activity and immunoreactivity (using GGFII polyclonal antisera) was eluted with 50 mM Hepes, 500 mM NaCl pH 8.0. An additional peak was observed at 50 mM Hepes, 1M NaCl pH 8.0 with both proliferation as well as immunoreactivity (FIG. 51).

rGGF-II can be further purified using Hydrophobic Interaction Chromatography as a high resolution step; Cation Exchange/Reverse phase Chromatography (if needed as second high resolution step); a viral inactivation step and a DNA removal step such as Anion Exchange chromatography.

Detailed description of procedures used are as follows:

Schwann Cell Proliferation Activity of the recombinant GGF-II peak eluted from the Cation Exchange column was determined as follows: Mitogenic responses of the cultured Schwann cells were measured in the presence of 5 μM forskolin using the peak eluted by 50 mM Tris 1M NaCl. pH 8.0. The peak was added at 20 1, 10 1 (1:10) 10 1 and (1:100) 10 1. Incorporation of $^{125}$I-Uridine was determined and expressed as (CPM) following an 18–24 hour exposure.

An immunoblot using polyclonal antibody raised against a peptide of GGF-II was carried out as follows: 10 μl of different fractions were run on 4–12% gradient gels. The gels were transferred on to Nitrocellulose paper, and the nitrocellulose blots were blocked with 5% BSA and probed with GGF-II-specific antibody (1:250 dilution). $^{125}$I protein A (1:500 dilution, Specific Activity=9.0/ci/g) was used as the secondary antibody. The immunoblots were exposed to Kodax X-Ray films for 6 hours. The peak fractions eluted with 1M NaCl showed a broad immunoreactive band at 65–90 Kd which is the expected size range for GGFII and higher molecular weight glycoforms.

GGF-II purification on cation exchange columns was performed as follows: CHO cell conditioned media expressing rGGFII was loaded on the cation exchange column at 10 ml/min. The column was equilibrated with PBS pH 7.4. The elution was achieved with 50 mM Hepes 500 mM NaCl pH 8.0 and 50 mM Hepes 1M NaCl pH 8.0 respectively. All fractions were analyzed using the Schwann cell proliferation assay (CPM) described herein. The protein concentration (mg/ml) was determined by the Bradford assay using BSA as the standard.

Figure 51A:
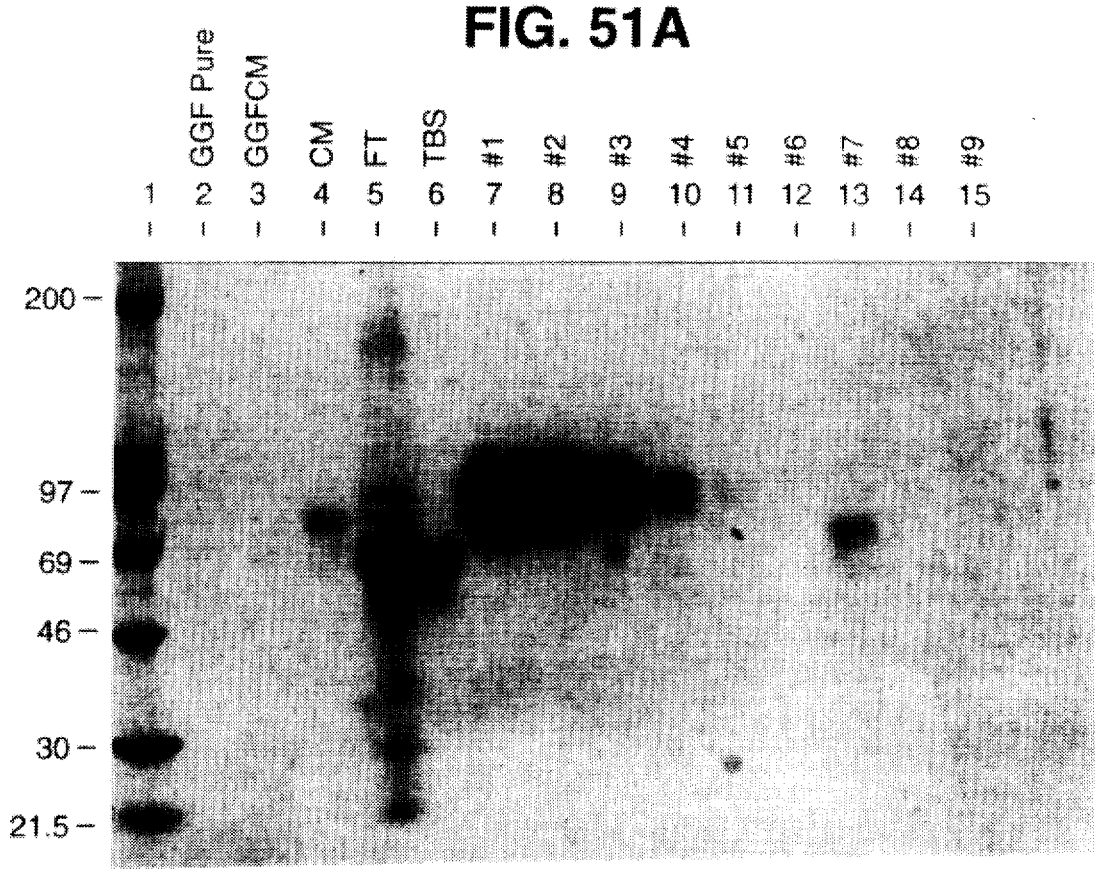
Figure 51B:
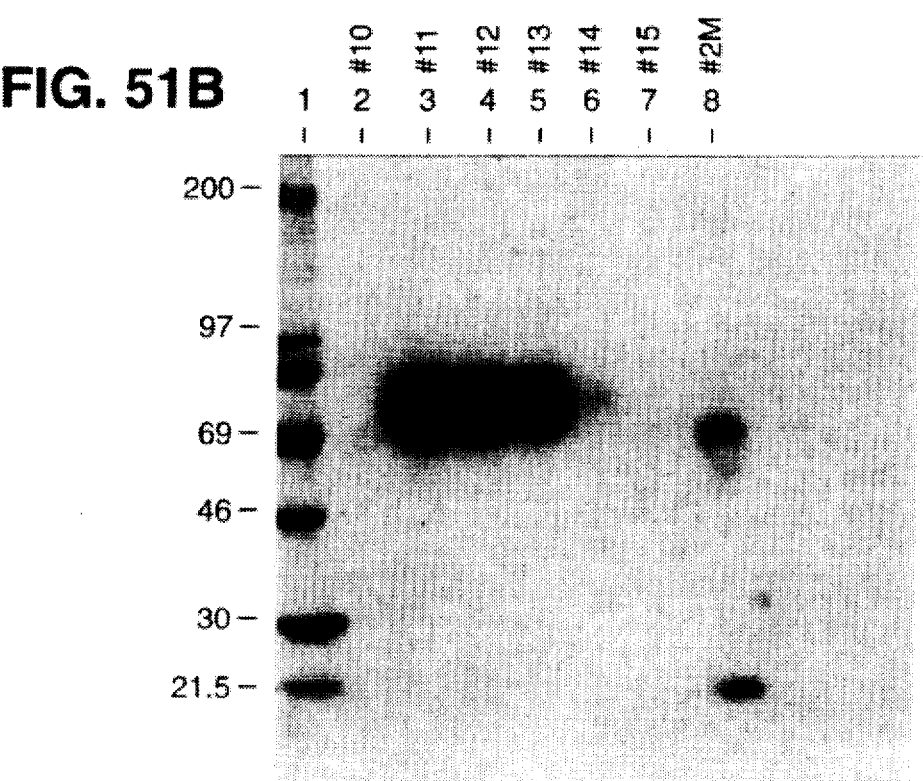

A Western blot using 10 μl of each fraction was performed. As indicated in FIG. 51A and 51B, immunoreactivity and the Schwann cell activity co-migrates.

The Schwann cell mitogenic assay described herein may be used to assay the expressed product of the full length clone or any biologically active portions thereof. The full length clone GGF2BPP5 has been expressed transiently in COS cells. Intracellular extracts of transfected COS cells show biological activity when assayed in the Schwann cell proliferation assay described in Example 1. In addition, the full length close encoding GGF2HBS5 has been expressed stably in CHO and insect vital systems (Example 7) cells. In this case both cell extract and conditioned media show biological activity in the Schwann cell proliferation assay described in Example 1. Any member of the family of splicing variant complementary DNA's derived from the GGF gene (including the Heregulins) can be expressed in this manner and assayed in the Schwann cell proliferation assay by one skilled in the art.

Alternatively, recombinant material may be isolated from other variants according to Wen et al. (Cell 69, 559 (1992)) who expressed the splicing variant Ned differentiation factor (NDF) in COS-7 cells. cDNA clones inserted in the pJT-2 eukaryotic plasmid vector are under the control of the SV40 early promoter, and are 3'-flanked with the SV40 termination and polyadenylation signals. COS-7 cells were transfected with the pJT-2 plasmid DNA by electropotation as follows: 6×10$^6$ cells (in 0.8 ml of DMEM and 10% FEBS) were transferred to a 0.4 cm cuvette and mixed with 20 μg of plasmid DNA in 10 μl of TE solution (10 mM Tris-HCl (pH 8.0), 1 mM EDTA). Electropotation was performed at room temperature at 1600 V and 25 μF using a Bio-Rad Gens Pulser apparatus with the pulse controller unit set at 200 ohms. The cells were then diluted into 20 ml of DMEM, 10% FBS and transferred into a T75 flask (Falcon). After 14 hr. of incubation at 37° C., the medium was replaced with DMEM, 1% FBS, and the incubation continued for an additional 48 hr. Conditioned medium containing recombinant protein which was harvested from the cells demonstrated biological activity in a cell line expressing the receptor for this protein. This cell line (cultured human breast carcinoma cell line AU 565) was treated with recombinant material. The treated cells exhibited a morphology change which is characteristic of the activation of the erbB2 receptor. Conditioned medium of this type also can be tested in the Schwann cell proliferation assay.

EXAMPLE 13

Purification and Assay of other Proteins which bind p185$^{erbB2}$ Receptor

I. Purification of gp30 and p70

Lupu et al. (Science 249, 1552 (1990)) and Lippman and Lupu (patent application number PCT/US91/03443 (1990)), hereby incorporated by reference, have purified a protein from conditioned media of a human breast cancer cell line MDA-MB-231, as follows.

Conditioned media collections were carried using well-known procedures. The media was concentrated 100-fold in an Amicon ultra-filtration cell (YM5 membrane) (Amicon, Danvers, Mass.). Once clarified and concentrated, the media were stored at −20° C. while consecutive collections were made during the following days. The concentrated media were dialyzed using Spectra/por® 3 tubing (Spectrum Medical Industries, Los Angeles, Calif.) against 100 volumes of 0.1M acetic acid over a two day period at 4° C. The material that precipitated during dialysis was removed by centrifugation at 4000 rpm for 30 min. at 4° C.; protease inhibitors were added. The clarified sample was then lyophilized.

Lyophilized conditioned medium was dissolved in 1M acetic acid to a final concentration of about 25 mg/ml total protein. Insoluble material was removed by centrifugation at 10,000 rpm for 15 minutes. The sample was then loaded onto a Sephadex G-100 column (XK 16, Pharmacia, Piscataway, N.J.), was equilibrated and was subjected to elution with 1M acetic acid at 4° C. with an upward flow of 30 ml/hr. 100 ng of protein was processed from 4 ml of 100-fold concentrated medium. Fractions containing 3 ml of eluate were lyophilized and resuspended in 300 μl PBS for assay and served as a source for further purification.

Sephadex G-100 purified material was run on reversed-phase high pressure liquid chromatography (HPLC). The first step involved a steep acetonitrile gradient. Steep acetonitrile gradient and all other HPLC steps were carried out at room temperature after equilibration of the C3-Reversed phase column with 0.05% TFA (Trifluoroacetic acid) An water (HPLC-grade). The samples were loaded and fractions were eluted with a linear gradient (0–45% acetonitrile An 0.05% TFA) at a flow rate of 1 ml/min. over a 30 minute period. Absorbance was monitored at 280 nm. One ml fractions were collected and lyophilized before analysis for EGF receptor-competing activity.

A second HPLC step involved a shallow acetonitrile gradient. The pool of active fractions from the previous HPLC step was rechromatographed over the same column. Elution was performed with a 0–18% acetonitrile gradient in 0.05% TFA over a 5 minute period followed by a linear 18–45% acetonitrile gradient in 0.05% TFA over a 30 minute period. The flow rate was 1.0 ml/min. and 1 ml fractions were collected. Human TGFα-like factor was eluted at a 30–32% acetonitrile-concentration as a single peak detectable by RRA.

Lupu et al. (Proc. Natl. Acad. Sci. 89, 2287 (1992)) purified another protein which binds to the p185$^{erbB2}$ receptor. This particular protein, p75, was purified from conditioned medium used for the growth of SKBr-3 (a human breast cancer cell line) propagated in improved Eagle's medium (IMEM: GIBCO) supplemented with 10% fetal bovine serum (GIBCO). Protein p75 was purified from concentrated (100X) conditioned medium using a p185$^{erbB2}$ affinity column. The 94 Kilodalton extracellular domain of p185$^{erbB2}$ (which binds p75) was produced via recombinant expression and was coupled to a polyacrylamide hydrazido-Sepharose affinity chromatography matrix. Following coupling the matrix was washed extensively with ice cold 1.0M HCl and the beads were activated with 0.5M NaNO$_2$. The temperature was maintained at 0° C. for 20 minutes and this was followed by filtration and washing with ice cold 0.1M HCl. 500 ml of concentrated conditioned medium was run through the beads by gravity. The column was washed and eluted stepwise with 1.0M citric acid at pH values from 4.0 to 2.0 (to allow dissociation of the erbB2 and p75). All fractions were desalted on Pharmacia PD10 columns. Purification yielded a homogeneous polypeptide of 75 kDa at 3.0–3.5 elution pH (confirmed by analysis on SDS/PAGE by silver staining).

II. Binding of gp30 to p185$^{erb}$B2

The purified gp30 protein was tested in an assay to determine if it bound to p185$^{erbB2}$. A competition assay with a monoclonal antibody against p185$^{erbB2}$. The gp30 protein displaced antibody binding to p185$^{erbB2}$ in SK-BR-3 and MDA-MB-453 cells (human breast carcinoma cell lines expressing the p185$^{erbB2}$ receptor). Schwann cell proliferation activity of gp30 can also be demonstrated by treating Schwann cell cultures with purified gp30 using the assay procedure described in Examples 1–3.

III. Binding of D75 to D185$^{erbB}$2

To assess whether the 75-kDa polypeptide (p75) obtained from SKBr-3 conditioned medium was indeed a ligand for the erbB2 oncoprotein in SKBr-3 cells, a competition assay as described above for gp30 was used. It was found that the p75 exhibited binding activity, whereas material from other chromatography fractions did not show such activity (data not shown). The flow-through material showed some binding activity. This might be due to the presence of shed erbB2 ECD.

IV. Other p185$^{erbB2}$ ligands

Pales et al. (Cell 69, 205 (1992)) have also purified a 185$^{erbB2}$ stimulating ligand from rat cells, (NDF, see Example 8 for method). Holmes et al. (Science 256, 1205 (1992)) have purified Heregulin a from human cells which binds and stimulates 185$^{erbB2}$ (see example 6). Tarakovsky et al. Oncogene 6:218 (1991) have demonstrated bending of a 25 kD polypeptide isolated from activated macrophages to the Ned receptor, a p185$^{erbB2}$ homology, herein incorporated by reference.

VI. NDF Isolation

Yarden and Peles (Biochemistry 30, 3543 (1991)) have identified a 35 kilodalton glycoprotein which will stimulate the 185$^{erbB2}$ receptor. The protein was identified conditioned medium according to the following procedure. Rat I-EJ cells were grown to confluence in 175-cm$^2$ flasks (Falcon). Monolayers were washed with PBS and left serum-free medium for 10–16 h. The medium was discarded and replaced by fresh serum-free medium that was collected after 3 days in culture. The conditioned medium was cleared by low-speed centrifugation and concentrated 100-fold in an Amicon ultrafiltration cell with a YM2 membrane (molecular weight cutoff of 2000). Biochemical analyses of the neu stimulatory activity in conditioned medium indicate that the ligand is a 35-kD glycoprotein that it is heat stable but sensitive to reduction. The factor is precipitable by either high salt concentrations or acidic alcohol. Partial purification of the molecule by selective precipitation, heparin-agarose chromatography, and gel filtration in dilute acid resulted in an active ligand, which is capable of stimulating the protooncogenic receptor but is ineffective on the oncogenic neu protein, which is constitutively active. The purified fraction, however, retained the ability to stimulate also the related receptor for EGF, suggesting that these two receptors are functionally coupled through a bidirectional mechanism. Alternatively, the presumed ligand interacts simultaneously with both receptors. The presented biochemical characteristic of the factor may be used to enable a completely purified factor with which to explore these possibilities.

In other publications, Davis et al. (Biochem. Biophys. Res. Commun. 179, 1536 (1991), Proc. Natl. Acad. Sci.88, 8582 (1991) and Greene et al., PCT patent application PCT/US91/02331 (1990)) describe the purification of a protein from conditioned medium of a human T-cell (ATL-2) cell line.

ATL-2 cell line is an IL-2-independent HTLV-1 (+) T cell line. Mycoplasm-free ATL-2 cells were maintained in RPMI 1640 medium containing 10% PCB as the culture medium (10% FCS-RPMI 1640) at 37° C. in a humidified atmosphere with 5% $CO_2$.

For purification of the proteinaceous substance, ATL-2 cells were washed twice in 1×PBS and cultured at $3\times10^5$ ml in serum-free RPMI 1640 medium/2 mM L-glutamine for seventy-two hours followed by pelleting of the cells. The culture supernatant so produced is termed "conditioned medium" (C.M.).

C.M. was concentrated 100 fold, from 1 liter to 10 ml, using a YM-2 Diaflo membrane (Amicon, Boston, Mass.) with a 1000d cutoff. For use in some assays, concentrated C.M. containing components greater than 1000 MW were rediluted to original volume with RPMI medium. Gel electrophoresis using a polyacrylamide gradient gel (Integrated Separation Systems, Hyde Park, Md. or Phorecast System by Amersham, Arlington Heights, Ill.) followed by silver staining of some of this two column purified material from the one liter preparation revealed at least four to five bands of which the 10 kD and 20 kD bands were unique to this material. Passed C.M. containing components less than 1000 NW were used without dilution.

Concentrated conditioned medium was filter sterilized with a 0.45µ uniflo filter (Schleicher and Schuell, Keene, N.H.) and then further purified by application to a DEAE-SW artion exchange column (Waters, Inc., Milford, Mass.) which had been preequilibrated with 10 mM Tris-Cl, pH 8.1 Concentrated C.M. proteins representing one liter of original ATL-2 conditioned medium per HPLC run were absorbed to the column and then eluted with a linear gradient of 0 mM to 40 mM NaCl at a flow rate of 4 ml/min. Fractions were assayed using an in vitro immune complex kinase assay with 10% of the appropriate DEAE fraction (1 column purified material) or 1% of the appropriate C18 fractions (two column purified material). The activity which increased the tyrosine kinase activity of p185c-neu in a dose-dependent manner using the in vitro immune complex kinase assay was eluted as one dominant peak across 4 to 5 fractions (36–40) around 220 to 240 mM of NaCl. After HPLC-DEAE purification, the proteins in the active fractions were concentrated and pooled, concentrated and subjected to C18 (million matrix) reverse phase chromatography (Waters, Inc., Milford, Mass.) (referred to as the C18+1 step or two column purified material). Elution was performed under a linear gradient of 2-propanol against 0.1% TFA. All the fractions were dialyzed against RPMI 1640 medium to remove the 2-propanol and assayed using the in vitro immune complex kinase assay, described below, and a 1% concentration of the appropriate fraction. The activity increasing the tyrosine kinas activity of p185c-neu was eluted in two peaks. One eluted in fraction 11–13, while a second, slightly less active peak of activity eluted in fractions 20–23. These two peaks correspond to around 5 to 7% of isopropanol and 11 to 14% isopropanol respectively. C18#1 generated fractions 11–13 were used in the characterization studies. Active fractions obtained from the second chromatographic step were pooled, and designated as the proteinaceous substance sample.

A twenty liter preparation employed the same purification strategy. The DEAE active fractions 35–41 were pooled and subjected to c18 chromatography as discussed above. C18#1 fractions 11–13 and 21–24 both had dose-dependent activity. The pool of fractions 11–13 was subjected to an additional C18 chromatographic step (referred to as C18#2 or three column purified material). Again, fractions 11–13 and 21–24 had activity. The dose response of fraction 23 determined by in vitro immune complex kinase assay as described in Example 8 may be obtained upon addition of 0.005% by volume fraction 23 and 0.05% by volume fraction 23. This represents the greatest purity achieved.

Molecular weight ranges were determined based on gel filtration chromatography and ultrafiltration membrane analysis. Near equal amounts of tyrosine kinass activity were retained and passed by a 10,000 molecular weight cut off filter. Almost all activity was passed by a 30,000 molecular weight cut off filter. Molecular weight ranges for active chromatographic fractions were determined by comparing fractions containing dose-dependent neu-activating activity to the elution profiles of a set of protein molecular weight standards (Sigma Chemical Co., St. Louis, Mo.) generated using the same running conditions. A low molecular weight region of activity was identified between 7,000 and 14,000 daltons. A second range of activity ranged from about 14,000 to about 24,000 daltons.

After gel electrophoresis using a polyacrylamide gradient gel (Integrated Separation Systems, Hyde Park, Md. or Phorecase System by Amersham, Arlington Heights, Ill.), silver staining of the three-column purified material (c18#2) was done with a commercially available silver staining kit (BioRad, Rockville Centre, N.Y.). Fraction 21, 22, 23, and 24 from c18#2 purification of the twenty liter preparation were run with markers. Fractions 22 and 23 showed the most potent dose response in the $185^{erbB2}$ (neu) kinass assay (see below). The fact that selected molecular weight fractions interact with $185^{erbB2}$ was demonstrated with an immune complex kinass assay.

Huang et al. (1992, J. Biol. Chem. 257:11508–11512), hereby incorporated by reference, have isolated an additional neu/erb B2 ligand growth factor from bovine kidney. The 25 kD polypeptide factor was isolated by a procedure of column fractionation, followed by sequential column chromatography on DEAE/cellulose (DE52), Sulfadex (sulfated Sephadex G-50), heparin-Sepharose 4B, and Superdex 75 (fast protein liquid chromatography). The factor, NEL-GF, stimulates tyrosine-specific autophosphorylation of the neu/ erb B2 gene product.

VII, Immune complex assay NDF for ligand binding to p185$^{erb}$B2

This assay reflects the differences in the autophosphorylation activity of immunoprecipitated p185 driven by preincubation of PN-NR6 cell lysate with varying amounts of ATL-2 conditioned medium (C.H.) or proteinaceous substance and is referred to hereinafter as neu-activating activity.

Cell lines used in the immune complex kinase assay were obtained, prepared and cultured according to the methods disclosed in Kokai et al., Cell 55, 287–292 (Jul. 28, 1989) the disclosures of which are hereby incorporated by reference as if fully set forth herein, and U.S. application Ser. No. 386,820 filed Jul. 27, 1989 in the name of Mark I. Green entitled "Methods of Treating Cancerous Cells with Anti-Receptor Antibodies", the disclosures of which are hereby incorporated by reference as if fully set forth herein.

Cell lines were all maintained in DMEM medium containing 5% FCS as the culture medium (5% FCS-DMEM) at 37° C. in a humidified atmosphere with 5% $CO_2$.

Dense cultures of cells in 150 mm dishes were washed twice with cold PBS, scraped into 10 ml of freeze-thaw buffer (150 mM NaCl, 1 mM $MgCl_2$, 20 mM Hepes, pH 7.2, 10% Glycerol, 1 mM EDTA, 1% Aprotinin), and centrifuged (600×6, 10 minutes). Cell pellets were resuspended in 1 ml Lysis buffer (50 mM Hepes, pH 7.5, 150 mM NaCl, 3% Brij 35, 1 mM EDTA, 1.5 mM $MgCl_2$, 1% Aprotinin, 1 mM EGTA, 20 µM $Na_3VO_4$, 10% Glycerol) and rotated for thirty minutes at 4° C. All chemicals were from Sigma Chemical Co., St. Louis, Mo., unless otherwise indicated. The insoluble materials were removed by centrifugation at 40,000× g for thirty minutes. The clear supernatant which was subsequently used is designated as cell lysate.

The cell lysates were incubated for fifteen minutes with 50 μl of 50% (volume/voluane) Protein A-sepharose (Sigma Chemical Co., St. Louis, Mo.), and centrifugated for two minutes to preclear the lysates. 50 μl aliquots of precleared cell lyeate were incubated on ice for fifteen minutes with conditioned medium, proteinaceous substance, or other factors as specified, in a final volume of 1 ml with lysis buffer. The sample was then incubated with 5 μg of 7.16.4 monoclonal antibody, which recognizes the extracellular domain of the p185neu and p185c-neu, or other appropriate antibodies, for twenty minutes on ice, followed by a twenty minute incubation with 50 μl of 50% (vol/vol) protein A-Sepharose with rotation at 4° C. Immune complexes were collected by centrifugation, washed four times with 500 μl of washing buffer (50 mM Hepes, pH 7.5, 0.1%, Brij 35, 150 mM NaCl, 2 mM EDTA, 1% Aprontinin, 30 μm $Na_3VO_4$), then twice with reaction buffer (20 mM Hepes (pH 7.4), 3 mM $MnCl_2$ and 0.1% Brij 35, 30 μm $Na_3VO_4$). Pellets were resuspended in 50 μl of reaction buffer and (Gamma-$^{32}$P]-ATP (Amersham, Arlington Heights, Ill.) was added giving a final concentration of 0.2 μm. The samples were incubated at 27° C. for twenty minutes or at 4° C. for 25 minutes with purer samples. The reactions were terminated by addition of 3× SDS sample buffer containing 2 mMATP and 2 mM EDTA and then incubating them at 100° C. for five minutes. The samples were then subjected to SDS-PAGE analysis on 10% acrylamide gels. Gels were stained, dried, and exposed to Kodak XAR or XRP film with intensifying screens.

VIII. Purification of acetylcholine receptor inducing activity (ARIA)

ARIA, a 42 kD protein which stimulates acetylcholine receptor synthesis, has been isolated in the laboratory of Gerald Fischbach (Falls et al., Cell 72:801–815 (1993)). ARIA induces tyrosine phosphorylation of a 185 Kda muscle transmembrane protein which resembles p185$^{erbB2}$, and stimulates acetylcholine receptor synthesis in cultured embryonic myotubes. Sequence analysis of cDNA clones which encode ARIA shows that ARIA is a member of the GGF/erbB2 ligand group of proteins, and this is potentially useful in the glial cell mitogenesis stimulation and other applications of, e.g., GGF2 described herein.

EXAMPLE 14

Protein Tyrosine Phosphorylation Mediated by GGF in Schwann Cells

Figure 36:
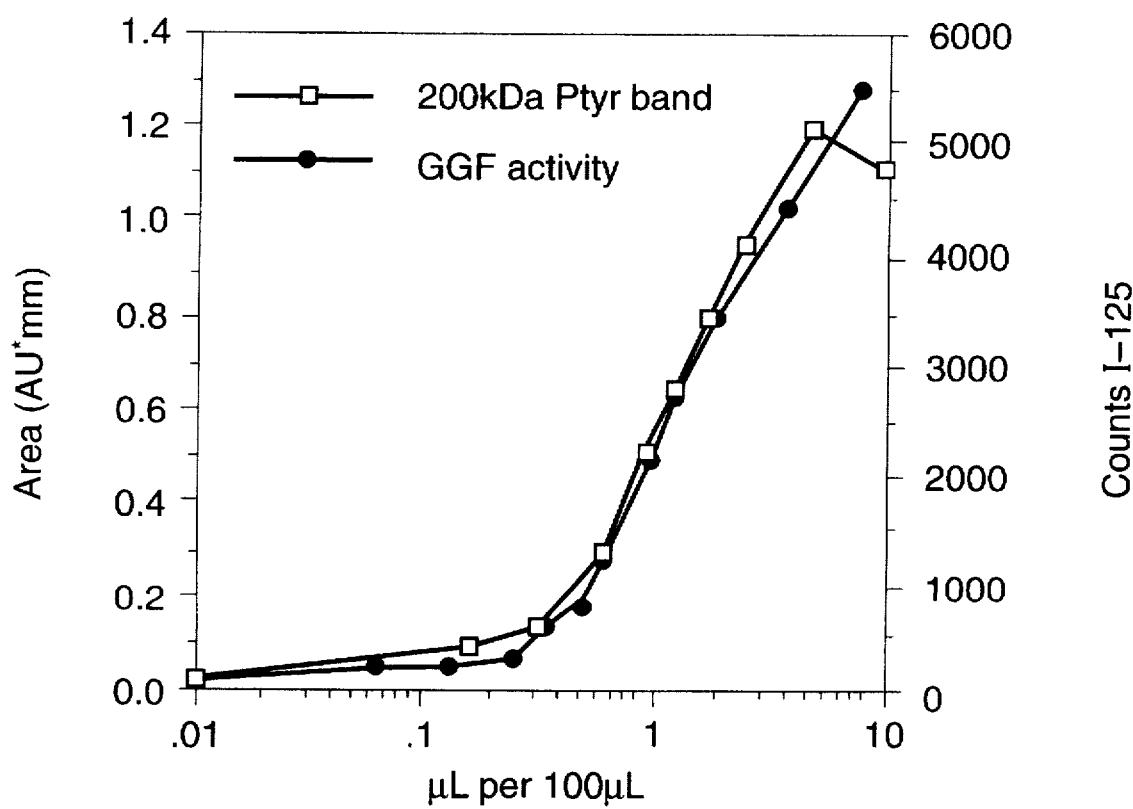

Rat Schwann cells, following treatment with sufficient levels of Glial Growth Factor to induce proliferation, show stimulation of protein tyrosine phosphorylation (FIG. 36). Varying amounts of partially purified GGF were applied to a primary culture of rat Schwann cells according to the procedure outlined in Example 3. Schwann cells were grown in DMEM/10% fetal calf serum/5 μM forskolin/0.5 μg per mL GGF-CM (0.5 mL per well) in poly D-lysine coated 24 well plates. When confluent, the cells were fed with DMEM/10% fetal calf serum at 0.5 mL per well and left in the incubator overnight to quiesce. The following day, the cells were fed with 0.2 mL of DMEM/10% fetal calf serum and left in the incubator for 1 hour. Test samples were then added directly to the medium at different concentrations and for different lengths of time as required. The cells were then lysed in boiling lysis buffer (sodium phosphate, 5 mM, pH 6.8; SDS, 2%, β-mercapteothanol, 5%; dithiothreitol, 0.114; glycerol, 10%; Bromophenol Blue, 0.4%; sodium vanadate, 10 mM), incubated in a boiling water bath for 10 minutes and then either analyzed directly or frozen at −70° C. Samples were analyzed by running on 7.5% SDS-PAGE gels and then electroblotting onto nitrocellulose using standard procedures as described by Towbin et al. (1979) Proc. Natl. Acad. Sci. USA 76:4350–4354. The blotted nitrocellulose was probed with antiphosphotyrosine antibodies using standard methods as described in Kamps and Selton (1988) Oncogene 2:305–315. The probed blots were exposed to autoradiography film overnight and developed using a standard laboratory processor. Densitometric measurements were carried out using an Ultrascan XL enhanced laser densitometer (LKB). Molecular weight assignments were made relative to prestained high molecular weight standards (Sigma). The dose responses of protein phosphorylation and Schwann cell proliferation are very similar (FIG. 36). The molecular weight of the phosphorylated band is very close to the molecular weight of p185$^{erbB2}$. Similar results were obtained when Schwann cells were treated with conditioned media prepared from COS cells translates with the GGF2HBS5 clone. These results correlate well with the expected interaction of the GGFs with and activation of 185$^{erbB2}$.

Figure 52:
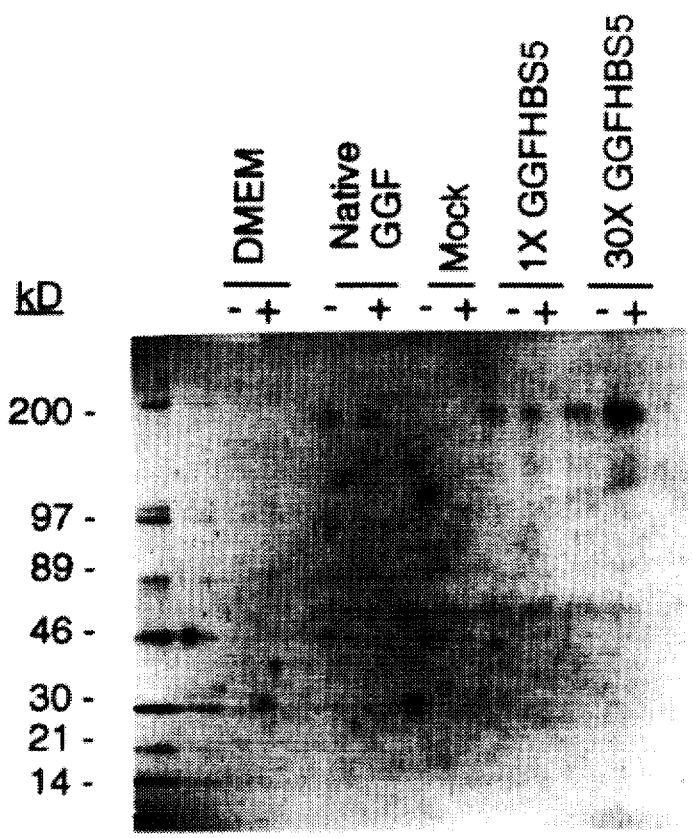
FIG. 52 is a photograph of a gel depicting tyrosine phosphorylation in Schwann cells treated with recombinant glial growth factors.

This experiment has been repeated with recombinant GGF-II. Conditioned medium derived from a CHO cell line stably transformed with the GGF-II clone (GGF2HBS5) stimulates protein tyrosine phosphorylation using the assay described above. Mock transfected CHO cells fail to stimulate this activity (FIG. 52).

EXAMPLE 15

Assay for Schwinn Cell Proliferation by Protein Factor from the MDA-M231 Cell Line.

Schwann cell proliferation is mediated by conditioned medium derived from the human breast cancer cell line MDA-MB-231. On day 1 of the assay, $10^4$ primary rat Schwann cells were plated in 100 μl of Dulbecco's Modified Eagle's medium supplemented with 5% fetal bovine plasma per well in a 96 well microtiter plate. On day 2 of the assay, 10 μl of conditioned medium (from the human breast cancer cell line MDA-MB-231, cultured as described in Example 6) was added to each well of the microtiter plate. One day 6, the number of Schwann cells per plate was determined using an acid phosphatase assay (according to the procedure of Connolly et al. Anal. Biochem. 152: 136 (1986)). The plate was washed with 100 μl of phosphate buffered saline (PBS) and 100 μl of reaction buffer (0.1M sodium acetate, (pH 5.5) ), 0.1% Triton X-100, and 10 mM p-nitrophenyl phosphate) was added per well. The plate was incubated at 37° C. for two hours and the reaction was stopped by the addition of 10 μl of 1N NaOH. The optical density of each sample was read in a spectrophotometer at 410 nm. A 38% stimulation of cell number over Schwann cells treated with conditioned medium from a control cell line (HS-294T, a non-producer of erbB-2 ligand) was observed. This result shows that a protein secreted by the MDA-MB-231 cell line (which secretes a p185$^{erbB2}$ binding activity) stimulates Schwann cell proliferation.

EXAMPLE 16

N-glycosylation of GGF

The protein sequence predicted from the cDNA sequence of GGF-II candidate clones GGF2BPP1,2 and 3 contains a number of consensus N-glycosylation motifs. A gap in the GGFIIO2 peptide sequence coincides with the asparagine residue in one of these motifs, indicating that carbohydrate is probably bound at this site.

N-glycosylation of the GGFs was studied by observing mobility changes on SDS-PAGE after incubation with N-glycanase, an enzyme that cleaves the covalent linkages between carbohydrate and aspargine residues in proteins.

N-Glycanase treatment of GGF-II yielded a major band of MW 40–42 kDa and a minor band at 45–48 kDa. Activity elution experiments under non-reducing conditions showed a single active deglycosylated species at ca 45–50 kDa.

Activity elution experiments with GGF-I also demonstrate an increase in electrophoretic mobility when treated with N-Glycanase, giving an active species of MW 26–28 kDa. Silver staining confirmed that there is a mobility shift, although no N-deglycosylated band could be assigned because of background staining in the sample used.

Deposit

Nucleic acid encoding GGF-II (cDNA, GGF2HBS5) protein (Example 6) in a plasmid pBluescript 5 k, under the control of the T7 promoter, was deposited in the American Type Culture Collection, Rockville, Md., on Sep. 2, 1992, and given ATCC Accession No. 75298. Applicant acknowledges its responsibility to replace this plasmid should it become non-viable before the end of the term of a patent issued hereon, and its responsibility to notify the ATCC of the issuance of such a patent, at which time the deposit will be made available to the public. Prior to that time the deposit will be made available to the Commissioner of Patents under the terms of 37 CFR §1.14 and 35 USC §112.

What is claimed is:

1. A method for obtaining a basic polypeptide factor having a molecular weight of from about 30 kD to about 36 kD on SDS-polyacrylamide gel electrophoresis which has mitogenic activity on rat Schwann cells in the presence of fetal calf plasma and, when isolated using reversed-phase HPLC retains at least 50% of its activity after 10 weeks incubation in 0.1% trifluoroacetic acid at 4° C., comprising extracting vertebrate brain material to obtain protein, subjecting said protein to chromatographic purification comprising hydroxylapatite HPLC and thereafter to SDS-polyacrylamide gel electrophoresis, and collecting a fraction therefrom which has an observed molecular weight of about 30 kD to 36 kD which stimulates division of rat Schwann cells against a background of fetal calf plasma.

2. The method of claim 1, wherein the vertebrate brain material is pituitary material.

3. The method of claim 2, wherein said pituitary material is bovine pituitary material.

4. The method of claim 1, comprising subjecting said vertebrate brain material to carboxymethyl cellulose chromatography prior to hydroxylapatite HPLC.

5. The method as claimed in claim 1 further comprising carrying out at least one step selected from the group consisting of cation exchange chromatography, gel filtration and reversed-phase HPLC, following said hydroxylapatite HPLC.

6. The method of claim 1 further comprising assaying for mitogenic activity by assaying purified fractions for stimulating the division of rat Schwann cells in the presence of fetal calf plasma following each step.

7. A method for obtaining basic polypeptide factor having a molecular weight, under non-reducing conditions, of from about 55 kD to about 63 kD via SDS-polyacrylamide gel electrophoresis, said polypeptide factor having mitogenic activity on rat Schwann cells in the presence of fetal calf plasma, and when isolated using reversed-phase HPLC retains at least about 50% of said mitogenic activity after 4 days incubation in 0.1% trifluoroacetic acid at 4° C., comprising extracting vertebrate brain material to obtain protein, subjecting said protein to chromatographic purification comprising hydroxylapatite HPLC and thereafter to SDS-polyacrylamide gel electrophoresis and collecting a fraction therefrom which has an observed molecular weight of about 55 kD to 63 kD and under non-reducing conditions, and which exhibits mitogenic activity by stimulating the division of rat Schwann cells against a background of fetal calf plasma.

8. The method of claim 7, wherein said vertebrate brain material is pituitary material.

9. The method of claim 7, wherein said pituitary material is bovine pituitary material.

10. The method of claim 7 wherein said comprising subjecting said vertebrate brain material to carboxymethyl cellulose chromatography prior to hydroxylapatite HPLC.

11. The method of claim 7, further comprising carrying out at least one step selected from the group consisting of cation exchange chromatography, gel filtration, and reversed-phase HPLC following hydroxylapatite HPLC.

12. The method of claim 7, further comprising assessing for mitogenic activity by assaying purified fractions for stimulating the division of rat Schwann cells in the presence of fetal calf plasma following each step.

* * * * *

SEQUENCE LISTING ( 1 ) GENERAL INFORMATION:

( i i i ) NUMBER OF SEQUENCES: 184

( 2 ) INFORMATION FOR SEQ ID NO: 1:

( i ) SEQUENCE CHARACTERISTICS:
( A ) LENGTH: 8
( B ) TYPE: amino acid
( C ) STRANDEDNESS:
( D ) TOPOLOGY: linear ( x i ) SEQUENCE DESCRIPTION: SEQ ID NO: 1:

Phe Lys Gly Asp Ala His Thr Glu
 1                   5

( 2 ) INFORMATION FOR SEQ ID NO: 2:

( i ) SEQUENCE CHARACTERISTICS:
( A ) LENGTH: 13
( B ) TYPE: amino acid
( C ) STRANDEDNESS:
( D ) TOPOLOGY: linear ( i x ) FEATURE:
( D ) OTHER INFORMATION: Xaa in position 1 is Lysine or
Arginine; Xaa in position 12 is unknown.

( x i ) SEQUENCE DESCRIPTION: SEQ ID NO: 2:

Xaa Ala Ser Leu Ala Asp Glu Tyr Glu Tyr Met Xaa Lys
             5                        1 0

( 2 ) INFORMATION FOR SEQ ID NO: 3:

( i ) SEQUENCE CHARACTERISTICS:
( A ) LENGTH: 12
( B ) TYPE: amino acid
( C ) STRANDEDNESS:
( D ) TOPOLOGY: linear ( i x ) FEATURE:
( D ) OTHER INFORMATION: Xaa in position 1 is Lysine or
Arginine; Xaa in position 10 is unknown.

( x i ) SEQUENCE DESCRIPTION: SEQ ID NO: 3:

Xaa Thr Glu Thr Ser Ser Ser Gly Leu Xaa Leu Lys
 1               5                    1 0

( 2 ) INFORMATION FOR SEQ ID NO: 4:

( i ) SEQUENCE CHARACTERISTICS:
            ( A ) LENGTH: 9
            ( B ) TYPE: amino acid
            ( C ) STRANDEDNESS:
            ( D ) TOPOLOGY: linear ( i x ) FEATURE:
            ( D ) OTHER INFORMATION: Xaa in position 1 is Lysine or
                Arginine.

( x i ) SEQUENCE DESCRIPTION: SEQ ID NO: 4:

Xaa Lys Leu Gly Glu Met Trp Ala Glu
 1                   5

( 2 ) INFORMATION FOR SEQ ID NO: 5:

( i ) SEQUENCE CHARACTERISTICS:
            ( A ) LENGTH: 7
            ( B ) TYPE: amino acid
            ( C ) STRANDEDNESS:
            ( D ) TOPOLOGY: linear ( i x ) FEATURE:
            ( D ) OTHER INFORMATION: Xaa in position 1 is Lysine or
                Arginine.

( x i ) SEQUENCE DESCRIPTION: SEQ ID NO: 5:

Xaa Leu Gly Glu Lys Arg Ala
 1                   5

( 2 ) INFORMATION FOR SEQ ID NO: 6:

( i ) SEQUENCE CHARACTERISTICS:
            ( A ) LENGTH: 16
            ( B ) TYPE: amino acid
            ( C ) STRANDEDNESS:
            ( D ) TOPOLOGY: linear ( i x ) FEATURE:
            ( D ) OTHER INFORMATION: Xaa in position 1 is Lysine or
                Arginine.

( x i ) SEQUENCE DESCRIPTION: SEQ ID NO: 6:

Xaa Ile Lys Ser Glu His Ala Gly Leu Ser Ile Gly Asp Thr Ala Lys
 1                   5                  10                  15

( 2 ) INFORMATION FOR SEQ ID NO: 7:

( i ) SEQUENCE CHARACTERISTICS:
            ( A ) LENGTH: 13
            ( B ) TYPE: amino acid
            ( C ) STRANDEDNESS:
            ( D ) TOPOLOGY: linear ( i x ) FEATURE:
            ( D ) OTHER INFORMATION: Xaa in position 1 is Lysine or
                Arginine.

( x i ) SEQUENCE DESCRIPTION: SEQ ID NO: 7:

Xaa Ala Ser Leu Ala Asp Glu Tyr Glu Tyr Met Arg Lys
 1                   5                  10

( 2 ) INFORMATION FOR SEQ ID NO: 8:

( i ) SEQUENCE CHARACTERISTICS:
            ( A ) LENGTH: 16
            ( B ) TYPE: amino acid
            ( C ) STRANDEDNESS:
            ( D ) TOPOLOGY: linear ( i x ) FEATURE:
            ( D ) OTHER INFORMATION: Xaa in position 1 is Lysine or Arginine.

( x i ) SEQUENCE DESCRIPTION: SEQ ID NO: 8:

```
Xaa Ile Lys Gly Glu His Pro Gly Leu Ser Ile Gly Asp Val Ala Lys
 1               5                   10                  15
```

( 2 ) INFORMATION FOR SEQ ID NO: 9:

( i ) SEQUENCE CHARACTERISTICS:
        ( A ) LENGTH: 13
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is Lysine or
        Arginine and Xaa in position 12 is unknown.

( x i ) SEQUENCE DESCRIPTION: SEQ ID NO: 9:

```
Xaa Met Ser Glu Tyr Ala Phe Phe Val Gln Thr Xaa Arg
 1               5                   10
```

( 2 ) INFORMATION FOR SEQ ID NO: 10:

( i ) SEQUENCE CHARACTERISTICS:
        ( A ) LENGTH: 14
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is Lysine or
        Arginine.

( x i ) SEQUENCE DESCRIPTION: SEQ ID NO: 10:

```
Xaa Ser Glu His Pro Gly Leu Ser Ile Gly Asp Thr Ala Lys
 1               5                   10
```

( 2 ) INFORMATION FOR SEQ ID NO: 11:

( i ) SEQUENCE CHARACTERISTICS:
        ( A ) LENGTH: 10
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is Lysine or
        Arginine; Xaa in position 8 is unknown.

( x i ) SEQUENCE DESCRIPTION: SEQ ID NO: 11:

```
Xaa Ala Gly Tyr Phe Ala Glu Xaa Ala Arg
 1               5                   10
```

( 2 ) INFORMATION FOR SEQ ID NO: 12:

( i ) SEQUENCE CHARACTERISTICS:
        ( A ) LENGTH: 9
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is Lysine or
        Arginine; Xaa in position 7 is unknown.

( x i ) SEQUENCE DESCRIPTION: SEQ ID NO: 12:

```
Xaa Lys Leu Glu Phe Leu Xaa Ala Lys
 1               5
```

( 2 ) INFORMATION FOR SEQ ID NO: 13:

( i ) SEQUENCE CHARACTERISTICS:
        ( A ) LENGTH: 11
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is Lysine or Arginine.

( x i ) SEQUENCE DESCRIPTION: SEQ ID NO: 13:

```
Xaa  Thr  Thr  Glu  Met  Ala  Ser  Glu  Gln  Gly  Ala
 1                 5                           10
```

( 2 ) INFORMATION FOR SEQ ID NO: 14:

( i ) SEQUENCE CHARACTERISTICS:
        ( A ) LENGTH: 10
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is Lysine or Arginine.

( x i ) SEQUENCE DESCRIPTION: SEQ ID NO: 14:

```
Xaa  Ala  Lys  Glu  Ala  Leu  Ala  Ala  Leu  Lys
 1                 5                           10
```

( 2 ) INFORMATION FOR SEQ ID NO: 15:

( i ) SEQUENCE CHARACTERISTICS:
        ( A ) LENGTH: 8
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is Lysine or Arginine.

( x i ) SEQUENCE DESCRIPTION: SEQ ID NO: 15:

```
Xaa  Phe  Val  Leu  Gln  Ala  Lys  Lys
 1                 5
```

( 2 ) INFORMATION FOR SEQ ID NO: 16:

( i ) SEQUENCE CHARACTERISTICS:
        ( A ) LENGTH: 6
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is Lysine or Arginine.

( x i ) SEQUENCE DESCRIPTION: SEQ ID NO: 16:

```
Xaa  Leu  Gly  Glu  Met  Trp
 1                 5
```

( 2 ) INFORMATION FOR SEQ ID NO: 17:

( i ) SEQUENCE CHARACTERISTICS:
        ( A ) LENGTH: 16
        ( B ) TYPE: amino acid
        ( C ) STRANDEDNESS:
        ( D ) TOPOLOGY: linear ( x i ) SEQUENCE DESCRIPTION: SEQ ID NO: 17:

Glu Tyr Lys Cys Leu Lys Phe Lys Trp Phe Lys Lys Ala Thr Val Met
1               5                   10                  15

( 2 ) INFORMATION FOR SEQ ID NO: 18:

( i ) SEQUENCE CHARACTERISTICS:
        ( A ) LENGTH: 10
        ( B ) TYPE: amino acid
        ( C ) STRANDEDNESS:
        ( D ) TOPOLOGY: linear ( i x ) FEATURE:
        ( D ) OTHER INFORMATION: Xaa in position 8 is unknown.

( x i ) SEQUENCE DESCRIPTION: SEQ ID NO: 18:

Glu Ala Lys Tyr Phe Ser Lys Xaa Asp Ala
1               5                   10

( 2 ) INFORMATION FOR SEQ ID NO: 19:

( i ) SEQUENCE CHARACTERISTICS:
        ( A ) LENGTH: 7
        ( B ) TYPE: amino acid
        ( C ) STRANDEDNESS:
        ( D ) TOPOLOGY: linear ( i x ) FEATURE:
        ( D ) OTHER INFORMATION: Xaa in position 2 is unknown.

( x i ) SEQUENCE DESCRIPTION: SEQ ID NO: 19:

Glu Xaa Lys Phe Tyr Val Pro
1               5

( 2 ) INFORMATION FOR SEQ ID NO: 20:

( i ) SEQUENCE CHARACTERISTICS:
        ( A ) LENGTH: 26
        ( B ) TYPE: amino acid
        ( C ) STRANDEDNESS:
        ( D ) TOPOLOGY: linear ( x i ) SEQUENCE DESCRIPTION: SEQ ID NO: 20:

Glu Leu Ser Phe Ala Ser Val Arg Leu Pro Gly Cys Pro Pro Gly Val
1               5                   10                  15

Asp Pro Met Val Ser Phe Pro Val Ala Leu
                20                  25

( 2 ) INFORMATION FOR SEQ ID NO: 21:

( i ) SEQUENCE CHARACTERISTICS:
        ( A ) LENGTH: 2003
        ( B ) TYPE: nucleic acid
        ( C ) STRANDEDNESS: single
        ( D ) TOPOLOGY: linear ( i x ) FEATURE:
        ( D ) OTHER INFORMATION: N in positions 31 and 32 could be
            either A or G.

( x i ) SEQUENCE DESCRIPTION: SEQ ID NO: 21:

| | | | | | |
|---|---|---|---|---|---|
| GGAATTCCTT | TTTTTTTTTT | TTTTTTTCTT | NNTTTTTTTT | TGCCCTTATA | CCTCTTCGCC | 60 |
| TTTCTGTGGT | TCCATCCACT | TCTTCCCCCT | CCTCCTCCCA | TAAACAACTC | TCCTACCCCT | 120 |
| GCACCCCCAA | TAAATAAATA | AAAGGAGGAG | GGCAAGGGGG | GAGGAGGAGG | AGTGGTGCTG | 180 |
| CGAGGGGAAG | GAAAAGGGAG | GCAGCGCGAG | AAGAGCCGGG | CAGAGTCCGA | ACCGACAGCC | 240 |
| AGAAGCCCGC | ACGCACCTCG | CACC ATG AGA | TGG CGA CGC | GCC CCG CGC | CGC | 291 |

```
                      Met Arg Trp Arg Arg Ala Pro Arg Arg
                       1                   5

TCC GGG CGT CCC GGC CCC CGG GCC CAG CGC CCC GGC TCC GCC GCC CGC      339
Ser Gly Arg Pro Gly Pro Arg Ala Gln Arg Pro Gly Ser Ala Ala Arg
 10              15                  20                  25

TCG TCG CCG CCG CTG CCG CTG CTG CCA CTA CTG CTG CTG CTG GGG ACC      387
Ser Ser Pro Pro Leu Pro Leu Leu Pro Leu Leu Leu Leu Leu Gly Thr
             30                  35                  40

GCG GCC CTG GCG CCG GGG GCG GCG GCC GGC AAC GAG GCG GCT CCC GCG      435
Ala Ala Leu Ala Pro Gly Ala Ala Ala Gly Asn Glu Ala Ala Pro Ala
         45                  50                  55

GGG GCC TCG GTG TGC TAC TCG TCC CCG CCC AGC GTG GGA TCG GTG CAG      483
Gly Ala Ser Val Cys Tyr Ser Ser Pro Pro Ser Val Gly Ser Val Gln
     60                  65                  70

GAG CTA GCT CAG CGC GCC GCG GTG GTG ATC GAG GGA AAG GTG CAC CCG      531
Glu Leu Ala Gln Arg Ala Ala Val Val Ile Glu Gly Lys Val His Pro
 75                  80                  85

CAG CGG CGG CAG CAG GGG GCA CTC GAC AGG AAG GCG GCG GCG GCG GCG      579
Gln Arg Arg Gln Gln Gly Ala Leu Asp Arg Lys Ala Ala Ala Ala Ala
 90                  95                 100                 105

GGC GAG GCA GGG GCG TGG GGC GGC GAT CGC GAG CCG CCA GCC GCG GGC      627
Gly Glu Ala Gly Ala Trp Gly Gly Asp Arg Glu Pro Pro Ala Ala Gly
             110                 115                 120

CCA CGG GCG CTG GGG CCG CCC GCC GAG GAG CCG CTC CTC GCC GCC AAC      675
Pro Arg Ala Leu Gly Pro Pro Ala Glu Glu Pro Leu Leu Ala Ala Asn
         125                 130                 135

GGG ACC GTG CCC TCT TGG CCC ACC GCC CCG GTG CCC AGC GCC GGC GAG      723
Gly Thr Val Pro Ser Trp Pro Thr Ala Pro Val Pro Ser Ala Gly Glu
     140                 145                 150

CCC GGG GAG GAG GCG CCC TAT CTG GTG AAG GTG CAC CAG GTG TGG GCG      771
Pro Gly Glu Glu Ala Pro Tyr Leu Val Lys Val His Gln Val Trp Ala
 155                 160                 165

GTG AAA GCC GGG GGC TTG AAG AAG GAC TCG CTG CTC ACC GTG CGC CTG      819
Val Lys Ala Gly Gly Leu Lys Lys Asp Ser Leu Leu Thr Val Arg Leu
 170                 175                 180                 185

GGG ACC TGG GGC CAC CCC GCC TTC CCC TCC TGC GGG AGG CTC AAG GAG      867
Gly Thr Trp Gly His Pro Ala Phe Pro Ser Cys Gly Arg Leu Lys Glu
             190                 195                 200

GAC AGC AGG TAC ATC TTC TTC ATG GAG CCC GAC GCC AAC AGC ACC AGC      915
Asp Ser Arg Tyr Ile Phe Phe Met Glu Pro Asp Ala Asn Ser Thr Ser
             205                 210                 215

CGC GCG CCG GCC GCC TTC CGA GCC TCT TTC CCC CCT CTG GAG ACG GGC      963
Arg Ala Pro Ala Ala Phe Arg Ala Ser Phe Pro Pro Leu Glu Thr Gly
         220                 225                 230

CGG AAC CTC AAG AAG GAG GTC AGC CGG GTG CTG TGC AAG CGG TGC GCC     1011
Arg Asn Leu Lys Lys Glu Val Ser Arg Val Leu Cys Lys Arg Cys Ala
 235                 240                 245

TTG CCT CCC CAA TTG AAA GAG ATG AAA AGC CAG GAA TCG GCT GCA GGT     1059
Leu Pro Pro Gln Leu Lys Glu Met Lys Ser Gln Glu Ser Ala Ala Gly
 250                 255                 260                 265

TCC AAA CTA GTC CTT CGG TGT GAA ACC AGT TCT GAA TAC TCC TCT CTC     1107
Ser Lys Leu Val Leu Arg Cys Glu Thr Ser Ser Glu Tyr Ser Ser Leu
             270                 175                 180

AGA TTC AAG TGG TTC AAG AAT GGG AAT GAA TTG AAT CGA AAA AAC AAA     1155
Arg Phe Lys Trp Phe Lys Asn Gly Asn Glu Leu Asn Arg Lys Asn Lys
             185                 190                 195

CCA CAA AAT ATC AAG ATA CAA AAA AAG CCA GGG AAG TCA GAA CTT CGC     1203
Pro Gln Asn Ile Lys Ile Gln Lys Lys Pro Gly Lys Ser Glu Leu Arg
         200                 205                 210

ATT AAC AAA GCA TCA CTG GCT GAT TCT GGA GAG TAT ATG TGC AAA GTG     1251
```

| | | | | | | | | | | | | | | |
|---|---|---|---|---|---|---|---|---|---|---|---|---|---|---|
| Ile | Asn | Lys | Ala | Ser | Leu | Ala | Asp | Ser | Gly | Glu | Tyr | Met | Cys | Lys | Val |
| 215 | | | | | 220 | | | | | | 225 | | | | |

| ATC | AGC | AAA | TTA | GGA | AAT | GAC | AGT | GCC | TCT | GCC | AAT | ATC | ACC | ATC | GTG | 1299 |
|---|---|---|---|---|---|---|---|---|---|---|---|---|---|---|---|---|
| Ile | Ser | Lys | Leu | Gly | Asn | Asp | Ser | Ala | Ser | Ala | Asn | Ile | Thr | Ile | Val | |
| 230 | | | | | 235 | | | | | 240 | | | | | 245 | |

| GAA | TCA | AAC | GCT | ACA | TCT | ACA | TCC | ACC | ACT | GGG | ACA | AGC | CAT | CTT | GTA | 1347 |
|---|---|---|---|---|---|---|---|---|---|---|---|---|---|---|---|---|
| Glu | Ser | Asn | Ala | Thr | Ser | Thr | Ser | Thr | Thr | Gly | Thr | Ser | His | Leu | Val | |
| | | | | 250 | | | | | 255 | | | | | 260 | | |

| AAA | TGT | GCG | GAG | AAG | GAG | AAA | ACT | TTC | TGT | GTG | AAT | GGA | GGG | GAG | TGC | 1395 |
|---|---|---|---|---|---|---|---|---|---|---|---|---|---|---|---|---|
| Lys | Cys | Ala | Glu | Lys | Glu | Lys | Thr | Phe | Cys | Val | Asn | Gly | Gly | Glu | Cys | |
| | | | 265 | | | | | 270 | | | | 275 | | | | |

| TTC | ATG | GTG | AAA | GAC | CTT | TCA | AAC | CCC | TCG | AGA | TAC | TTG | TGC | AAG | TGC | 1443 |
|---|---|---|---|---|---|---|---|---|---|---|---|---|---|---|---|---|
| Phe | Met | Val | Lys | Asp | Leu | Ser | Asn | Pro | Ser | Arg | Tyr | Leu | Cys | Lys | Cys | |
| | | 280 | | | | | 285 | | | | 290 | | | | | |

| CCA | AAT | GAG | TTT | ACT | GGT | GAT | CGC | TGC | CAA | AAC | TAC | GTA | ATG | GCC | AGC | 1491 |
|---|---|---|---|---|---|---|---|---|---|---|---|---|---|---|---|---|
| Pro | Asn | Glu | Phe | Thr | Gly | Asp | Arg | Cys | Gln | Asn | Tyr | Val | Met | Ala | Ser | |
| 295 | | | | | 300 | | | | | | 305 | | | | | |

| TTC | TAC | AGT | ACG | TCC | ACT | CCC | TTT | CTG | TCT | CTG | CCT | GAA | | | | 1530 |
|---|---|---|---|---|---|---|---|---|---|---|---|---|---|---|---|---|
| Phe | Tyr | Ser | Thr | Ser | Thr | Pro | Phe | Leu | Ser | Leu | Pro | Glu | | | | |
| 400 | | | | | 405 | | | | | 410 | | | | | | |

| TAGGAGCATG | CTCAGTTGGT | GCTGCTTTCT | TGTTGCTGCA | TCTCCCCTCA | GATTCCACCT | 1590 |
|---|---|---|---|---|---|---|
| AGAGCTAGAT | GTGTCTTACC | AGATCTAATA | TTGACTGCCT | CTGCCTGTCG | CATGAGAACA | 1650 |
| TTAACAAAAG | CAATTGTATT | ACTTCCTCTG | TTCGCGACTA | GTTGGCTCTG | AGATACTAAT | 1710 |
| AGGTGTGTGA | GGCTCCGGAT | GTTTCTGGAA | TTGATATTGA | ATGATGTGAT | ACAAATTGAT | 1770 |
| AGTCAATATC | AAGCAGTGAA | ATATGATAAT | AAAGGCATTT | CAAAGTCTCA | CTTTTATTGA | 1830 |
| TAAAATAAAA | ATCATTCTAC | TGAACAGTCC | ATCTTCTTTA | TACAATGACC | ACATCCTGAA | 1890 |
| AAGGGTGTTG | CTAAGCTGTA | ACCGATATGC | ACTTGAAATG | ATGGTAAGTT | AATTTTGATT | 1950 |
| CAGAATGTGT | TATTTGTCAC | AAATAAACAT | AATAAAAGGA | AAAAAAAAA | AAA | 2003 |

( 2 ) INFORMATION FOR SEQ ID NO: 22:

( i ) SEQUENCE CHARACTERISTICS:
        ( A ) LENGTH: 12
        ( B ) TYPE: amino acid
        ( C ) STRANDEDNESS:
        ( D ) TOPOLOGY: linear ( i x ) FEATURE:
        ( D ) OTHER INFORMATION: Xaa in position 11 is unknown.

( x i ) SEQUENCE DESCRIPTION: SEQ ID NO: 22:

| Ala | Ser | Leu | Ala | Asp | Glu | Tyr | Glu | Tyr | Met | Xaa | Lys |
|---|---|---|---|---|---|---|---|---|---|---|---|
| 1 | | | | 5 | | | | | 10 | | |

( 2 ) INFORMATION FOR SEQ ID NO: 23:

( i ) SEQUENCE CHARACTERISTICS:
        ( A ) LENGTH: 11
        ( B ) TYPE: amino acid
        ( C ) STRANDEDNESS:
        ( D ) TOPOLOGY: linear ( i x ) FEATURE:

( D ) OTHER INFORMATION: Xaa in position 9 is unknown.

( x i ) SEQUENCE DESCRIPTION: SEQ ID NO: 23:

| Thr | Glu | Thr | Ser | Ser | Ser | Gly | Leu | Xaa | Leu | Lys |
|---|---|---|---|---|---|---|---|---|---|---|
| 1 | | | | 5 | | | | | 10 | |

( 2 ) INFORMATION FOR SEQ ID NO: 24:

(i) SEQUENCE CHARACTERISTICS:
        (A) LENGTH: 12
        (B) TYPE: amino acid
        (C) STRANDEDNESS:
        (D) TOPOLOGY: linear (xi) SEQUENCE DESCRIPTION: SEQ ID NO: 24:

Ala Ser Leu Ala Asp Glu Tyr Glu Tyr Met Arg Lys
 1               5                   10

(2) INFORMATION FOR SEQ ID NO: 25:

(i) SEQUENCE CHARACTERISTICS:
        (A) LENGTH: 9
        (B) TYPE: amino acid
        (C) STRANDEDNESS:
        (D) TOPOLOGY: linear (ix) FEATURE:
        (D) OTHER INFORMATION: Xaa in position 7 is unknown.

(xi) SEQUENCE DESCRIPTION: SEQ ID NO: 25:

Ala Gly Tyr Phe Ala Glu Xaa Ala Arg
 1               5

(2) INFORMATION FOR SEQ ID NO: 26:

(i) SEQUENCE CHARACTERISTICS:
        (A) LENGTH: 10
        (B) TYPE: amino acid
        (C) STRANDEDNESS:
        (D) TOPOLOGY: linear (xi) SEQUENCE DESCRIPTION: SEQ ID NO: 26:

Thr Thr Glu Met Ala Ser Glu Gln Gly Ala
 1               5                   10

(2) INFORMATION FOR SEQ ID NO: 27:

(i) SEQUENCE CHARACTERISTICS:
        (A) LENGTH: 9
        (B) TYPE: amino acid
        (C) STRANDEDNESS:
        (D) TOPOLOGY: linear (xi) SEQUENCE DESCRIPTION: SEQ ID NO: 27:

Ala Lys Glu Ala Leu Ala Ala Leu Lys
 1               5

(2) INFORMATION FOR SEQ ID NO: 28:

(i) SEQUENCE CHARACTERISTICS:
        (A) LENGTH: 7
        (B) TYPE: amino acid
        (C) STRANDEDNESS:
        (D) TOPOLOGY: linear (xi) SEQUENCE DESCRIPTION: SEQ ID NO: 28:

Phe Val Leu Gln Ala Lys Lys
 1               5

(2) INFORMATION FOR SEQ ID NO: 29:

(i) SEQUENCE CHARACTERISTICS:
        (A) LENGTH: 21
        (B) TYPE: amino acid
        (C) STRANDEDNESS:
        (D) TOPOLOGY: linear ( x i ) SEQUENCE DESCRIPTION: SEQ ID NO: 29:

Glu Thr Gln Pro Asp Pro Gly Gln Ile Leu Lys Lys Val Pro Met Val
1               5                   10                  15

( 2 ) INFORMATION FOR SEQ ID NO: 30:

( i ) SEQUENCE CHARACTERISTICS:
        ( A ) LENGTH: 21
        ( B ) TYPE: amino acid
        ( C ) STRANDEDNESS:
        ( D ) TOPOLOGY: linear ( i x ) FEATURE:
        ( D ) OTHER INFORMATION: Xaa in positions 1, 3, 17 and 19 is
           unknown.

( x i ) SEQUENCE DESCRIPTION: SEQ ID NO: 30:

Xaa Glu Xaa Lys Glu Gly Arg Gly Lys Gly Lys Gly Lys Lys Lys Glu
1               5                   10                  15
Xaa Gly Xaa Gly Lys
                20

( 2 ) INFORMATION FOR SEQ ID NO: 31:

( i ) SEQUENCE CHARACTERISTICS:
        ( A ) LENGTH: 13
        ( B ) TYPE: amino acid
        ( C ) STRANDEDNESS:
        ( D ) TOPOLOGY: linear ( x i ) SEQUENCE DESCRIPTION: SEQ ID NO: 31:

Ala Glu Lys Glu Lys Thr Phe Cys Val Asn Gly Gly Glu
1               5                   10

( 2 ) INFORMATION FOR SEQ ID NO: 32:

( i ) SEQUENCE CHARACTERISTICS:
        ( A ) LENGTH: 8
        ( B ) TYPE: amino acid
        ( C ) STRANDEDNESS:
        ( D ) TOPOLOGY: linear ( i x ) FEATURE:
        ( D ) OTHER INFORMATION: Xaa in position 6 is unknown.

( x i ) SEQUENCE DESCRIPTION: SEQ ID NO: 32:

Lys Leu Glu Phe Leu Xaa Ala Lys
1               5

( 2 ) INFORMATION FOR SEQ ID NO: 33:

( i ) SEQUENCE CHARACTERISTICS:
        ( A ) LENGTH: 9
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is Lysine or
           Arginine.

( x i ) SEQUENCE DESCRIPTION: SEQ ID NO: 33:

Xaa Val His Gln Val Trp Ala Ala Lys
1               5

( 2 ) INFORMATION FOR SEQ ID NO: 34:

( i ) SEQUENCE CHARACTERISTICS:
        ( A ) LENGTH: 14

(B) TYPE: amino acid
(C) STRANDEDNESS:
(D) TOPOLOGY: linear (ix) FEATURE:
(D) OTHER INFORMATION: Xaa in position 1 is Lysine or Arginine, Xaa in position 11 is unknown.

(xi) SEQUENCE DESCRIPTION: SEQ ID NO: 34:

Xaa Tyr Ile Phe Phe Met Glu Pro Glu Ala Xaa Ser Ser Gly
 1               5                   10

(2) INFORMATION FOR SEQ ID NO: 35:

(i) SEQUENCE CHARACTERISTICS:
(A) LENGTH: 14
(B) TYPE: amino acid
(C) STRANDEDNESS:
(D) TOPOLOGY: linear (ix) FEATURE:
(D) OTHER INFORMATION: Xaa in position 1 is Lysine or Arginine, Xaa in position 13 is unknown.

(xi) SEQUENCE DESCRIPTION: SEQ ID NO: 35:

Xaa Leu Gly Ala Trp Gly Pro Pro Ala Phe Pro Val Xaa Tyr
 1               5                   10

(2) INFORMATION FOR SEQ ID NO: 36:

(i) SEQUENCE CHARACTERISTICS:
(A) LENGTH: 9
(B) TYPE: amino acid
(C) STRANDEDNESS:
(D) TOPOLOGY: linear (ix) FEATURE:
(D) OTHER INFORMATION: Xaa in position 1 is Lysine or Arginine.

(xi) SEQUENCE DESCRIPTION: SEQ ID NO: 36:

Xaa Trp Phe Val Val Ile Glu Gly Lys
 1               5

(2) INFORMATION FOR SEQ ID NO: 37:

(i) SEQUENCE CHARACTERISTICS:
(A) LENGTH: 16
(B) TYPE: amino acid
(C) STRANDEDNESS:
(D) TOPOLOGY: linear (ix) FEATURE:
(D) OTHER INFORMATION: Xaa in position 1 is Lysine or Arginine.

(xi) SEQUENCE DESCRIPTION: SEQ ID NO: 37:

Xaa Ala Ser Pro Val Ser Val Gly Ser Val Gln Glu Leu Val Gln Arg
 1               5                   10                  15

(2) INFORMATION FOR SEQ ID NO: 38:

(i) SEQUENCE CHARACTERISTICS:
(A) LENGTH: 13
(B) TYPE: amino acid
(C) STRANDEDNESS:
(D) TOPOLOGY: linear (ix) FEATURE:
(D) OTHER INFORMATION: Xaa in position 1 is Lysine or Arginine.

( x i ) SEQUENCE DESCRIPTION: SEQ ID NO: 38:

Xaa Val Cys Leu Leu Thr Val Ala Ala Leu Pro Pro Thr
1               5                   10

( 2 ) INFORMATION FOR SEQ ID NO: 39:

( i ) SEQUENCE CHARACTERISTICS:
       ( A ) LENGTH: 7
       ( B ) TYPE: amino acid
       ( C ) STRANDEDNESS:
       ( D ) TOPOLOGY: linear ( i x ) FEATURE:
       ( D ) OTHER INFORMATION: Xaa in position 1 is Lysine or
            Arginine; Xaa in position 6 is unknown.

( x i ) SEQUENCE DESCRIPTION: SEQ ID NO: 39:

Xaa Asp Leu Leu Leu Xaa Val
1               5

( 2 ) INFORMATION FOR SEQ ID NO: 40:

( i ) SEQUENCE CHARACTERISTICS:
       ( A ) LENGTH: 39
       ( B ) TYPE: amino acid
       ( C ) STRANDEDNESS:
       ( D ) TOPOLOGY: linear ( x i ) SEQUENCE DESCRIPTION: SEQ ID NO: 40:

Cys Thr Cys Gly Cys Cys Lys Cys Cys Arg Thr Thr Cys Ala Cys Arg
1               5                   10                  15
Cys Ala Gly Ala Ala Gly Gly Thr Cys Thr Thr Cys Thr Cys Cys Thr
                20                  25                  30
Thr Cys Thr Cys Ala Gly Cys
                35

( 2 ) INFORMATION FOR SEQ ID NO: 41:

( i ) SEQUENCE CHARACTERISTICS:
       ( A ) LENGTH: 24
       ( B ) TYPE: amino acid
       ( C ) STRANDEDNESS:
       ( D ) TOPOLOGY: linear ( x i ) SEQUENCE DESCRIPTION: SEQ ID NO: 41:

Cys Cys Thr Cys Gly Cys Thr Cys Cys Thr Thr Cys Thr Thr Cys Thr
1               5                   10                  15
Thr Gly Cys Cys Cys Thr Thr Cys
                20

( 2 ) INFORMATION FOR SEQ ID NO: 42:

( i ) SEQUENCE CHARACTERISTICS:
       ( A ) LENGTH: 60
       ( B ) TYPE: nucleic acid
       ( C ) STRANDEDNESS: single
       ( D ) TOPOLOGY: linear ( x i ) SEQUENCE DESCRIPTION: SEQ ID NO: 42:

AAGTGCCCAA ATGAGTTTAC TGGTGATCGC TGCCAAAACT ACGTAATGGC CAGCTTCTAC          60

( 2 ) INFORMATION FOR SEQ ID NO: 43:

( i ) SEQUENCE CHARACTERISTICS:
       ( A ) LENGTH: 36
       ( B ) TYPE: nucleic acid
       ( C ) STRANDEDNESS: single ( D ) TOPOLOGY: linear ( x i ) SEQUENCE DESCRIPTION: SEQ ID NO: 43:

| | | | | | |
|---|---|---|---|---|---|
| AGTACGTCCA | CTCCCTTTCT | GTCTCTGCCT | GAATAG | | 36 |

( 2 ) INFORMATION FOR SEQ ID NO: 44:

( i ) SEQUENCE CHARACTERISTICS:
        ( A ) LENGTH: 569
        ( B ) TYPE: nucleic acid
        ( C ) STRANDEDNESS: single
        ( D ) TOPOLOGY: linear ( x i ) SEQUENCE DESCRIPTION: SEQ ID NO: 44:

| | | | | | |
|---|---|---|---|---|---|
| AAGGCGGAGG | AGCTGTACCA | GAAGAGAGTG | CTGACCATAA | CCGGCATCTG | CATCGCCCTC | 60 |
| CTTGTGGTCG | GCATCATGTG | TGTGGTGGCC | TACTGCAAAA | CCAAGAAACA | GCGGAAAAAG | 120 |
| CTGCATGACC | GTCTTCGGCA | GAGCCTTCGG | TCTGAACGAA | ACAATATGAT | GAACATTGCC | 180 |
| AATGGGCCTC | ACCATCCTAA | CCCACCCCCC | GAGAATGTCC | AGCTGGTGAA | TCAATACGTA | 240 |
| TCTAAAAACG | TCATCTCCAG | TGAGCATATT | GTTGAGAGAG | AAGCAGAGAC | ATCCTTTTCC | 300 |
| ACCAGTCACT | ATACTTCCAC | AGCCCATCAC | TCCACTACTG | TCACCCAGAC | TCCTAGCCAC | 360 |
| AGCTGGAGCA | ACGGACACAC | TGAAAGCATC | CTTTCCGAAA | GCCACTCTGT | AATCGTGATG | 420 |
| TCATCCGTAG | AAAACAGTAG | GCACAGCAGC | CCAACTGGGG | GCCCAAGAGG | ACGTCTTAAT | 480 |
| GGCACAGGAG | GCCCTCGTGA | ATGTAACAGC | TTCCTCAGGC | ATGCCAGAGA | AACCCCTGAT | 540 |
| TCCTACCGAG | ACTCTCCTCA | TAGTGAAAG | | | | 569 |

( 2 ) INFORMATION FOR SEQ ID NO: 45:

( i ) SEQUENCE CHARACTERISTICS:
        ( A ) LENGTH: 8
        ( B ) TYPE: amino acid
        ( C ) STRANDEDNESS:
        ( D ) TOPOLOGY: linear ( x i ) SEQUENCE DESCRIPTION: SEQ ID NO: 45:

Val His Gln Val Trp Ala Ala Lys
 1                   5

( 2 ) INFORMATION FOR SEQ ID NO: 46:

( i ) SEQUENCE CHARACTERISTICS:
        ( A ) LENGTH: 13
        ( B ) TYPE: amino acid
        ( C ) STRANDEDNESS:
        ( D ) TOPOLOGY: linear ( i x ) FEATURE:
        ( D ) OTHER INFORMATION: Xaa in position 10 is unknown.

( x i ) SEQUENCE DESCRIPTION: SEQ ID NO: 46:

Tyr Ile Phe Phe Met Glu Pro Glu Ala Xaa Ser Ser Gly
 1              5                       10

( 2 ) INFORMATION FOR SEQ ID NO: 47:

( i ) SEQUENCE CHARACTERISTICS:
        ( A ) LENGTH: 13
        ( B ) TYPE: amino acid
        ( C ) STRANDEDNESS:
        ( D ) TOPOLOGY: linear ( i x ) FEATURE:
        ( D ) OTHER INFORMATION: Xaa in position 12 is unknown.

( x i ) SEQUENCE DESCRIPTION: SEQ ID NO: 47:

Leu Gly Ala Trp Gly Pro Pro Ala Phe Pro Val Xaa Tyr
 1               5                   10

( 2 ) INFORMATION FOR SEQ ID NO: 48:

( i ) SEQUENCE CHARACTERISTICS:
        ( A ) LENGTH: 8
        ( B ) TYPE: amino acid
        ( C ) STRANDEDNESS:
        ( D ) TOPOLOGY: linear ( x i ) SEQUENCE DESCRIPTION: SEQ ID NO: 48:

Trp Phe Val Val Ile Glu Gly Lys
 1               5

( 2 ) INFORMATION FOR SEQ ID NO: 49:

( i ) SEQUENCE CHARACTERISTICS:
        ( A ) LENGTH: 15
        ( B ) TYPE: amino acid
        ( C ) STRANDEDNESS:
        ( D ) TOPOLOGY: linear ( x i ) SEQUENCE DESCRIPTION: SEQ ID NO: 49:

Ala Ser Pro Val Ser Val Gly Ser Val Gln Glu Leu Val Gln Arg
 1               5                   10                  15

( 2 ) INFORMATION FOR SEQ ID NO: 50:

( i ) SEQUENCE CHARACTERISTICS:
        ( A ) LENGTH: 12
        ( B ) TYPE: amino acid
        ( C ) STRANDEDNESS:
        ( D ) TOPOLOGY: linear ( x i ) SEQUENCE DESCRIPTION: SEQ ID NO: 50:

Val Cys Leu Leu Thr Val Ala Ala Leu Pro Pro Thr
 1               5                   10

( 2 ) INFORMATION FOR SEQ ID NO: 51:

( i ) SEQUENCE CHARACTERISTICS:
        ( A ) LENGTH: 9
        ( B ) TYPE: amino acid
        ( C ) STRANDEDNESS:
        ( D ) TOPOLOGY: linear ( x i ) SEQUENCE DESCRIPTION: SEQ ID NO: 51:

Lys Val His Gln Val Trp Ala Ala Lys
 1               5

( 2 ) INFORMATION FOR SEQ ID NO: 52:

( i ) SEQUENCE CHARACTERISTICS:
        ( A ) LENGTH: 13
        ( B ) TYPE: amino acid
        ( C ) STRANDEDNESS:
        ( D ) TOPOLOGY: linear ( i x ) FEATURE:
        ( D ) OTHER INFORMATION: Xaa in position 12 is unknown.

( x i ) SEQUENCE DESCRIPTION: SEQ ID NO: 52:

Lys Ala Ser Leu Ala Asp Ser Gly Glu Tyr Met Xaa Lys
 1               5                   10

( 2 ) INFORMATION FOR SEQ ID NO: 53:

```
( i ) SEQUENCE CHARACTERISTICS:
        ( A ) LENGTH: 6
        ( B ) TYPE: amino acid
        ( C ) STRANDEDNESS:
        ( D ) TOPOLOGY: linear ( i x ) FEATURE:
        ( D ) OTHER INFORMATION: Xaa in position 5 is unknown.

( x i ) SEQUENCE DESCRIPTION: SEQ ID NO: 53:
```

Asp Leu Leu Leu Xaa Val
 1               5

( 2 ) INFORMATION FOR SEQ ID NO: 54:

```
( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 54:
```

TTYAARGGNG AYGCNCAYAC                              20

( 2 ) INFORMATION FOR SEQ ID NO: 55:

```
( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( x i ) SEQUENCE DESCRIPTION: SEQ ID NO: 55:
```

CATRTAYTCR TAYTCRTCNG C                            21

( 2 ) INFORMATION FOR SEQ ID NO: 56:

```
( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 56:
```

TGYTCNGANG CCATYTCNGT                              20

( 2 ) INFORMATION FOR SEQ ID NO: 57:

```
( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 57:
```

TGYTCRCTNG CCATYTCNGT                              20

( 2 ) INFORMATION FOR SEQ ID NO: 58:

```
( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 58:
```

CCDATNACCA TNGGIJACYTT                             20

( 2 ) INFORMATION FOR SEQ ID NO: 59:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 59:

GCNGCCCANA CYTGRTGNAC     20

( 2 ) INFORMATION FOR SEQ ID NO: 60:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 60:

GCYTCNGGYT CCATRAARAA     20

( 2 ) INFORMATION FOR SEQ ID NO: 61:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 61:

CCYTCDATNA CNACRAACCA     20

( 2 ) INFORMATION FOR SEQ ID NO: 62:

( i ) SEQUENCE CHARACTERISTICS:
        ( A ) LENGTH: 17
        ( B ) TYPE: nucleic acid
        ( C ) STRANDEDNESS: single
        ( D ) TOPOLOGY: linear ( x i ) SEQUENCE DESCRIPTION: SEQ ID NO: 62:

TCNGCRAART ANCCNGC     17

( 2 ) INFORMATION FOR SEQ ID NO: 63:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 63:

GCNGCNAGNG CYTCYTTNGC     20

( 2 ) INFORMATION FOR SEQ ID NO: 64:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 64:

GCNGCYAANG CYTCYTTNGC     20

( 2 ) INFORMATION FOR SEQ ID NO: 65:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( x i ) SEQUENCE DESCRIPTION: SEQ ID NO: 65:

TTYTTNGCYT GNAGNACRAA                    20

( 2 ) INFORMATION FOR SEQ ID NO: 66:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 66:

TTYTTNGCYT GYAANACRAA                    20

( 2 ) INFORMATION FOR SEQ ID NO: 67:

( i ) SEQUENCE CHARACTERISTICS:
        ( A ) LENGTH: 17
        ( B ) TYPE: nucleic acid
        ( C ) STRANDEDNESS: single
        ( D ) TOPOLOGY: linear ( x i ) SEQUENCE DESCRIPTION: SEQ ID NO: 67:

TGNACNAGYT CYTGNAC                       17

( 2 ) INFORMATION FOR SEQ ID NO: 68:

( i ) SEQUENCE CHARACTERISTICS:
        ( A ) LENGTH: 17
        ( B ) TYPE: nucleic acid
        ( C ) STRANDEDNESS: single
        ( D ) TOPOLOGY: linear ( x i ) SEQUENCE DESCRIPTION: SEQ ID NO: 68:

TGNACYAAYT CYTGNAC                       17

( 2 ) INFORMATION FOR SEQ ID NO: 69:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( x i ) SEQUENCE DESCRIPTION: SEQ ID NO: 69:

CATRTAYTCN CCNGARTCNG C                  21

( 2 ) INFORMATION FOR SEQ ID NO: 70:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( x i ) SEQUENCE DESCRIPTION: SEQ ID NO: 70:

CATRTAYTCN CCRCTRTCNG C                  21

( 2 ) INFORMATION FOR SEQ ID NO: 71:

( i ) SEQUENCE CHARACTERISTICS:

(A) LENGTH: 21
(B) TYPE: nucleic acid
(C) STRANDEDNESS: single
(D) TOPOLOGY: linear (xi) SEQUENCE DESCRIPTION: SEQ ID NO: 71:

NGARTCNGCY AANGANGCYT T                    21

(2) INFORMATION FOR SEQ ID NO: 72:

(i) SEQUENCE CHARACTERISTICS:
(A) LENGTH: 21
(B) TYPE: nucleic acid
(C) STRANDEDNESS: single
(D) TOPOLOGY: linear (xi) SEQUENCE DESCRIPTION: SEQ ID NO: 72:

NGARTCNGCN AGNGANGCYT T                    21

(2) INFORMATION FOR SEQ ID NO: 73:

(i) SEQUENCE CHARACTERISTICS:
(A) LENGTH: 21
(B) TYPE: nucleic acid
(C) STRANDEDNESS: single
(D) TOPOLOGY: linear (xi) SEQUENCE DESCRIPTION: SEQ ID NO: 73:

RCTRTCNGCY AANGANGCYT T                    21

(2) INFORMATION FOR SEQ ID NO: 74:

(i) SEQUENCE CHARACTERISTICS:
(A) LENGTH: 21
(B) TYPE: nucleic acid
(C) STRANDEDNESS: single
(D) TOPOLOGY: linear (xi) SEQUENCE DESCRIPTION: SEQ ID NO: 74:

RCTRTCNGCN AGNGANGCYT T                    21

(2) INFORMATION FOR SEQ ID NO: 75:

(i) SEQUENCE CHARACTERISTICS:
(A) LENGTH: 21
(B) TYPE: nucleic acid
(C) STRANDEDNESS: single
(D) TOPOLOGY: linear (xi) SEQUENCE DESCRIPTION: SEQ ID NO: 75:

NGARTCNGCY AARCTNGCYT T                    21

(2) INFORMATION FOR SEQ ID NO: 76:

(i) SEQUENCE CHARACTERISTICS:
(A) LENGTH: 21
(B) TYPE: nucleic acid
(C) STRANDEDNESS: single
(D) TOPOLOGY: linear (xi) SEQUENCE DESCRIPTION: SEQ ID NO: 76:

NGARTCNGCN AGRCTNGCYT T                    21

(2) INFORMATION FOR SEQ ID NO: 77:

(i) SEQUENCE CHARACTERISTICS:
(A) LENGTH: 730
(B) TYPE: nucleic acid (C) STRANDEDNESS: single
(D) TOPOLOGY: linear (xi) SEQUENCE DESCRIPTION: SEQ ID NO: 77:

| | | | | | | |
|---|---|---|---|---|---|---|
| GTATGTGTCA | GCCATGACCA | CCCCGGCTCG | TATGTCACCT | GTAGATTTCC | ACACGCCAAG | 60 |
| CTCCCCCAAA | TCGCCCCCTT | CGGAAATGTC | TCCACCCGTG | TCCAGCATGA | CGGTGTCCAT | 120 |
| GCCTTCCATG | GCGGTCAGCC | CCTTCATGGA | AGAAGAGAGA | CCTCTACTTC | TCGTGACACC | 180 |
| ACCAAGGCTG | CGGGAGAAGA | AGTTTGACCA | TCACCCTCAG | CAGTTCAGCT | CCTTCCACCA | 240 |
| CAACCCCGCG | CATGACAGTA | ACAGCCTCCC | TGCTAGCCCC | TTGAGGATAG | TGGAGGATGA | 300 |
| GGAGTATGAA | ACGACCCAAG | AGTACGAGCC | AGCCCAAGAG | CCTGTTAAGA | AACTCGCCAA | 360 |
| TAGCCGGCGG | GCCAAAAGAA | CCAAGCCCAA | TGGCCACATT | GCTAACAGAT | TGGAAGTGGA | 420 |
| CAGCAACACA | AGCTCCCAGA | GCAGTAACTC | AGAGAGTGAA | ACAGAAGATG | AAAGAGTAGG | 480 |
| TGAAGATACG | CCTTTCCTGG | GCATACAGAA | CCCCCTGGCA | GCCAGTCTTG | AGGCAACACC | 540 |
| TGCCTTCCGC | CTGGCTGACA | GCAGGACTAA | CCCAGCAGGC | CGCTTCTCGA | CACAGGAAGA | 600 |
| AATCCAGGCC | AGGCTGTCTA | GTGTAATTGC | TAACCAAGAC | CCTATTGCTG | TATAAAACCT | 660 |
| AAATAAACAC | ATAGATTCAC | CTGTAAAACT | TTATTTTATA | TAATAAAGTA | TTCCACCTTA | 720 |
| AATTAAACAA | | | | | | 730 |

(2) INFORMATION FOR SEQ ID NO: 78:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 78:

| | | |
|---|---|---|
| RCTRTCNGCY | AARCTNGCYT T | 21 |

(2) INFORMATION FOR SEQ ID NO: 79:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 79:

| | | |
|---|---|---|
| RCTRCTNGCN | AGRCTNGCYT T | 21 |

(2) INFORMATION FOR SEQ ID NO: 80:

(i) SEQUENCE CHARACTERISTICS:
        (A) LENGTH: 20
        (B) TYPE: nucleic acid
        (C) STRANDEDNESS: single
        (D) TOPOLOGY: linear (xi) SEQUENCE DESCRIPTION: SEQ ID NO: 80:

| | | |
|---|---|---|
| ACNACNGARA | TGGCTCNNGA | 20 |

(2) INFORMATION FOR SEQ ID NO: 81:

(i) SEQUENCE CHARACTERISTICS:
        (A) LENGTH: 20
        (B) TYPE: nucleic acid
        (C) STRANDEDNESS: single
        (D) TOPOLOGY: linear (xi) SEQUENCE DESCRIPTION: SEQ ID NO: 81:

ACNACNGARA TGGCAGYNGA    20

( 2 ) INFORMATION FOR SEQ ID NO: 82:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 82:

CAYCARGTNT GGGCNGCNAA    20

( 2 ) INFORMATION FOR SEQ ID NO: 83:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 83:

TTYGTNGTNA THGARGGNAA    20

( 2 ) INFORMATION FOR SEQ ID NO: 84:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 84:

AARGGNGAYG CNCAYACNGA    20

( 2 ) INFORMATION FOR SEQ ID NO: 85:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 85:

GARGCNYTNG CNGCNYTNAA    20

( 2 ) INFORMATION FOR SEQ ID NO: 86:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 86:

GTNGGNTCNG TNCARGARYT    20

( 2 ) INFORMATION FOR SEQ ID NO: 87:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 87:

GTNGGNAGYG TNCARGARYT    20

(2) INFORMATION FOR SEQ ID NO: 88:

(i) SEQUENCE CHARACTERISTICS:
 (A) LENGTH: 21
 (B) TYPE: nucleic acid
 (C) STRANDEDNESS: single
 (D) TOPOLOGY: linear (xi) SEQUENCE DESCRIPTION: SEQ ID NO: 88:

NACYTTYTTN ARDATYTGNC C    21

(2) INFORMATION FOR SEQ ID NO: 89:

(i) SEQUENCE CHARACTERISTICS:
 (A) LENGTH: 417
 (B) TYPE: nucleic acid
 (C) STRANDEDNESS: single
 (D) TOPOLOGY: linear (ix) FEATURE:
 (D) OTHER INFORMATION: Xaa in positions 14, 23, 90, 100,
  126, and 135 is a stop codon.

(xi) SEQUENCE DESCRIPTION: SEQ ID NO: 89:

```
TCTAA AAC TAC AGA GAC TGT ATT TTC ATG ATC ATC ATA GTT CTG TGA AAT ATA   53
      Asn Tyr Arg Asp Cys Ile Phe Met Ile Ile Ile Val Leu Xaa Asn Ile
      1           5                   10                  15

CTT AAA CCG CTT TGG TCC TGA TCT TGT AGG AAG TCA GAA CTT CGC ATT          101
Leu Lys Pro Leu Trp Ser Xaa Ser Cys Arg Lys Ser Glu Leu Arg Ile
            20              25                  30

AGC AAA GCG TCA CTG GCT GAT TCT GGA GAA TAT ATG TGC AAA GTG ATC          149
Ser Lys Ala Ser Leu Ala Asp Ser Gly Glu Tyr Met Cys Lys Val Ile
        35              40                  45

AGC AAA CTA GGA AAT GAC AGT GCC TCT GCC AAC ATC ACC ATT GTG GAG          197
Ser Lys Leu Gly Asn Asp Ser Ala Ser Ala Asn Ile Thr Ile Val Glu
    50              55                  60

TCA AAC GGT AAG AGA TGC CTA CTG CGT GCT ATT TCT CAG TCT CTA AGA          245
Ser Asn Gly Lys Arg Cys Leu Leu Arg Ala Ile Ser Gln Ser Leu Arg
65          70                  75                  80

GGA GTG ATC AAG GTA TGT GGT CAC ACT TGA ATC ACG CAG GTG TGT GAA          293
Gly Val Ile Lys Val Cys Gly His Thr Xaa Ile Thr Gln Val Cys Glu
            85                  90                  95

ATC TCA TTG TGA ACA AAT AAA AAT CAT GAA AGG AAA ACT CTA TGT TTG          341
Ile Ser Cys Xaa Thr Asn Lys Asn His Glu Arg Lys Thr Leu Cys Leu
            100             105                 110

AAA TAT CTT ATG GGT CCT CCT GTA AAG CTC TTC ACT CCA TAA GGT GAA          389
Lys Tyr Leu Met Gly Pro Pro Val Lys Leu Phe Thr Pro Xaa Gly Glu
        115             120                 125

ATA GAC CTG AAA TAT ATA TAG ATT ATT T                                    
Ile Asp Leu Lys Tyr Ile Xaa Ile Ile
    130             135
```

(2) INFORMATION FOR SEQ ID NO: 90:

(i) SEQUENCE CHARACTERISTICS:
 (A) LENGTH: 33
 (B) TYPE: nucleic acid
 (C) STRANDEDNESS: single
 (D) TOPOLOGY: linear (ix) FEATURE:
 (D) OTHER INFORMATION: N at positions 19, 25, and 31 is
  Inosine. Y can be cytidine or thymidine.

(xi) SEQUENCE DESCRIPTION: SEQ ID NO: 90:

CCGAATTCTG CAGGARACNC ARCCNGAYCC NGG    33

( 2 ) INFORMATION FOR SEQ ID NO: 91:

( i ) SEQUENCE CHARACTERISTICS:
        ( A ) LENGTH: 37
        ( B ) TYPE: nucleic acid
        ( C ) STRANDEDNESS: single
        ( D ) TOPOLOGY: linear ( i x ) FEATURE:
        ( D ) OTHER INFORMATION: N at positions 14, 20, 23, 29, and
            35 is Inosine.

( x i ) SEQUENCE DESCRIPTION: SEQ ID NO: 91:

AAGGATCCTG CAGNGTRTAN GCNCCDATNA CCATNGG    37

( 2 ) INFORMATION FOR SEQ ID NO: 92:

( i ) SEQUENCE CHARACTERISTICS:
        ( A ) LENGTH: 34
        ( B ) TYPE: nucleic acid
        ( C ) STRANDEDNESS: single
        ( D ) TOPOLOGY: linear ( i x ) FEATURE:
        ( D ) OTHER INFORMATION: N at positions 16, 21, and 24
            is Inosine. Y can be cytidine or thymidine.

( x i ) SEQUENCE DESCRIPTION: SEQ ID NO: 92:

CCGAATTCTG CAGGCNGAYT CNGGNGARTA YATG    34

( 2 ) INFORMATION FOR SEQ ID NO: 93:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( i x ) FEATURE:
        ( D ) OTHER INFORMATION: N at positions 16 and 25 is Inosine.
            Y can be cytidine or thymidine.

( x i ) SEQUENCE DESCRIPTION: SEQ ID NO: 93:

CCGAATTCTG CAGGCNGAYA GYGGNGARTA YAT    33

( 2 ) INFORMATION FOR SEQ ID NO: 94:

( i ) SEQUENCE CHARACTERISTICS:
        ( A ) LENGTH: 34
        ( B ) TYPE: nucleic acid
        ( C ) STRANDEDNESS: single
        ( D ) TOPOLOGY: linear ( i x ) FEATURE:
        ( D ) OTHER INFORMATION: N at positions 14, 15, 16, 26, and
            29 is Inosine. Y can be cytidine or thymidine.

( x i ) SEQUENCE DESCRIPTION: SEQ ID NO: 94:

AAGGATCCTG CAGNNNCATR TAYTCNCCNG ARTC    34

( 2 ) INFORMATION FOR SEQ ID NO: 95:

( i ) SEQUENCE CHARACTERISTICS:
        ( A ) LENGTH: 34
        ( B ) TYPE: nucleic acid
        ( C ) STRANDEDNESS: single
        ( D ) TOPOLOGY: linear ( i x ) FEATURE:

( D ) OTHER INFORMATION: N at positions 14, 15, 16, and 26
                        is Inosine. Y can be cytidine or thymidine.

( x i ) SEQUENCE DESCRIPTION: SEQ ID NO: 95:

AAGGATCCTG CAGNNNCATR TAYTCNCCRC TRTC                34

( 2 ) INFORMATION FOR SEQ ID NO: 96:

( i ) SEQUENCE CHARACTERISTICS:
                ( A ) LENGTH: 33
                ( B ) TYPE: nucleic acid
                ( C ) STRANDEDNESS: single
                ( D ) TOPOLOGY: linear ( i x ) FEATURE:
                ( D ) OTHER INFORMATION: N at positions 21, 28, and 31
                        is Inosine. Y can be cytidine or thymidine.

( x i ) SEQUENCE DESCRIPTION: SEQ ID NO: 96:

CCGAATTCTG CAGCAYCARG TNTGGGCNGC NAA                 33

( 2 ) INFORMATION FOR SEQ ID NO: 97:

( i ) SEQUENCE CHARACTERISTICS:
                ( A ) LENGTH: 35
                ( B ) TYPE: nucleic acid
                ( C ) STRANDEDNESS: single
                ( D ) TOPOLOGY: linear ( i x ) FEATURE:
                ( D ) OTHER INFORMATION: N at position 31 is Inosine. Y can be
                        cytidine or thymidine.

( x i ) SEQUENCE DESCRIPTION: SEQ ID NO: 97:

CCGAATTCTG CAGATHTTYT TYATGGARCC NGARG               35

( 2 ) INFORMATION FOR SEQ ID NO: 98:

( i ) SEQUENCE CHARACTERISTICS:
                ( A ) LENGTH: 25
                ( B ) TYPE: nucleic acid
                ( C ) STRANDEDNESS: single
                ( D ) TOPOLOGY: linear ( i x ) FEATURE:
                ( D ) OTHER INFORMATION: N at positions 18, 21, 24, 27, and
                        33 is Inosine. Y can be cytidine or thymidine.

( x i ) SEQUENCE DESCRIPTION: SEQ ID NO: 98:

CCGAATTCTC CAGGGGGNCC NCCIJGCNTTY CCNGT              35

( 2 ) INFORMATION FOR SEQ ID NO: 99:

( i ) SEQUENCE CHARACTERISTICS:
                ( A ) LENGTH: 33
                ( B ) TYPE: nucleic acid
                ( C ) STRANDEDNESS: single
                ( D ) TOPOLOGY: linear ( i x ) FEATURE:
                ( D ) OTHER INFORMATION: N at positions 21 and 24 is Inosine.
                        Y can be cytidine or thymidine.

( x i ) SEQUENCE DESCRIPTION: SEQ ID NO: 99:

CCGAATTCTG CAGTGGTTYG TNGTNATHGA RGG                 33

( 2 ) INFORMATION FOR SEQ ID NO: 100:

( i ) SEQUENCE CHARACTERISTICS:
                ( A ) LENGTH: 35

( B ) TYPE: nucleic acid
( C ) STRANDEDNESS: single
( D ) TOPOLOGY: linear ( i x ) FEATURE:
( D ) OTHER INFORMATION: N at positions 17, 20, and 26 is
Inosine. Y can be cytidine or thymidine.

( x i ) SEQUENCE DESCRIPTION: SEQ ID NO: 100:

AAGGATCCTG CAGYTTNGCU NGCCCANACY TGRTG    35

( 2 ) INFORMATION FOR SEQ ID NO: 101:

( i ) SEQUENCE CHARACTERISTICS:
( A ) LENGTH: 33
( B ) TYPE: nucleic acid
( C ) STRANDEDNESS: single
( D ) TOPOLOGY: linear ( i x ) FEATURE:
( D ) OTHER INFORMATION: N at position 19 is Inosine. Y
can be cytidine or thymidine.

( x i ) SEQUENCE DESCRIPTION: SEQ ID NO: 101:

AAGGATCCTG CAGGCYTCNG GYTCCATRAA RAA    33

( 2 ) INFORMATION FOR SEQ ID NO: 102:

( i ) SEQUENCE CHARACTERISTICS:
( A ) LENGTH: 33
( B ) TYPE: nucleic acid
( C ) STRANDEDNESS: single
( D ) TOPOLOGY: linear ( i x ) FEATURE:
( D ) OTHER INFORMATION: N at positions 16, 22, 25, 28, and
31 is Inosine.

( x i ) SEQUENCE DESCRIPTION: SEQ ID NO: 102:

AAGGATCCTG CAGACNGGRA ANGCNGGNGG NCC    33

( 2 ) INFORMATION FOR SEQ ID NO: 103:

( i ) SEQUENCE CHARACTERISTICS:
( A ) LENGTH: 35
( B ) TYPE: nucleic acid
( C ) STRANDEDNESS: single
( D ) TOPOLOGY: linear ( i x ) FEATURE:
( D ) OTHER INFORMATION: N at positions 17, 26, and 29 is
Inosine. Y can be cytidine or thymidine.

( x i ) SEQUENCE DESCRIPTION: SEQ ID NO: 103:

AAGGATCCTG CAGYTTNCCY TCDATNACNA CRAAC    35

( 2 ) INFORMATION FOR SEQ ID NO: 104:

( i ) SEQUENCE CHARACTERISTICS:
( A ) LENGTH: 33
( B ) TYPE: nucleic acid
( C ) STRANDEDNESS: single
( D ) TOPOLOGY: linear ( i x ) FEATURE:
( D ) OTHER INFORMATION: N at position 18 is Inosine. Y
can be cytidine or thymidine.

( x i ) SEQUENCE DESCRIPTION: SEQ ID NO: 104:

CATRTAYTCR TAYTCTCNGC AAGGATCCTG CAG    33

( 2 ) INFORMATION FOR SEQ ID NO: 105:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( i x ) FEATURE:
        ( D ) OTHER INFORMATION: N at position 19, 25, and 31 is
            Inosine. Y can be cytidine or thymidine.

( x i ) SEQUENCE DESCRIPTION: SEQ ID NO: 105:

CCGAATTCTG CAGAARGGNG AYGCNCAYAC NGA        33

( 2 ) INFORMATION FOR SEQ ID NO: 106:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( i x ) FEATURE:
        ( D ) OTHER INFORMATION: N at position 3 and 18 is Inosine.
            Y can be cytidine or thymidine.

( x i ) SEQUENCE DESCRIPTION: SEQ ID NO: 106:

GCNGCYAANG CYTCYTTNGC AAGGATCCTG CAG        33

( 2 ) INFORMATION FOR SEQ ID NO: 107:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( i x ) FEATURE:
        ( D ) OTHER INFORMATION: N at position 3, 6, 9, and 18 is
            Inosine. Y can be cytidine or thymidine.

( x i ) SEQUENCE DESCRIPTION: SEQ ID NO: 107:

GCNGCNAGNG CYTCYTTNGC AAGGATCCTG CAG        33

( 2 ) INFORMATION FOR SEQ ID NO: 108:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( i x ) FEATURE:
        ( D ) OTHER INFORMATION: N at position 3, 12, and 15 is
            Inosine. Y can be cytidine or thymidine.

( x i ) SEQUENCE DESCRIPTION: SEQ ID NO: 108:

TCNGCRAART ANCCNGCAAG GATCCTGCAG        30

( 2 ) INFORMATION FOR SEQ ID NO: 109:

( i ) SEQUENCE CHARACTERISTICS:
        ( A ) LENGTH: 38
        ( B ) TYPE: nucleic acid
        ( C ) STRANDEDNESS: single
        ( D ) TOPOLOGY: linear ( x i ) SEQUENCE DESCRIPTION: SEQ ID NO: 109:

CATCGATCTG CAGGCTGATT CTGCAGAATA TATGTGCA        38

( 2 ) INFORMATION FOR SEQ ID NO: 110:

( i ) SEQUENCE CHARACTERISTICS:
        ( A ) LENGTH: 37
        ( B ) TYPE: nucleic acid
        ( C ) STRANDEDNESS: single
        ( D ) TOPOLOGY: linear ( x i ) SEQUENCE DESCRIPTION: SEQ ID NO: 110:

AAGGATCCTG CAGCCACATC TCGAGTCGAC ATCGATT     37

( 2 ) INFORMATION FOR SEQ ID NO: 111:

( i ) SEQUENCE CHARACTERISTICS:
        ( A ) LENGTH: 37
        ( B ) TYPE: nucleic acid
        ( C ) STRANDEDNESS: single
        ( D ) TOPOLOGY: linear ( x i ) SEQUENCE DESCRIPTION: SEQ ID NO: 111:

CCGAATTCTG CAGTGATCAG CAAACTAGGA AATGACA     37

( 2 ) INFORMATION FOR SEQ ID NO: 112:

( i ) SEQUENCE CHARACTERISTICS:
        ( A ) LENGTH: 37
        ( B ) TYPE: nucleic acid
        ( C ) STRANDEDNESS: single
        ( D ) TOPOLOGY: linear ( x i ) SEQUENCE DESCRIPTION: SEQ ID NO: 112:

CATCGATCTG CAGCCTAGTT TGCTGATCAC TTTGCAC     37

( 2 ) INFORMATION FOR SEQ ID NO: 113:

( i ) SEQUENCE CHARACTERISTICS:
        ( A ) LENGTH: 37
        ( B ) TYPE: nucleic acid
        ( C ) STRANDEDNESS: single
        ( D ) TOPOLOGY: linear ( x i ) SEQUENCE DESCRIPTION: SEQ ID NO: 113:

AAGGATCCTG CAGTATATTC TCCAGAATCA GCCAGTG     37

( 2 ) INFORMATION FOR SEQ ID NO: 114:

( i ) SEQUENCE CHARACTERISTICS:
        ( A ) LENGTH: 34
        ( B ) TYPE: nucleic acid
        ( C ) STRANDEDNESS: single
        ( D ) TOPOLOGY: linear ( x i ) SEQUENCE DESCRIPTION: SEQ ID NO: 114:

AAGGATCCTG CAGGCACGCA GTAGGCATCT CTTA     34

( 2 ) INFORMATION FOR SEQ ID NO: 115:

( i ) SEQUENCE CHARACTERISTICS:
        ( A ) LENGTH: 35
        ( B ) TYPE: nucleic acid
        ( C ) STRANDEDNESS: single
        ( D ) TOPOLOGY: linear ( x i ) SEQUENCE DESCRIPTION: SEQ ID NO: 115:

CCGAATTCTG CAGCAGAACT TCGCATTAGC AAAGC     35

( 2 ) INFORMATION FOR SEQ ID NO: 116:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( x i ) SEQUENCE DESCRIPTION: SEQ ID NO: 116:

CATCCCGGGA TGAAGAGTCA GGAGTCTGTG GCA        33

( 2 ) INFORMATION FOR SEQ ID NO: 117:

( i ) SEQUENCE CHARACTERISTICS:
        ( A ) LENGTH: 39
        ( B ) TYPE: nucleic acid
        ( C ) STRANDEDNESS: single
        ( D ) TOPOLOGY: linear ( x i ) SEQUENCE DESCRIPTION: SEQ ID NO: 117:

ATACCCGGGC TGCAGACAAT GAGATTTCAC ACACCTGCG        39

( 2 ) INFORMATION FOR SEQ ID NO: 118:

( i ) SEQUENCE CHARACTERISTICS:
        ( A ) LENGTH: 36
        ( B ) TYPE: nucleic acid
        ( C ) STRANDEDNESS: single
        ( D ) TOPOLOGY: linear ( x i ) SEQUENCE DESCRIPTION: SEQ ID NO: 118:

AAGGATCCTG CAGTTTGGAA CCTGCCACAG ACTCCT        36

( 2 ) INFORMATION FOR SEQ ID NO: 119:

( i ) SEQUENCE CHARACTERISTICS:
        ( A ) LENGTH: 39
        ( B ) TYPE: nucleic acid
        ( C ) STRANDEDNESS: single
        ( D ) TOPOLOGY: linear ( x i ) SEQUENCE DESCRIPTION: SEQ ID NO: 119:

ATACCCGGGC TGCAGATGAG ATTTCACACA CCTGCGTGA        39

( 2 ) INFORMATION FOR SEQ ID NO: 120:

( i ) SEQUENCE CHARACTERISTICS:
        ( A ) LENGTH: 12
        ( B ) TYPE: amino acid
        ( C ) STRANDEDNESS:
        ( D ) TOPOLOGY: linear ( x i ) SEQUENCE DESCRIPTION: SEQ ID NO: 120:

His Gln Val Trp Ala Ala Lys Ala Ala Gly Leu Lys
1                5                  10

( 2 ) INFORMATION FOR SEQ ID NO: 121:

( i ) SEQUENCE CHARACTERISTICS:
        ( A ) LENGTH: 16
        ( B ) TYPE: amino acid
        ( C ) STRANDEDNESS:
        ( D ) TOPOLOGY: linear ( x i ) SEQUENCE DESCRIPTION: SEQ ID NO: 121:

Gly Gly Leu Lys Lys Asp Ser Leu Leu Thr Val Arg Leu Gly Ala Asn
1                5                  10                  15

( 2 ) INFORMATION FOR SEQ ID NO: 122:

( i ) SEQUENCE CHARACTERISTICS:
        ( A ) LENGTH: 13
        ( B ) TYPE: amino acid
        ( C ) STRANDEDNESS:
        ( D ) TOPOLOGY: linear ( i x ) FEATURE:
        ( D ) OTHER INFORMATION: Xaa in position 12 is unknown.

( x i ) SEQUENCE DESCRIPTION: SEQ ID NO: 122:

```
Leu Gly Ala Trp Gly Pro Pro Ala Phe Pro Val Xaa Tyr
 1               5                  10
```

( 2 ) INFORMATION FOR SEQ ID NO: 123:

( i ) SEQUENCE CHARACTERISTICS:
        ( A ) LENGTH: 23
        ( B ) TYPE: amino acid
        ( C ) STRANDEDNESS:
        ( D ) TOPOLOGY: linear ( x i ) SEQUENCE DESCRIPTION: SEQ ID NO: 123:

```
Leu Leu Thr Val Arg Leu Gly Ala Trp Gly His Pro Ala Phe Pro Ser
 1               5                  10                  15
Cys Gly Arg Leu Lys Glu Asp
                20
```

( 2 ) INFORMATION FOR SEQ ID NO: 124:

( i ) SEQUENCE CHARACTERISTICS:
        ( A ) LENGTH: 13
        ( B ) TYPE: amino acid
        ( C ) STRANDEDNESS:
        ( D ) TOPOLOGY: linear ( i x ) FEATURE:
        ( D ) OTHER INFORMATION: Xaa in position 10 is unknown.

( x i ) SEQUENCE DESCRIPTION: SEQ ID NO: 124:

```
Tyr Ile Phe Phe Met Glu Pro Glu Ala Xaa Ser Ser Gly
 1               5                  10
```

( 2 ) INFORMATION FOR SEQ ID NO: 125:

( i ) SEQUENCE CHARACTERISTICS:
        ( A ) LENGTH: 23
        ( B ) TYPE: amino acid
        ( C ) STRANDEDNESS:
        ( D ) TOPOLOGY: linear ( x i ) SEQUENCE DESCRIPTION: SEQ ID NO: 125:

```
Lys Glu Asp Ser Arg Tyr Ile Phe Phe Met Glu Pro Glu Ala Asn Ser
 1               5                  10                  15
Ser Gly Gly Pro Gly Arg Leu
                20
```

( 2 ) INFORMATION FOR SEQ ID NO: 126:

( i ) SEQUENCE CHARACTERISTICS:
        ( A ) LENGTH: 14
        ( B ) TYPE: amino acid
        ( C ) STRANDEDNESS:
        ( D ) TOPOLOGY: linear ( x i ) SEQUENCE DESCRIPTION: SEQ ID NO: 126:

```
Val Ala Gly Ser Lys Leu Val Leu Arg Cys Glu Thr Ser Ser
 1               5                  10
```

( 2 ) INFORMATION FOR SEQ ID NO: 127:

( i ) SEQUENCE CHARACTERISTICS:
        ( A ) LENGTH: 16
        ( B ) TYPE: amino acid
        ( C ) STRANDEDNESS:
        ( D ) TOPOLOGY: linear ( x i ) SEQUENCE DESCRIPTION: SEQ ID NO: 127:

```
Glu  Tyr  Lys  Cys  Leu  Lys  Phe  Lys  Trp  Phe  Lys  Lys  Ala  Thr  Val  Met
 1                  5                        10                       15
```

( 2 ) INFORMATION FOR SEQ ID NO: 128:

( i ) SEQUENCE CHARACTERISTICS:
        ( A ) LENGTH: 26
        ( B ) TYPE: amino acid
        ( C ) STRANDEDNESS:
        ( D ) TOPOLOGY: linear ( x i ) SEQUENCE DESCRIPTION: SEQ ID NO: 128:

```
Cys  Glu  Thr  Ser  Ser  Glu  Tyr  Ser  Ser  Leu  Lys  Phe  Lys  Trp  Phe  Lys
 1                  5                        10                       15
Asn  Gly  Ser  Glu  Leu  Ser  Arg  Lys  Asn  Lys
                20                       25
```

( 2 ) INFORMATION FOR SEQ ID NO: 129:

( i ) SEQUENCE CHARACTERISTICS:
        ( A ) LENGTH: 13
        ( B ) TYPE: amino acid
        ( C ) STRANDEDNESS:
        ( D ) TOPOLOGY: linear ( i x ) FEATURE:
        ( D ) OTHER INFORMATION: Xaa in position 12 is unknown.

( x i ) SEQUENCE DESCRIPTION: SEQ ID NO: 129:

```
Lys  Ala  Ser  Leu  Ala  Asp  Ser  Gly  Glu  Tyr  Met  Xaa  Lys
 1                  5                        10
```

( 2 ) INFORMATION FOR SEQ ID NO: 130:

( i ) SEQUENCE CHARACTERISTICS:
        ( A ) LENGTH: 23
        ( B ) TYPE: amino acid
        ( C ) STRANDEDNESS:
        ( D ) TOPOLOGY: linear ( x i ) SEQUENCE DESCRIPTION: SEQ ID NO: 130:

```
Glu  Leu  Arg  Ile  Ser  Lys  Ala  Ser  Leu  Ala  Asp  Ser  Gly  Glu  Tyr  Met
 1                  5                        10                       15
Cys  Lys  Val  Ile  Ser  Lys  Leu
                20
```

( 2 ) INFORMATION FOR SEQ ID NO: 131:

( i ) SEQUENCE CHARACTERISTICS:
        ( A ) LENGTH: 12
        ( B ) TYPE: amino acid
        ( C ) STRANDEDNESS:
        ( D ) TOPOLOGY: linear ( x i ) SEQUENCE DESCRIPTION: SEQ ID NO: 131:

```
Ala  Ser  Leu  Ala  Asp  Glu  Tyr  Glu  Tyr  Met  Arg  Lys
 1                  5                        10
```

( 2 ) INFORMATION FOR SEQ ID NO: 132:

( i ) SEQUENCE CHARACTERISTICS:
    ( A ) LENGTH: 22
    ( B ) TYPE: amino acid
    ( C ) STRANDEDNESS:
    ( D ) TOPOLOGY: linear ( x i ) SEQUENCE DESCRIPTION: SEQ ID NO: 132:

```
Leu Arg Ile Ser Lys Ala Ser Leu Ala Asp Ser Gly Glu Tyr Met Cys
 1               5                  10                  15

Lys Val Ile Ser Lys Leu
            20
```

( 2 ) INFORMATION FOR SEQ ID NO: 133:

( i ) SEQUENCE CHARACTERISTICS:
    ( A ) LENGTH: 744
    ( B ) TYPE: nucleic acid
    ( C ) STRANDEDNESS: single
    ( D ) TOPOLOGY: linear ( x i ) SEQUENCE DESCRIPTION: SEQ ID NO: 133:

```
CCTGCAG CAT CAA GTG TGG GCG GCG
        His Gln Val Trp Ala Ala
         1               5

AAA GCC GGG GGC TTG AAG AAG GAC TCG CTG                        55
        Lys Ala Gly Gly Leu Lys Lys Asp Ser Leu
                 10                  15

CTC ACC GTG CGC CTG GGC GCC TGG GGC CAC CCC GCC TTC CCC TCC TGC       103
Leu Thr Val Arg Leu Gly Ala Trp Gly His Pro Ala Phe Pro Ser Cys
             20                  25                  30

GGG CGC CTC AAG GAG GAC AGC AGG TAC ATC TTC TTC ATG GAG CCC GAG       151
Gly Arg Leu Lys Glu Asp Ser Arg Tyr Ile Phe Phe Met Glu Pro Glu
         35                  40                  45

GCC AAC AGC AGC GGC GGG CCC GGC CGC CTT CCG AGC CTC CTT CCC CCC       199
Ala Asn Ser Ser Gly Gly Pro Gly Arg Leu Pro Ser Leu Leu Pro Pro
     50                  55                  60

TCT CGA GAC GGG CCG GAA CCT CAA GAA GGA GGT CAG CCG GGT GCT GTG       247
Ser Arg Asp Gly Pro Glu Pro Gln Glu Gly Gly Gln Pro Gly Ala Val
 65                  70                  75                  80

CAA CGG TGC GCC TTG CCT CCC CGC TTG AAA GAG ATG AAG AGT CAG GAG       295
Gln Arg Cys Ala Leu Pro Pro Arg Leu Lys Glu Met Lys Ser Gln Glu
                 85                  90                  95

TCT GTG GCA GGT TCC AAA CTA GTG CTT CGG TGC GAG ACC AGT TCT GAA       343
Ser Val Ala Gly Ser Lys Leu Val Leu Arg Cys Glu Thr Ser Ser Glu
             100                 105                 110

TAC TCC TCT CTC AAG TTC AAG TGG TTC AAG AAT GGG AGT GAA TTA AGC       391
Tyr Ser Ser Leu Lys Phe Lys Trp Phe Lys Asn Gly Ser Glu Leu Ser
         115                 120                 125

CGA AAG AAC AAA CCA GAA AAC ATC AAG ATA CAG AAA AGG CCG GGG AAG       439
Arg Lys Asn Lys Pro Glu Asn Ile Lys Ile Gln Lys Arg Pro Gly Lys
     130                 135                 140

TCA GAA CTT CGC ATT AGC AAA GCG TCA CTG GCT GAT TCT GGA GAA TAT       487
Ser Glu Leu Arg Ile Ser Lys Ala Ser Leu Ala Asp Ser Gly Glu Tyr
 145                 150                 155                 160

ATG TGC AAA GTG ATC AGC AAA CTA GGA AAT GAC AGT GCC TCT GCC AAC       535
Met Cys Lys Val Ile Ser Lys Leu Gly Asn Asp Ser Ala Ser Ala Asn
                 165                 170                 175

ATC ACC ATT GTG GAG TCA AAC GGT AAG AGA TGC CTA CTG CGT GCT ATT       583
Ile Thr Ile Val Glu Ser Asn Gly Lys Arg Cys Leu Leu Arg Ala Ile
             180                 185                 190
```

| TCT | CAG | TCT | CTA | AGA | GGA | GTG | ATC | AAG | GTA | TGT | GGT | CAC | ACT | 625 |
| Ser | Gln | Ser | Leu | Arg | Gly | Val | Ile | Lys | Val | Cys | Gly | His | Thr | |
| | | 195 | | | | 200 | | | | | 205 | | | |

TGAATCACGC AGGTGTGTGA AATCTCATTG TGAACAAATA AAAATCATGA AAGGAAAAAA 685

AAAAAAAAAA AATCGATGTC GACTCGAGAT GTGGCTGCAG GTCGACTCTA GAGGATCCC 744

( 2 ) INFORMATION FOR SEQ ID NO: 134:

( i ) SEQUENCE CHARACTERISTICS:
        ( A ) LENGTH: 1193
        ( B ) TYPE: nucleic acid
        ( C ) STRANDEDNESS: single
        ( D ) TOPOLOGY: linear ( x i ) SEQUENCE DESCRIPTION: SEQ ID NO: 134:

| CCTGCAG | CAT | CAA | GTG | TGG | GCG | GCG | | | | | | | | | |
| | His | Gln | Val | Trp | Ala | Ala | | | | | | | | | |
| | 1 | | | | 5 | | | | | | | | | | |

| | AAA | GCC | GGG | GGC | TTG | AAG | AAG | GAC | TCG | CTG | | | | | 55 |
| | Lys | Ala | Gly | Gly | Leu | Lys | Lys | Asp | Ser | Leu | | | | | |
| | | | | 10 | | | | | 15 | | | | | | |

| CTC | ACC | GTG | CGC | CTG | GGC | GCC | TGG | GGC | CAC | CCC | GCC | TTC | CCC | TCC | TGC | 103 |
| Leu | Thr | Val | Arg | Leu | Gly | Ala | Trp | Gly | His | Pro | Ala | Phe | Pro | Ser | Cys | |
| | | | 20 | | | | | 25 | | | | | 30 | | | |

| GGG | CGC | CTC | AAG | GAG | GAC | AGC | AGG | TAC | ATC | TTC | TTC | ATG | GAG | CCC | GAG | 151 |
| Gly | Arg | Leu | Lys | Glu | Asp | Ser | Arg | Tyr | Ile | Phe | Phe | Met | Glu | Pro | Glu | |
| | | 35 | | | | | 40 | | | | | 45 | | | | |

| GCC | AAC | AGC | AGC | GGC | GGG | CCC | GGC | CGC | CTT | CCG | AGC | CTC | CTT | CCC | CCC | 199 |
| Ala | Lys | Ser | Ser | Gly | Gly | Pro | Gly | Arg | Leu | Pro | Ser | Leu | Leu | Pro | Pro | |
| | 50 | | | | | 55 | | | | | 60 | | | | | |

| TCT | CGA | GAC | GGG | CCG | GAA | CCT | CAA | GAA | GGA | GGT | CAG | CCG | GGT | GCT | GTG | 247 |
| Ser | Arg | Asp | Gly | Pro | Glu | Pro | Gln | Glu | Gly | Gly | Gln | Pro | Gly | Ala | Val | |
| 65 | | | | | 70 | | | | | 75 | | | | | 80 | |

| CAA | CGG | TGC | GCC | TTG | CCT | CCC | CGC | TTG | AAA | GAG | ATG | AAG | AGT | CAG | GAG | 295 |
| Gln | Arg | Cys | Ala | Leu | Pro | Pro | Arg | Leu | Lys | Glu | Met | Lys | Ser | Gln | Glu | |
| | | | | 85 | | | | | 90 | | | | | 95 | | |

| TCT | GTG | GCA | GGT | TCC | AAA | CTA | GTG | CTT | CGG | TGC | GAG | ACC | AGT | TCT | GAA | 343 |
| Ser | Val | Ala | Gly | Ser | Lys | Leu | Val | Leu | Arg | Cys | Glu | Thr | Ser | Ser | Glu | |
| | | | 100 | | | | | 105 | | | | | 110 | | | |

| TAC | TCC | TCT | CTC | AAG | TTC | AAG | TGG | TTC | AAG | AAT | GGG | AGT | GAA | TTA | AGC | 391 |
| Tyr | Ser | Ser | Leu | Lys | Phe | Lys | Trp | Phe | Lys | Asn | Gly | Ser | Glu | Leu | Ser | |
| | | 115 | | | | | 120 | | | | | 125 | | | | |

| CGA | AAG | AAC | AAA | CCA | GAA | AAC | ATC | AAG | ATA | CAG | AAA | AGG | CCG | GGG | AAG | 439 |
| Arg | Lys | Asn | Lys | Gly | Gly | Asn | Ile | Lys | Ile | Gln | Lys | Arg | Pro | Gly | Lys | |
| | 130 | | | | | 135 | | | | | 140 | | | | | |

| TCA | GAA | CTT | CGC | ATT | AGC | AAA | GCG | TCA | CTG | GCT | GAT | TCT | GGA | GAA | TAT | 487 |
| Ser | Glu | Leu | Arg | Ile | Ser | Lys | Ala | Ser | Leu | Ala | Asp | Ser | Gly | Glu | Tyr | |
| 145 | | | | | 150 | | | | | 155 | | | | | 160 | |

| ATG | TGC | AAA | GTG | ATC | AGC | AAA | CTA | GGA | AAT | GAC | AGT | GCC | TCT | GCC | AAC | 535 |
| Met | Cys | Lys | Val | Ile | Ser | Lys | Leu | Gly | Asn | Asp | Ser | Ala | Ser | Ala | Asn | |
| | | | | 165 | | | | | 170 | | | | | 175 | | |

| ATC | ACC | ATT | GTG | GAG | TCA | AAC | GCC | ACA | TCC | ACA | TCT | ACA | GCT | GGG | ACA | 583 |
| Ile | Thr | Ile | Val | Glu | Ser | Asn | Ala | Thr | Ser | Thr | Ser | Thr | Ala | Gly | Thr | |
| | | | 180 | | | | | 185 | | | | | 190 | | | |

| AGC | CAT | CTT | GTC | AAG | TGT | GCA | GAG | AAG | GAG | AAA | ACT | TTC | TGT | GTG | AAT | 631 |
| Ser | His | Leu | Val | Lys | Ser | Ala | Glu | Lys | Glu | Lys | Thr | Phe | Cys | Val | Asn | |
| | | 195 | | | | | 200 | | | | | 205 | | | | |

| GGA | GGC | GAG | TGC | TTC | ATG | GTG | AAA | GAC | CTT | TCA | AAT | CCC | TCA | AGA | TAC | 679 |
| Gly | Gly | Glu | Cys | Phe | Met | Val | Lys | Asp | Leu | Ser | Asn | Pro | Ser | Arg | Tyr | |
| | 210 | | | | | 215 | | | | | 220 | | | | | |

| TTG | TGC | AAG | TGC | CAA | CCT | GGA | TTC | ACT | GGA | GCG | AGA | TGT | ACT | GAG | AAT | 727 |

| | | | | | | | | | | | | | | | |
|---|---|---|---|---|---|---|---|---|---|---|---|---|---|---|---|
| Leu | Cys | Lys | Cys | Gln | Pro | Gly | Phe | Thr | Gly | Ala | Arg | Cys | Thr | Glu | Asn |
| 225 | | | | | 230 | | | | | 235 | | | | | 240 |

| GTG | CCC | ATG | AAA | GTC | CAA | ACC | CAA | GAA | AGT | GCC | CAA | ATG | AGT | TTA | CTG | 775 |
|---|---|---|---|---|---|---|---|---|---|---|---|---|---|---|---|---|
| Val | Pro | Met | Lys | Val | Gln | Thr | Gln | Glu | Ser | Ala | Gln | Met | Ser | Leu | Leu | |
| | | | 245 | | | | | 250 | | | | | 255 | | | |

| GTG | ATC | GCT | GCC | AAA | ACT | ACG | TAATGGCCAG | CTTCTACAGT | ACGTCCACTC |
|---|---|---|---|---|---|---|---|---|---|
| Val | Ile | Ala | Ala | Lys | Thr | Thr | | | |
| | | | 260 | | | | | | |

| CCTTTCTGTC | TCTGCCTGAA | TAGCGCATCT | CAGTCGGTGC | CGCTTTCTTG | TTGCCGCATC | 886 |
|---|---|---|---|---|---|---|
| TCCCCTCAGA | TTCCTCCTAG | AGCTAGATGC | GTTTTACCAG | GTCTAACATT | GACTGCCTCT | 946 |
| GCCTGTCGCA | TGAGAACATT | AACACAAGCG | ATTGTATGAC | TTCCTCTGTC | CGTGACTAGT | 1006 |
| GGGCTCTGAG | CTACTCGTAG | GTGCGTAAGG | CTCCAGTGTT | TCTGAAATTG | ATCTTGAATT | 1066 |
| ACTGTGATAC | GACATGATAG | TCCCTCTCAC | CCAGTGCAAT | GACAATAAAG | GCCTTGAAAA | 1126 |
| GTCAAAAAAA | AAAAAAAAAA | AAAAAATCGA | TGTCGACTCG | AGATGTGGCT | GCAGGTCGAC | 1186 |
| TCTAGAG | | | | | | 1193 |

( 2 ) INFORMATION FOR SEQ ID NO: 135:

( i ) SEQUENCE CHARACTERISTICS:
        ( A ) LENGTH: 1108
        ( B ) TYPE: nucleic acid
        ( C ) STRANDEDNESS: single
        ( D ) TOPOLOGY: linear ( x i ) SEQUENCE DESCRIPTION: SEQ ID NO: 135:

| CCTGCAG | CAT | CAA | GTG | TGG | GCG | GCG | | | | | | | | | | |
|---|---|---|---|---|---|---|---|---|---|---|---|---|---|---|---|---|
| | His | Gln | Val | Trp | Ala | Ala | | | | | | | | | | |
| | 1 | | | | 5 | | | | | | | | | | | |

| | AAA | GCC | GGG | GGC | TTG | AAG | AAG | GAC | TCG | CTG | | | | | | 55 |
|---|---|---|---|---|---|---|---|---|---|---|---|---|---|---|---|---|
| | Lys | Ala | Gly | Gly | Leu | Lys | Lys | Asp | Ser | Leu | | | | | | |
| | | | | 10 | | | | | 15 | | | | | | | |

| CTC | ACC | GTG | CGC | CTG | GGC | GCC | TGG | GGC | CAC | CCC | GCC | TTC | CCC | TCC | TGC | 103 |
|---|---|---|---|---|---|---|---|---|---|---|---|---|---|---|---|---|
| Leu | Thr | Val | Arg | Leu | Gly | Ala | Trp | Gly | His | Pro | Ala | Phe | Pro | Ser | Cys | |
| | | | 20 | | | | 25 | | | | | 30 | | | | |

| GGG | CGC | CTC | AAG | GAG | GAC | AGC | AGG | TAC | ATC | TTC | TTC | ATG | GAG | CCC | GAG | 151 |
|---|---|---|---|---|---|---|---|---|---|---|---|---|---|---|---|---|
| Gly | Arg | Leu | Lys | Glu | Asp | Ser | Arg | Tyr | Ile | Phe | Phe | Met | Glu | Pro | Glu | |
| | | 35 | | | | | 40 | | | | | 45 | | | | |

| GCC | AAC | AGC | AGC | GGC | GGG | CCC | GGC | CGC | CTT | CCG | AGC | CTC | CTT | CCC | CCC | 199 |
|---|---|---|---|---|---|---|---|---|---|---|---|---|---|---|---|---|
| Ala | Asn | Ser | Ser | Gly | Gly | Pro | Gly | Arg | Leu | Pro | Ser | Leu | Leu | Pro | Pro | |
| | 50 | | | | | 55 | | | | | 60 | | | | | |

| TCT | CGA | GAC | GGG | CCG | GAA | CCT | CAA | GAA | GGA | GGT | CAG | CCG | GGT | GCT | GTG | 247 |
|---|---|---|---|---|---|---|---|---|---|---|---|---|---|---|---|---|
| Ser | Arg | Asp | Gly | Pro | Glu | Pro | Gln | Glu | Gly | Gly | Gln | Pro | Gly | Ala | Val | |
| 65 | | | | | 70 | | | | | 75 | | | | | 80 | |

| CAA | CGG | TGC | GCC | TTG | CCT | CCC | CGC | TTG | AAA | GAG | ATG | AAG | AGT | CAG | GAG | 295 |
|---|---|---|---|---|---|---|---|---|---|---|---|---|---|---|---|---|
| Gln | Arg | Cys | Ala | Leu | Pro | Pro | Arg | Leu | Lys | Glu | Met | Lys | Ser | Gln | Glu | |
| | | | | 85 | | | | | 90 | | | | | 95 | | |

| TCT | GTG | GCA | GGT | TCC | AAA | CTA | GTG | CTT | CGG | TGC | GAG | ACC | AGT | TCT | GAA | 343 |
|---|---|---|---|---|---|---|---|---|---|---|---|---|---|---|---|---|
| Ser | Val | Ala | Gly | Ser | Lys | Leu | Val | Leu | Arg | Cys | Glu | Thr | Ser | Ser | Glu | |
| | | | 100 | | | | | 105 | | | | | 110 | | | |

| TAC | TCC | TCT | CTC | AAG | TTC | AAG | TGG | TTC | AAG | AAT | GGG | AGT | GAA | TTA | AGC | 391 |
|---|---|---|---|---|---|---|---|---|---|---|---|---|---|---|---|---|
| Tyr | Ser | Ser | Leu | Lys | Phe | Lys | Trp | Phe | Lys | Asn | Gly | Ser | Glu | Leu | Ser | |
| | | | 115 | | | | 120 | | | | | 125 | | | | |

| CGA | AAG | AAC | AAA | CCA | GAA | AAC | ATC | AAG | ATA | CAG | AAA | AGG | CCG | GGG | AAG | 439 |
|---|---|---|---|---|---|---|---|---|---|---|---|---|---|---|---|---|
| Arg | Lys | Asn | Lys | Pro | Glu | Asn | Ile | Lys | Ile | Gln | Lys | Arg | Pro | Pro | Lys | |
| | | 130 | | | | | 135 | | | | | 140 | | | | |

| TCA | GAA | CTT | CGC | ATT | AGC | AAA | GCG | TCA | CTG | GCT | GAT | TCT | GGA | GAA | TAT | 487 |
|---|---|---|---|---|---|---|---|---|---|---|---|---|---|---|---|---|
| Ser | Glu | Leu | Arg | Ile | Ser | Lys | Ala | Ser | Leu | Ala | Asp | Ser | Gly | Glu | Tyr | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ATG | TGC | AAA | GTG | ATC | AGC | AAT | CTA | GGA | AAT | GAC | AGT | GCC | TCT | GCC | AAC | 535 |
| Met | Cys | Lys | Val | Ile | Ser | Lys | Leu | Gly | Asn | Asp | Ser | Ala | Ser | Ala | Asn | |
| | | | | 165 | | | | | 170 | | | | | 175 | | |
| ATC | ACC | ATT | GTG | GAG | TCA | GTG | GCC | ACA | TCC | ACA | TCT | ACA | GCT | GGG | ACA | 583 |
| Ile | Arg | Ile | Val | Glu | Ser | Asn | Ala | Thr | Ser | Thr | Ser | Thr | Ala | Gly | Thr | |
| | | | 180 | | | | | 185 | | | | | 190 | | | |
| AGC | CAT | CTT | GTC | AAG | TGT | GTG | GAG | AAG | GAG | AAA | ACT | TTC | TGT | GTG | AAT | 631 |
| Ser | His | Leu | Val | Lys | Cys | Ala | Glu | Lys | Glu | Lys | Thr | Phe | Cys | Val | Asn | |
| | | 195 | | | | | 200 | | | | | 205 | | | | |
| GGA | GGC | GAG | TGC | TTC | ATG | GTG | AAA | GAC | CTT | TCA | AAT | CCC | TCA | AGA | TAC | 679 |
| Gly | Gly | Glu | Cys | Phe | Met | Val | Lys | Asp | Leu | Ser | Asn | Pro | Ser | Arg | Tyr | |
| 210 | | | | | 215 | | | | | 220 | | | | | | |
| TTG | TGC | AAG | TGC | CCA | AAT | GAG | TTT | ACT | GGT | GAT | CGC | TGC | CAA | AAC | TAC | 727 |
| Leu | Cys | Lys | Cys | Pro | Asn | Glu | Phe | Thr | Gly | Asp | Arg | Cys | Gln | Asn | Tyr | |
| 225 | | | | | 230 | | | | | 235 | | | | | 240 | |
| GTA | ATG | GCC | AGC | TTC | TAC | AGT | ACG | TCC | ACT | CCC | TTT | CTG | TCT | CTG | CCT | 775 |
| Val | Met | Ala | Ser | Phe | Tyr | Ser | Thr | Ser | Thr | Pro | Phe | Leu | Ser | Leu | Pro | |
| | | | | 245 | | | | | 250 | | | | | 255 | | |

| | | | | | |
|---|---|---|---|---|---|
| GAA | TAGCGCATCT | CAGTCGGTGC | CGCTTTCTTG | TTGCCGCATC | TCCCCTCAGA TTCCGCTAG 838 |
| Glu | | | | | |
| AGCTAGATGC | GTTTTACCAG | GTCTAACATT | GACTGCCTCT | GCCTGTCGCA | TGAGAACATT 898 |
| AACACAAGCG | ATTGTATGAC | TTCCTCTGTC | CGTGACTAGT | GGGCTCTGAG | CTACTCGTAG 958 |
| GTGCGTAAGG | CTCCAGTGTT | TCTGAAATTG | ATCTTGAATT | ACTGTGATAC | GACATGATAG 1018 |
| TCCCTCTCAC | CCAGTGCAAT | GACAATAAAG | GCCTTGAAAA | GTCAAAAAAA | AAAAAAAAA 1078 |
| AAAAATCGAT | GTCGACTCGA | GATGTGGCTG | | | 1108 |

( 2 ) INFORMATION FOR SEQ ID NO: 136:

( i ) SEQUENCE CHARACTERISTICS:
        ( A ) LENGTH: 559
        ( B ) TYPE: nucleic acid
        ( C ) STRANDEDNESS: single
        ( D ) TOPOLOGY: linear ( i x ) FEATURE:
        ( D ) OTHER INFORMATION: N in position 214 is unknown.

( x i ) SEQUENCE DESCRIPTION: SEQ ID NO: 136:

| | | | | | |
|---|---|---|---|---|---|
| AGTTTCCCCC | CCCAACTTGT | CGGAACTCTG | GGCTCGCGCG | CAGGGCAGGA | GCGGAGCGGC 60 |
| GGCGGCTGCC | CAGGCGATGC | GAGCGCGGGC | CGGACGGTAA | TCGCCTCTCC | CTCCTCGGGC 120 |
| TGCGAGCGCG | CCGGACCGAG | GCAGCGACAG | GAGCGGACCG | CGGCGGGAAC | CGAGGACTCC 180 |
| CCAGCGGCGC | GCCAGCAGGA | GCCACCCCGC | GAGNCGTGCG | ACCGGGACGG | AGCGCCCGCC 240 |
| AGTCCCAGGT | GGCCCGGACC | GCACGTTGCG | TCCCCGCGCT | CCCCGCCGGC | GACAGGAGAC 300 |
| GCTCCCCCCC | ACGCCGCGCG | CGCCTCGGCC | CGGTCGCTGG | CCCGCCTCCA | CTCCGGGGAC 360 |
| AAACTTTTCC | CGAAGCCGAT | CCCAGCCCTC | GGACCCAAAC | TTGTCGCGCG | TCGCCTTCGC 420 |
| CGGGAGCCGT | CCGCGCAGAG | CGTGCACTTC | TCGGGCGAG | | |

| | | | | | | | | |
|---|---|---|---|---|---|---|---|---|
| | | | | | ATG | TCG | GAG | CGC AGA 474 |
| | | | | | Met | Ser | Glu | Arg Arg |
| | | | | | 1 | | | 5 |
| GAA | GGC | AAA | GGC | AAG | GGG | AAG | GGC | GGC AAG AAG GAC CGA GGC TCC GGG 522 |
| Glu | Gly | Lys | Gly | Lys | Gly | Lys | Gly | Gly Lys Lys Asp Arg Gly Ser Gly |
| | | | 10 | | | | 15 | 20 |
| AAG | AAG | CCC | GTG | CCC | GCG | GCT | GGC | GGC CCG AGC CCA G 559 |
| Lys | Lys | Pro | Val | Pro | Ala | Ala | Gly | Gly Pro Ser Pro Ala |
| | | | 25 | | | | 30 | |

( 2 ) INFORMATION FOR SEQ ID NO: 137:

(i) SEQUENCE CHARACTERISTICS:
    (A) LENGTH: 252
    (B) TYPE: nucleic acid
    (C) STRANDEDNESS: single
    (D) TOPOLOGY: linear (ix) FEATURE:
    (D) OTHER INFORMATION: N in position 8 could be either A or G.

(xi) SEQUENCE DESCRIPTION: SEQ ID NO: 137:

| | | | | | | | | | | | | | | | | |
|---|---|---|---|---|---|---|---|---|---|---|---|---|---|---|---|---|
| CC CAT | CAN | GTG | TGG | GCG | GCG | AAA | GCC | GGG | GGC | TTG | AAG | AAG | GAC | TCG | | 47 |
| His | Gln | Val | Trp | Ala | Ala | Lys | Ala | Gly | Gly | Leu | Lys | Lys | Asp | Ser | | |
| 1 | | | | 5 | | | | | 10 | | | | | 15 | | |
| CTG | CTC | ACC | GTG | CGC | CTG | GGC | GCC | TGG | GGC | CAC | CCC | GCC | TTC | CCC | TCC | 95 |
| Leu | Leu | Thr | Val | Arg | Leu | Gly | Ala | Trp | Gly | His | Pro | Ala | Phe | Pro | Ser | |
| | | | | 20 | | | | | 25 | | | | | 30 | | |
| TGC | GGG | CGC | CTC | AAG | GAG | GAC | AGC | AGG | TAC | ATC | TTC | TTC | ATG | GAG | CCC | 143 |
| Cys | Gly | Arg | Leu | Lys | Glu | Asp | Ser | Arg | Tyr | Ile | Phe | Phe | Met | Glu | Pro | |
| | | | 35 | | | | | 40 | | | | | 45 | | | |
| GAG | GCC | AAC | AGC | AGC | GGC | GLG | CCC | GGC | CGC | CTT | CCG | AGC | CTC | CTT | CCC | 191 |
| Glu | Ala | Asn | Ser | Ser | Gly | Gly | Pro | Gly | Arg | Leu | Pro | Ser | Leu | Leu | Pro | |
| | | 50 | | | | | 55 | | | | | 60 | | | | |
| CCC | TCT | CGA | GAC | GGG | CCG | GAA | CCT | CAA | GAA | GGA | GGT | CAG | CCG | GGT | GCT | 239 |
| Pro | Ser | Arg | Asp | Gly | Pro | Glu | Pro | Gln | Glu | Gly | Gly | Gln | Pro | Gly | Ala | |
| | 65 | | | | | 70 | | | | | 75 | | | | | |
| GTG | CAA | CGG | TGC | G | | | | | | | | | | | | 252 |
| Val | Gln | Arg | Cys | | | | | | | | | | | | | |
| 80 | | | | | | | | | | | | | | | | |

(2) INFORMATION FOR SEQUEIZCE IDENTIFICATION NUMBER: 138:

(i) SEQUENCE CHARACTERISTICS:
    (A) LENGTH: 178
    (B) TYPE: nucleic acid
    (C) STRANDEDNESS: single
    (D) TOPOLOGY: linear (xi) SEQUENCE DESCRIPTION: SEQ ID NO: 138:

| | | | | | | | | | | | | | | | | |
|---|---|---|---|---|---|---|---|---|---|---|---|---|---|---|---|---|
| CCT | TGC | CTC | CCC | GCT | TGA | AAG | AGA | TGA | AGA | GTC | AGG | AGT | CTG | TGG | CAG | 48 |
| Leu | Pro | Pro | Arg | Leu | Lys | Glu | His | Lys | Ser | Gln | Glu | Ser | Val | Ala | Gly | |
| 1 | | | | 5 | | | | | 10 | | | | | 15 | | |
| GTT | CCA | AAC | TAG | TGC | TTC | GGT | GCG | AGA | CCA | GTT | CTG | AAT | ACT | CCT | CTC | 96 |
| Ser | Lys | Leu | Val | Leu | Arg | Cys | Glu | Thr | Ser | Ser | Glu | Tyr | Ser | Ser | Leu | |
| | | | 20 | | | | | 25 | | | | | 30 | | | |
| TCA | AGT | TCA | AGT | GGT | TCA | AGA | ATG | GGA | GTG | AAT | TAA | GCC | GAA | AGA | ACA | 144 |
| Lys | Phe | Lys | Trp | Phe | Lys | Asn | Gly | Ser | Glu | Leu | Ser | Arg | Lys | Asn | Lys | |
| | | 35 | | | | | 40 | | | | | 45 | | | | |
| AAC | CAC | AAA | ACA | TCA | AGA | TAC | AGA | AAA | GGC | CGG | G | | | | | 178 |
| Pro | Gly | Asn | Ile | Lys | Ile | Gln | Lys | Arg | Pro | Gly | | | | | | |
| | 50 | | | | | 55 | | | | | | | | | | |

(2) INFORMATION FOR SEQ ID NO: 139:

(i) SEQUENCE CHARACTERISTICS:
    (A) LENGTH: 122
    (B) TYPE: nucleic acid
    (C) STRANDEDNESS: single
    (D) TOPOLOGY: linear (xi) SEQUENCE DESCRIPTION: SEQ ID NO: 139:

| | | | | | | | | | | | | | | | | |
|---|---|---|---|---|---|---|---|---|---|---|---|---|---|---|---|---|
| G AAG | TCA | GAA | CTT | CGC | ATT | AGC | AAA | GCG | TCA | CTG | GCT | GAT | TCT | GGA | | 46 |
| Lys | Ser | Glu | Leu | Arg | Ile | Ser | Lys | Ala | Ser | Leu | Ala | Asp | Ser | Gly | | |
| 1 | | | | 5 | | | | | 10 | | | | | 15 | | |
| GAA | TAT | ATG | TGC | AAA | GTG | ATC | ACC | AAA | CTA | GGA | AAT | GAC | AGT | GCC | TCT | 94 |
| Glu | Tyr | Met | Cys | Lys | Val | Ile | Thr | Lys | Leu | Gly | Asn | Asp | Ser | Ala | Ser | |
| | | | | 20 | | | | | 25 | | | | | 30 | | |

```
GCC AAC ATC ACC ATT GTG GAG TCA AAC G                                              122
Ala Asn Ile Thr Ile Val Glu Ser Asn Ala
             35
```

( 2 ) INFORMATION FOR SEQ ID NO: 140:

( i ) SEQUENCE CHARACTERISTICS:
        ( A ) LENGTH: 417
        ( B ) TYPE: nucleic acid
        ( C ) STRANDEDNESS: single
        ( D ) TOPOLOGY: linear ( x i ) SEQUENCE DESCRIPTION: SEQ ID NO: 140:

```
TCTAAAACTA CAGAGACTGT ATTTTCATGA TCATCATAGT TCTGTGAAAT ATACTTAAAC                   60

CGCTTTGGTC CTGATCTTGT AGG AAG TCA GAA CTT CGC ATT AGC AAA GCG                      110
                         Lys Ser Glu Leu Arg Ile Ser Lys Ala
                          1               5

TCA CTG GCT GAT TCT GGA GAA TAT ATG TGC AAA GTG ATC AGC AAA CTA                    158
Ser Leu Ala Asp Ser Gly Glu Tyr Met Cys Lys Val Ile Ser Lys Leu
 10              15                   20                      25

GGA AAT GAC AGT GCC TCT GCC AAC ATC ACC ATT GTG GAG TCA AAC GGT                    206
Gly Asn Asp Ser Ala Ser Ala Asn Ile Thr Ile Val Glu Ser Asn Gly
             30                   35                      40

AAG AGA TGC CTA CTG CGT GCT ATT TCT CAG TCT CTA AGA GGA GTG ATC                    254
Lys Arg Cys Leu Leu Arg Ala Ile Ser Gln Ser Leu Arg Gly Val Ile
             45                   50                55

AAG GTA TGT GGT CAC ACT TGAATCACGC AGGTGTGTGA AATCTCATTG                           302
Lys Val Cys Gly His Thr
             60

TGAACAAATA AAAATCATGA AAGGAAAACT CTATGTTTGA AATATCTTAT GGGTCCTCCT                   362

GTAAAGCTCT TCACTCCATA AGGTGAAATA GACCTGAAAT ATATATAGAT TATTT                       417
```

( 2 ) INFORMATION FOR SEQ ID NO: 141:

( i ) SEQUENCE CHARACTERISTICS:
        ( A ) LENGTH: 102
        ( B ) TYPE: nucleic acid
        ( C ) STRANDEDNESS: single
        ( D ) TOPOLOGY: linear ( x i ) SEQUENCE DESCRIPTION: SEQ ID NO: 141:

```
AG  ATC ACC ACT GGC ATG CCA GCC TCA ACT GAG ACA GCG TAT GTG TCT                    47
Glu Ile Thr Thr Gly Met Pro Ala Ser Thr Glu Thr Ala Tyr Val Ser
 1               5                   10                      15

TCA GAG TCT CCC ATT AGA ATA TCA GTA TCA ACA GAA GGA ACA AAT ACT                    95
Ser Glu Ser Pro Ile Arg Ile Ser Val Ser Thr Glu Gly Thr Asn Thr
             20                   25                  30

TCT TCA T                                                                          102
Ser Ser Ser
         35
```

( 2 ) INFORMATION FOR SEQ ID NO: 142:

( i ) SEQUENCE CHARACTERISTICS:
        ( A ) LENGTH: 69
        ( B ) TYPE: nucleic acid
        ( C ) STRANDEDNESS: single
        ( D ) TOPOLOGY: linear ( x i ) SEQUENCE DESCRIPTION: SEQ ID NO: 142:

```
AAG TGC CAA CCT GGA TTC ACT GGA GCG AGA TGT ACT GAG AAT GTG CCC                    48
Lys Cys Gln Pro Gly Phe Thr Gly Ala Arg Cys Thr Glu Asn Val Pro
 1               5                   10                      15
```

```
ATG  AAG  GTC  CAA  ACC  CAA  GAA                                                              69
Met  Lys  Val  Gln  Thr  Gln  Glu
              20
```

( 2 ) INFORMATION FOR SEQ ID NO: 143:

( i ) SEQUENCE CHARACTERISTICS:
        ( A ) LENGTH: 60
        ( B ) TYPE: nucleic acid
        ( C ) STRANDEDNESS: single
        ( D ) TOPOLOGY: linear ( x i ) SEQUENCE DESCRIPTION: SEQ ID NO: 143:

```
AAG  TGC  CCA  AAT  GAG  TTT  ACT  GGT  GAT  CGC  TGC  CAA  AAC  TAC  GTA  ATG          48
Lys  Cys  Pro  Asn  Glu  Phe  Thr  Gly  Asp  Arg  Cys  Gln  Asn  Tyr  Val  Met
 1                    5                       10                      15

GCC  AGC  TTC  TAC                                                                       60
Ala  Ser  Phe  Tyr
              20
```

( 2 ) INFORMATION FOR SEQ ID NO: 144:

( i ) SEQUENCE CHARACTERISTICS:
        ( A ) LENGTH: 36
        ( B ) TYPE: nucleic acid
        ( C ) STRANDEDNESS: single
        ( D ) TOPOLOGY: linear ( x i ) SEQUENCE DESCRIPTION: SEQ ID NO: 144:

```
AGT  ACG  TCC  ACT  CCC  TTT  CTG  TCT  CTG  CCT  GAA  TAG                               36
Ser  Thr  Ser  Thr  Pro  Phe  Leu  Ser  Leu  Pro  Glu
 1                    5                       10
```

( 2 ) INFORMATION FOR SEQ ID NO: 145:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( x i ) SEQUENCE DESCRIPTION: SEQ ID NO: 145:

```
AAG  CAT  CTT  GGG  ATT  GAA  TTT  ATG  GAG                                              27
Lys  His  Leu  Gly  Ile  Glu  Phe  Met  Glu
 1                    5
```

( 2 ) INFORMATION FOR SEQ ID NO: 146:

( i ) SEQUENCE CHARACTERISTICS:
        ( A ) LENGTH: 569
        ( B ) TYPE: nucleic acid
        ( C ) STRANDEDNESS: single
        ( D ) TOPOLOGY: linear ( x i ) SEQUENCE DESCRIPTION: SEQ ID NO: 146:

```
AAA  GCG  GAG  GAG  CTC  TAC  CAG  AAG  AGA  GTG  CTC  ACC  ATT  ACC  GGC  ATT          48
Lys  Ala  Glu  Glu  Leu  Tyr  Gln  Lys  Arg  Val  Leu  Thr  Ile  Thr  Gly  Ile
 1                    5                       10                      15

TGC  ATC  GCG  CTG  CTC  GTG  GTT  GGC  ATC  ATG  TGT  GTG  GTG  GTC  TAC  TGC          96
Cys  Ile  Ala  Leu  Leu  Val  Val  Gly  Ile  Met  Cys  Val  Val  Val  Tyr  Cys
              20                      25                      30

AAA  ACC  AAG  AAA  CAA  CGG  AAA  AAG  CTT  CAT  GAC  CGG  CTT  CGG  CAG  AGC         144
Lys  Thr  Lys  Lys  Gln  Arg  Leu  Lys  Leu  His  Asp  Arg  Leu  Arg  Gln  Ser
         35                      40                      45

CTT  CGG  TCT  GAA  AGA  AAC  ACC  ATG  ATG  AAC  GTA  GCC  AAC  GGG  CCC  CAC         192
Leu  Arg  Ser  Glu  Arg  Asn  Thr  Met  Met  Asn  Val  Ala  Asn  Gly  Pro  His
         50                      55                      60
```

| | | | | | | | | | | | | | | | | |
|---|---|---|---|---|---|---|---|---|---|---|---|---|---|---|---|---|
| CAC | CCC | AAT | CCG | CCC | CCC | GAG | AAC | GTG | CAG | CTG | GTG | AAT | CAA | TAC | GTA | 240 |
| His | Pro | Asn | Pro | Pro | Pro | Glu | Asn | Val | Gln | Leu | Val | Asn | Gln | Tyr | Val | |
| 65 | | | | | 70 | | | | 75 | | | | | | 80 | |
| TCT | AAA | AAT | GTC | ATC | TCT | AGC | GAG | CAT | ATT | GTT | GAG | AGA | GAG | GCG | GAG | 288 |
| Ser | Lys | Asn | Val | Ile | Ser | Ser | Glu | His | Ile | Val | Glu | Arg | Glu | Ala | Glu | |
| | | | | 85 | | | | | 90 | | | | | 95 | | |
| AGC | TCT | TTT | TCC | ACC | AGT | CAC | TAC | ACT | TCG | ACA | GCT | CAT | CAT | TCC | ACT | 336 |
| Ser | Ser | Phe | Ser | Thr | Ser | His | Tyr | Thr | Ser | Thr | Ala | His | His | Ser | Thr | |
| | | | 100 | | | | | 105 | | | | 110 | | | | |
| ACT | GTC | ACT | CAG | ACT | CCC | AGT | CAC | AGC | TGG | AGC | AAT | GGA | CAC | ACT | GAA | 384 |
| Thr | Val | Thr | Gln | Thr | Pro | Ser | His | Ser | Trp | Ser | Asn | Gly | His | Thr | Glu | |
| | | 115 | | | | | 120 | | | | | 125 | | | | |
| AGC | ATC | ATT | TCG | GAA | AGC | CAC | TCT | GTC | ATC | GTG | ATG | TCA | TCC | GTA | GAA | 432 |
| Ser | Ile | Ile | Ser | Glu | Ser | His | Ser | Val | Ile | Val | Met | Ser | Ser | Val | Glu | |
| | 130 | | | | | 135 | | | | | 140 | | | | | |
| AAC | AGT | AGG | CAC | AGC | AGC | CCG | ACT | GGG | GGC | CCG | AGA | GGA | CGT | CTC | AAT | 480 |
| Asn | Ser | Arg | His | Ser | Ser | Pro | Thr | Gly | Gly | Pro | Arg | Gly | Arg | Leu | Asn | |
| 145 | | | | | 150 | | | | | 155 | | | | | 160 | |
| GGC | TTG | GGA | GGC | CCT | CGT | GAA | TGT | AAC | AGC | TTC | CTC | AGG | CAT | GCC | AGA | 528 |
| Gly | Leu | Gly | Gly | Pro | Arg | Glu | Cys | Asn | Ser | Phe | Leu | Arg | His | Ala | Arg | |
| | | | | 165 | | | | | 170 | | | | | 175 | | |
| GAA | ACC | CCT | GAC | TCC | TAC | CGA | GAC | TCT | CCT | CAT | AGT | G | AAAG | | | 569 |
| Glu | Thr | Pro | Asp | Ser | Tyr | Arg | Asp | Ser | Pro | His | Ser | | | | | |
| | | | 180 | | | | | 185 | | | | | | | | |

( 2 ) INFORMATION FOR SEQ ID NO: 147:

( i ) SEQUENCE CHARACTERISTICS:
( A ) LENGTH: 730
( B ) TYPE: nucleic acid
( C ) STRANDEDNESS: single
( D ) TOPOLOGY: linear ( x i ) SEQUENCE DESCRIPTION: SEQ ID NO: 147:

| | | | | | | | | | | | | | | | | |
|---|---|---|---|---|---|---|---|---|---|---|---|---|---|---|---|---|
| G | TAT | GTA | TCA | GCA | ATG | ACC | ACC | CCG | GCT | CGT | ATG | TCA | CCT | GTA | GAT | 46 |
| | Tyr | Val | Ser | Ala | Met | Thr | Thr | Pro | Ala | Arg | Met | Ser | Pro | Val | Asp | |
| | 1 | | | | 5 | | | | | 10 | | | | | 15 | |
| TTC | CAC | ACG | CCA | AGC | TCC | CCC | AAG | TCA | CCC | CCT | TCG | GAA | ATG | TCC | CCG | 94 |
| Phe | His | Thr | Pro | Ser | Ser | Pro | Lys | Ser | Pro | Pro | Ser | Glu | Met | Ser | Pro | |
| | | | | 20 | | | | | 25 | | | | | 30 | | |
| CCC | GTG | TCC | AGC | ACG | ACG | GTC | TCC | ATG | CCC | TCC | ATG | GCG | GTC | AGT | CCC | 142 |
| Pro | Val | Ser | Ser | Thr | Thr | Val | Ser | Met | Pro | Ser | Met | Ala | Val | Ser | Pro | |
| | | | 35 | | | | | 40 | | | | | 45 | | | |
| TTC | GTG | GAA | GAG | GAG | AGA | CCC | CTG | CTC | CTT | GTG | ACG | CCA | CCA | CGG | CTG | 190 |
| Phe | Val | Glu | Glu | Glu | Arg | Pro | Leu | Leu | Leu | Val | Thr | Pro | Pro | Arg | Leu | |
| | | 50 | | | | | 55 | | | | | 60 | | | | |
| CGG | GAG | AAG | TAT | GAC | CAC | CAC | GCC | CAG | CAA | TTC | AAC | TCG | TTC | CAC | TGC | 238 |
| Arg | Glu | Lys | Tyr | Asp | His | His | Ala | Gln | Gln | Phe | Asn | Ser | Phe | His | Cys | |
| | 65 | | | | 70 | | | | | 75 | | | | | | |
| AAC | CCC | GCG | CAT | GAG | AGC | AAC | AGC | CTG | CCC | CCC | AGC | CCC | TTG | AGG | ATA | 286 |
| Asn | Pro | Ala | His | Glu | Ser | Asn | Ser | Leu | Pro | Pro | Ser | Pro | Leu | Arg | Ile | |
| 80 | | | | | 85 | | | | | 90 | | | | | 95 | |
| GTG | GAG | GAT | GAG | GAA | TAT | GAA | ACG | ACC | CAG | GAG | TAC | GAA | CCA | GCT | CAA | 334 |
| Val | Glu | Asp | Glu | Glu | Tyr | Glu | Thr | Thr | Gln | Glu | Tyr | Glu | Pro | Ala | Gln | |
| | | | | 100 | | | | | 105 | | | | | 110 | | |
| GAG | CCG | GTT | AAG | AAA | CTC | ACC | AAC | AGC | AGC | CGG | CGG | GCC | AAA | AGA | ACC | 382 |
| Glu | Pro | Val | Lys | Lys | Leu | Thr | Asn | Ser | Ser | Arg | Arg | Ala | Lys | Arg | Thr | |
| | | | 115 | | | | | 120 | | | | | 125 | | | |
| AAG | CCC | AAT | GGT | CAC | ATT | GCC | CAC | AGG | TTG | GAA | ATG | GAC | AAC | AAC | ACA | 430 |
| Lys | Pro | Asn | Gly | His | Ile | Ala | His | Arg | Leu | Glu | Met | Asp | Asn | Asn | Thr | |
| | | | 130 | | | | | 135 | | | | | 140 | | | |
| GGC | GCT | GAC | AGC | AGT | AAC | TCA | GAG | AGC | GAA | ACA | GAG | GAT | GAA | AGA | GTA | 478 |

| | | | | | | | | | | | | | | | |
|---|---|---|---|---|---|---|---|---|---|---|---|---|---|---|---|
| Gly | Ala | Asp | Ser | Ser | Asn | Ser | Glu | Ser | Glu | Thr | Glu | Asp | Glu | Arg | Val |
| | 145 | | | | 150 | | | | | 155 | | | | | |

| | | | | | | | | | | | | | | | | |
|---|---|---|---|---|---|---|---|---|---|---|---|---|---|---|---|---|
| GGA | GAA | GAT | ACG | CCT | TTC | CTG | GCC | ATA | CAG | AAC | CCC | CTG | GCA | GCC | AGT | 526 |
| Gly | Glu | Asp | Thr | Pro | Phe | Leu | Ala | Ile | Gln | Asn | Pro | Leu | Ala | Ala | Ser | |
| 160 | | | | | 165 | | | | | 170 | | | | | 175 | |

| | | | | | | | | | | | | | | | | |
|---|---|---|---|---|---|---|---|---|---|---|---|---|---|---|---|---|
| CTC | GAG | GCG | GCC | CCT | GCC | TTC | CGC | CTG | GTC | GAC | AGC | AGG | ACT | AAC | CCA | 574 |
| Leu | Glu | Ala | Ala | Pro | Ala | Phe | Arg | Leu | Val | Asp | Ser | Arg | Thr | Asn | Pro | |
| | | | | 180 | | | | | 185 | | | | | 190 | | |

| | | | | | | | | | | | | | | | | |
|---|---|---|---|---|---|---|---|---|---|---|---|---|---|---|---|---|
| ACA | GGC | GGC | TTC | TCT | CCG | CAG | GAA | GAA | TTG | CAG | GCC | AGG | CTC | TCC | GGT | 622 |
| Thr | Gly | Gly | Phe | Ser | Pro | Gln | Glu | Glu | Leu | Gln | Ala | Arg | Leu | Ser | Gly | |
| | | | 195 | | | | | 200 | | | | | 205 | | | |

| | | | | | | | | | | |
|---|---|---|---|---|---|---|---|---|---|---|
| GTA | ATC | GCT | AAC | CAA | GAC | CCT | ATC | GCT | GTC | TAAAACGAA ATACACCCAT | 672 |
| Val | Ile | Ala | Asn | Gln | Asp | Pro | Ile | Ala | Val | |
| | | 210 | | | | | 215 | | | |

AGATTCACCT GTAAAACTTT ATTTTATATA ATAAAGTATT CCACCTTAAA TTAAACAA    730

( 2 ) INFORMATION FOR SEQ ID NO: 148:

( i ) SEQUENCE CHARACTERISTICS:
        ( A ) LENGTH: 1652
        ( B ) TYPE: nucleic acid
        ( C ) STRANDEDNESS: single
        ( D ) TOPOLOGY: linear ( x i ) SEQUENCE DESCRIPTION: SEQ ID NO: 148:

AGTTTCCCCC CCCAACTTGT CGGAACTCTG GGCTCGCGCG CAGGGCAGGA GCGGAGCGGC    60

GGCGGCTGCC CAGGCGATGC GAGCGCGGGC CGGACGGTAA TCGCCTCTCC CTCCTCGGGC    120

TGCGAGCGCG CCGGACCGAG GCAGCGACAG GAGCGGACCG CGGCGGGAAC CGAGGACTCC    180

CCAGCGGCGC GCCAGCAGGA GCCACCCCGC GAGCGTGCGA CCGGGACGGA GCGCCCGCCA    240

GTCCAGGTG GCCCGGACCG CACGTTGCGT CCCCGCGCTC CCCGCCGGCG ACAGGAGACG     300

CTCCCCCCCA CGCCGCGCGC GCCTCGGCCC GGTCGCTGGC CCGCCTCCAC TCCGGGGACA    360

AACTTTTCCC GAAGCCGATC CCAGCCCTCG ACCCAAACT TGTCGCGCGT CGCCTTCGCC     420

GGGAGCCGTC CGCGCAGAGC GTGCACTTCT CGGGCGAG ATG TCG GAG CGC AGA        473
                                                               Met Ser Glu Arg Arg
                                                                1                5

| | | | | | | | | | | | | | | | | |
|---|---|---|---|---|---|---|---|---|---|---|---|---|---|---|---|---|
| GAA | GGC | AAA | GGC | AAG | GGG | AAG | GGC | GGC | AAG | AAG | GAC | CGA | GGC | TCC | GGG | 521 |
| Glu | Gly | Lys | Gly | Lys | Gly | Lys | Gly | Gly | Lys | Lys | Asp | Arg | Gly | Ser | Gly | |
| | | | | 10 | | | | | 15 | | | | | 20 | | |

| | | | | | | | | | | | | | | | | |
|---|---|---|---|---|---|---|---|---|---|---|---|---|---|---|---|---|
| AAG | AAG | CCC | GTG | CCC | GCG | GCT | GGC | GGC | CCG | AGC | CCA | GCC | TTG | CCT | CCC | 569 |
| Lys | Lys | Pro | Val | Pro | Ala | Ala | Gly | Gly | Pro | Ser | Pro | Ala | Leu | Pro | Pro | |
| | | | | 25 | | | | | 30 | | | | | 35 | | |

| | | | | | | | | | | | | | | | | |
|---|---|---|---|---|---|---|---|---|---|---|---|---|---|---|---|---|
| CGC | TTG | AAA | GAG | ATG | AAG | ATG | CAG | GAG | TCT | GTG | GCA | GGT | TCC | AAA | CTA | 617 |
| Arg | Leu | Lys | Glu | Met | Lys | Met | Gln | Glu | Ser | Val | Ala | Gly | Ser | Lys | Leu | |
| | | | 40 | | | | | 45 | | | | | 50 | | | |

| | | | | | | | | | | | | | | | | |
|---|---|---|---|---|---|---|---|---|---|---|---|---|---|---|---|---|
| GTG | CTT | CGG | TGC | GAG | ACC | AGT | TCT | GAA | TAC | TCC | TCT | CTC | AAG | TTC | AAG | 665 |
| Val | Leu | Arg | Cys | Glu | Thr | Ser | Ser | Glu | Tyr | Ser | Ser | Leu | Lys | Phe | Lys | |
| | | 55 | | | | | 60 | | | | | 65 | | | | |

| | | | | | | | | | | | | | | | | |
|---|---|---|---|---|---|---|---|---|---|---|---|---|---|---|---|---|
| TGG | TTC | AAG | AAT | GGG | AGT | GAA | TTA | AGC | CGA | AAG | AAC | AAA | CCA | CAA | AAC | 713 |
| Trp | Phe | Lys | Asn | Gly | Ser | Glu | Leu | Ser | Arg | Lys | Asn | Lys | Pro | Gln | Asn | |
| | 70 | | | | 75 | | | | | 80 | | | | | | |

| | | | | | | | | | | | | | | | | |
|---|---|---|---|---|---|---|---|---|---|---|---|---|---|---|---|---|
| ATC | AAG | ATA | CAG | AAA | AGG | CCG | GGG | AAG | TCA | GAA | CTT | CGC | ATT | AGC | AAA | 761 |
| Ile | Lys | Ile | Gln | Lys | Arg | Pro | Gly | Lys | Ser | Glu | Leu | Arg | Ile | Ser | Lys | |
| 85 | | | | | 90 | | | | | 95 | | | | | 100 | |

| | | | | | | | | | | | | | | | | |
|---|---|---|---|---|---|---|---|---|---|---|---|---|---|---|---|---|
| GCG | TCA | CTG | GCT | GAT | TCT | GGA | GAA | TAT | ATG | TGC | AAA | GTG | ATC | AGC | AAA | 809 |
| Ala | Ser | Leu | Ala | Asp | Ser | Gly | Glu | Tyr | Met | Cys | Lys | Val | Ile | Ser | Lys | |
| | | | | 105 | | | | | 110 | | | | | 115 | | |

| | | | | | | | | | | | | | | | | |
|---|---|---|---|---|---|---|---|---|---|---|---|---|---|---|---|---|
| CTA | GGA | AAT | GAC | AGT | GCC | TCT | GCC | AAC | ATC | ACC | ATT | GTG | GAG | TCA | AAC | 857 |
| Leu | Gly | Asn | Asp | Ser | Ala | Ser | Ala | Asn | Ile | Thr | Ile | Val | Glu | Ser | Asn | |

| | | | | | | | | | | | | | | | | |
|---|---|---|---|---|---|---|---|---|---|---|---|---|---|---|---|---|
| | | | 120 | | | | | 125 | | | | | 130 | | | |
| GAG | ATC | ACC | ACT | GGC | ATG | CCA | GCC | TCA | ACT | GAG | ACA | GCG | TAT | GTG | TCT | 905 |
| Glu | Ile | Thr | Thr | Gly | Met | Pro | Ala | Ser | Thr | Glu | Thr | Ala | Tyr | Val | Ser | |
| | | 135 | | | | | 140 | | | | | 145 | | | | |
| TCA | GAG | TCT | CCC | ATT | AGA | ATA | TCA | GTA | TCA | ACA | GAA | GGA | ACA | AAT | ACT | 953 |
| Ser | Glu | Ser | Pro | Ile | Arg | Ile | Ser | Val | Ser | Thr | Glu | Gly | Thr | Asn | Thr | |
| | 150 | | | | | 155 | | | | | 160 | | | | | |
| TCT | TCA | TCC | ACA | TCC | ACA | TCT | ACA | GCT | GGG | ACA | AGC | CAT | CTT | GTC | AAG | 1001 |
| Ser | Ser | Ser | Thr | Ser | Thr | Ser | Thr | Ala | Gly | Thr | Ser | His | Leu | Val | Lys | |
| 165 | | | | | 170 | | | | | 175 | | | | | 180 | |
| TGT | GCA | GAG | AAG | GAG | AAA | ACT | TTC | TGT | GTG | AAT | GGA | GGC | GAG | TGC | TTC | 1049 |
| Cys | Ala | Glu | Lys | Glu | Lys | Thr | Phe | Cys | Val | Asn | Gly | Gly | Glu | Cys | Phe | |
| | | | | 185 | | | | | 190 | | | | | 195 | | |
| ATG | GTG | AAA | GAC | CTT | TCA | APT | CCC | TCA | AGA | TAC | TTG | TGC | AAG | TGC | CCA | 1097 |
| Met | Val | Lys | Asp | Leu | Ser | Asn | Pro | Ser | Arg | Tyr | Leu | Cys | Lys | Cys | Pro | |
| | | | 200 | | | | | 205 | | | | | 210 | | | |
| AAT | GAG | TTT | ACT | GGT | GAT | CGC | TGC | CAA | AAC | TAC | GTA | ATG | GCC | AGC | TTC | 1145 |
| Asn | Glu | Phe | Thr | Gly | Asp | Arg | Cys | Gln | Asn | Tyr | Val | Met | Ala | Ser | Phe | |
| | | 215 | | | | | 220 | | | | | 225 | | | | |
| TAC | AGT | ACG | TCC | ACT | CCC | TTT | CTG | TCT | CTG | CCT | GAA | TAGGCGCATG | | | | 1193 |
| Tyr | Ser | Thr | Ser | Thr | Pro | Phe | Leu | Ser | Leu | Pro | Glu | | | | | |
| | 230 | | | | | 235 | | | | | 240 | | | | | |

| | | | | |
|---|---|---|---|---|
| CTCAGTCGGT | GCCGCTTTCT | TGTTGCCGCA | TCTCCCCTCA | GATTCAACCT AGAGCTAGAT | 1253 |
| GCGTTTTACC | AGGTCTAACA | TTGACTGCCT | CTGCCTGTCG | CATGAGAACA TTAACACAAG | 1313 |
| CGATTGTATG | ACTTCCTCTG | TCCGTGACTA | GTGGGCTCTG | AGCTACTCGT AGGTGCGTAA | 1373 |
| GGCTCCAGTG | TTTCTGAAAT | TGATCTTGAA | TTACTGTGAT | ACGACATGAT AGTCCCTCTC | 1433 |
| ACCCAGTGCA | ATGACAATAA | AGGCCTTGAA | AAGTCTCACT | TTTATTGAGA AAATAAAAAT | 1493 |
| CGTTCCACGG | GACAGTCCCT | CTTCITTATA | AAATGACCCT | ATCCTTGAAA AGGAGGTGTG | 1553 |
| TTAAGTTGTA | ACCAGTACAC | ACTTGAAATG | ATGGTAAGTT | CGCTTCGGTT CAGAATGTGT | 1613 |
| TCTTTCTGAC | AAATAAACAG | AATAAAAAAA | AAAAAAAAA | A | 1652 |

( 2 ) INFORMATION FOR SEQ ID NO: 149:

( i ) SEQUENCE CHARACTERISTICS:
        ( A ) LENGTH: 1140
        ( B ) TYPE: nucleic acid
        ( C ) STRANDEDNESS: single
        ( D ) TOPOLOGY: linear ( x i ) SEQUENCE DESCRIPTION: SEQ ID NO: 149:

| | | | | | | | | | | | | | | | | |
|---|---|---|---|---|---|---|---|---|---|---|---|---|---|---|---|---|
| CAT | CAN | GTG | TGG | GCG | GCG | AAA | GCC | GGG | GGC | TTG | AAG | AAG | GAC | TCG | CTG | 48 |
| His | Gln | Val | Trp | Ala | Ala | Leu | Ala | Gly | Gly | Leu | Lys | Lys | Asp | Ser | Leu | |
| 1 | | | | 5 | | | | | 10 | | | | | 15 | | |
| CTC | ACC | GTG | CGC | CTG | GGC | GCC | TGG | GGC | CAC | CCC | GCC | TTC | CCC | TCC | TGC | 96 |
| Leu | Thr | Val | Arg | Leu | Gly | Ala | Trp | Gly | His | Pro | Ala | Phe | Pro | Ser | Cys | |
| | | | 20 | | | | | 25 | | | | | 30 | | | |
| GGG | CGC | CTC | AAG | GAG | GAC | AGC | AGG | TAC | ATC | TTC | TTC | ATG | GAG | CCC | GAG | 144 |
| Gly | Arg | Leu | Lys | Glu | Asp | Ser | Arg | Tyr | Ile | Phe | Phe | Met | Glu | Pro | Glu | |
| | | 35 | | | | | 40 | | | | | 45 | | | | |
| GCC | AAC | AGC | AGC | GGC | GGG | CCC | GGC | CGC | CTT | CCG | AGC | CTC | CTT | CCC | CCC | 192 |
| Ala | Asn | Ser | Ser | Gly | Gly | Pro | Gly | Arg | Leu | Pro | Ser | Leu | Leu | Pro | Pro | |
| | 50 | | | | | 55 | | | | | 60 | | | | | |
| TCT | CGA | GAC | GGG | CCG | GAA | CCT | CAA | GAA | GGA | GGT | CAG | CCG | GGT | GCT | GTG | 240 |
| Ser | Arg | Asp | Gly | Pro | Glu | Pro | Gln | Glu | Gly | Gly | Gln | Pro | Gly | Ala | Val | |
| 65 | | | | | 70 | | | | | 75 | | | | | 80 | |
| CAA | CGG | TGC | GCC | TTG | CCT | CCC | CGC | TTG | AAA | GAG | ATG | AAG | AGT | CAG | GAG | 288 |
| Gln | Arg | Cys | Ala | Leu | Pro | Pro | Arg | Leu | Lys | Glu | Met | Lys | Ser | Gln | Glu | |
| | | | | 85 | | | | | 90 | | | | | 95 | | |

| | | | | | | | | | | | | | | | | |
|---|---|---|---|---|---|---|---|---|---|---|---|---|---|---|---|---|
| TCT | GTG | GCA | GGT | TCC | AAA | CTA | GTG | CTT | CGG | TGC | GAG | ACC | AGT | TCT | GAA | 336 |
| Ser | Val | Ala | Gly | Ser | Lys | Leu | Val | Leu | Arg | Cys | Glu | Thr | Ser | Ser | Glu | |
| | | | 100 | | | | 105 | | | | | | 110 | | | |
| TAC | TCC | TCT | CTC | AAG | TTC | AAG | TGG | TTC | AAG | AAT | GGG | AGT | GAA | TTA | AGC | 384 |
| Tyr | Ser | Ser | Leu | Lys | Phe | Lys | Trp | Phe | Lys | Asn | Gly | Ser | Glu | Leu | Ser | |
| | | 115 | | | | | 120 | | | | | 125 | | | | |
| CGA | AAG | AAC | AAA | CCA | GAA | AAC | ATC | AAG | ATA | CAG | AAA | AGG | CCG | GGG | AAG | 432 |
| Arg | Lys | Asn | Lys | Pro | Glu | Asn | Ile | Lys | Ile | Gln | Lys | Arg | Pro | Gly | Lys | |
| | 130 | | | | | 135 | | | | | 140 | | | | | |
| TCA | GAA | CTT | CGC | ATT | AGC | AAA | GCG | TCA | CTG | GCT | GAT | TCT | GGA | GAA | TAT | 480 |
| Ser | Glu | Leu | Arg | Ile | Ser | Lys | Ala | Ser | Leu | Ala | Asp | Ser | Gly | Glu | Tyr | |
| 145 | | | | | 150 | | | | | 155 | | | | | 160 | |
| ATG | TGC | AAA | GTG | ATC | AGC | AAA | CTA | GGA | AAT | GAC | AGT | GCC | TCT | GCC | AAC | 528 |
| Met | Cys | Lys | Val | Ile | Ser | Lys | Leu | Gly | Asn | Asp | Ser | Ala | Ser | Ala | Asn | |
| | | | | 165 | | | | | 170 | | | | | 175 | | |
| ATC | ACC | ATT | GTG | GAG | TCA | ACA | GCC | ACA | TCC | ACA | TCT | ACA | GCT | GGG | ACA | 576 |
| Ile | Thr | Ile | Val | Glu | Ser | Asn | Ala | Thr | Ser | Thr | Ser | Thr | Ala | Gly | Thr | |
| | | | 180 | | | | | 185 | | | | | 190 | | | |
| AGC | CAT | CTT | GTC | AAG | TGT | GCA | GAG | AAG | GAG | AAA | ACT | TTC | TGT | GTG | AAT | 624 |
| Ser | His | Leu | Val | Lys | Cys | Ala | Glu | Lys | Glu | Lys | Thr | Phe | Cys | Val | Asn | |
| | | 195 | | | | | 200 | | | | | 205 | | | | |
| GGA | GGC | GAG | TGC | TTC | ATG | GTG | AAA | GAC | CTT | TCA | AAT | CCC | TCA | AGA | TAC | 672 |
| Gly | Gly | Glu | Cys | Phe | Met | Val | Lys | Asp | Leu | Ser | Asn | Pro | Ser | Arg | Tyr | |
| | 210 | | | | | 215 | | | | | 220 | | | | | |
| TTG | TGC | AAG | TGC | CAA | CCT | GGA | TTC | ACT | GGA | GCG | AGA | TGT | ACT | GAG | AAT | 720 |
| Leu | Cys | Lys | Cys | Gln | Pro | Gly | Phe | Thr | Gly | Ala | Arg | Cys | Thr | Glu | Asn | |
| 225 | | | | | 230 | | | | | 235 | | | | | 240 | |
| GTG | CCC | ATG | AAA | GTC | CAA | ACC | CAA | GAA | AAG | TGC | CCA | AAT | GAG | TTT | ACT | 768 |
| Val | Pro | Met | Lys | Val | Gln | Thr | Gln | Glu | Lys | Cys | Pro | Asn | Glu | Phe | Thr | |
| | | | | 245 | | | | | 250 | | | | | 255 | | |
| GGT | GAT | CGC | TGC | CAA | AAC | TAC | GTA | ATG | GCC | AGC | TTC | TAC | AGT | ACG | TCC | 816 |
| Gly | Asp | Arg | Cys | Gln | Asn | Tyr | Val | Met | Ala | Ser | Phe | Tyr | Ser | Thr | Ser | |
| | | | 260 | | | | | 265 | | | | | 270 | | | |
| ACT | CCC | TTT | CTG | TCT | CTG | CCT | GAA | TAGCGCATCT | | CAGTCGGTGC | | CGCTTTCTTG | | | | 870 |
| Thr | Pro | Phe | Leu | Ser | Leu | Pro | Glu | | | | | | | | | |
| | | 275 | | | | | 280 | | | | | | | | | |

| | | | | |
|---|---|---|---|---|
| TTGCCGCATC | TCCCCTCAGA | TTCCNCCTAG | AGCTAGATGC | GTTTTACCAG | GTCTAACATT | 930 |
| GACTGCCTCT | GCCTGTCGCA | TGAGXACATT | AACACAAGCG | ATTGTATGAC | TTCCTCTGTC | 990 |
| CGTGACTAGT | GGGCTCTGAG | CTACTCGTAG | GTGCGTAAGG | CTCCAGTGTT | TCTGAAATTG | 1050 |
| ATCTTGAATT | ACTGTGATAC | GACATGATAG | TCCCTCTCAC | CCAGTGCAAT | GACAATAAAG | 1110 |
| GCCTTGAAAA | GTCAAAAAAA | AAAAAAAAAA | | | | 1140 |

( 2 ) INFORMATION FOR SEQ ID NO: 150:

( i ) SEQUENCE CHARACTERISTICS:
        ( A ) LENGTH: 1764
        ( B ) TYPE: nucleic acid
        ( C ) STRANDEDNESS: single
        ( D ) TOPOLOGY: linear ( x i ) SEQUENCE DESCRIPTION: SEQ ID NO: 150:

| | | | | | | | | | | | | | | | | |
|---|---|---|---|---|---|---|---|---|---|---|---|---|---|---|---|---|
| G | AAG | TCA | GAA | CTT | CGC | ATT | AGC | AAA | GCG | TCA | CTG | GCT | GAT | TCT | GGA | GAA | 49 |
| | Lys | Ser | Glu | Leu | Arg | Ile | Ser | Lys | Ala | Ser | Leu | Ala | Asp | Ser | Gly | Glu | |
| | 1 | | | | 5 | | | | | 10 | | | | | 15 | | |
| TAT | ATG | TGC | AAA | GTG | ATC | AGC | AAA | CTA | GGA | AAT | GAC | AGT | GCC | TCT | GCC | 97 |
| Tyr | Met | Cys | Lys | Val | Ile | Ser | Lys | Leu | Gly | Asn | Asp | Ser | Ala | Ser | Ala | |
| | | | 20 | | | | | 25 | | | | | 30 | | | |
| AAC | ATC | ACC | ATT | GTG | GAG | TCA | AAC | GCC | ACA | TCC | ACA | TCT | ACA | GCT | GGG | 145 |
| Asn | Ile | Thr | Ile | Val | Glu | Ser | Asn | Ala | Thr | Ser | Thr | Ser | Thr | Ala | Gly | |

|  |  |  |  |  |  |  |  |  |  |  |  |  |  |  |  |
|---|---|---|---|---|---|---|---|---|---|---|---|---|---|---|---|
|  |  | 35 |  |  |  |  | 40 |  |  |  |  | 45 |  |  |  |
| ACA | AGC | CAT | CTT | GTC | AAG | TGT | GCA | GAG | AAG | GAG | AAA | ACT | TTC | TGT | GTG | 193 |
| Thr | Ser | His | Leu | Val | Lys | Cys | Ala | Glu | Lys | Glu | Lys | Thr | Phe | Cys | Val |
|  | 50 |  |  |  | 55 |  |  |  |  | 60 |  |  |  |  |  |
| AAT | GGA | GGC | GAC | TGC | TTC | ATG | GTG | AAA | GAC | CTT | TCA | AAT | CCC | TCA | AGA | 241 |
| Asn | Gly | Gly | Asp | Cys | Phe | Met | Val | Lys | Asp | Leu | Ser | Asn | Pro | Ser | Arg |
| 65 |  |  |  |  | 70 |  |  |  |  | 75 |  |  |  |  | 80 |
| TAC | TTG | TGC | AAG | TGC | CAA | CCT | GGA | TTC | ACT | GGA | GCG | AGA | TGT | ACT | GAG | 289 |
| Tyr | Leu | Cys | Lys | Cys | Gln | Pro | Gly | Phe | Thr | Gly | Ala | Arg | Cys | Thr | Glu |
|  |  |  |  | 85 |  |  |  |  | 90 |  |  |  |  | 95 |  |
| AAT | GTG | CCC | ATG | AAA | GTC | CAA | ACC | CAA | GAA | AAA | GCG | GAG | GAG | CTC | TAC | 337 |
| Asn | Val | Pro | Met | Lys | Val | Gln | Thr | Gln | Glu | Lys | Ala | Glu | Glu | Leu | Tyr |
|  |  |  | 100 |  |  |  |  | 105 |  |  |  |  | 110 |  |  |
| CAG | AAG | AGA | GTG | CTC | ACC | ATT | ACC | GGC | ATT | TGC | ATC | GCG | CTG | CTC | GTG | 385 |
| Gln | Lys | Arg | Val | Leu | Thr | Ile | Thr | Gly | Ile | Cys | Ile | Ala | Leu | Leu | Val |
|  |  | 115 |  |  |  |  | 120 |  |  |  |  | 125 |  |  |  |
| GTT | GGC | ATC | ATG | TGT | GTG | GTG | GTC | TAC | TGC | AAA | ACC | AAG | AAA | CAA | CGG | 433 |
| Val | Gly | Ile | Met | Cys | Val | Val | Val | Tyr | Cys | Lys | Thr | Lys | Lys | Gln | Arg |
|  | 130 |  |  |  |  | 135 |  |  |  |  | 140 |  |  |  |  |
| AAA | AAG | CTT | CAT | GAC | CGG | CTT | CGG | CAG | AGC | CTT | CGG | TCT | GAA | AGA | AAC | 481 |
| Lys | Lys | Leu | His | Asp | Arg | Leu | Arg | Gln | Ser | Leu | Arg | Ser | Glu | Arg | Asn |
| 145 |  |  |  |  | 150 |  |  |  |  | 155 |  |  |  |  | 160 |
| ACC | ATG | ATG | AAC | GTA | GCC | AAC | GGG | CCC | CAC | CAC | CCC | AAT | CCG | CCC | CCC | 529 |
| Thr | Met | Met | Asn | Val | Ala | Asn | Gly | Pro | His | His | Pro | Asn | Pro | Pro | Pro |
|  |  |  |  | 165 |  |  |  |  | 170 |  |  |  |  | 175 |  |
| GAG | AAC | GTG | CAG | CTG | GTG | AAT | CAA | TAC | GTA | TCT | AAA | AAT | GTC | ATC | TCT | 577 |
| Glu | Asn | Val | Gln | Leu | Val | Asn | Gln | Tyr | Val | Ser | Lys | Asn | Val | Ile | Ser |
|  |  |  | 180 |  |  |  |  | 185 |  |  |  |  | 190 |  |  |
| AGC | GAG | CAT | ATT | GTT | GAG | AGA | GAG | GCG | GAG | AGC | TCT | TTT | TCC | ACC | AGT | 625 |
| Ser | Glu | His | Ile | Val | Glu | Arg | Glu | Ala | Glu | Ser | Ser | Phe | Ser | Thr | Ser |
|  |  | 195 |  |  |  |  | 200 |  |  |  |  | 205 |  |  |  |
| CAC | TAC | ACT | TCG | ACA | GCT | CAT | CAT | TCC | ACT | ACT | GTC | ACT | CAG | ACT | CCC | 673 |
| His | Tyr | Thr | Ser | Thr | Ala | His | His | Ser | Thr | Thr | Val | Thr | Gln | Thr | Pro |
|  | 210 |  |  |  |  | 215 |  |  |  |  | 220 |  |  |  |  |
| AGT | CAC | AGC | TGG | AGC | AAT | GGA | CAC | ACT | GAA | AGC | ATC | ATT | TCG | GAA | AGC | 721 |
| Ser | His | Ser | Trp | Ser | Asn | Gly | His | Thr | Glu | Ser | Ile | Ile | Ser | Glu | Ser |
| 225 |  |  |  |  | 230 |  |  |  |  | 235 |  |  |  |  | 240 |
| CAC | TCT | GTC | ATC | GTG | ATG | TCA | TCC | GTA | GAA | AAC | AGT | AGG | CAC | AGC | AGC | 769 |
| His | Ser | Val | Ile | Val | Met | Ser | Ser | Val | Glu | Asn | Ser | Arg | His | Ser | Ser |
|  |  |  |  | 245 |  |  |  |  | 250 |  |  |  |  | 255 |  |
| CCG | ACT | GGG | GGC | CCG | AGA | GGA | CGT | CTC | AAT | GGC | TTG | GGA | GGC | CCT | CGT | 817 |
| Pro | Thr | Gly | Gly | Pro | Arg | Gly | Arg | Leu | Asn | Gly | Leu | Gly | Gly | Pro | Arg |
|  |  |  | 260 |  |  |  |  | 265 |  |  |  |  | 270 |  |  |
| GAA | TGT | AAC | AGC | TTC | CTC | AGG | CAT | GCC | AGA | GAA | ACC | CCT | GAC | TCC | TAC | 865 |
| Glu | Cys | Asn | Ser | Phe | Leu | Arg | His | Ala | Arg | Glu | Thr | Pro | Asp | Ser | Tyr |
|  |  | 275 |  |  |  |  | 280 |  |  |  |  | 285 |  |  |  |
| CGA | GAC | TCT | CCT | CAT | AGT | GAA | AGA | CAT | AAC | CTT | ATA | GCT | GAG | CTA | AGG | 913 |
| Arg | Asp | Ser | Pro | His | Ser | Glu | Arg | His | Asn | Leu | Ile | Ala | Glu | Leu | Arg |
|  | 290 |  |  |  |  | 295 |  |  |  |  | 300 |  |  |  |  |
| AGA | AAC | AAG | GCC | CAC | AGA | TCC | AAA | TGC | ATG | CAG | ATC | CAG | CTT | TCC | GCA | 961 |
| Arg | Asn | Lys | Ala | His | Arg | Ser | Lys | Cys | Met | Gln | Ile | Gln | Leu | Ser | Ala |
| 305 |  |  |  |  | 310 |  |  |  |  | 315 |  |  |  |  | 320 |
| ACT | CAT | CTT | AGA | GCT | TCT | TCC | ATT | CCC | CAT | TGG | GCT | TCA | TTC | TCT | AAG | 1009 |
| Thr | His | Leu | Arg | Ala | Ser | Ser | Ile | Pro | His | Trp | Ala | Ser | Phe | Ser | Lys |
|  |  |  |  | 325 |  |  |  |  | 330 |  |  |  |  | 335 |  |
| ACC | CCT | TGG | CCT | TTA | GGA | AGG | TAT | GTA | TCA | GCA | ATG | ACC | ACC | CCG | GCT | 1057 |
| Thr | Pro | Trp | Pro | Leu | Gly | Arg | Tyr | Val | Ser | Ala | Met | Thr | Thr | Pro | Ala |
|  |  |  | 340 |  |  |  |  | 345 |  |  |  |  | 350 |  |  |
| CGT | ATG | TCA | CCT | GTA | GAT | TTC | CAC | ACG | CCA | AGC | TCC | CCC | AAG | TCA | CCC | 1105 |
| Arg | Met | Ser | Pro | Val | Asp | Phe | His | Thr | Pro | Ser | Ser | Pro | Lys | Ser | Pro |

|  |  |  |  |  |  |  |  |  |  |  |  |  |  |  |  |  |
|---|---|---|---|---|---|---|---|---|---|---|---|---|---|---|---|---|
|  |  | 355 |  |  |  |  | 360 |  |  |  |  |  | 365 |  |  |  |
| CCT | TCG | GAA | ATG | TCC | CCG | CCC | GTG | TCC | AGC | ACG | ACG | GTC | TCC | ATG | CCC | 1153 |
| Pro | Ser | Glu | Met | Ser | Pro | Pro | Val | Ser | Ser | Thr | Thr | Val | Ser | Met | Pro |  |
|  | 370 |  |  |  | 375 |  |  |  |  | 380 |  |  |  |  |  |  |
| TCC | ATG | GCG | GTC | AGT | CCC | TTC | GTG | GAA | GAG | GAG | AGA | CCC | CTG | CTC | CTT | 1201 |
| Ser | Met | Ala | Val | Ser | Pro | Phe | Val | Glu | Glu | Glu | Arg | Pro | Leu | Leu | Leu |  |
| 385 |  |  |  |  | 390 |  |  |  |  | 395 |  |  |  |  | 400 |  |
| GTG | ACG | CCA | CCA | CGG | CTG | CGG | GAG | AAG | TAT | GAC | CAC | CAC | GCC | CAG | CAA | 1249 |
| Val | Thr | Pro | Pro | Arg | Leu | Arg | Glu | Lys | Tyr | Asp | His | His | Ala | Gln | Gln |  |
|  |  |  |  | 405 |  |  |  |  | 410 |  |  |  |  | 415 |  |  |
| TTC | AAC | TCG | TTC | CAC | TGC | AAC | CCC | GCG | CAT | GAG | AGC | AAC | AGC | CTG | CCC | 1297 |
| Phe | Asn | Ser | Phe | His | Cys | Asn | Pro | Ala | His | Glu | Ser | Asn | Ser | Leu | Pro |  |
|  |  |  | 420 |  |  |  |  | 425 |  |  |  |  | 430 |  |  |  |
| CCC | AGC | CCC | TTG | AGG | ATA | GTG | GAG | GAT | GAG | GAA | TAT | GAA | ACG | ACC | CAG | 1345 |
| Pro | Ser | Pro | Leu | Arg | Ile | Val | Glu | Asp | Glu | Glu | Tyr | Glu | Thr | Thr | Gln |  |
|  |  | 435 |  |  |  |  | 440 |  |  |  |  | 445 |  |  |  |  |
| GAG | TAC | GAA | CCA | GCT | CAA | GAG | CCG | GTT | AAG | AAA | CTC | ACC | AAC | AGC | AGC | 1393 |
| Glu | Tyr | Glu | Pro | Ala | Gln | Glu | Pro | Val | Lys | Lys | Leu | Thr | Asn | Ser | Ser |  |
|  | 450 |  |  |  |  | 455 |  |  |  |  | 460 |  |  |  |  |  |
| CGG | CGG | GCC | AAA | AGA | ACC | AAG | CCC | AAT | GGT | CAC | ATT | GCC | CAC | AGG | TTG | 1441 |
| Arg | Arg | Ala | Lys | Arg | Thr | Lys | Pro | Asn | Gly | His | Ile | Ala | His | Arg | Leu |  |
| 465 |  |  |  |  | 470 |  |  |  |  | 475 |  |  |  |  | 480 |  |
| GAA | ATG | GAC | AAC | AAC | ACA | GGC | GCT | GAC | AGC | AGT | AAC | TCA | GAG | AGC | GAA | 1489 |
| Glu | Met | Asp | Asn | Asn | Thr | Gly | Ala | Asp | Ser | Ser | Asn | Ser | Glu | Ser | Glu |  |
|  |  |  |  | 485 |  |  |  |  | 490 |  |  |  |  | 495 |  |  |
| ACA | GAG | GAT | GAA | AGA | GTA | GGA | GAA | GAT | ACG | CCT | TTC | CTG | GCC | ATA | CAG | 1537 |
| Thr | Glu | Asp | Glu | Arg | Val | Gly | Glu | Asp | Thr | Pro | Phe | Leu | Ala | Ile | Gln |  |
|  |  |  | 500 |  |  |  |  | 505 |  |  |  |  | 510 |  |  |  |
| AAC | CCC | CTG | GCA | GCC | AGT | CTC | GAG | GCG | GCC | CCT | GCC | TTC | CGC | CTG | GTC | 1585 |
| Asn | Pro | Leu | Ala | Ala | Ser | Leu | Glu | Ala | Ala | Pro | Ala | Phe | Arg | Leu | Val |  |
|  |  | 515 |  |  |  |  | 520 |  |  |  |  | 525 |  |  |  |  |
| GAC | AGC | AGG | ACT | AAC | CCA | ACA | GGC | GGC | TTC | TCT | CCG | CAG | GAA | GAA | TTG | 1633 |
| Asp | Ser | Arg | Thr | Asn | Pro | Thr | Gly | Gly | Phe | Ser | Pro | Gln | Glu | Glu | Leu |  |
|  | 530 |  |  |  |  | 535 |  |  |  |  | 540 |  |  |  |  |  |
| CAG | GCC | AGG | CTC | TCC | GGT | GTA | ATC | GCT | AAC | CAA | GAC | CCT | ATC | GCT | GTC | 1681 |
| Gln | Ala | Arg | Leu | Ser | Gly | Val | Ile | Ala | Asn | Gln | Asp | Pro | Ile | Ala | Val |  |
| 545 |  |  |  |  | 550 |  |  |  |  | 555 |  |  |  |  | 560 |  |
| TAAAACCGAA | ATACACCCAT | AGATTCACCT | GTAAAACTTT | ATTTTATATA | ATAAAGTATT |  |  |  |  |  |  |  |  |  |  | 1741 |
| CCACCTTAAA | TTAAACAAAA | AAA |  |  |  |  |  |  |  |  |  |  |  |  |  | 1764 |

( 2 ) INFORMATION FOR SEQ ID NO: 151:

( i ) SEQUENCE CHARACTERISTICS:
        ( A ) LENGTH: 50
        ( B ) TYPE: amino acid
        ( C ) STRANDEDNESS:
        ( D ) TOPOLOGY: linear ( x i ) SEQUENCE DESCRIPTION: SEQ ID NO: 151:

| Lys | Cys | Ala | Glu | Lys | Glu | Lys | Thr | Phe | Cys | Val | Asn | Gly | Gly | Glu | Cys |
|---|---|---|---|---|---|---|---|---|---|---|---|---|---|---|---|
| 1 |  |  |  | 5 |  |  |  |  | 10 |  |  |  |  | 15 |  |
| Phe | Met | Val | Lys | Asp | Leu | Ser | Asn | Pro | Ser | Arg | Tyr | Leu | Cys | Lys | Cys |
|  |  |  | 20 |  |  |  |  | 25 |  |  |  |  | 30 |  |  |
| Pro | Asn | Glu | Phe | Thr | Gly | Asp | Arg | Cys | Gln | Asn | Tyr | Val | Met | Ala | Ser |
|  |  | 35 |  |  |  |  | 40 |  |  |  |  | 45 |  |  |  |
| Phe | Tyr |  |  |  |  |  |  |  |  |  |  |  |  |  |  |
|  | 50 |  |  |  |  |  |  |  |  |  |  |  |  |  |  |

( 2 ) INFORMATION FOR SEQ ID NO: 152:

( i ) SEQUENCE CHARACTERISTICS:
    ( A ) LENGTH: 50
    ( B ) TYPE: amino acid
    ( C ) STRANDEDNESS:
    ( D ) TOPOLOGY: linear ( x i ) SEQUENCE DESCRIPTION: SEQ ID NO: 152:

```
Lys Cys Ala Glu Lys Glu Lys Thr Phe Cys Val Asn Gly Gly Glu Cys
 1               5                  10                  15
Phe Met Val Lys Asp Leu Ser Asn Pro Ser Arg Tyr Leu Cys Lys Cys
            20                  25                  30
Gln Pro Gly Phe Thr Gly Ala Arg Cys Thr Glu Asn Val Pro Met Lys
            35                  40                  45
Val Gln
 50
```

( 2 ) INFORMATION FOR SEQ ID NO: 153:

( i ) SEQUENCE CHARACTERISTICS:
        ( A ) LENGTH: 46
        ( B ) TYPE: amino acid
        ( C ) STRANDEDNESS:
        ( D ) TOPOLOGY: linear ( x i ) SEQUENCE DESCRIPTION: SEQ ID NO: 153:

```
Glu Cys Leu Arg Lys Tyr Lys Asp Phe Cys Ile His Gly Glu Cys Lys
 1               5                  10                  15
Tyr Val Lys Glu Leu Arg Ala Pro Ser Cys Lys Cys Gln Gln Glu Tyr
            20                  25                  30
Phe Gly Glu Arg Cys Gly Glu Lys Ser Asn Lys Thr His Ser
            35                  40                  45
```

( 2 ) INFORMATION FOR SEQ ID NO: 154:

( i ) SEQUENCE CHARACTERISTICS:
        ( A ) LENGTH: 198
        ( B ) TYPE: nucleic acid
        ( C ) STRANDEDNESS: single
        ( D ) TOPOLOGY: linear ( x i ) SEQUENCE DESCRIPTION: SEQ ID NO: 154:

```
AGC CAT CTT GTC AAG TGT GCA GAG AAG GAG AAA ACT TTC TGT GTG AAT    48
Ser His Leu Val Lys Cys Ala Glu Lys Glu Lys Thr Phe Cys Val Asn
 1               5                  10                  15

GGA GGC GAG TGC TTC ATG GTG AAA GAC CTT TCA AAT CCC TCA AGA TAC    96
Gly Gly Glu Cys Phe Met Val Lys Asp Leu Ser Asn Pro Ser Arg Tyr
            20                  25                  30

TTG TGC AAG TGC CCA AAT GAG TTT ACT GGT GAT CGC TGC CAA AAC TAC   144
Leu Cys Lys Cys Pro Asn Glu Phe Thr Gly Asp Arg Cys Gln Asn Tyr
            35                  40                  45

GTA ATG GCC AGC TTC TAC AGT ACG TCC ACT CCC TTT CTG TCT CTG CCT   192
Val Met Ala Ser Phe Tyr Ser Thr Ser Thr Pro Phe Leu Ser Leu Pro
      50                  55                  60

GAA TAG
Glu
 65
```

( 2 ) INFORMATION FOR SEQ ID NO: 155:

( i ) SEQUENCE CHARACTERISTICS:
        ( A ) LENGTH: 192
        ( B ) TYPE: nucleic acid
        ( C ) STRANDEDNESS: single
        ( D ) TOPOLOGY: linear ( x i ) SEQUENCE DESCRIPTION: SEQ ID NO: 155:

| | | | | | | | | | | | | | | | | |
|---|---|---|---|---|---|---|---|---|---|---|---|---|---|---|---|---|
| AGC | CAT | CTT | GTC | AAG | TGT | GCA | GAG | AAG | GAG | AAA | ACT | TTC | TGT | GTG | AAT | 48 |
| Ser | His | Leu | Val | Lys | Cys | Ala | Glu | Lys | Glu | Lys | Thr | Phe | Cys | Val | Asn | |
| 1 | | | | 5 | | | | | 10 | | | | | 15 | | |
| GGA | GGC | GAG | TGC | TTC | ATG | GTG | AAA | GAC | CTT | TCA | AAT | CCC | TCA | AGA | TAC | 96 |
| Gly | Gly | Glu | Cys | Phe | Met | Val | Lys | Asp | Leu | Ser | Asn | Pro | Ser | Arg | Tyr | |
| | | | 20 | | | | | 25 | | | | | 30 | | | |
| TTG | TGC | AAG | TGC | CAA | CCT | GCA | TTC | ACT | GGA | GCG | AGA | TGT | ACT | GAG | AAT | 144 |
| Leu | Cys | Lys | Cys | Gln | Pro | Gly | Phe | Thr | Gly | Ala | Arg | Cys | Thr | Glu | Asn | |
| | | 35 | | | | | 40 | | | | | 45 | | | | |
| GTG | CCC | ATG | AAA | GTC | CAA | ACC | CAA | GAA | AAA | GCG | GAG | GAG | CTC | TAC | TAA | 192 |
| Val | Pro | Met | Lys | Val | Gln | Thr | Gln | Glu | Lys | Ala | Glu | Glu | Leu | Tyr | | |
| | 50 | | | | 55 | | | | | 60 | | | | | | |

( 2 ) INFORMATION FOR SEQ ID NO: 156:

( i ) SEQUENCE CHARACTERISTICS:
    ( A ) LENGTH: 183
    ( B ) TYPE: nucleic acid
    ( C ) STRANDEDNESS: single
    ( D ) TOPOLOGY: linear ( x i ) SEQUENCE DESCRIPTION: SEQ ID NO: 156:

| | | | | | | | | | | | | | | | | |
|---|---|---|---|---|---|---|---|---|---|---|---|---|---|---|---|---|
| AGC | CAT | CTT | GTC | AAG | TGT | GCA | GAG | AAG | GAG | AAA | ACT | TTC | TGT | GTG | AAT | 48 |
| Ser | His | Leu | Val | Lys | Cys | Ala | Glu | Lys | Glu | Lys | Thr | Phe | Cys | Val | Asn | |
| 1 | | | | 5 | | | | | 10 | | | | | 15 | | |
| GGA | GGC | GAG | TGC | TTC | ATG | GTG | AAA | GAC | CTT | TCA | AAT | CCC | TCA | AGA | TAC | 96 |
| Gly | Gly | Glu | Cys | Phe | Met | Val | Lys | Asp | Leu | Ser | Asn | Pro | Ser | Arg | Tyr | |
| | | | 20 | | | | | 25 | | | | | 30 | | | |
| TTG | TGC | AAG | TGC | CCA | AAT | GXG | TTT | ACT | GGT | GAT | CGC | TGC | CAA | AAC | TAC | 144 |
| Leu | Cys | Lys | Cys | Pro | Asn | Glu | Phe | Thr | Gly | Asp | Arg | Cys | Gln | Asn | Tyr | |
| | | 35 | | | | | 40 | | | | | 45 | | | | |
| GTA | ATG | GCC | AGC | TTC | TAC | AAA | GCG | GAG | GAG | CTC | TAC | TAA | | | | 183 |
| Val | Met | Ala | Ser | Phe | Tyr | Lys | Ala | Glu | Glu | Leu | Tyr | | | | | |
| | 50 | | | | 55 | | | | | 60 | | | | | | |

( 2 ) INFORMATION FOR SEQ ID NO: 157:

( i ) SEQUENCE CHARACTERISTICS:
    ( A ) LENGTH: 210
    ( B ) TYPE: nucleic acid
    ( C ) STRANDEDNESS: single
    ( D ) TOPOLOGY: linear ( x i ) SEQUENCE DESCRIPTION: SEQ ID NO: 157:

| | | | | | | | | | | | | | | | | |
|---|---|---|---|---|---|---|---|---|---|---|---|---|---|---|---|---|
| AGC | CAT | CTT | GTC | AAG | TGT | GCA | GAG | AAG | GAG | AAA | ACT | TTC | TGT | GTG | AAT | 48 |
| Ser | His | Leu | Val | Lys | Cys | Ala | Glu | Lys | Glu | Lys | Thr | Phe | Cys | Val | Asn | |
| 1 | | | | 5 | | | | | 10 | | | | | 15 | | |
| GGA | GGC | GAG | TGC | TTC | ATG | GTG | AAA | GAC | CTT | TCA | AAT | CCC | TCA | AGA | TAC | 96 |
| Gly | Gly | Glu | Cys | Phe | Met | Val | Lys | Asp | Leu | Ser | Asn | Pro | Ser | Arg | Tyr | |
| | | | 20 | | | | | 25 | | | | | 30 | | | |
| TTG | TGC | AAG | TGC | CCA | AAT | GAG | TTT | ACT | GGT | GAT | CGC | TGC | CAA | AAC | TAC | 144 |
| Leu | Cys | Lys | Cys | Pro | Asn | Glu | Phe | Thr | Gly | Asp | Arg | Cys | Gln | Asn | Tyr | |
| | | 35 | | | | | 40 | | | | | 45 | | | | |
| GTA | ATG | GCC | AGC | TTC | TAC | AAG | CAT | CTT | GGG | ATT | GAA | TTT | ATG | GAG | AAA | 192 |
| Val | Met | Ala | Ser | Phe | Tyr | Lys | His | Leu | Gly | Ile | Glu | Phe | Met | Glu | Lys | |
| | 50 | | | | 55 | | | | | 60 | | | | | | |
| GCG | GAG | GAG | CTC | TAC | TAA | | | | | | | | | | | 210 |
| Ala | Glu | Glu | Leu | Tyr | | | | | | | | | | | | |
| 65 | | | | | | | | | | | | | | | | |

( 2 ) INFORMATION FOR SEQ ID NO: 158:

( i ) SEQUENCE CHARACTERISTICS:

( A ) LENGTH: 267
( B ) TYPE: nucleic acid
( C ) STRANDEDNESS: single
( D ) TOPOLOGY: linear ( x i ) SEQUENCE DESCRIPTION: SEQ ID NO: 158:

| AGC | CAT | CTT | GTC | AAG | TGT | GCA | GAG | AAG | GAG | AAA | ACT | TTC | TGT | GTG | AAT | 48 |
| Ser | His | Leu | Val | Lys | Cys | Ala | Glu | Lys | Glu | Lys | Thr | Phe | Cys | Val | Asn | |
| 1 | | | | 5 | | | | | 10 | | | | | 15 | | |

| GGA | GGC | GAG | TGC | TTC | ATG | GTG | AAA | GAC | CTT | TCA | AAT | CCC | TCA | AGA | TAC | 96 |
| Gly | Gly | Glu | Cys | Phe | Met | Val | Lys | Asp | Leu | Ser | Asn | Pro | Ser | Arg | Tyr | |
| | | | 20 | | | | | 25 | | | | | 30 | | | |

| TTG | TGC | AAG | TGC | CAA | CCT | GGA | TTC | ACT | GGA | GCG | AGA | TGT | ACT | GAG | AAT | 144 |
| Leu | Cys | Lys | Cys | Gln | Pro | Gly | Phe | Thr | Gly | Ala | Arg | Cys | Thr | Glu | Asn | |
| | | 35 | | | | | 40 | | | | | 45 | | | | |

| GTG | CCC | ATG | AAA | GTC | CAA | ACC | CAA | GAA | AAG | TGC | CCA | AAT | GAG | TTT | ACT | 192 |
| Val | Pro | Met | Lys | Val | Gln | Thr | Gln | Glu | Lys | Cys | Pro | Asn | Glu | Phe | Thr | |
| | | 50 | | | | 55 | | | | | 60 | | | | | |

| GGT | GAT | CGC | TGC | CAA | AAC | TAC | GTA | ATG | GCC | AGC | TTC | TAC | AGT | ACG | TCC | 240 |
| Gly | Asp | Arg | Cys | Gln | Asn | Tyr | Val | Met | Ala | Ser | Phe | Tyr | Ser | Thr | Ser | |
| 65 | | | | | 70 | | | | | 75 | | | | | 80 | |

| ACT | CCC | TTT | CTG | TCT | CTG | CCT | GAA | TAG | | | | | | | | 267 |
| Thr | Pro | Phe | Leu | Ser | Leu | Pro | Glu | | | | | | | | | |
| | | | | 85 | | | | | | | | | | | | |

( 2 ) INFORMATION FOR SEQ ID NO: 159:

( i ) SEQUENCE CHARACTERISTICS:
( A ) LENGTH: 252
( B ) TYPE: nucleic acid
( C ) STRANDEDNESS: single
( D ) TOPOLOGY: linear ( x i ) SEQUENCE DESCRIPTION: SEQ ID NO: 159:

| AGC | CAT | CTT | GTC | AAG | TGT | GCA | GAG | AAG | GAG | AAA | ACT | TTC | TGT | GTG | AAT | 48 |
| Ser | His | Leu | Val | Lys | Cys | Ala | Glu | Lys | Glu | Lys | Thr | Phe | Cys | Val | Asn | |
| 1 | | | | 5 | | | | | 10 | | | | | 15 | | |

| GGA | GGC | GAG | TGC | TTC | ATG | GTG | AAA | GAC | CTT | TCA | AAT | CCC | TCA | AGA | TAC | 96 |
| Gly | Gly | Glu | Cys | Phe | Met | Val | Lys | Asp | Leu | Ser | Asn | Pro | Ser | Arg | Tyr | |
| | | | 20 | | | | | 25 | | | | | 30 | | | |

| TTG | TGC | AAG | TGC | CAA | CCT | GGA | TTC | ACT | GGA | GCG | AGA | TGT | ACT | GAG | AAT | 144 |
| Leu | Cys | Lys | Cys | Gln | Pro | Gly | Phe | Thr | Gly | Ala | Arg | Cys | Thr | Glu | Asn | |
| | | 35 | | | | | 40 | | | | | 45 | | | | |

| GTG | CCC | ATG | AAA | GTC | CAA | ACC | CAA | GAA | AAG | TGC | CCA | AAT | GAG | TTT | ACT | 192 |
| Val | Pro | Met | Lys | Val | Gln | Thr | Gln | Glu | Lys | Cys | Pro | Asn | Glu | Phe | Thr | |
| | | 50 | | | | 55 | | | | | 60 | | | | | |

| GGT | GAT | CGC | TGC | CAA | AAC | TAC | GTA | ATG | GCC | AGC | TTC | TAC | AAA | GCG | GAG | 240 |
| Gly | Asp | Arg | Cys | Gln | Asn | Tyr | Val | Met | Ala | Ser | Phe | Tyr | Lys | Ala | Glu | |
| 65 | | | | | 70 | | | | | 75 | | | | | 80 | |

| GAG | CTC | TAC | TAA | | | | | | | | | | | | | 252 |
| Glu | Leu | Tyr | | | | | | | | | | | | | | |

( 2 ) INFORMATION FOR SEQ ID NO: 160:

( i ) SEQUENCE CHARACTERISTICS:
( A ) LENGTH: 128
( B ) TYPE: nucleic acid
( C ) STRANDEDNESS: single
( D ) TOPOLOGY: linear ( x i ) SEQUENCE DESCRIPTION: SEQ ID NO: 160:

| CC | ACA | TCC | ACA | TCT | ACA | GCT | GGG | ACA | AGC | CAT | CTT | GTC | AAG | TGT | GCA | 47 |
| | Thr | Ser | Thr | Ser | Thr | Ala | Gly | Thr | Ser | His | Leu | Val | Lys | Cys | Ala | |
| | 1 | | | | 5 | | | | | 10 | | | | | 15 | |

```
GAG  AAG  GAG  AAA  ACT  TTC  TGT  GTG  AAT  GGA  GGC  GAG  TGC  TTC  ATG  GTG         95
Glu  Lys  Glu  Lys  Thr  Phe  Cys  Val  Asn  Gly  Gly  Glu  Cys  Phe  Met  Val
                    20                       25                           30

AAA  GAC  CTT  TCA  AAT  CCC  TCA  AGA  TAC  TTG  TGC                                 128
Lys  Asp  Leu  Ser  Asn  Pro  Ser  Arg  Tyr  Leu
                    35                  40
```

( 2 ) INFORMATION FOR SEQ ID NO: 161:

( i ) SEQUENCE CHARACTERISTICS:
        ( A ) LENGTH: 141
        ( B ) TYPE: nucleic acid
        ( C ) STRANDEDNESS: single
        ( D ) TOPOLOGY: linear ( x i ) SEQUENCE DESCRIPTION: SEQ ID NO: 161:

```
A  CAT  AAC  CTT  ATA  GCT  GAG  CTA  AGG  AGA  AAC  AAG  GCC  CAC  AGA  TCC          46
   His  Asn  Leu  Ile  Ala  Glu  Leu  Arg  Arg  Asn  Lys  Ala  His  Arg  Ser
   1                   5                        10                       15

AAA  TGC  ATG  CAG  ATC  CAG  CTT  TCC  GCA  ACT  CAT  CTT  AGA  GCT  TCT  TCC         94
Lys  Cys  Met  Gln  Ile  Gln  Leu  Ser  Ala  Thr  His  Leu  Arg  Ala  Ser  Ser
                    20                       25                           30

ATT  CCC  CAT  TGG  GCT  TCA  TTC  TCT  AAG  ACC  CCT  TGG  CCT  TTA  GGA  AG        141
Ile  Pro  His  Trp  Ala  Ser  Pro  Ser  Lys  Thr  Pro  Trp  Pro  Leu  Gly  Arg
                    35                       40                           45
```

( 2 ) INFORMATION FOR SEQ ID NO: 162:

( i ) SEQUENCE CHARACTERISTICS:
        ( A ) LENGTH: 24
        ( B ) TYPE: amino acid
        ( C ) STRANDEDNESS:
        ( D ) TOPOLOGY: linear ( i x ) FEATURE:
        ( D ) OTHER INFORMATION: Xaa in positions 15 and 22 is unknown.

( x i ) SEQUENCE DESCRIPTION: SEQ ID NO: 162:

```
Ala  Ala  Glu  Lys  Glu  Lys  Thr  Phe  Cys  Val  Asn  Gly  Gly  Glu  Xaa  Phe
1                   5                        10                           15

Met  Val  Lys  Asp  Leu  Xaa  Asn  Pro
                    20
```

( 2 ) INFORMATION FOR SEQ ID NO: 163:

( i ) SEQUENCE CHARACTERISTICS:
        ( A ) LENGTH: 745
        ( B ) TYPE: nucleic acid
        ( C ) STRANDEDNESS: single
        ( D ) TOPOLOGY: linear ( x i ) SEQUENCE DESCRIPTION: SEQ ID NO: 163:

```
ATG  AGA  TGG  CGA  CGC  GCC  CCG  CGC  CGC  TCC  GGG  CGT  CCC  GGC  CCC  CGG         48
Met  Arg  Trp  Arg  Arg  Ala  Pro  Arg  Arg  Ser  Gly  Arg  Pro  Gly  Pro  Arg
1                   5                        10                           15

GCC  CAG  CGC  CCC  GGC  TCC  GCC  GCC  CGC  TCG  TCG  CCG  CCG  CTG  CCG  CTG         96
Ala  Gln  Arg  Pro  Gly  Ser  Ala  Ala  Arg  Ser  Ser  Pro  Pro  Leu  Pro  Leu
                    20                       25                           30

CTG  CCA  CTA  CTG  CTG  CTG  CTG  GGG  ACC  GCG  GCC  CTG  GCG  CCG  GGG  GCG        144
Leu  Pro  Leu  Leu  Leu  Leu  Leu  Gly  Thr  Ala  Ala  Leu  Ala  Pro  Gly  Ala
                    35                       40                           45

GCG  GCC  GGC  AAC  GAG  GCG  GCT  CCC  GCG  GGG  GCC  TCG  GTG  TGC  TAC  TCG        192
Ala  Ala  Gly  Asn  Glu  Ala  Ala  Pro  Ala  Gly  Ala  Ser  Val  Cys  Tyr  Ser
               50                       55                           60

TCC  CCG  CCC  AGC  GTG  GGA  TCG  GTG  CAG  GAG  CTA  GCT  CAG  CGC  GCC  GCG        240
Ser  Pro  Pro  Ser  Val  Gly  Ser  Val  Gln  Glu  Leu  Ala  Gln  Arg  Ala  Ala
```

```
         65                          70                          75                          80
GTG  GTG  ATC  GAG  GGA  AAG  GTG  CAC  CCG  CAG  CGG  CGG  CAG  CAG  GGG  GCA        288
Val  Val  Ile  Glu  Gly  Lys  Val  His  Pro  Gln  Arg  Arg  Gln  Gln  Gly  Ala
                         85                          90                          95

CTC  GAC  AGG  AAG  GCG  GCG  GCG  GCG  GCG  GGC  GAG  GCA  GGG  GCG  TGG  GGC        336
Leu  Asp  Arg  Lys  Ala  Ala  Ala  Ala  Ala  Gly  Glu  Ala  Gly  Ala  Trp  Gly
               100                           105                           110

GGC  GAT  CGC  GAG  CCG  CCA  GCC  GCG  GGC  CCA  CGG  GCG  CTG  GGG  CCG  CCC        384
Gly  Asp  Arg  Glu  Pro  Pro  Ala  Ala  Gly  Pro  Arg  Ala  Leu  Gly  Pro  Pro
          115                           120                           125

GCC  GAG  GAG  CCG  CTG  CTC  GCC  GCC  AAC  GGG  ACC  GTG  CCC  TCT  TGG  CCC        432
Ala  Glu  Glu  Pro  Leu  Leu  Ala  Ala  Asn  Gly  Thr  Val  Pro  Ser  Trp  Pro
     130                           135                           140

ACC  GCC  CCG  GTG  CCC  AGC  GCC  GGC  GAG  CCC  GGG  GAG  GAG  GCG  CCC  TAT        480
Thr  Ala  Pro  Val  Pro  Ser  Ala  Gly  Glu  Pro  Gly  Glu  Glu  Ala  Pro  Tyr
145                           150                           155                           160

CTG  GTG  AAG  GTG  CAC  CAG  GTG  TGG  GCG  GTG  AAA  GCC  GGG  GGC  TTG  AAG        528
Leu  Val  Lys  Val  His  Gln  Val  Trp  Ala  Val  Lys  Ala  Gly  Gly  Leu  Lys
                    165                           170                           175

AAG  GAC  TCG  CTG  CTC  ACC  GTG  CGC  CTG  GGG  ACC  TGG  GGC  CAC  CCC  GCC        576
Lys  Asp  Ser  Leu  Leu  Thr  Val  Arg  Leu  Gly  Thr  Trp  Gly  His  Pro  Ala
               180                           185                           190

TTC  CCC  TCC  TGC  GGG  AGG  CTC  AAG  GAG  GAC  AGC  AGG  TAC  ATC  TTC  TTC        624
Phe  Pro  Ser  Cys  Gly  Arg  Leu  Lys  Glu  Asp  Ser  Arg  Tyr  Ile  Phe  Phe
          195                           200                           205

ATG  GAG  CCC  GAC  GCC  AAC  AGC  ACC  AGC  CGC  GCG  CCG  GCC  GCC  TTC  CGA        672
Met  Glu  Pro  Asp  Ala  Asn  Ser  Thr  Ser  Arg  Ala  Pro  Ala  Ala  Phe  Arg
     210                           215                           220

GCC  TCT  TTC  CCC  CCT  CTG  GAG  ACG  GGC  CGG  AAC  CTC  AAG  AAG  GAG  GTC        720
Ala  Ser  Phe  Pro  Pro  Leu  Glu  Thr  Gly  Arg  Asn  Leu  Lys  Lys  Glu  Val
225                           230                           235                           240

AGC  CGG  GTG  CTG  TGC  AAG  CGG  TGC  G                                              745
Ser  Arg  Val  Leu  Cys  Lys  Arg  Cys
                    245
```

( 2 ) INFORMATION FOR SEQ ID NO: 164:

( i ) SEQUENCE CHARACTERISTICS:
        ( A ) LENGTH: 12
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is unknown.

( x i ) SEQUENCE DESCRIPTION: SEQ ID NO: 164:

```
Xaa  Ala  Leu  Ala  Ala  Ala  Gly  Tyr  Asp  Val  Glu  Lys
  1                   5                         10
```

( 2 ) INFORMATION FOR SEQUEIJCE IDENTIFICATION NUMBER: 165:

( i ) SEQUENCE CHARACTERISTICS:
        ( A ) LENGTH: 5
        ( B ) TYPE: amino acid
        ( C ) STRANDEDNESS:
        ( D ) TOPOLOGY: linear ( i x ) FEATURE:
        ( D ) OTHER INFOPI4ATION: Xaa in position 1 is unknown.

( x i ) SEQUENCE DESCRIPTION: SEQ ID NO: 165:

```
Xaa  Leu  Val  Leu  Arg
  1             5
```

( 2 ) INFORMATION FOR SEQ ID NO: 166:

( i ) SEQUENCE CHARACTERISTICS:
        ( A ) LENGTH: 11
        ( B ) TYPE: amino acid
        ( C ) STRANDEDNESS:
        ( D ) TOPOLOGY: linear ( i x ) FEATURE:
        ( D ) OTHER INFORMATION:
            Xaa in positions 1, 2, and 3 is unknown.

( x i ) SEQUENCE DESCRIPTION: SEQ ID NO: 166:

Xaa Xaa Xaa Tyr Pro Gly Gln Ile Thr Ser Asn
 1              5                    10

( 2 ) INFORMATION FOR SEQ ID NO: 167:

( i ) SEQUENCE CHARACTERISTICS:
        ( A ) LENGTH: 60
        ( B ) TYPE: nucleic acid
        ( C ) STRANDEDNESS: single
        ( D ) TOPOLOGY: linear ( i x ) FEATURE:
        ( D ) OTHER INFORMATION: N in positions 25 and 36 is unknown.

( x i ) SEQUENCE DESCRIPTION: SEQ ID NO: 167:

ATAGGGAAGG GCGGGGGAAG GGTCNCCCTC NGCAGGGCCG GGCTTGCCTC TGGAGCCTCT    60

( 2 ) INFORMATION FOR SEQ ID NO: 168:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i x ) FEATURE:
        ( D ) OTHER INFORMATION: N in position 16 is unknown.

( x i ) SEQUENCE DESCRIPTION: SEQ ID NO: 168:

TTTACACATA TATTCNCC    18

( 2 ) INFORMATION FOR SEQ ID NO: 169:

( i ) SEQUENCE CHARACTERISTICS:
        ( A ) LENGTH: 21
        ( B ) TYPE: amino acid
        ( C ) STRANDEDNESS:
        ( D ) TOPOLOGY: linear ( x i ) SEQUENCE DESCRIPTION: SEQ ID NO: 169:

Glu Thr Gln Pro Asp Pro Gly Gln Ile Leu Lys Lys Val Pro Met Val
 1              5                  10                15

Ile Gly Ala Tyr Thr
              20

( 2 ) INFORMATION FOR SEQUEIICE IDENTIFICATION NUMBER: 170:

( i ) SEQUENCE CHARACTZRISTICS:
        ( A ) LENGTH: 422
        ( B ) TYPE: amino acid
        ( C ) STRANDEDNESS:
        ( D ) TOPOLOGY: linear ( x i ) SEQUENCE DESCRIPTION: SEQ ID NO: 170:

Met Arg Trp Arg Arg Ala Pro Arg Arg Ser Gly Arg Pro Gly Pro Arg
 1              5                  10                15

| | | | | | | | | | | | | | | |
|---|---|---|---|---|---|---|---|---|---|---|---|---|---|---|
| Ala | Gln | Arg | Pro | Gly | Ser | Ala | Ala | Arg | Ser | Ser | Pro | Pro | Leu | Pro | Leu |
| | | | 20 | | | | 25 | | | | 30 | | | |
| Leu | Pro | Leu | Leu | Leu | Leu | Leu | Gly | Thr | Ala | Ala | Leu | Ala | Pro | Gly | Ala |
| | | 35 | | | | 40 | | | | 45 | | | | | |
| Ala | Ala | Gly | Asn | Glu | Ala | Ala | Pro | Ala | Gly | Ala | Ser | Val | Cys | Tyr | Ser |
| 50 | | | | | 55 | | | | 60 | | | | | | |
| Ser | Pro | Pro | Ser | Val | Gly | Ser | Val | Gln | Glu | Leu | Ala | Gln | Arg | Ala | Ala |
| 65 | | | | 70 | | | | 75 | | | | 80 | | | |
| Val | Val | Ile | Glu | Gly | Lys | Val | His | Pro | Gln | Arg | Arg | Gln | Gln | Gly | Ala |
| | | | | 85 | | | | 90 | | | | 95 | | | |
| Leu | Asp | Arg | Lys | Ala | Ala | Ala | Ala | Gly | Glu | Ala | Gly | Ala | Trp | Gly |
| | | | 100 | | | | 105 | | | | 110 | | | |
| Gly | Asp | Arg | Glu | Pro | Pro | Ala | Ala | Gly | Pro | Arg | Ala | Leu | Gly | Pro | Pro |
| | | 115 | | | | 120 | | | | 125 | | | | | |
| Ala | Glu | Glu | Pro | Leu | Leu | Ala | Ala | Asn | Gly | Thr | Val | Pro | Ser | Trp | Pro |
| | 130 | | | | 135 | | | | 140 | | | | | | |
| Thr | Ala | Pro | Val | Pro | Ser | Ala | Gly | Glu | Pro | Gly | Glu | Glu | Ala | Pro | Tyr |
| 145 | | | | 150 | | | | 155 | | | | 160 | | | |
| Leu | Val | Lys | Val | His | Gln | Val | Trp | Ala | Val | Lys | Ala | Gly | Gly | Leu | Lys |
| | | | 165 | | | | 170 | | | | 175 | | | | |
| Lys | Asp | Ser | Leu | Leu | Thr | Val | Arg | Leu | Gly | Thr | Trp | Gly | His | Pro | Ala |
| | | | 180 | | | | 185 | | | | 190 | | | | |
| Phe | Pro | Ser | Cys | Gly | Arg | Leu | Lys | Glu | Asp | Ser | Arg | Tyr | Ile | Phe | Phe |
| | | 195 | | | | 200 | | | | 205 | | | | | |
| Met | Glu | Pro | Asp | Ala | Asn | Ser | Thr | Ser | Arg | Ala | Pro | Ala | Ala | Phe | Arg |
| | 210 | | | | 215 | | | | 220 | | | | | | |
| Ala | Ser | Phe | Pro | Pro | Leu | Glu | Thr | Gly | Arg | Asn | Leu | Lys | Lys | Glu | Val |
| 225 | | | | 230 | | | | 235 | | | | 240 | | | |
| Ser | Arg | Val | Leu | Cys | Lys | Arg | Cys | Ala | Leu | Pro | Pro | Gln | Leu | Lys | Glu |
| | | | 245 | | | | 250 | | | | 255 | | | | |
| Met | Lys | Ser | Gln | Glu | Ser | Ala | Ala | Gly | Ser | Lys | Leu | Val | Leu | Arg | Cys |
| | | 260 | | | | 265 | | | | 270 | | | | | |
| Glu | Thr | Ser | Ser | Glu | Tyr | Ser | Ser | Leu | Arg | Phe | Lys | Trp | Phe | Lys | Asn |
| | 275 | | | | 280 | | | | 285 | | | | | | |
| Gly | Asn | Glu | Leu | Asn | Arg | Phe | Asn | Lys | Pro | Gln | Asn | Ile | Lys | Ile | Gln |
| 290 | | | | 295 | | | | 300 | | | | | | | |
| Lys | Lys | Pro | Gly | Lys | Ser | Glu | Leu | Arg | Ile | Asn | Lys | Ala | Ser | Leu | Ala |
| 305 | | | | 310 | | | | 315 | | | | 320 | | | |
| Asp | Ser | Gly | Glu | Tyr | Met | Cys | Lys | Val | Ile | Ser | Lys | Leu | Gly | Asn | Asp |
| | | | 325 | | | | 330 | | | | 335 | | | | |
| Ser | Ala | Ser | Ala | Asn | Ile | Thr | Ile | Val | Glu | Ser | Asn | Ala | Thr | Ser | Thr |
| | | | 340 | | | | 345 | | | | 350 | | | | |
| Ser | Thr | Thr | Gly | Thr | Ser | His | Leu | Val | Lys | Cys | Ala | Glu | Lys | Glu | Lys |
| | | 355 | | | | 360 | | | | 365 | | | | | |
| Thr | Phe | Cys | Val | Asn | Gly | Gly | Glu | Cys | Phe | Met | Val | Lys | Asp | Leu | Ser |
| | 370 | | | | 375 | | | | 380 | | | | | | |
| Asn | Pro | Ser | Arg | Tyr | Leu | Cys | Lys | Cys | Pro | Asn | Glu | Phe | Thr | Gly | Asp |
| 385 | | | | 390 | | | | 395 | | | | 400 | | | |
| Arg | Cys | Gln | Asn | Tyr | Val | Met | Ala | Ser | Phe | Tyr | Ser | Thr | Ser | Thr | Pro |
| | | | 405 | | | | 410 | | | | 415 | | | | |
| Phe | Leu | Ser | Leu | Pro | Glu |
| | | | 420 | | |

( 2 ) INFORMATION FOR SEQ ID NO: 171:

( i ) SEQUENCE CHARACTERISTICS:
        ( A ) LENGTH: 69
        ( B ) TYPE: amino acid
        ( C ) STRANDEDNESS:
        ( D ) TOPOLOGY: linear ( x i ) SEQUENCE DESCRIPTION: SEQ ID NO: 171:

```
Met Ser Glu Arg Lys Glu Cys Arg Gly Lys Gly Lys Gly Lys Lys Lys
 1               5                  10                  15
Glu Arg Gly Ser Gly Lys Lys Pro Glu Ser Ala Ala Gly Ser Gln Ser
             20                  25                  30
Pro Arg Glu Ile Ile Thr Gly Met Pro Ala Ser Thr Glu Gly Ala Tyr
         35                  40                  45
Val Ser Ser Glu Ser Pro Ile Arg Ile Ser Val Ser Thr Glu Gly Ala
     50                  55                  60
Asn Thr Ser Ser Ser
 65
```

( 2 ) INFORMATION FOR SEQ ID NO: 172:

( i ) SEQUENCE CHARACTERISTICS:
        ( A ) LENGTH: 19
        ( B ) TYPE: amino acid
        ( C ) STRANDEDNESS:
        ( D ) TOPOLOGY: linear ( x i ) SEQUENCE DESCRIPTION: SEQ ID NO: 172:

```
Arg Lys Gly Asp Val Pro Gly Pro Arg Val Lys Ser Ser Arg Ser Thr
 1               5                  10                  15
Thr Thr Ala
```

( 2 ) INFORMATION FOR SEQ ID NO: 173:

( i ) SEQUENCE CHARACTERISTICS:
        ( A ) LENGTH: 231
        ( B ) TYPE: nucleic acid
        ( C ) STRANDEDNESS: single
        ( D ) TOPOLOGY: linear ( x i ) SEQUENCE DESCRIPTION: SEQ ID NO: 173:

```
CGCGAGCGCC TCAGCGCGGC CGCTCGCTCT CCCCCTCGAG GGACAAACTT TTCCCAAACC     60
CGATCCGAGC CCTTGGACCA AACTCGCCTG CGCCGAGAGC CGTCCGCGTA GAGCGCTCCG    120
TCTCCGGCGA GATGTCCGAG CGCAAAGAAG GCAGAGGCAA AGGGAAGGGC AAGAAGAAGG    180
AGCGAGGCTC CGGCAAGAAG CCGGAGTCCG CGGCGGGCAG CCAGAGCCCA G             231
```

( 2 ) INFORMATION FOR SEQ ID NO: 174:

( i ) SEQUENCE CHARACTERISTICS:
        ( A ) LENGTH: 178
        ( B ) TYPE: nucleic acid
        ( C ) STRANDEDNESS: single
        ( D ) TOPOLOGY: Linear ( x i ) SEQUENCE DESCRIPTION: SEQ ID NO: 174:

```
CCTTGCCTCC CCGATTGAAA GAGATGAAAA GCCAGGAATC GGCTGCAGGT TCCAAACTAG     60
TCCTTCGGTG TGAAACCAGT TCTGAATACT CCTCTCTCAG ATTCAAGTGG TTCAAGAATG    120
GGAATGAATT GAATCGAAAA AACAAACCAC AAAATATCAA GATACAAAAA AAGCCAGG     178
```

( 2 ) INFORMATION FOR SEQ ID NO: 175:

( i ) SEQUENCE CHARACTERISTICS:
    ( A ) LENGTH: 122
    ( B ) TYPE: nucleic acid
    ( C ) STRANDEDNESS: single
    ( D ) TOPOLOGY: linear ( x i ) SEQUENCE DESCRIPTION: SEQ ID NO: 175:

```
GAAGTCAGAA CTTCGCATTA ACAAAGCATC ACTGGCTGAT TCTGGAGAGT ATATGTGCAA      60
AGTGATCAGC AAATTAGGAA ATGACAGTGC CTCTGCCAAT ATCACCATCG TGGAATCAAA     120
CG                                                                    122
```

( 2 ) INFORMATION FOR SEQ ID NO: 176:

( i ) SEQUENCE CHARACTERISTICS:
    ( A ) LENGTH: 102
    ( B ) TYPE: nucleic acid
    ( C ) STRANDEDNESS: single
    ( D ) TOPOLOGY: linear ( x i ) SEQUENCE DESCRIPTION: SEQ ID NO: 176:

```
AGATCATCAC TGGTATGCCA GCCTCAACTG AAGGAGCATA TGTGTCTTCA GAGTCTCCCA      60
TTAGAATATC AGTATCCACA GAAGGAGCAA ATACTTCTTC AT                        102
```

( 2 ) INFORMATION FOR SEQ ID NO: 177:

( i ) SEQUENCE CHARACTERISTICS:
    ( A ) LENGTH: 128
    ( B ) TYPE: nucleic acid
    ( C ) STRANDEDNESS: single
    ( D ) TOPOLOGY: linear ( x i ) SEQUENCE DESCRIPTION: SEQ ID NO: 177:

```
CTACATCTAC ATCCACCACT GGGACAAGCC ATCTTGTAAA ATGTGCGGAG AAGGAGAAAA      60
CTTTCTGTGT GAATGGAGGG GAGTGCTTCA TGGTGAAAGA CCTTTCAAAC CCCTCGAGAT     120
ACTTGTGC                                                              128
```

( 2 ) INFORMATION FOR SEQ ID NO: 178:

( i ) SEQUENCE CHARACTERISTICS:
    ( A ) LENGTH: 69
    ( B ) TYPE: nucleic acid
    ( C ) STRANDEDNESS: single
    ( D ) TOPOLOGY: linear ( x i ) SEQUENCE DESCRIPTION: SEQ ID NO: 178:

```
AAGTGCCAAC CTGGATTCAC TGGAGCAAGA TGTACTGAGA ATGTGCCCAT GAAAGTCCAA      60
AACCAAGAA                                                              69
```

( 2 ) INFORMATION FOR SEQ ID NO: 179:

( i ) SEQUENCE CHARACTERISTICS:
    ( A ) LENGTH: 23
    ( B ) TYPE: nucleic acid
    ( C ) STRANDEDNESS: single
    ( D ) TOPOLOGY: linear ( x i ) SEQUENCE DESCRIPTION: SEQ ID NO: 179:

```
TCGGGCTCCA TGAAGAAGAT GTA                                              23
```

( 2 ) INFORMATION FOR SEQ ID NO: 180

( i ) SEQUENCE CHARACTERISTICS:
    ( A ) LENGTH: 23

(B) TYPE: nucleic acid
    (C) STRANDEDNESS: single
    (D) TOPOLOGY: linear ( x i ) SEQUENCE DESCRIPTION: SEQ ID NO: 180:

TCCATGAAGA AGATGTACCT GCT 23

( 2 ) INFORMATION FOR SEQ ID NO: 181

( i ) SEQUENCE CHARACTERISTICS:
    (A) LENGTH: 22
    (B) TYPE: nucleic acid
    (C) STRANDEDNESS: single
    (D) TOPOLOGY: linear ( x i ) SEQUENCE DESCRIPTION: SEQ ID NO: 181:

ATGTACCTGC TGTCCTCCTT GA 22

( 2 ) INFORMATION FOR SEQ ID NO: 182

( i ) SEQUENCE CHARACTAISTICS:
    (A) LENGTH: 22
    (B) TYPE: nucleic acid
    (C) STRANDEDNESS: single
    (D) TOPOLOGY: linear ( x i ) SEQUENCE DESCRIPTION: SEQ ID NO: 182:

TTGAAGAAGG ACTCGCTGCT CA 22

( 2 ) INFORMATION FOR SEQ ID NO: 183

( i ) SEQUENCE CHARACTERISTICS:
    (A) LENGTH: 20
    (B) TYPE: nucleic acid
    (C) STRANDEDNESS: single
    (D) TOPOLOGY: linear ( x i ) SEQUENCE DESCRIPTION: SEQ ID NO: 183:

AAAGCCGGGG GCTTGAAGAA 20

( 2 ) INFORMATION FOR SEQ ID NO: 184

( i ) SEQUENCE CHARACTERISTICS:
    (A) LENGTH: 20
    (B) TYPE: nucleic acid
    (C) STRANDEDNESS: single
    (D) TOPOLOGY: linear ( x i ) SEQUENCE DESCRIPTION: SEQ ID NO: 184:

ATGARGTGTG GGCGGCGAAA 20